United States Patent
Zabrocki et al.

(10) Patent No.: US 10,238,713 B2
(45) Date of Patent: Mar. 26, 2019

(54) CYCLIC TETRAPEPTIDES AND THERAPEUTIC APPLICATIONS THEREOF

(71) Applicants: LODZ UNIVERSITY OF TECHNOLOGY, Lodz (PL); PEPTADERM SP. Z O.O., Warsaw (PL)

(72) Inventors: Janusz Zabrocki, Lodz (PL); Michal Zimecki, Wroclaw (PL); Andrzej Kaszuba, Lodz (PL); Krzysztof Kaczmarek, Lodz (PL)

(73) Assignees: LODZ UNIVERSITY OF TECHNOLOGY, Lodz (PL); PEPTADERM SP. Z O.O., Warsaw (PL)

( * ) Notice: Subject to any disclaimer, the term of this patent is extended or adjusted under 35 U.S.C. 154(b) by 0 days.

(21) Appl. No.: 15/201,565

(22) Filed: Jul. 4, 2016

(65) Prior Publication Data
US 2017/0157204 A1 Jun. 8, 2017

Related U.S. Application Data

(63) Continuation of application No. 13/593,716, filed on Aug. 24, 2012, now Pat. No. 9,382,292, which is a continuation-in-part of application No. 13/579,933, filed as application No. PCT/US2011/025571 on Feb. 19, 2011, now abandoned.

(30) Foreign Application Priority Data

Feb. 19, 2010 (PL) .......................................... 390493

(51) Int. Cl.
| | |
|---|---|
| A61K 38/00 | (2006.01) |
| A61K 38/12 | (2006.01) |
| C07K 5/02 | (2006.01) |
| C07K 5/12 | (2006.01) |
| C07K 7/56 | (2006.01) |
| C07K 7/64 | (2006.01) |
| A61K 9/06 | (2006.01) |
| A61K 45/06 | (2006.01) |

(52) U.S. Cl.
CPC ................ *A61K 38/12* (2013.01); *A61K 9/06* (2013.01); *A61K 45/06* (2013.01); *C07K 5/0202* (2013.01); *C07K 5/126* (2013.01); *C07K 7/56* (2013.01); *C07K 7/64* (2013.01)

(58) Field of Classification Search
CPC ........ A61K 38/00; A61K 38/12; A61K 38/07; C07K 5/126; C07K 7/64
See application file for complete search history.

(56) References Cited

U.S. PATENT DOCUMENTS

| | | | |
|---|---|---|---|
| 3,842,067 | A | 10/1974 | Sarantakis |
| 3,862,925 | A | 1/1975 | Sarantakis |
| 3,972,859 | A | 8/1976 | Fujino |
| 4,105,603 | A | 8/1978 | Vale, Jr. |
| 5,216,124 | A | 6/1993 | Hansen, Jr. |
| 5,541,287 | A | 7/1996 | Yau |
| 6,015,881 | A | 1/2000 | Kang |
| 6,197,927 | B1 | 3/2001 | Braisted |
| 7,439,222 | B2 | 10/2008 | Guinn |
| 2013/0224232 | A1 | 8/2013 | Zabrocki |

FOREIGN PATENT DOCUMENTS

| | | |
|---|---|---|
| DE | 19816922 | 10/1999 |
| WO | 00/21979 | 4/2000 |
| WO | 00/47608 | 8/2000 |
| WO | 2006/049597 | 5/2006 |
| WO | 2008/023378 | 2/2008 |
| WO | 2009/107139 | 9/2009 |
| WO | 2010/006267 | 1/2010 |
| WO | 2011/048390 | 4/2011 |

OTHER PUBLICATIONS

Blakskjær et al., (2004) An improved protocol for the Sml2-promoted C-alkylation of peptides: degradation and functionalization of serine residues in linear and cyclic peptides. Tetrahedron Letters 45(49): 9091-9094.
Bray (2003) Large-scale manufacture of peptide therapeutics by chemical synthesis. Nat Rev Drug Discov 2(7): 587-93.
Cebrat et al., (1997) Sulfonated analogues of cyclolinopeptide A. Synthesis, immunosuppressive activity and CD studies. J Pept Res 49(5): 415-20.
Cebrat et al., (1997) The cyclolinopeptide A analogues with D-Phe, D-Tyr, and L- and D-Trp residues. Polish J Chem 71: 1401-12.
Che and, Marshall (2006) Engineering cyclic tetrapeptides containing chimeric amino acids as preferred reverse-turn scaffolds. J Med Chem 49(1): 111-24.
Choi, Morning Report. May 4, 2004 (available online at: http://www.google.com/url?sa=t&rct=j&q=aspirin%20toxicity%20choi%20&source=web&cd=1&cad=rja&ved=0CCoQFjAA&url=http%3A%2F%2Fwww.med.unc.edu%2Fmedicine%2Fweb%2FAapirin%2520Toxicity.pdf&ei=9ZcCUtHnCJS44AP1vlC4CA&usg=AFQjCNFf5jIXTKNzTdksHcSu2WfScZvqog).

(Continued)

*Primary Examiner* — Rachael E Bredefeld
*Assistant Examiner* — Kaipeen E Yang
(74) *Attorney, Agent, or Firm* — Wenderoth, Lind & Ponack, L.LP.

(57) ABSTRACT

There are provided compounds of formula I:

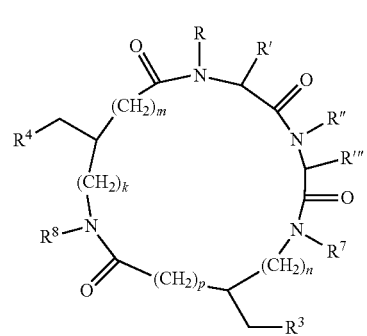

wherein k, m, n, p, R, R', R", R''', $R^3$, $R^4$, $R^7$ and $R^8$ are as defined in the application. Other embodiments are also disclosed.

5 Claims, 17 Drawing Sheets

(56) References Cited

OTHER PUBLICATIONS

Datta et al., (2009) Calcineurin inhibitors activate the proto-oncogene Ras and promote protumorigenic signals in renal cancer cells. Cancer Res 69(23): 8902-9.
Davies (2003) The cyclization of peptides and depsipeptides. J Pept Sci 9(8): 471-501.
Fredericks and Holt (2003) Pharmacogenomics of immunosuppressive drug metabolism. Curr Opin Nephrol Hypertens 12(6): 607-13.
Gallo et al., (1995) Specific interaction between cyclophilin and cyclic peptides. Biopolymers 36(3): 273-81.
Gaymes et al., (1997) Cyclolinopeptide A (CLA) mediates its immunosuppressive activity through cyclophilin-dependent calcineurin inactivation. FEBS Lett. 418(1-2): 224-7.
Giolitti et al., (2002) Monocyclic human tachykinin NK-2 receptor antagonists as evolution of a potent bicyclic antagonist: QSAR and site-directed mutagenesis studies. J Med Chem 45(16): 3418-29.
Glenn et al., (2003) Conformationally homogeneous cyclic tetrapeptides: useful new three-dimensional scaffolds. J Am Chem Soc 125(3): 640-1.
Hernández-Espinosa and Morton (2006) Calcineurin inhibitors cause an acceleration of the neurological phenotype in a mouse transgenic for the human Huntington's disease mutation. Brain Res Bull 69(6): 669-79.
Houghten (1985) General method for the rapid solid-phase synthesis of large numbers of peptides: specificity of antigen-antibody interaction at the level of individual amino acids. Proc Natl Arad Sci U S A 82(15): 5131-5.
Kaczmarek et al., (2002) Tetrazole analogues of cyclolinopeptide A: synthesis, conformation, and biology. Biopolymers 63(6): 343-57.
Kaczmarek et al., (2009) Synthesis, conformational analysis and immunological activity of beta3Phe-substituted Cyclolinopeptide A analogues. J Pept Sci 15(3): 166-74.
Katarzyńska et al., (2008) Synthesis and immunosuppressive activity of new cyclolinopeptide A analogs modified with beta-prolines. J Pept Sci 14(12): 1283-94.
Kaufmann and Tobschirbel (1959) Über ein Oligopeptid aus Leinsamen. Chemische Berichte 92(11): 2805-9; machine translation of the title and abstract.
Kovarik and Burtin (2003) Immunosuppressants in advanced clinical development for organ transplantation and selected autoimmune diseases. Expert Opin Emerg Drugs 8(1): 47-62.
Liu et al., (2009) Synthesis and screening of a cyclic peptide library: discovery of small-molecule ligands against human prolactin receptor. Bioorg Med Chem 17(3): 1026-33.
Lloyd-Williams et al., (1993) Convergent solid-phase peptide synthesis. Tetrahedron 49(48): 11065-11133.
Mergler et al., (1988) Peptide synthesis by a combination of solid-phase and solution methods I: A new very acid-labile anchor group for the solid phase synthesis of fully protected fragments. Tetrahedron Letters 29(32): 4005-4008.
Mergler et al., (1988) Peptide synthesis by a combination of solid-phase and solution methods II synthesis of fully protected peptide fragments on 2-methoxy-4-alkoxy-benzyl alcohol resin. Tetrahedron Letters 29(32): 4009-4012.
Merrifield (1963) Solid Phase Peptide Synthesis. I. The Synthesis of a Tetrapeptide. J Am Chem Soc 85(14): 2149-2154.
Norgren et al., (2006) Beta2-amino acids in the design of conformationally homogeneous cyclo-peptide scaffolds. J Org Chem 71(18): 6814-21.
Olsen and Ghadiri (2009) Discovery of potent and selective histone deacetylase inhibitors via focused combinatorial libraries of cyclic alpha3beta-tetrapeptides. J Med Chem 52(23): 7836-46.
Riniker et al., (1993) A General Strategy for the Synthesis of Large Peptides: the Combined Solid-Phase and Solution Approach. Tetrahedron 49(41): 9307-9320.
Schumann et al., (2000) Are beta-amino acids gamma-turn mimetics? Exploring a new design principle for bioactive cyclopeptides. J Am Chem Soc 122(48): 12009-12010.
Seebach et al., (2008) New Open-Chain and Cyclic Tetrapeptides, Consisting of α-, β2-, and β3-Amino-Acid Residues, as Somatostatin Mimics—a Survey. Helvetica Chimica Acta 91(9): 1736-1786.
Siemion et al., (1992) Immunosuppressive activity of threonine-containing analogues of cyclolinopeptide A. Arch Immunol Ther Exp (Warsz) 40(5-6): 257-61.
Siemion et al., (1994) Synthesis and biological studies on analogs of cyclolinopeptide A with a shortened peptide chain. Arch Immunol Ther Exp (Warsz) 42(5-6): 459-65.
Siemion et al., (1999) Cyclolinopeptides and their analogs—a new family of peptide immunosuppressants affecting the calcineurin system. Arch Immunol Ther Exp (Warsz) 47(3): 143-53.
Terracciano et al., (2008) Synthetic and pharmacological studies on new simplified analogues of the potent actin-targeting Jaspamide. Bioorg Med Chem 16(13): 6580-8.
Wieczorek et al., (1991) Immunosuppressive activity of cyclolinopeptide A. Pept Res 4(5): 275-83.
Wieczorek et al., (1992) Immunosuppressive activity of tyrosine analogues of cyclolinopeptide A. Arch Immunol Ther Exp (Warsz) 40(3-4): 213-6.
Wieczorek et al., (1993) Immunosuppressive activity of alanine analogs of cyclolinopeptide A. Arch Immunol Ther Exp (Warsz) 41(5-6): 291-6.
Zubrzak et al., (2005) Analogues of cyclolinopeptide A containing alpha-hydroxymethyl amino acid residues. Biopolymers 80(2-3): 347-56.
Opinion of the Scientific Committee on Food on the Tolerable Upper Intake Level of Vitamin E, (European Commission Health & Consumer Protection Directorate-General, p. 1-18, published on Apr. 23, 2003).
Andersson et al., (2000) Large-scale synthesis of peptides. Biopolymers 55(3): 227-250.
Espevik and Nissen-Meyer (1986) A highly sensitive cell line, WEHI 164 clone 13, for measuring cytotoxic factor/tumor necrosis factor from human monocytes. J Immunol Methods 95(1): 99-105.
Goindi et al., (2014) Novel flexible vesicles based topical formulation of levocetirizine: in vivo evaluation using oxazolone-induced atopic dermatitis in murine model. J Liposome Res 24(3): 249-257.
Gorbachev and Fairchild (2001) Induction and regulation of T-cell priming for contact hypersensitivity. Crit Rev Immunol 21(5): 451-472.
Guiller et al., (2000) Linkers and Cleavage Strategies in Solid-Phase Organic Synthesis and Combinatorial Chemistry. Chem Rev 100(6): 2091-2158.
Hansen et al., (1989) Re-examination and further development of a precise and rapid dye method for measuring cell growth/cell kill. J Immunol Methods 119(2): 203-210.
Hofmann et al., (2018) Non-invasive bioluminescence imaging as a standardized assessment measure in mouse models of dermal inflammation. J Dermatol Sci 91(2) 153-163.
Kim et al., (2014) Panduratin A, an activator of PPAR-α/δ, suppresses the development of oxazolone-induced atopic dermatitis-like symptoms in hairless mice. Life Sci 100(1): 45-54.
Lv et al., (2015) Leukotriene $B_4$-leukotriene $B_4$ receptor axis promotes oxazolone-induced contact dermatitis by directing skin homing of neutrophils and $CD8^+T$ cells. Immunology 146(1): 50-58.
Mishell and Dutton (1967) Immunization of dissociated spleen cell cultures from normal mice. J Exp Med 126(3): 423-442.
Nam et al., (2016) Selective Cannabinoid Receptor-1 Agonists Regulate Mast Cell Activation in an Oxazolone-Induced Atopic Dermatitis Model. Ann Dermatol 28(1): 22-29.
Nolte et al., (2013) Induction of oxazolone-mediated features of atopic dermatitis in NOD-scid IL2Rγnull mice engrafted with human peripheral blood mononuclear cells. Dis Model Mech 6(1): 125-134
Noonan and Hallida (1978) Studies of contact hypersensitivity and tolerance in vivo and in vitro. I. Basic characteristics of the reactions and confirmation of an immune response in tolerant mice. Int Arch Allergy Appl Immunol 56(6): 523-53.
Yamamoto et al., (2006) Pharmacological profile of a novel phosphodiesterase 7A and -4 dual inhibitor, YM-393059, on acute and chronic inflammation models. Eur J Pharmacol 550(1-3): 166-172.

CYCLIC TETRAPEPTIDES AND THERAPEUTIC APPLICATIONS THEREOF

STATEMENT REGARDING RELATED APPLICATIONS

This application is a continuation of U.S. Ser. No. 13/593,716, entitled "CYCLIC TETRAPEPTIDES AND THERAPEUTIC APPLICATIONS THEREOF" and filed August 2012 as a continuation-in-part of U.S. Ser. No. 13/579,933, also entitled "CYCLIC TETRAPEPTIDES AND THERAPEUTIC APPLICATIONS THEREOF" and filed Aug. 19, 2012 (but given a filing date of Aug. 29, 2012) per 35 U.S.C. § 371 as a national phase application of PCT/US2011/025571, filed Feb. 19, 2011 and claiming priority from Polish patent application no. P.390493, filed Feb. 19, 2010, the contents of all of which are incorporated herein by reference. Priority from the Polish application, and the benefit of the PCT and US applications, is claimed.

BACKGROUND

Immunosuppressive drugs are commonly used in transplantation and in treatment of autoimmune diseases. Production of these drugs is expensive, and the most frequently used of these drugs, namely cyclosporine A, tacrolimus and rapamycin, exhibit undesirable side-effects. The search for new immunosuppressive drugs devoid of side-effects, particularly in the class of natural peptide immunoregulators and their analogues, represents a serious challenge for medicinal chemistry.

Cyclolinopeptide A (CLA), a very hydrophobic cyclic nonapeptide, was first isolated from linen seeds in 1959. CLA is strongly immunosuppressive, with a potency comparable to that of cyclosporine A (CsA). The mechanism of action of CLA was shown to be similar to that of CsA, i.e. CLA formed a complex with cyclophilin A causing inactivation of calcineurin, albeit at much lower affinity (Gaymes et al., *Febs Lett*, 1997, 418, 224-227). CLA inhibited both humoral and cellular immune response and graft-versus-host reaction; prolonged survival of allogeneic skin grafts; tempered post-adjuvant polyarthritis in rats and hemolytic anemia of New Zealand Black mice; and, similarly to CsA, inhibited IL1 and IL-2 production. Unfortunately, the high hydrophobicity of CLA presents an obstacle for the potential application of the compound in therapy.

Linear CLA analogues containing alanine residue in successive positions of the peptide chain were found to be immunosuppressive (Wieczorek et al., *Arch Immunol Ther Exp*, 1992, 40, 213-216). It was also found that the activity of linear CLA analogues gradually decreased with shortening of the peptide chain from the N-terminus, at the same time showing an increase of activity for C-terminal tetra- and tripeptides (Siemion et al., *Arch Immunol Ther Exp*, 1994, 42, 459-465). The introduction of a single, hydrophilic threonine residue into the CLA molecule did not result in improved solubility in water. However, an improvement in solubility was achieved by the introduction of a sulphonic group in the para-position of the phenyl ring of one or two phenyloalanine residues, without loss of biological activity (Siemion et al., *Arch Immunol Ther Exp*, 1992, 40, 257-261; Cebrat et al., *J Peptide Res.*, 1997, 49, 415-420). In addition, it has been observed that the inclusion of tetrapeptidic (Pro-Pro-Phe-Phe) or tripeptidic (Pro-Phe-Phe) fragments in longer linear peptides chains seem to have significance for immunosuppressive activity (Wieczorek et al., *Arch Immunol Ther Exp,* 1993, 41, 291-296; Cebrat et al., *Pol. J Chem,* 1997, 71, 1401).

A series of analogues in which the cis-peptide bond between proline residues was replaced with 1,5-disubstituted tetrazole ring (a good mimetic of amide bonds in cis configuration) showed immunosuppressive activity comparable to CsA. (Karczmarek et al., *Biopolymers,* 2002, 63, 343-357).

Synthetic CLA analogues in which leucine residues in position 5 and/or 8 were replaced with their hydroxymethyl analogue displayed a four-fold increase in solubility in water in comparison to CLA, but also showed a 25% diminution in biological activity compared to native CLA (Zubrzak et al., *Biopolymers (Peptide Science),* 2005, 80, 347-356).

A series of nine CLA analogues was obtained by replacement of CLA proline residues with $\beta^2$-isoproline and $\beta^3$-homoproline. In comparison to CsA, these CLA analogues displayed strong inhibitory properties in the cellular immune response. The majority of these analogs were practically devoid of cell toxicity (Katarzyliska et al., *J Pept Sci*, 2009, 14, 1283-1294).

BRIEF DESCRIPTION OF THE INVENTION

There are provided in accordance with an embodiment of the present invention compounds having the formula I:

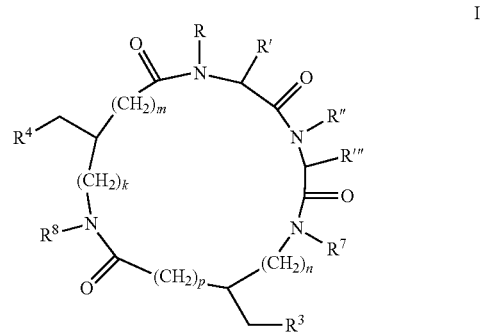

wherein k, m, n and p are each independently 0, 1 or 2, provided that at least one of k, m, n and p is not zero;

R is selected from H and $C_{1-3}$ alkyl and R' is selected from H and optionally substituted $C_{1-3}$ alkyl, or, when taken together, R and R', together with the peptide backbone atoms to which they are attached, form an optionally substituted 5- or 6-membered ring or an optionally substituted 9- or 10-membered bicyclic ring, said 5- or 6-membered ring or said 9- or 10-membered bicyclic ring being saturated or unsaturated;

R" is selected from H and $C_{1-3}$ alkyl and R'" is selected from H and optionally substituted $C_{1-3}$ alkyl, or, when taken together, R" and R'", together with the peptide backbone atoms to which they are attached, form an optionally substituted 5- or 6-membered ring or an optionally substituted 9- or 10-membered bicyclic ring, said 5- or 6-membered ring or said 9- or 10-membered bicyclic ring being saturated or unsaturated;

$R^7$ and $R^8$ are each H; and $R^3$ and $R^4$ are each independently selected from aryl $(C_y alkyl)$, substituted aryl$(C_y alkyl)$, heteroaryl$(C_y alkyl)$ and substituted heteroaryl$(C_y alkyl)$, wherein y is 0, 1 or 2; or $R^3$ may be taken together with $R^7$ and the intervening carbon and nitrogen atoms to form a 5- or 6-membered ring or a 9- or 10-membered bicyclic ring, which 5- or 6-membered ring or a 9- or 10-membered bicyclic ring may contain unsaturation, and $R^4$ may be taken together with $R^8$ and the intervening carbon and nitrogen atoms to form a 5- or 6-membered ring or a 9- or 10-membered bicyclic ring, which 5- or 6-membered ring or a 9- or 10-membered bicyclic ring may contain unsaturation;

or a pharmaceutically acceptable salt thereof. In the claims, unless specified otherwise or illogical in the given context, when reference is made to a compound of formula I or a subgenus or sub-species thereof, such reference is intended to include such compound in the form of a pharmaceutically acceptable salt thereof.

In some embodiments, at least one of $R^3$ and $R^4$ is phenyl. In some embodiments, at least one of $R^3$ and $R^4$ is substituted phenyl. In some embodiments, at least one of $R^3$ and $R^4$ is 4-hydroxyphenyl. In some embodiments, at least one of $R^3$ and $R^4$ is 4-t-butoxyphenyl. In some embodiment the substituted phenyl is 4-methylphenyl. In some embodiments, the substituted phenyl is halo-substituted phenyl. In some embodiments, the halo-substituted phenyl is 4-halophenyl. In some embodiments the 4-halophenyl is selected from the group consisting of 4-iodophenyl, 4-chlorophenyl and 4-fluorophenyl. In some embodiments, the substituted phenyl is 4-phenylphenyl. In some embodiments, at least one of $R^3$ and $R^4$ is indolyl. In some embodiments, the indolyl is 2-indolyl. In some embodiments, the indolyl is 3-indolyl. In some embodiments, at least one of $R^3$ and $R^4$ is naphthyl. In some embodiments, the naphthyl is 2-naphthyl. In some embodiments, the naphthyl is 1-naphthyl. In some embodiments, at least one of $R^3$ and $R^4$ is pyridinyl. In some embodiments the pyridinyl is 3-pyridinyl. In some embodiments, at least one of $R^3$ and $R^4$ is phenylmethyl. In some embodiments, $R^3$ and $R^4$ are both phenyl. In some embodiments, one of $R^3$ and $R^4$ is phenyl and the other of $R^3$ and $R^4$ is 4-hydroxyphenyl. In some embodiments, one of $R^3$ and $R^4$ is phenyl and the other of $R^3$ and $R^4$ is 4-t-butoxyphenyl. In some embodiments, one of $R^3$ and $R^4$ is phenyl and the other of $R^3$ and $R^4$ is 2-indolyl. In some embodiments, one of $R^3$ and $R^4$ is phenyl and the other of $R^3$ and $R^4$ is 3-indolyl. In some embodiments, one of $R^3$ and $R^4$ is phenyl and the other of $R^3$ and $R^4$ is 4-methylphenyl. In some embodiments, one of $R^3$ and $R^4$ is phenyl and the other of $R^3$ and $R^4$ is 4-phenylphenyl. In some embodiments, one of $R^3$ and $R^4$ is phenyl and the other of $R^3$ and $R^4$ is 3-pyridyl. In some embodiments, one of $R^3$ and $R^4$ is phenyl and the other of $R^3$ and $R^4$ is phenylmethyl. In some embodiments, one of $R^3$ and $R^4$ is phenyl and the other of $R^3$ and $R^4$ is 2-naphthyl. In some embodiments, one of $R^3$ and $R^4$ is phenyl and the other of $R^3$ and $R^4$ is 1-naphthyl. In some embodiments, one of $R^3$ and $R^4$ is phenyl and the other of $R^3$ and $R^4$ is 4-halophenyl. In some embodiments the halo is iodo. In some embodiments the halo is chloro. In some embodiments the halo is fluoro. In some embodiments, $R^3$ is taken together with $R^7$ and the intervening carbon and nitrogen atoms to form a tetrahydroisoquinoline moiety. In some embodiments, $R^4$ is taken together with $R^8$ and the intervening carbon and nitrogen atoms to form a tetrahydroisoquinoline moiety. In some embodiments, the carbon to which —$CH_2$—$R^3$ is attached has absolute (R)-stereochemistry. In some embodiments, the carbon to which —$CH_2$—$R^3$ is attached has absolute (S)-stereochemistry. In some embodiments, the carbon to which —$CH_2$—$R^4$ is attached has absolute (R)-stereochemistry. In some embodiments, the carbon to which —$CH_2$—$R^4$ is attached has absolute (S)-stereochemistry. In some embodiments, one of k, m, n and p is 1, and the remainder of k, m, n and p are 0. In some embodiments, two of k, m, n and p are 1, and the remainder of k, m, n and p are 0. In some embodiments, at least one of k and m is not 0. In some embodiments, at least one of n and p is not 0. In some embodiments, at least one of k and m is not 0 and at least one of n and p is not 0. In some embodiments, both k and n are 0. In some embodiments, both k and n are 0, one of m and p is 0, and the other of m and p is 1. In some embodiments, both k and n are 0 and both m and p are 1. In some embodiments, all four amino acids are L-amino acids. In some embodiments, three of the amino acids are L-amino acids and one of the amino acids is a D-amino acid. In some embodiments, two of the amino acids are L-amino acids and two of the amino acids are D-amino acids. In some embodiments, one of the amino acids is an L-amino acid and three of the amino acids are D-amino acids. In some embodiments, all four amino acids are D-amino acids.

In some embodiments, R and R' are taken together to form a unit —$CR^1R^1$—X—$CR^2R^2$—, wherein $CR^1R^1$ is attached to the backbone nitrogen, $R^1$ and $R^2$ are independently selected at each instance from H, optionally substituted $C_{1-3}$ alkyl, and optionally substituted —$OC_{1-3}$ alkyl, X is selected from —$CR^5R^6$—, —$CR^5R^5CR^6R^6$—, —$NR^5CR^6R^6$—, —$CR^5R^5NR^6$—, —O—, —S—, —$NR^5$— and —$NR^6$—, wherein $R^5$ and $R^6$ are independently selected at each instance from H, optionally substituted $C_{1-3}$ alkyl, and, when $R^5$ or $R^6$ is attached to a carbon atom, optionally substituted $OC_{1-3}$ alkyl, and (a)(i) one $R^5$ may be taken together with one $R^1$ to form a bond, or (ii) one $R^5$ and the carbon or nitrogen atom to which it is attached may be taken together with one $R^1$ and the carbon atom to which it is attached to form saturated, partly unsaturated or fully unsaturated 5- or 6-membered ring, (b)(i) one $R^6$ may be taken together with one $R^2$ to form a bond, or (ii) one $R^6$ and the carbon or nitrogen atom to which it is attached may be taken together with one $R^2$ and the carbon atom to which it is attached to form saturated, partly unsaturated or fully unsaturated 5- or 6-membered ring, provided that when X is —$CR^5R^6$—, only one of $R^5$ and $R^6$ may be taken together with $R^1$ or $R^2$; or (c)(i) one $R^5$ and one $R^6$ which is not geminal thereto may be taken together to form a bond, or (ii) one $R^5$ and one $R^6$ which is not geminal thereto be taken together with the atoms to which they are attached to form a saturated, partly unsaturated or fully unsaturated 5- or 6-membered ring.

In some embodiments, R" and R'" are taken together to form a unit —$CR^{1'}R^{1'}$—X'—$CR^{2'}R^{2'}$—, wherein $CR^{1'}R^{1'}$ is attached to the backbone nitrogen, $R^{1'}$ and $R^{2'}$ are independently selected at each instance from H, optionally substituted $C_{1-3}$ alkyl, and optionally substituted $OC_{1-3}$ alkyl, X' is selected from —$CR^{5'}R^{6'}$—, —$CR^{5'}R^{5'}CR^{6'}R^{6'}$—, —$NR^{5'}CR^{6'}R^{6'}$—, —$CR^{5'}R^{5'}NR^{6'}$—, —O—, —S—, —$NR^{5'}$— and —$NR^{6'}$—, wherein $R^{5'}$ and $R^{6'}$ are independently selected at each instance from H, optionally substituted $C_{1-3}$ alkyl, and, when $R^{5'}$ or $R^{6'}$ is attached to a carbon atom, optionally substituted $OC_{1-3}$ alkyl, and (a)(i) one $R^{5'}$ may be taken together with one $R^{1'}$ to form a bond, or (ii) one $R^{5'}$ and the carbon or nitrogen atom to which it is attached may be taken together with one $R^{1'}$ and the carbon atom to which it is attached to form saturated, partly unsaturated or fully unsaturated 5- or 6-membered ring, (b)(i) one $R^{6'}$ may be taken together with one $R^{2'}$ to form a bond, or (ii) one $R^{6'}$ and the carbon or nitrogen atom to which it is attached may be taken together with one $R^{2'}$ and the carbon atom to which it is attached to form saturated, partly unsaturated or fully unsaturated 5- or 6-membered ring, provided that when X' is —$CR^{5'}R^{6'}$—, only one of $R^{5'}$ and $R^{6'}$ may be taken together with R¹' or R²'; or (c)(i) one R⁵' and one R⁶' which is not geminal thereto may be taken together to form a bond, or (ii) one R⁵' and one R⁶' which is not geminal thereto be taken together with the atoms to which they are attached to form a saturated, partly unsaturated or fully unsaturated 5- or 6-membered ring.

In some embodiments, R and R' are taken together to form —(CH₂)₃—, i.e. R and R' are taken together to form —CR¹R¹—X—CR²R²— wherein R¹ and R² in all instances are H and X is CH₂. In some embodiments, R" and R'" are taken together to form —(CH₂)₃—, i.e. R" and R'" are taken together to form —CR¹R¹'—X'—CR²R²'— wherein R¹' and R²' in all instances are H and X' is CH₂. In some embodiments, R and R' are taken together to form —(CH₂)₄—, i.e. R and R' are taken together to form —CR¹R¹—X—CR²R²— wherein R¹ and R² in all instances are H and X is (CH₂)₂. In some embodiments, R" and R'" are taken together to form —(CH₂)₄—, i.e. R" and R'" are taken together to form —CR¹R¹'—X'—CR²'R²'— wherein R¹' and R²' in all instances are H and X is (CH₂)₂. In some embodiments, R and R' are taken together to form —CH₂—CH(OH)—CH₂—, i.e. R and R' are taken together to form —CR¹R¹—X—CR²R²— wherein R¹ and R² in all instances are H and X is CH(OH). In some embodiments, R" and R'" are taken together to form —CH₂—CH(OH)—CH₂—, i.e. R" and R'" are taken together to form —CR¹R¹'—X'—CR²R²'— wherein R¹' and R²' in all instances are H and X' is CH(OH). In some embodiments, R and R' are taken together to form —CH₂—CH(O-t-Bu)-CH₂—, i.e. R and R' are taken together to form —CR¹R¹—X—CR²R²— wherein R¹ and R² in all instances are H and X is CH(O-t-Bu). In some embodiments, R" and R'" are taken together to form —CH₂—CH(O-t-Bu)-CH₂—, i.e. R" and R'" are taken together to form —CR¹R¹'—X'—CR²R²'— wherein R¹' and R²' in all instances are H and X' is CH(O-t-Bu). In some embodiments, R and R' are taken together to form —CH₂—CH=CH—, i.e. R and R' are taken together to form —CR¹R¹—X—CR²R²— wherein R⁶ is taken together with one R² to form a bond and the remaining R¹, R² and R⁵ in all instances are H. In some embodiments, R" and R'" are taken together to form —CH₂—CH=CH—, i.e. R" and R'" are taken together to form —CR¹R¹'—X'—CR²R²'— wherein R⁶' is taken together with one R²' to form a bond and the remaining R¹', R²' and R⁵' in all instances are H. In some embodiments, R and R' are taken together with the nitrogen and carbon atoms to which they are respectively attached to form a 1,2,3,4-tetrahydroisoquinoline moiety, i.e. R and R' are taken together to form —CR¹R¹—X—CR²R²— wherein R¹ and R² in all instances are H and X is CR⁵R⁵CR⁶R⁶ wherein an R⁵ and R⁶, together with the carbon atoms to which they are attached, form an aromatic 6-membered ring. In some embodiments, R" and R'" are taken together with the nitrogen and carbon atoms to which they are respectively attached to form a 1,2,3,4-tetrahydroisoquinoline moiety, i.e. R" and R'" are taken together to form —CR¹R¹'—X'—CR²R²'— wherein R¹' and R²' in all instances are H and X' is CR⁵R⁵'CR⁶R⁶' wherein an R⁵' and R⁶', together with the carbon atoms to which they are attached, form an aromatic 6-membered ring. In some embodiments, R and R' are taken together with the nitrogen and carbon atoms to which they are respectively attached to form an octahydroindole moiety, i.e. R and R' are taken together to form —CR¹R¹—X—CR²R²— wherein X is CR⁵R⁶, one R¹ is taken together with R⁵ to form —CH₂CH₂CH₂CH₂—, and the remaining R¹, R² and R⁶ in all instances are H. In some embodiments, R" and R'" are taken together with the nitrogen and carbon atoms to which they are respectively attached to form an octahydroindole moiety, i.e. R" and R'" are taken together to form —CR¹R¹'—X—CR²'R²'— wherein X is CR⁵'R⁶', one R¹' is taken together with R⁵' to form —CH₂CH₂CH₂CH₂—, and the remaining R¹', R²' and R⁶' in all instances are H. In some embodiments, R' is selected from the group consisting of —CH₂OH, —CH₂OCH₃ and —CH₂O-t-Bu. In some embodiments, R'" is selected from the group consisting of —CH₂OH, —CH₂OCH₃ and —CH₂O-t-Bu. In some embodiments in which R' is other than H, e.g. in which R and R' are taken together, the carbon at which R' is attached has absolute (S)-stereochemistry. In some embodiments in which R' is other than H, e.g. in which R and R' are taken together, the carbon at which R' is attached has absolute (R)-stereochemistry. In some embodiments in which R'" is other than H, e.g. in which R" and R'" are taken together, the carbon at which R'" is attached has absolute (S)-stereochemistry. In some embodiments in which R'" is other than H, e.g. in which R" and R'" are taken together, the carbon at which R'" is attached has absolute (R)-stereochemistry.

In some embodiments, the compound is selected from the group consisting of:

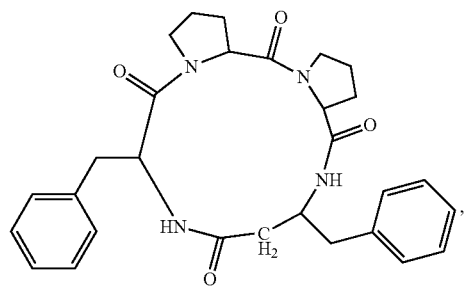

(cyclo(-Pro-Pro-β³hoPhe-Phe-))

I-1

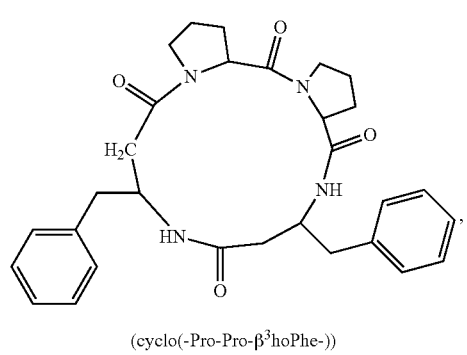

(cyclo(-Pro-Pro-β³hoPhe-))

I-2

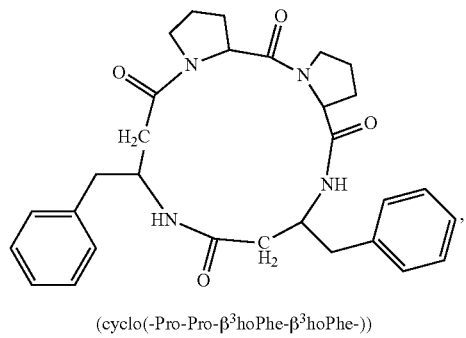

(cyclo(-Pro-Pro-β³hoPhe-β³hoPhe-))

I-3

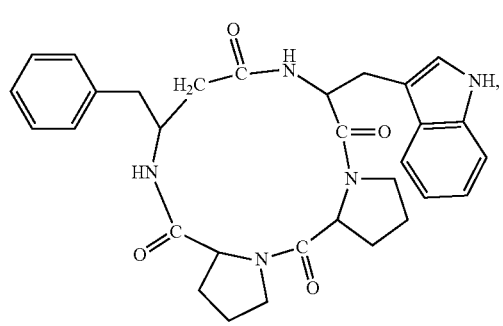
(cyclo(-Pro-Pro-β³hoPhe-Trp-))   I-4
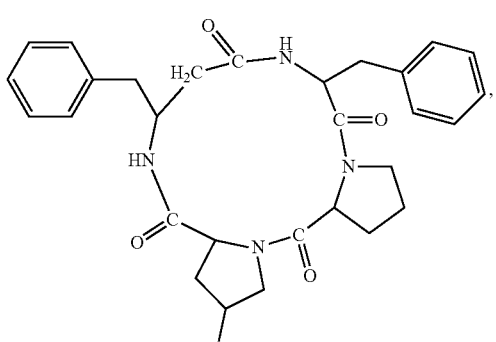
(cyclo(-Pro-Hyp-β³hoPhe-Phe-))   I-8
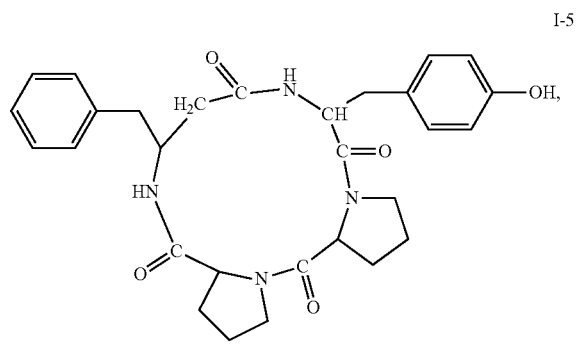
(cyclo(-Pro-Pro-β³hoPhe-Tyr-))   I-5
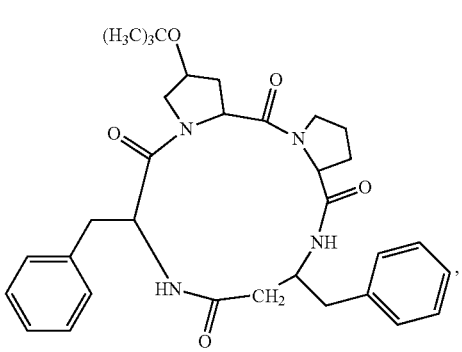
(cyclo(-Hyp(tBu)-Pro-β³hoPhe-Phe-))   I-9
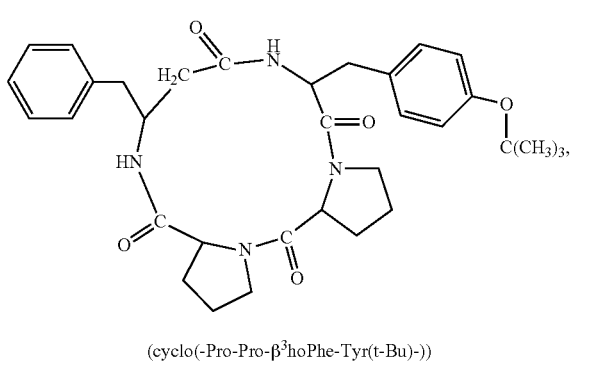
(cyclo(-Pro-Pro-β³hoPhe-Tyr(t-Bu)-))   I-6
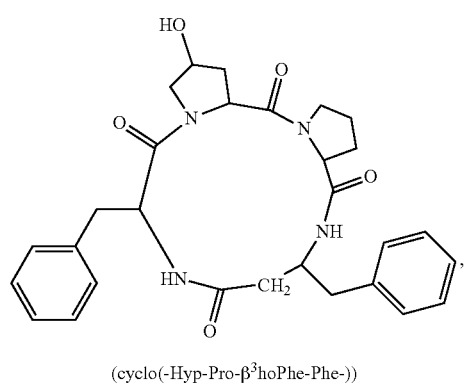
(cyclo(-Hyp-Pro-β³hoPhe-Phe-))   I-10
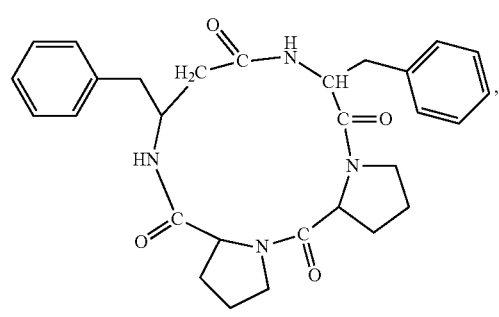
(cyclo(-Pro-Pip-β³hoPhe-Phe-))   I-7
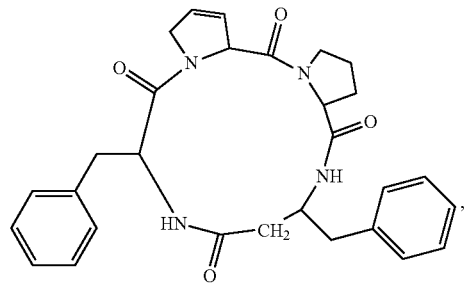
(cyclo(-ΔPro-Pro-β³hoPhe-Phe-))   I-11

I-12
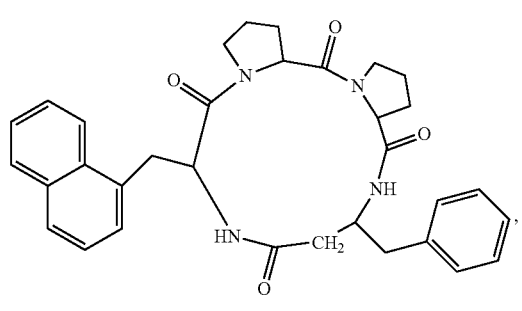
(cyclo(-Pro-Pro-β³hoPhe-1Nal))
I-13
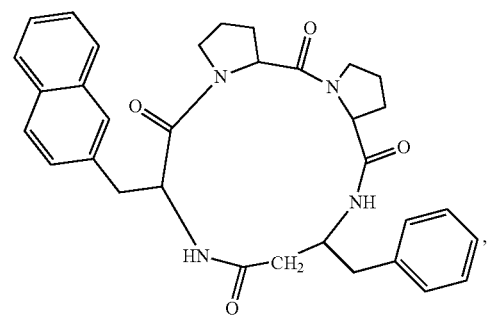
(cyclo(-Pro-Pro-β³hoPhe-2Nal))
I-14
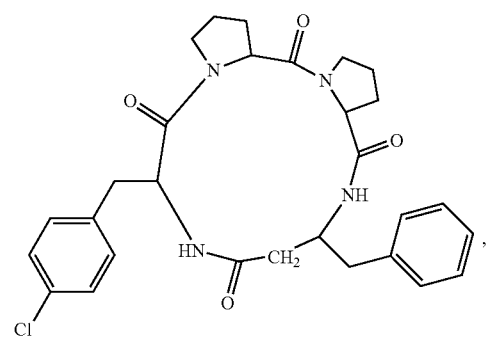
(cyclo(-Pro-Pro-β³hoPhe-Phe(4Cl)))
I-15
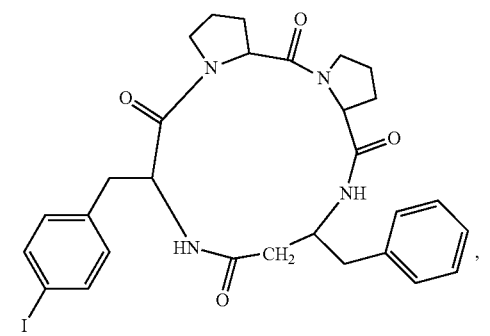
(cyclo(-Pro-Pro-β³hoPhe-Phe(4I)))
I-16
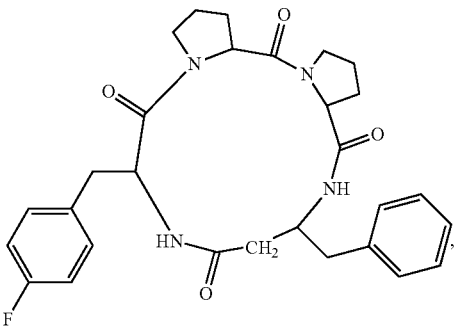
(cyclo(-Pro-Pro-β³hoPhe-Phe(4F)))
I-17
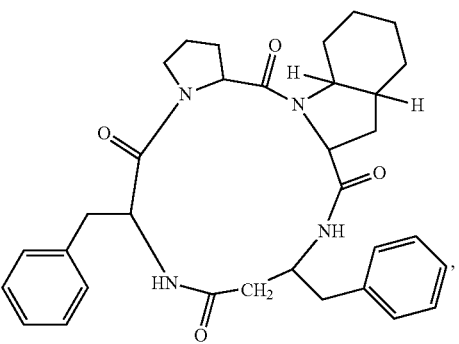
(cyclo(-Pro-Oic-β³hoPhe-Phe))
I-18
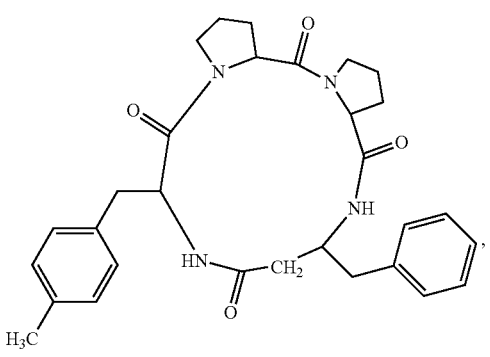
(cyclo(-Pro-Pro-β³hoPhe-Phe(4Me)))
I-19
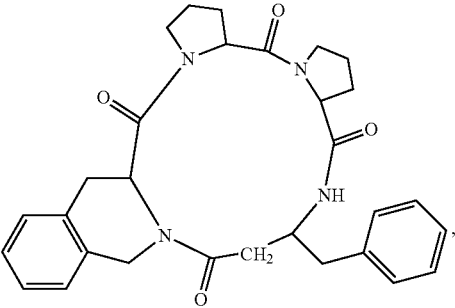
(cyclo(-Pro-Pro-β³hoPhe-Tic))

I-20
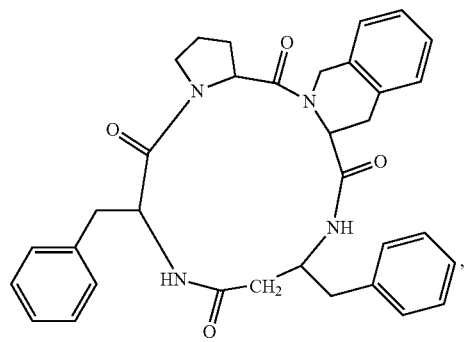
(cyclo(-Pro-Tic-β³hoPhe-Phe))
I-21
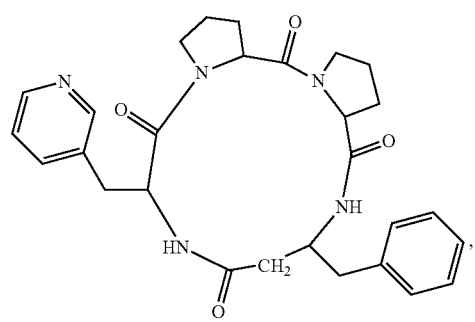
(cyclo(-Pro-Pro-β³hoPhe-3Pal))
I-22
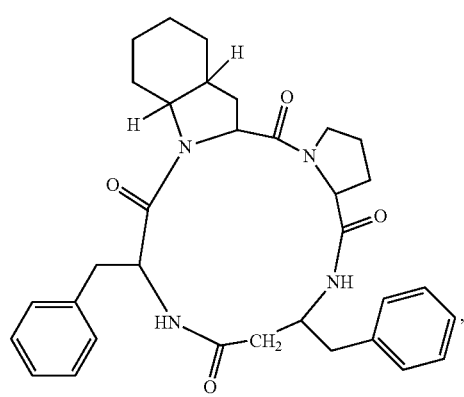
(cyclo(Oic-Pro-β³hoPhe-Phe-))
I-23
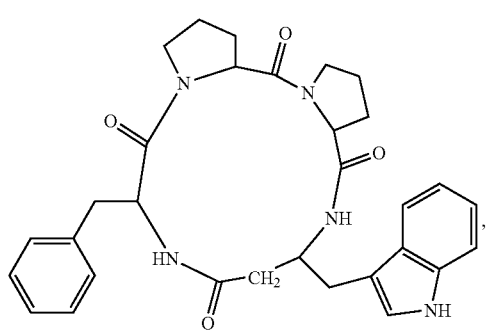
(cyclo(Pro-Pro-β³hoTrp-Phe-))
I-24
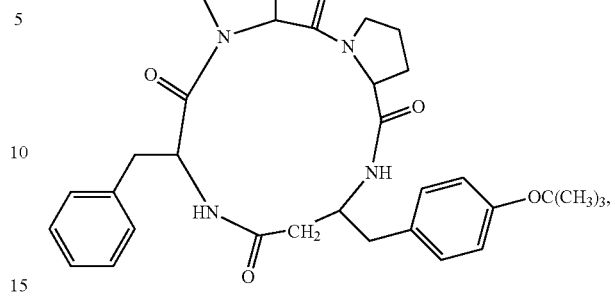
(cyclo(-Pro-Pro-β³hoTyr(tBu)-Phe-))
I-25
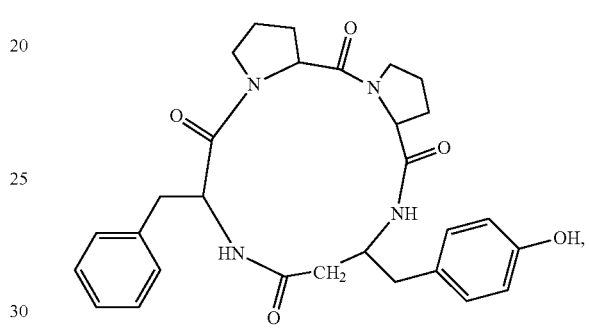
(cyclo(-Pro-Pro-β³hoTyr-Phe))
I-26
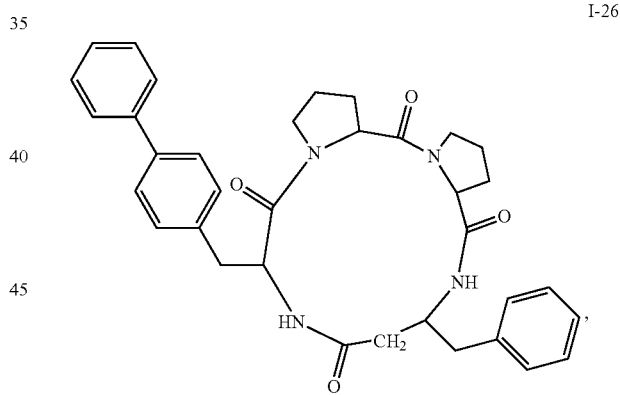
(cyclo(-Pro-Pro-β³hoPhe-Bip))
I-27
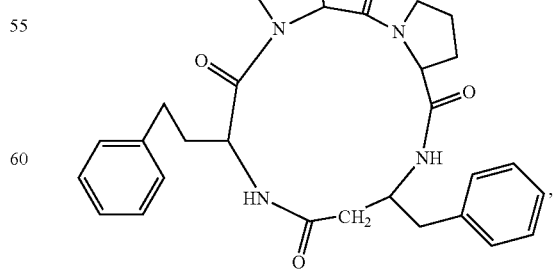
(cyclo(-Pro-Pro-β³hoPhe-hoPhe))

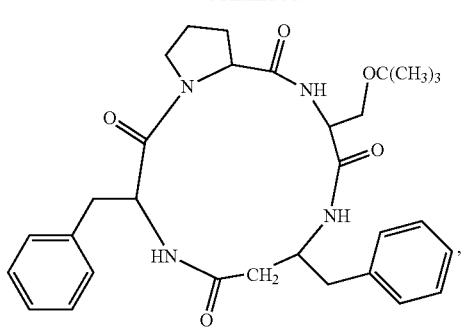

(cyclo(-Pro-Ser(tBu)-β³hoPhe-Phe))

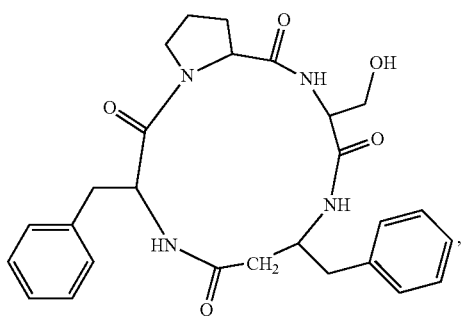

(cyclo(-Pro-Ser-β³hoPhe-Phe))

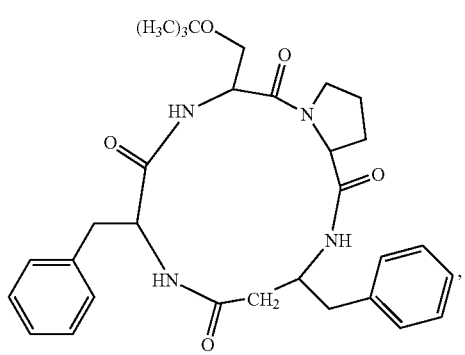

(cyclo(-Ser(tBu)-Pro-β³hoPhe-Phe)),  and

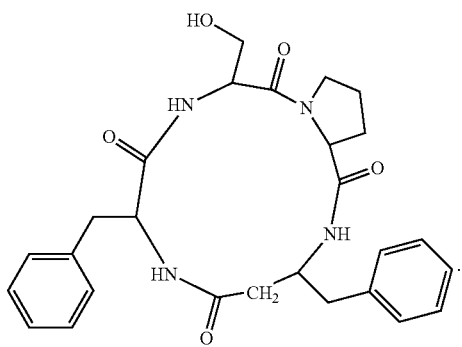

(cyclo(-Ser-Pro-β³hoPhe-Phe)).

In some embodiments, the compound is a compound of formula I-1. In some embodiments, the compound is a compound of formula I-2. In some embodiments, the compound is a compound of formula I-3. In some embodiments, the compound is a compound of formula I-4. In some embodiments, the compound is a compound of formula I-5. In some embodiments, the compound is a compound of formula I-6. In some embodiments, the compound is a compound of formula I-7. In some embodiments, the compound is a compound of formula I-8. In some embodiments, the compound is a compound of formula I-9. In some embodiments, the compound is a compound of formula I-10. In some embodiments, the compound is a compound of formula I-11. In some embodiments, the compound is a compound of formula I-12. In some embodiments, the compound is a compound of formula I-13. In some embodiments, the compound is a compound of formula I-14. In some embodiments, the compound is a compound of formula I-15. In some embodiments, the compound is a compound of formula I-16. In some embodiments, the compound is a compound of formula I-17. In some embodiments, the compound is a compound of formula I-18. In some embodiments, the compound is a compound of formula I-19. In some embodiments, the compound is a compound of formula I-20. In some embodiments, the compound is a compound of formula I-21. In some embodiments, the compound is a compound of formula I-22. In some embodiments, the compound is a compound of formula I-23. In some embodiments, the compound is a compound of formula I-24. In some embodiments, the compound is a compound of formula I-25. In some embodiments, the compound is a compound of formula I-26. In some embodiments, the compound is a compound of formula I-27. In some embodiments, the compound is a compound of formula I-28. In some embodiments, the compound is a compound of formula I-29. In some embodiments, the compound is a compound of formula I-30. In some embodiments, the compound is a compound of formula I-31.

In some embodiments, the compound is selected from the group consisting of:

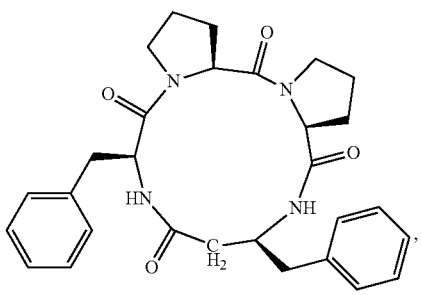

((cyclo(-L-Pro-L-Pro-L-β³hoPhe-L-Phe-))

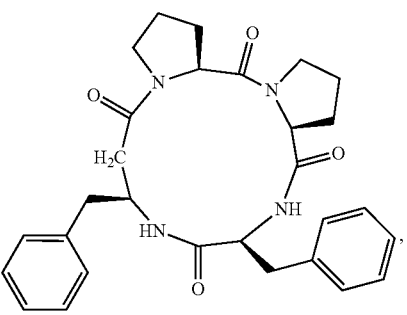

(cyclo(-L-Pro-L-Pro-L-Phe-LL-β³hoPhe-)),

I-C
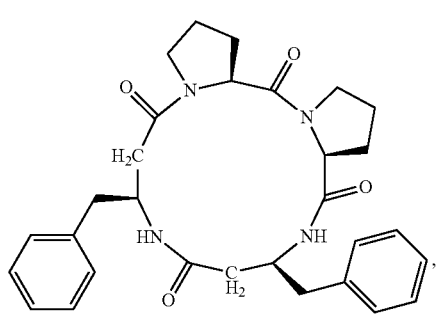
(cyclo(-L-Pro-L-Pro-L-β³hoPhe-L-β³hoPhe-)),
I-D
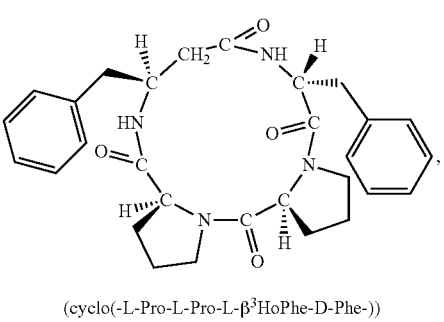
(cyclo(-L-Pro-L-Pro-L-β³HoPhe-D-Phe-)),
I-E
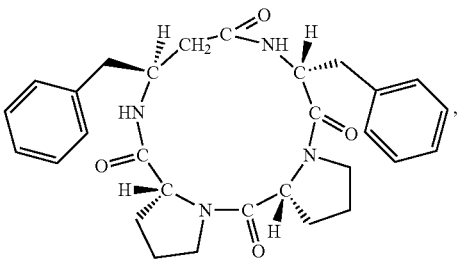
(cyclo(-D-Pro-D-Pro-L-β³HoPhe-D-Phe-)),
I-F
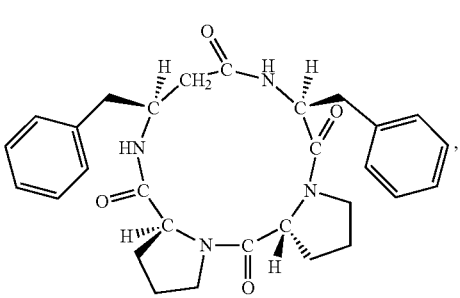
(cyclo(-D-Pro-L-Pro-L-β³HoPhe-L-Phe-)),
I-G
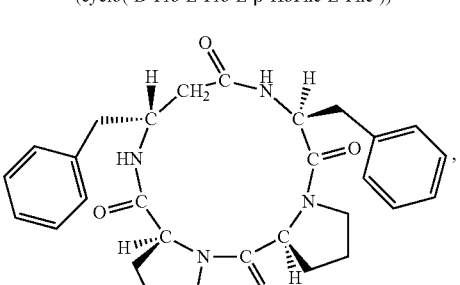
(cyclo(-L-Pro-L-Pro-D-β³HoPhe-L-Phe-)
I-H
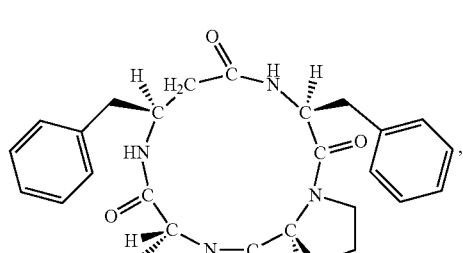
(cyclo(-L-Pro-D-Pro-L-β³HoPhe-L-Phe-)
I-J
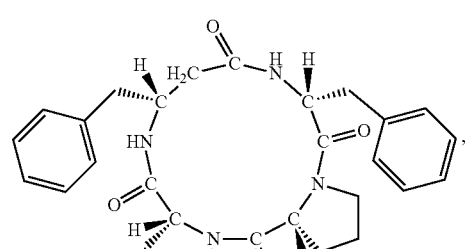
(cyclo(-D-Pro-D-Pro-D-β³HoPhe-D-Phe-)
I-K
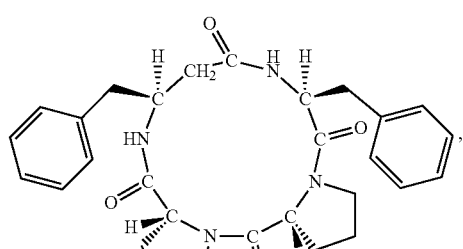
(cyclo(-D-Pro-D-Pro-L-β³HoPhe-L-Phe-)
I-L
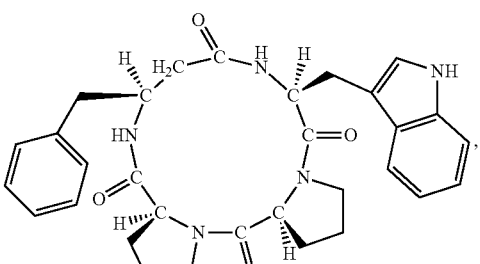
(cyclo(-L-Pro-L-Pro-L-β³HoPhe-L-Trp-)), -continued
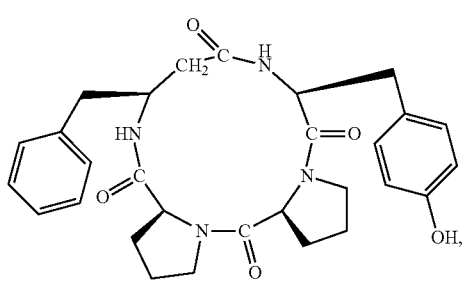
(c(-L-Pro-L-Pro-L-β³HoPhe-L-Tyr-))
I-M
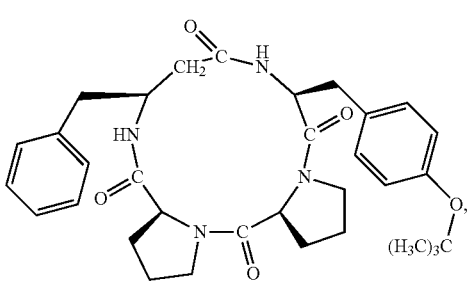
(cyclic[-L-Pro-L-Pro-L-β³HoPhe-L-Tyr(tBu)-])
I-N
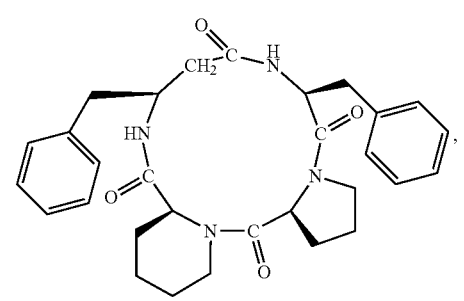
(cyclo(-L-Pro-L-Pip-L-β³HoPhe-L-Phe-))
I-O
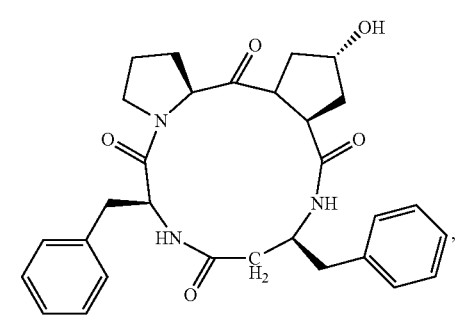
(cyclo(-L-Pro-L-t-Hyp-L-β³HoPhe-L-Phe-))
I-P
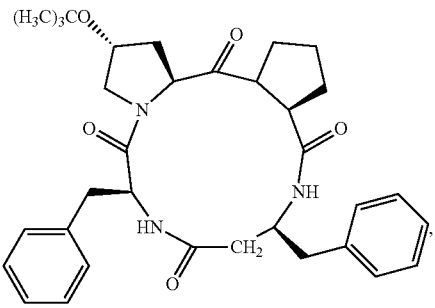
(cyclo(-L-Hyp(tBu)-L-Pro-L-β³hoPhe-L-Phe))
I-Q
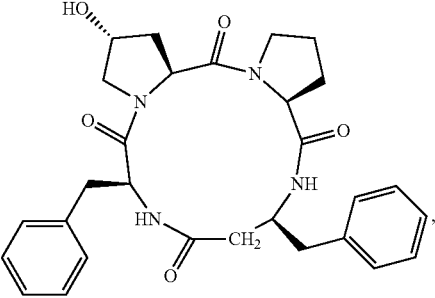
(cyclo(-L-Hyp-L-Pro-L-β³hoPhe-L-Phe-))
I-R
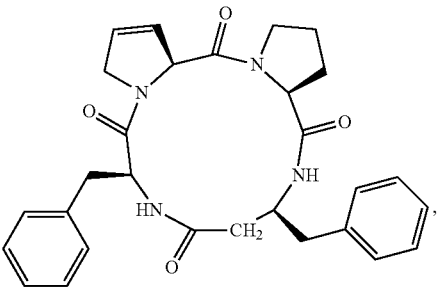
(cyclo(-L-ΔPro-L-Pro-L-β³hoPhe-L-Phe))
I-S
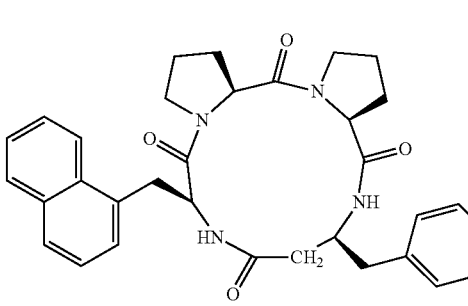
(cyclo(-L-Pro-L-Pro-L-β³hoPhe-L-1Nal))
I-T -continued
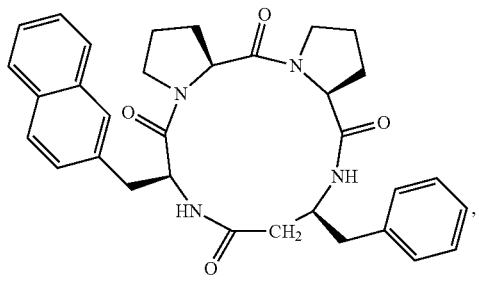
cyclo(-L-Pro-L-Pro-L-β³hoPhe-L-2Nal))
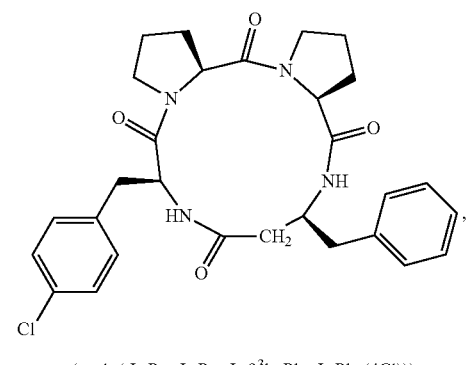
(cyclo(-L-Pro-L-Pro-L-β³hoPhe-L-Phe(4Cl)))
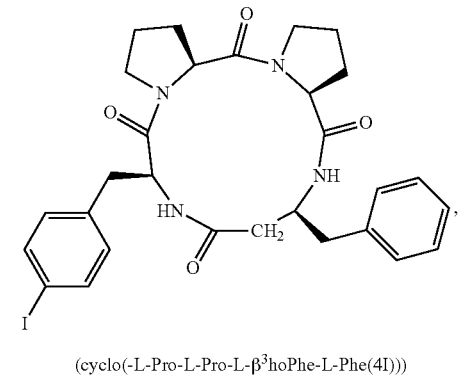
(cyclo(-L-Pro-L-Pro-L-β³hoPhe-L-Phe(4I)))
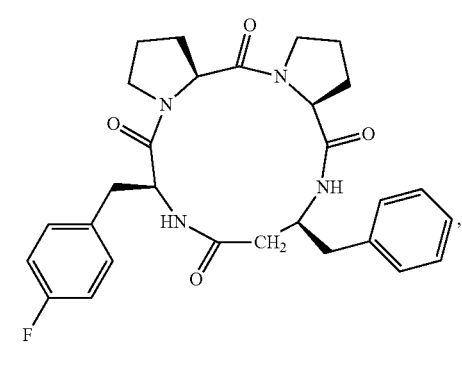
cyclo(-L-Pro-L-Pro-L-β³hoPhe-L-Phe(4F)))
-continued
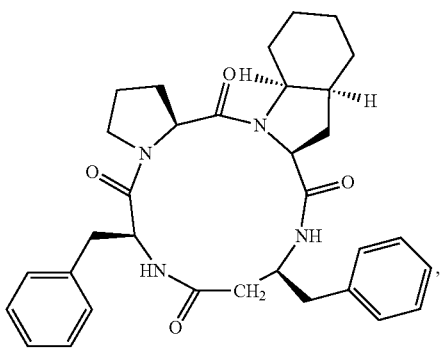
cyclo(-L-Pro-L-Oic-L-β³hoPhe-L-Phe))
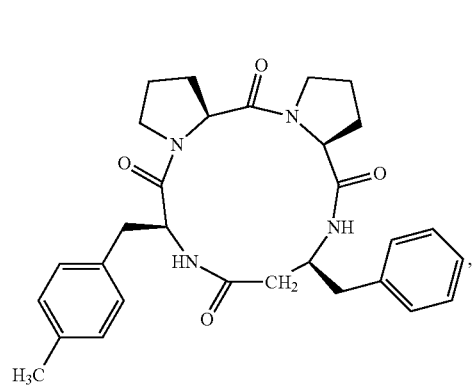
cyclo(-L-Pro-L-Pro-L-β³hoPhe-L-Phe(4Me)))
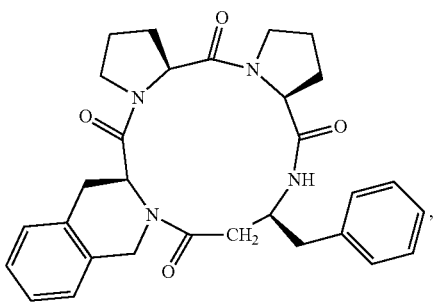
(cyclo(-L-Pro-L-Pro-L-β³hoPhe-L-Tic))
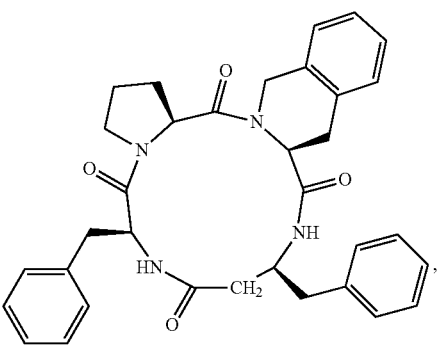
(cyclo(-L-Pro-L-Tic-L-β³hoPhe-L-Phe))

I-AC
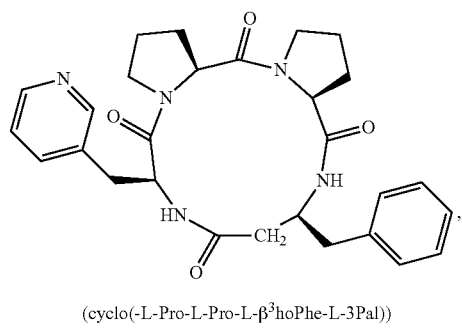
(cyclo(-L-Pro-L-Pro-L-β³hoPhe-L-3Pal))
I-AD
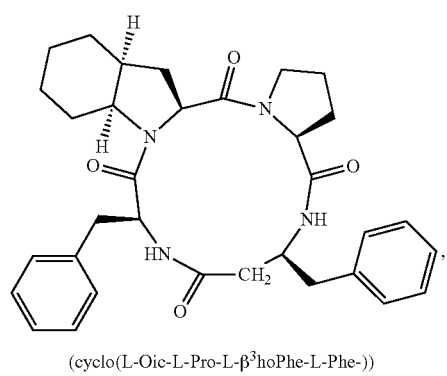
(cyclo(L-Oic-L-Pro-L-β³hoPhe-L-Phe-))
I-AE
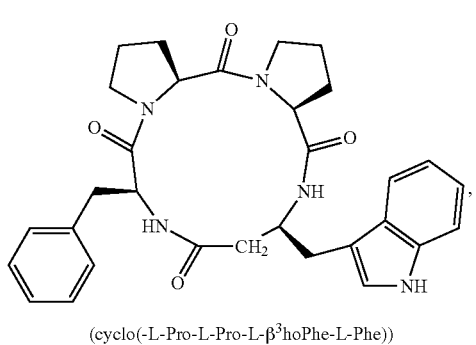
(cyclo(-L-Pro-L-Pro-L-β³hoPhe-L-Phe))
I-AF
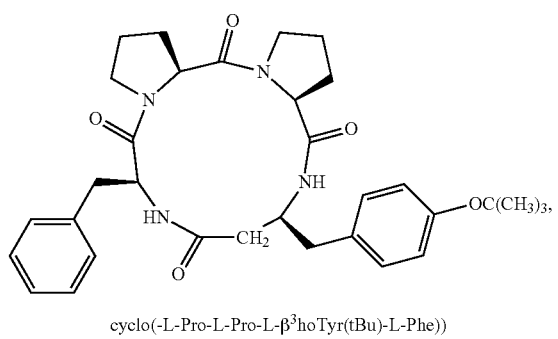
cyclo(-L-Pro-L-Pro-L-β³hoTyr(tBu)-L-Phe))
I-AG
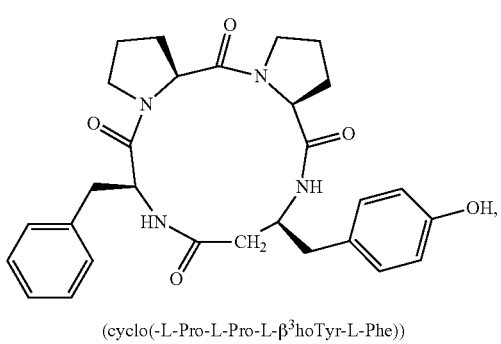
(cyclo(-L-Pro-L-Pro-L-β³hoTyr-L-Phe))
I-AH
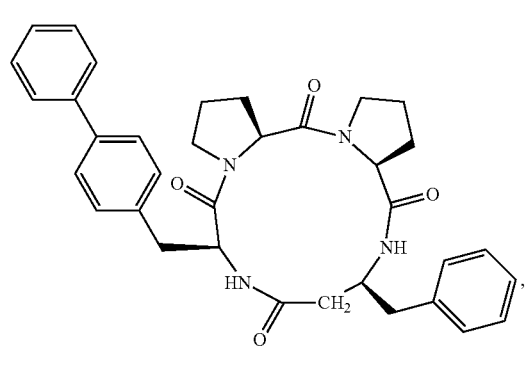
(cyclo(-L-Pro-L-Pro-L-β³hoPhe-L-Bip))
I-AI
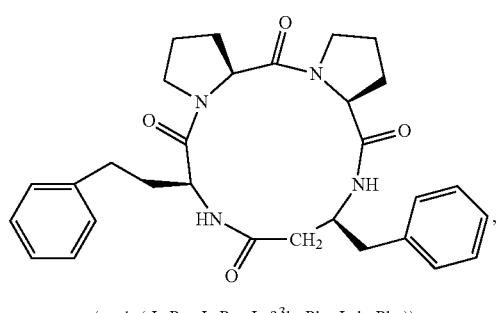
(cyclo(-L-Pro-L-Pro-L-β³hoPhe-L-hoPhe))
I-AJ
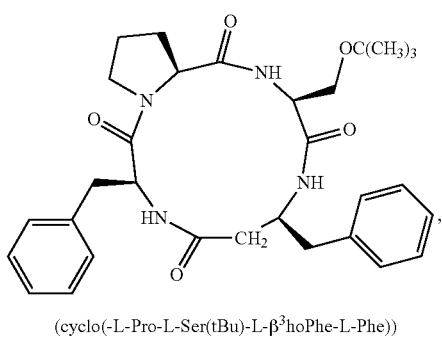
(cyclo(-L-Pro-L-Ser(tBu)-L-β³hoPhe-L-Phe))

-continued

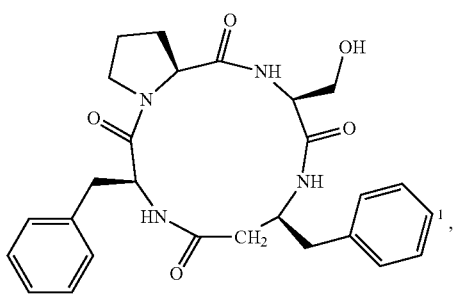

(cyclo(-L-Pro-L-Ser-L-β³hoPhe-L-Phe))    I-AK

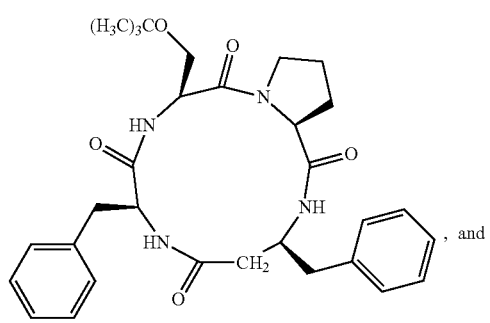

(cyclo(-L-Ser(tBu)-L-Pro-L-β³hoPhe-L-Phe)), and    I-AL

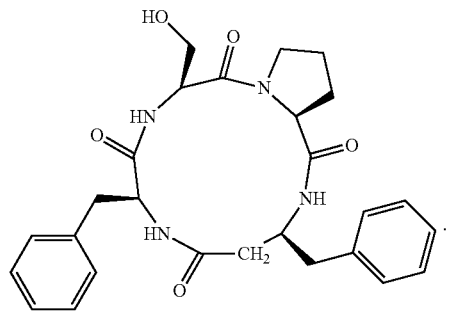

(cyclo(-L-Ser-L-Pro-L-β³hoPhe-L-Phe)).    I-AM

In some embodiments, the compound is a compound of formula I-A. In some embodiments, the corn-pound is a compound of formula I-B. In some embodiments, the compound is a compound of formula I-C. In some embodiments, the compound is a compound of formula I-D. In some embodiments, the compound is a compound of formula I-E. In some embodiments, the corn-pound is a compound of formula I-F. In some embodiments, the compound is a compound of formula I-G. In some embodiments, the compound is a compound of formula I-H. In some embodiments, the compound is a compound of formula I-I. In some embodiments, the compound is a compound of formula I-J. In some embodiments, the compound is a compound of formula I-K. In some embodiments, the compound is a compound of formula I-L. In some embodiments, the compound is a compound of formula I-M. In some embodiments, the corn-pound is a compound of formula I-N. In some embodiments, the compound is a compound of formula I-O. In some embodiments, the compound is a compound of formula I-P. In some embodiments, the compound is a compound of formula I-Q. In some embodiments, the compound is a compound of formula I-R. In some embodiments, the compound is a compound of formula I-S. In some embodiments, the compound is a compound of formula I-T. In some embodiments, the compound is a compound of formula I-U. In some embodiments, the compound is a compound of formula I-V. In some embodiments, the compound is a compound of formula I-W. In some embodiments, the compound is a compound of formula I-X. In some embodiments, the compound is a compound of formula I-Y. In some embodiments, the compound is a compound of formula I-Z. In some embodiments, the compound is a compound of formula I-AA. In some embodiments, the compound is a compound of formula I-AB. In some embodiments, the compound is a compound of formula I-AC. In some embodiments, the compound is a compound of formula I-AD. In some embodiments, the compound is a compound of formula I-AE. In some embodiments, the compound is a compound of formula I-AF. In some embodiments, the compound is a compound of formula I-AG. In some embodiments, the compound is a compound of formula I-AH. In some embodiments, the compound is a compound of formula I-AI. In some embodiments, the compound is a compound of formula I-AJ. In some embodiments, the compound is a compound of formula I-AK. In some embodiments, the compound is a compound of formula I-AL. In some embodiments, the compound is a compound of formula I-AM.

In some embodiments, one or more amino groups in the compound of Formula I are in protected form.

There is also provided, in accordance with an embodiment of the invention, a pharmaceutical composition comprising a compound of formula I and a pharmaceutically acceptable carrier, excipient or diluent therefor. In some embodiments, the compound is a compound of formula I-1. In some embodiments, the compound is a compound of formula I-2. In some embodiments, the compound is a compound of formula I-3. In some embodiments, the compound is a compound of formula I-4. In some embodiments, the compound is a compound of formula I-5. In some embodiments, the compound is a compound of formula I-6. In some embodiments, the compound is a compound of formula I-7. In some embodiments, the compound is a compound of formula I-8. In some embodiments, the compound is a compound of formula I-9. In some embodiments, the compound is a compound of formula I-10. In some embodiments, the compound is a compound of formula I-11. In some embodiments, the compound is a compound of formula I-12. In some embodiments, the compound is a compound of formula I-13. In some embodiments, the compound is a compound of formula I-14. In some embodiments, the compound is a compound of formula I-15. In some embodiments, the compound is a compound of formula I-16. In some embodiments, the compound is a compound of formula I-17. In some embodiments, the compound is a compound of formula I-18. In some embodiments, the compound is a compound of formula I-19. In some embodiments, the compound is a compound of formula I-20. In some embodiments, the compound is a compound of formula I-21. In some embodiments, the compound is a compound of formula I-22. In some embodiments, the compound is a compound of formula I-23. In some embodiments, the compound is a compound of formula I-24. In some embodiments, the compound is a compound of formula I-25. In some embodiments, the compound is a compound of formula I-26. In some embodiments, the compound is a compound of formula I-27. In some embodiments, the compound is a compound of formula I-28. In some embodiments, the compound is a compound of formula I-29. In some embodiments, the compound is a compound of formula I-30. In some embodiments, the compound is a compound of formula I-31. In some embodiments, the compound is a compound of formula I-A. In some embodiments, the compound is a compound of formula I-B. In some embodiments, the compound is a compound of formula I-C. In some embodiments, the compound is a compound of formula I-D. In some embodiments, the compound is a compound of formula I-E. In some embodiments, the compound is a compound of formula I-F. In some embodiments, the compound is a compound of formula I-G. In some embodiments, the compound is a compound of formula I-H. In some embodiments, the compound is a compound of formula I-I. In some embodiments, the compound is a compound of formula I-J. In some embodiments, the compound is a compound of formula I-K. In some embodiments, the compound is a com-pound of formula I-L. In some embodiments, the compound is a compound of formula I-M. In some embodiments, the compound is a compound of formula I-N. In some embodiments, the compound is a compound of formula I-O. In some embodiments, the compound is a compound of formula I-P. In some embodiments, the compound is a compound of formula I-Q. In some embodiments, the compound is a compound of formula I-R. In some embodiments, the compound is a compound of formula I-S. In some embodiments, the compound is a compound of formula I-T. In some embodiments, the compound is a compound of formula I-U. In some embodiments, the compound is a compound of formula IV. In some embodiments, the compound is a compound of formula I-W. In some embodiments, the compound is a compound of formula I-X. In some embodiments, the compound is a compound of formula I-Y. In some embodiments, the compound is a compound of formula I-Z. In some embodiments, the compound is a compound of formula I-AA. In some embodiments, the compound is a compound of formula I-AB. In some embodiments, the compound is a compound of formula I-AC. In some embodiments, the compound is a compound of formula I-AD. In some embodiments, the compound is a compound of formula I-AE. In some embodiments, the compound is a compound of formula I-AF. In some embodiments, the compound is a compound of formula I-AG. In some embodiments, the compound is a compound of formula I-AH. In some embodiments, the compound is a compound of formula I-AI. In some embodiments, the compound is a compound of formula I-AJ. In some embodiments, the compound is a compound of formula I-AK. In some embodiments, the compound is a compound of formula I-AL. In some embodiments, the compound is a compound of formula I-AM.

There is also provided, in accordance with an embodiment of the invention, a method of suppressing immune response in a patient, comprising administering to a patient in need thereof an efficacious amount of a compound of formula I. In some embodiments, the immune response which is suppressed is inflammation. In some embodiments the immune response which is suppressed is transplant rejection. In some embodiments, the compound is a compound of formula I-1. In some embodiments, the compound is a compound of formula I-2. In some embodiments, the compound is a compound of formula I-3. In some embodiments, the compound is a compound of formula I-4. In some embodiments, the compound is a compound of formula I-5. In some embodiments, the compound is a compound of formula I-6. In some embodiments, the compound is a compound of formula I-7. In some embodiments, the compound is a compound of formula I-8. In some embodiments, the compound is a compound of formula I-9. In some embodiments, the compound is a compound of formula I-10. In some embodiments, the compound is a compound of formula I-11. In some embodiments, the compound is a compound of formula I-12. In some embodiments, the compound is a compound of formula I-13. In some embodiments, the compound is a compound of formula I-14. In some embodiments, the compound is a compound of formula I-15. In some embodiments, the compound is a compound of formula I-16. In some embodiments, the compound is a compound of formula I-17. In some embodiments, the compound is a compound of formula I-18. In some embodiments, the compound is a compound of formula I-19. In some embodiments, the compound is a compound of formula I-20. In some embodiments, the compound is a compound of formula I-21. In some embodiments, the compound is a compound of formula I-22. In some embodiments, the compound is a compound of formula I-23. In some embodiments, the compound is a compound of formula I-24. In some embodiments, the compound is a compound of formula I-25. In some embodiments, the compound is a compound of formula I-26. In some embodiments, the compound is a compound of formula I-27. In some embodiments, the compound is a compound of formula I-28. In some embodiments, the compound is a compound of formula I-29. In some embodiments, the compound is a compound of formula I-30. In some embodiments, the compound is a compound of formula I-31. In some embodiments, the compound is a compound of formula I-A. In some embodiments, the compound is a compound of formula I-B. In some embodiments, the compound is a compound of formula I-C. In some embodiments, the com-pound is a compound of formula I-D. In some embodiments, the compound is a compound of formula I-E. In some embodiments, the compound is a compound of formula I-F. In some embodiments, the compound is a compound of formula I-G. In some embodiments, the com-pound is a compound of formula I-H. In some embodiments, the compound is a compound of formula I-I. In some embodiments, the compound is a compound of formula I-J. In some embodiments, the compound is a compound of formula I-K. In some embodiments, the com-pound is a compound of formula I-L. In some embodiments, the compound is a compound of formula I-M. In some embodiments, the compound is a compound of formula I-N. In some embodiments, the compound is a compound of formula I-O. In some embodiments, the compound is a compound of formula I-P. In some embodiments, the compound is a compound of formula I-Q. In some embodiments, the compound is a compound of formula I-R. In some embodiments, the compound is a compound of formula I-S. In some embodiments, the compound is a compound of formula I-T. In some embodiments, the compound is a compound of formula I-U. In some embodiments, the compound is a compound of formula I-V. In some embodiments, the compound is a compound of formula I-W. In some embodiments, the compound is a compound of formula I-X. In some embodiments, the compound is a compound of formula I-Y. In some embodiments, the compound is a compound of formula I-Z. In some embodiments, the compound is a compound of formula I-AA. In some embodiments, the compound is a compound of formula I-AB. In some embodiments, the compound is a compound of formula I-AC. In some embodiments, the compound is a compound of formula I-AD. In some embodiments, the compound is a compound of formula I-AE. In some embodiments, the compound is a compound of formula I-AF. In some embodiments, the compound is a compound of formula I-AG. In some embodiments, the compound is a compound of formula I-AH. In some embodiments, the compound is a compound of formula I-AI. In some embodiments, the compound is a compound of formula I-AJ. In some embodiments, the compound is a compound of formula I-AK. In some embodiments, the compound is a compound of formula I-AL. In some embodiments, the compound is a compound of formula I-AM.

There is also provided, in accordance with an embodiment of the invention, a method of treating or preventing an immune-mediated disease or condition in a patient, comprising administering to a patient in need thereof an efficacious amount of a compound of formula I. There is also provided, in accordance with an embodiment of the invention, a method for lowering the toxicity profile of a second drug, comprising administering a compound of formula I in conjunction with the second drug. In some embodiments, the immune-mediated disease or condition is selected from the group consisting of auto-immune diseases, inflammation processes, transplant rejection, and allergic reactions. In some embodiments, the immune-mediated disease or condition is selected from Psoriasis, lichen planus and other papulosquamous disorders. In some embodiments, the immune-mediated disease or condition is selected from eczema and dermatitis. In some embodiments, the eczemea or dermatitis is selected from eczema, atopic eczema, seborrheic dermatitis, and pompholyx. In some embodiments, the immune-mediated disease or condition is a skin reaction to sunlight. In some embodiments, the immune-mediated disease or condition selected from non-specific skin irritation and insect bite. In some embodiments, the immune-mediated disease or condition is a urticaria. In some embodiments, the immune-mediated disease or condition is selected from the group consisting of a primary skin tumor (e.g. melanoma); rheumatoid arthritis (both autoimmune and elicited by infection); Crohn's disease; inflammatory bowel disease; irritable bowel syndrome; a neurodegenerative disease (e.g. multiple sclerosis); Parkinson's disease; Graft-versus-Host reaction; severe psoriasis; and atopic dermatitis. In some embodiments, the compound of formula I is administered in conjunction with a chemotherapeutic drug in order to reduce the toxic effects of the chemotherapeutic drug. In some embodiments, the compound is a compound of formula I-1. In some embodiments, the compound is a compound of formula I-2. In some embodiments, the compound is a compound of formula I-3. In some embodiments, the compound is a compound of formula I-4. In some embodiments, the compound is a compound of formula I-5. In some embodiments, the compound is a compound of formula I-6. In some embodiments, the compound is a compound of formula I-7. In some embodiments, the compound is a compound of formula I-8. In some embodiments, the compound is a compound of formula I-9. In some embodiments, the compound is a compound of formula I-10. In some embodiments, the compound is a compound of formula I-11. In some embodiments, the compound is a compound of formula I-12. In some embodiments, the compound is a compound of formula I-13. In some embodiments, the compound is a compound of formula I-14. In some embodiments, the compound is a compound of formula I-15. In some embodiments, the compound is a compound of formula I-16. In some embodiments, the compound is a compound of formula I-17. In some embodiments, the compound is a compound of formula I-18. In some embodiments, the compound is a compound of formula I-19. In some embodiments, the compound is a compound of formula I-20. In some embodiments, the compound is a compound of formula I-21. In some embodiments, the compound is a compound of formula I-22. In some embodiments, the compound is a compound of formula I-23. In some embodiments, the compound is a compound of formula I-24. In some embodiments, the compound is a compound of formula I-25. In some embodiments, the compound is a compound of formula I-26. In some embodiments, the compound is a compound of formula I-27. In some embodiments, the compound is a compound of formula I-28. In some embodiments, the compound is a compound of formula I-29. In some embodiments, the compound is a compound of formula I-30. In some embodiments, the compound is a compound of formula I-31. In some embodiments, the compound is a com-pound of formula I-A. In some embodiments, the compound is a compound of formula I-B. In some embodiments, the compound is a compound of formula I-C. In some embodiments, the compound is a compound of formula I-D. In some embodiments, the compound is a compound of formula I-E. In some embodiments, the compound is a compound of formula I-F. In some embodiments, the compound is a compound of formula I-G. In some embodiments, the com-pound is a compound of formula I-H. In some embodiments, the compound is a compound of formula I-I. In some embodiments, the compound is a compound of formula I-J. In some embodiments, the compound is a compound of formula I-K. In some embodiments, the com-pound is a compound of formula I-L. In some embodiments, the compound is a compound of formula I-M. In some embodiments, the compound is a compound of formula I-N. In some embodiments, the compound is a compound of formula I-O. In some embodiments, the compound is a compound of formula I-P. In some embodiments, the compound is a compound of formula I-Q. In some embodiments, the compound is a compound of formula I-R. In some embodiments, the compound is a compound of formula I-S. In some embodiments, the compound is a compound of formula I-T. In some embodiments, the compound is a compound of formula I-U. In some embodiments, the compound is a compound of formula I-V. In some embodiments, the compound is a compound of formula I-W. In some embodiments, the compound is a compound of formula I-X. In some embodiments, the compound is a compound of formula I-Y. In some embodiments, the compound is a compound of formula I-Z. In some embodiments, the compound is a compound of formula I-AA. In some embodiments, the compound is a compound of formula I-AB. In some embodiments, the compound is a compound of formula I-AC. In some embodiments, the compound is a compound of formula I-AD. In some embodiments, the compound is a compound of formula I-AE. In some embodiments, the compound is a compound of formula I-AF. In some embodiments, the compound is a compound of formula I-AG. In some embodiments, the compound is a compound of formula I-AH. In some embodiments, the compound is a compound of formula I-AI. In some embodiments, the compound is a compound of formula I-AJ. In some embodiments, the compound is a compound of formula I-AK. In some embodiments, the compound is a compound of formula I-AL. In some embodiments, the compound is a compound of formula I-AM.

There is also provided, in accordance with an embodiment of the invention, a kit, comprising a compound of formula I and instructions for using the compound to (a) suppress an immune response in a patient, (b) treat or prevent an immune-mediated disease or condition in a patient, or (c) lower the toxicity profile of a second drug. In some embodiments, the immune response is inflammation. In some embodiments the immune response is transplant rejection. In some embodiments, the immune-mediated disease or condition is selected from the group consisting of auto-immune diseases, inflammation processes, transplant rejection, allergic reactions. In some embodiments, the immune-mediated disease or condition is selected from Psoriasis, lichen planus and other papulosquamous disorders. In some embodiments, the immune-mediated disease or condition is selected from eczema and dermatitis. In some embodiments, the eczemea or dermatitis is selected from eczema, atopic eczema, seborrheic dermatitis, and pompholyx. In some embodiments, the immune-mediated disease or condition is a skin reaction to sunlight. In some embodiments, the immune-mediated disease or condition selected from non-specific skin irritation and insect bite. In some embodiments, the immune-mediated disease or condition is a urticaria. In some embodiments, the immune-mediated disease or condition is selected from the group consisting of a primary skin tumor (e.g. melanoma); rheumatoid arthritis (both autoimmune and elicited by infection); Crohn's disease; inflammatory bowel disease; irritable bowel syndrome; a neurodegenerative disease (e.g. multiple sclerosis); Parkinson's disease; Graft-versus-Host reaction; severe psoriasis; and atopic dermatitis. In some embodiments, the instructions instruct administering the compound of formula I in conjunction with a chemotherapeutic drug in order to reduce the toxic effects of the chemotherapeutic drug. In some embodiments, the compound is a compound of formula I-1. In some embodiments, the compound is a compound of formula I-2. In some embodiments, the compound is a compound of formula I-3. In some embodiments, the compound is a compound of formula I-4. In some embodiments, the compound is a compound of formula I-5. In some embodiments, the compound is a compound of formula I-6. In some embodiments, the compound is a compound of formula I-7. In some embodiments, the compound is a compound of formula I-8. In some embodiments, the compound is a compound of formula I-9. In some embodiments, the compound is a compound of formula I-10. In some embodiments, the compound is a compound of formula I-11. In some embodiments, the compound is a compound of formula I-12. In some embodiments, the compound is a compound of formula I-13. In some embodiments, the compound is a compound of formula I-14. In some embodiments, the compound is a compound of formula I-15. In some embodiments, the compound is a compound of formula I-16. In some embodiments, the compound is a compound of formula I-17. In some embodiments, the compound is a compound of formula I-18. In some embodiments, the compound is a compound of formula I-19. In some embodiments, the compound is a compound of formula I-20. In some embodiments, the compound is a compound of formula I-21. In some embodiments, the compound is a compound of formula I-22. In some embodiments, the compound is a compound of formula I-23. In some embodiments, the compound is a compound of formula I-24. In some embodiments, the compound is a compound of formula I-25. In some embodiments, the compound is a compound of formula I-26. In some embodiments, the compound is a compound of formula I-27. In some embodiments, the compound is a compound of formula I-28. In some embodiments, the compound is a compound of formula I-29. In some embodiments, the compound is a compound of formula I-30. In some embodiments, the compound is a compound of formula I-31. In some embodiments, the compound is a compound of formula I-A. In some embodiments, the compound is a compound of formula I-B. In some embodiments, the compound is a compound of formula I-C. In some embodiments, the compound is a compound of formula I-D. In some embodiments, the compound is a compound of formula I-E. In some embodiments, the compound is a compound of formula I-F. In some embodiments, the compound is a compound of formula I-G. In some embodiments, the compound is a compound of formula I-H. In some embodiments, the compound is a compound of formula I-I. In some embodiments, the compound is a compound of formula I-J. In some embodiments, the compound is a compound of formula I-K. In some embodiments, the compound is a compound of formula I-L. In some embodiments, the compound is a compound of formula I-M. In some embodiments, the compound is a compound of formula I-N. In some embodiments, the compound is a compound of formula I-O. In some embodiments, the compound is a compound of formula I-P. In some embodiments, the compound is a compound of formula I-Q. In some embodiments, the compound is a compound of formula I-R. In some embodiments, the compound is a compound of formula I-S. In some embodiments, the compound is a compound of formula I-T. In some embodiments, the compound is a compound of formula I-U. In some embodiments, the compound is a compound of formula I-V. In some embodiments, the compound is a compound of formula I-W. In some embodiments, the compound is a compound of formula I-X. In some embodiments, the compound is a compound of formula I-Y. In some embodiments, the compound is a compound of formula I-Z. In some embodiments, the compound is a compound of formula I-AA. In some embodiments, the compound is a compound of formula I-AB. In some embodiments, the compound is a compound of formula I-AC. In some embodiments, the compound is a compound of formula I-AD. In some embodiments, the compound is a compound of formula I-AE. In some embodiments, the compound is a compound of formula I-AF. In some embodiments, the compound is a compound of formula I-AG. In some embodiments, the compound is a compound of formula I-AH. In some embodiments, the compound is a compound of formula I-AI. In some embodiments, the compound is a compound of formula I-AJ. In some embodiments, the compound is a compound of formula I-AK. In some embodiments, the compound is a compound of formula I-AL. In some embodiments, the compound is a compound of formula I-AM.

There is also provided, in accordance with an embodiment of the invention, a method for making a compound of formula I, comprising cyclizing a compound having the formula II-1, II-2, II-3 or II-4, wherein R, R', R", R''', $R^3$, $R^4$, k, m, n and p are as defined in formula I (collectively referred to hereinafter as compounds of formula II):

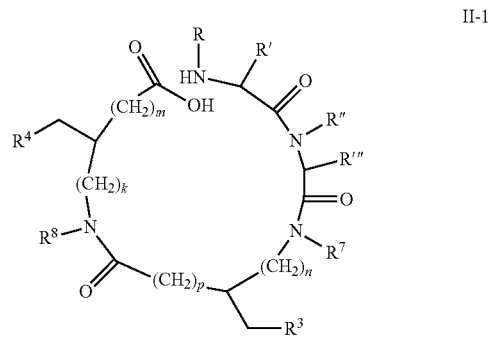

II-1

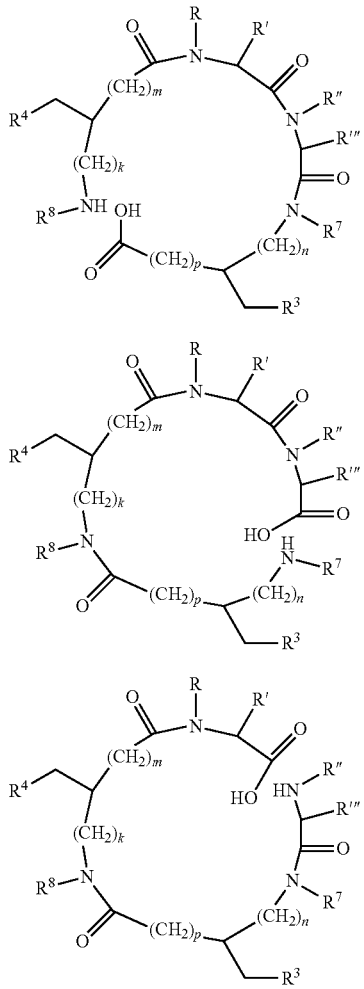

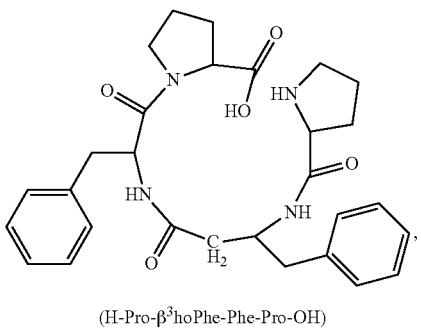

(H-Pro-β³hoPhe-Phe-Pro-OH)

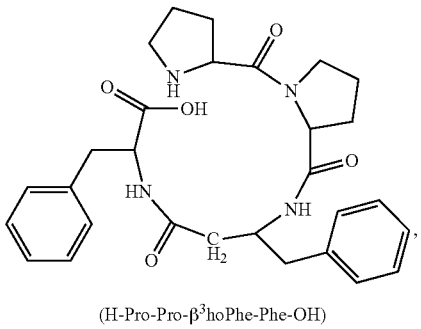

(H-Pro-Pro-β³hoPhe-Phe-OH)

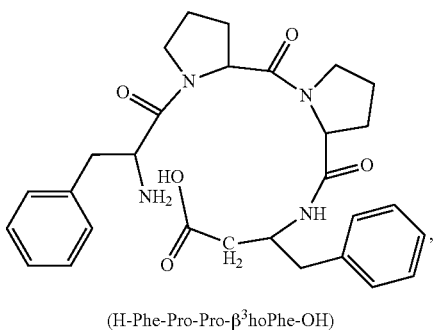

(H-Phe-Pro-Pro-β³hoPhe-OH)

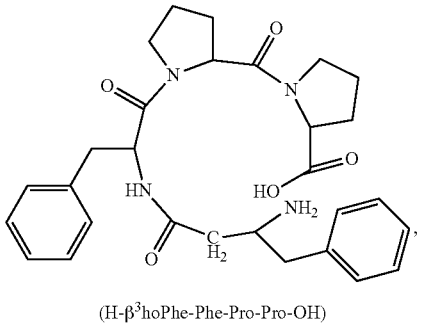

(H-β³hoPhe-Phe-Pro-Pro-OH)

to the corresponding compound of formula I. In some embodiments, the method further comprises synthesizing the compound of formula II-1, II-2, II-3 or II-4. In some embodiments, the compound of formula II-1, II-2, II-3 or II-4 is formed by solid-phase synthesis.

In accordance with embodiments of the invention, there are also provided compounds of formulae II-1, II-2, II-3 and II-4 per se, as well as protected versions of these compounds (e.g. in which one or more amino groups, such as the N-terminal amino group or a side chain amino group, are protected, e.g. by tert-butoxycarbonyl) and these compounds, in protected or unprotected form, when bound to a solid-phase resin. Hereinafter, unless specified otherwise or illogical in the given context, when reference is made to a compound of formula II or a subgenus or sub-species thereof, such reference is intended to include such compound in a form in which it is (a)(i) at least partly protected or (a)(ii) completely un- or deprotected; (b)(i) bound to a resin (1) directly or (2) through a linker, or (b)(ii) not bound to a resin; or a combination of conditions (a) and (b). Furthermore, as depicted herein, for the sake of convenience, free, non-protected linear peptides are shown as neutral molecules, viz. having H₂N— at the N-terminus and —COOH at the C-terminus; however, it will be appreciated that the actual charge on these moieties, as well as on any ionizable side chain moieties (e.g. carboxylic acid or amine moieties in the side chains) will depend on the pH of surroundings, and will not necessarily be as shown.

In some embodiments, the compound of formula II is selected from the group consisting of:

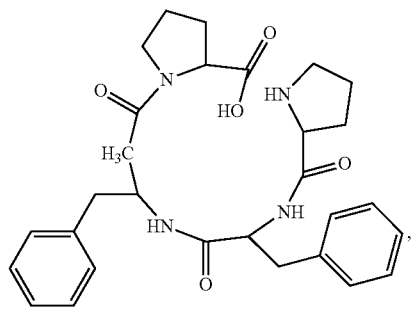
(H-Pro-Pro-Phe-β³hoPhe-OH)   II-4-b
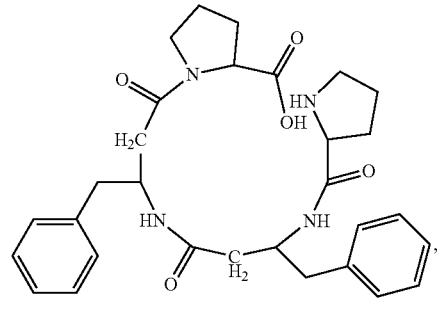
(H-Pro-β³hoPhe-β³hoPhe-Pro-OH)   II-4-c
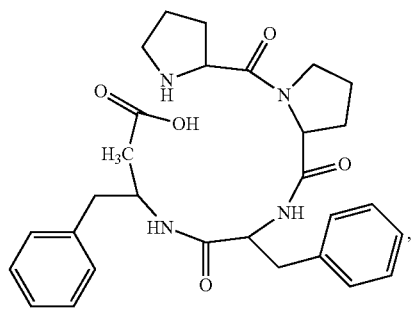
(H-Pro-Pro-Pre-β³hoPhe-OH)   II-1-b
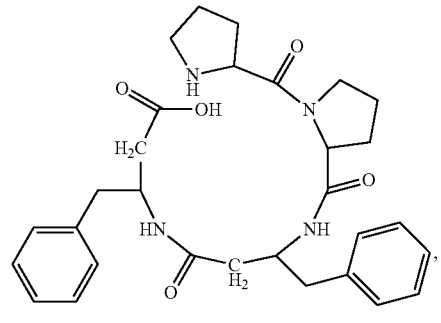
(H-Pro-Pro-β³hoPhe-β³hoPhe-OH)   II-1-c
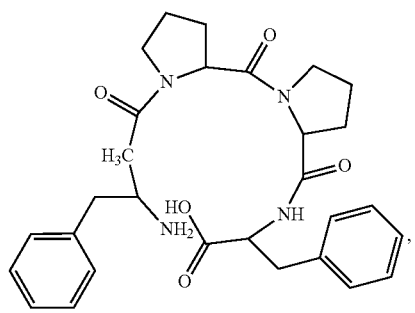
(H-β³hoPhe-Pro-Pro-Phe-OH)   II-2-b
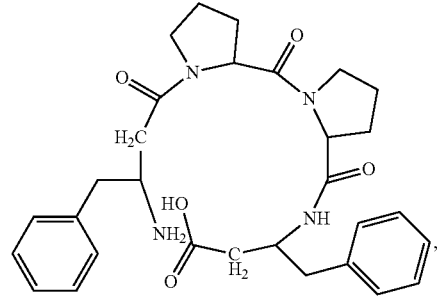
(H-β³hoPhe-Pro-Pro-β³hoPhe-OH)   II-2-c
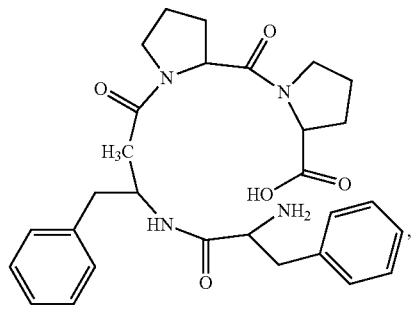
(H-Phe-β³hoPhe-Pro-Pro-OH)   II-3-b
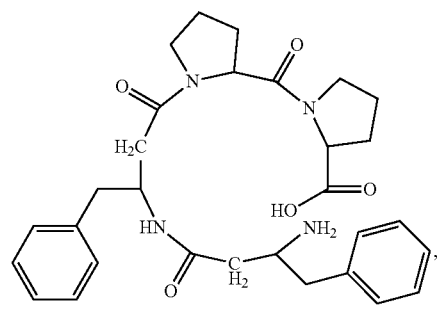
(H-β³hoPhe-β³hoPhe-Pro-Pro-OH)   II-3-c

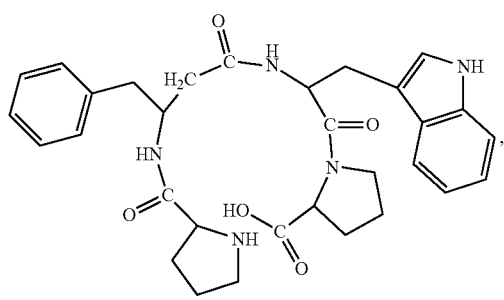
(H-Pro-Pro-β³hoPhe-Trp-Pro-OH)
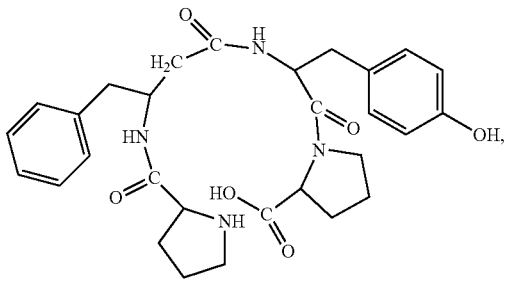
(H-Pro-β³hoPhe-Tyr-Pro-OH)
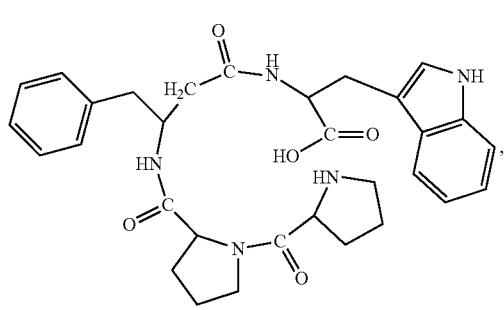
(H-Pro-Pro-β³hoPhe-Trp-OH)
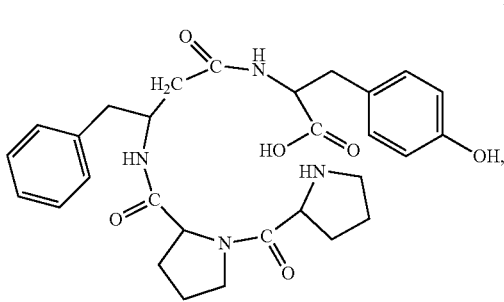
(H-Pro-Pro-β³hoPhe-Tyr-OH)
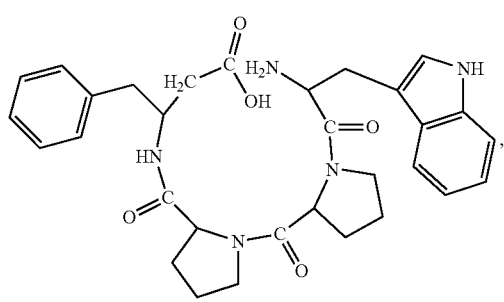
(H-Trp-Pro-Pro-β³hoPhe-OH)
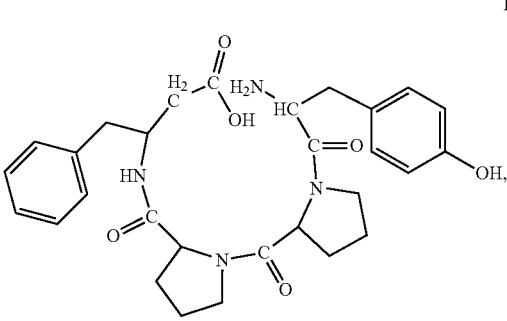
(H-Tyr-Pro-Pro-β³hoPhe-OH)
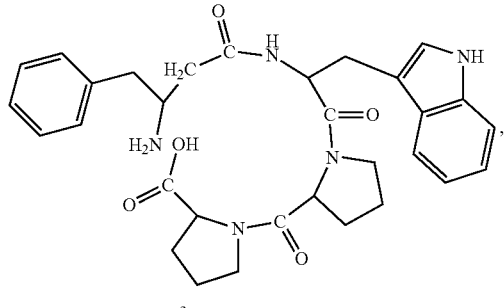
(H-β³hoPhe-Trp-Pro-Pro-OH)
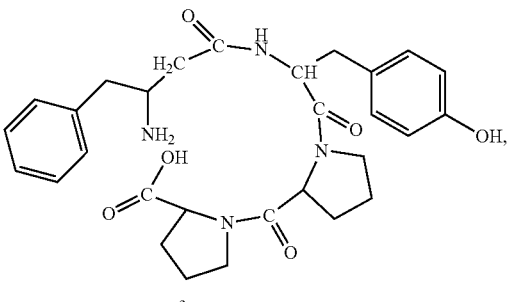
(H-β³hoPhe-Tyr-Pro-Pro-OH)

-continued
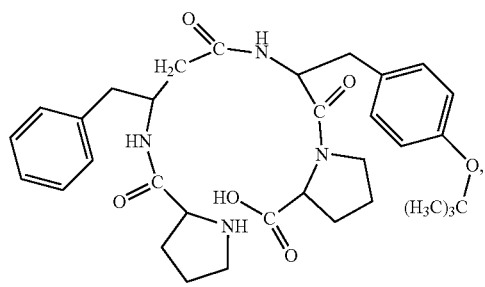
(H-Pro-β³hoPhe-Tyr(t-Bu)-Pro-OH)
II-4-f
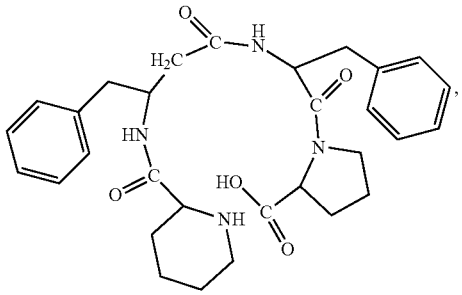
(H-Pip-β³hoPhe-Pre-Pro-OH)
II-4-g
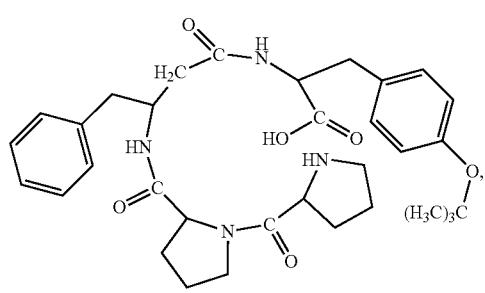
(H-Pro-Pro-β³hoPhe-Tyr(t-Bu)-OH)
II-1-f
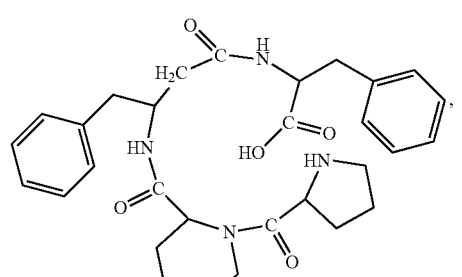
(H-Pro-Pip-β³hoPhe-Phe-OH)
II-1-g
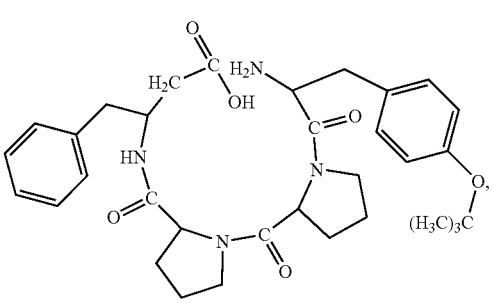
(H-Tyr(t-Bu)-Pro-Pro-β³hoPhe-OH)
II-2-f
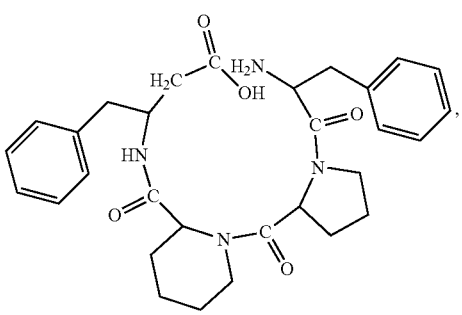
(H-Pre-Pro-Pip-β³hoPhe-OH)
II-2-g
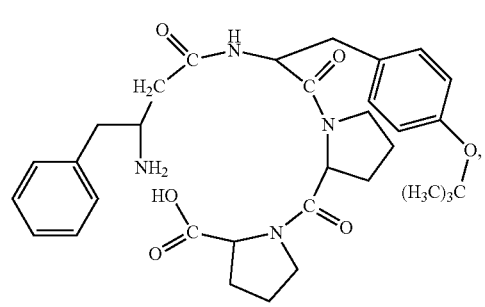
(H-β³hoPhe-Tyr(t-Bu)-Pro-Pro-OH)
II-3-f
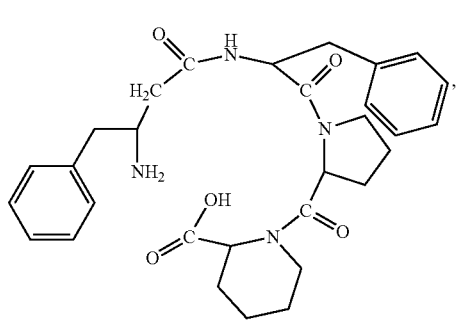
(H-β³hoPhe-Phe-Pro-Pip-OH)
II-3-g

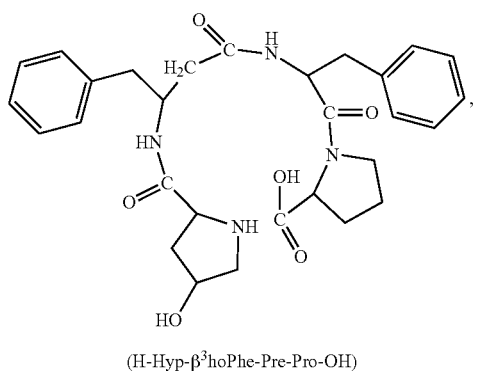
(H-Hyp-β³hoPhe-Pre-Pro-OH)
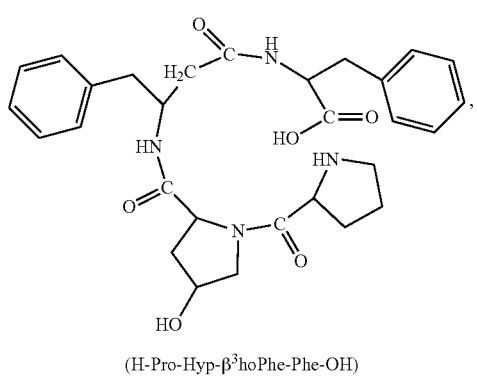
(H-Pro-Hyp-β³hoPhe-Phe-OH)
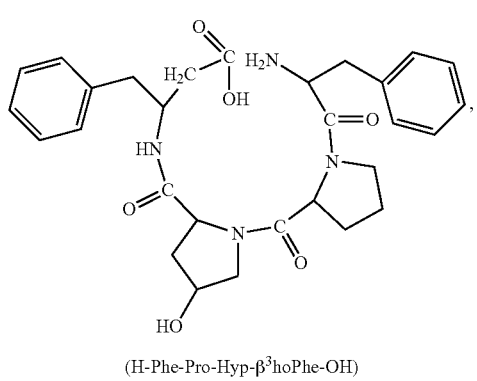
(H-Phe-Pro-Hyp-β³hoPhe-OH)
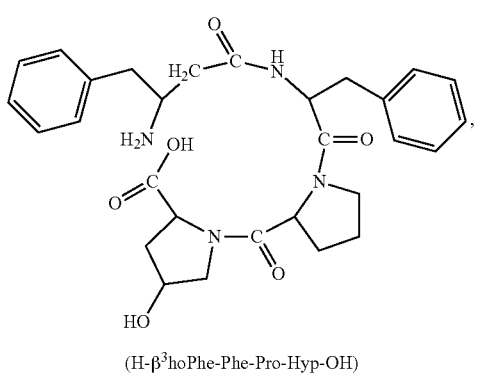
(H-β³hoPhe-Phe-Pro-Hyp-OH)
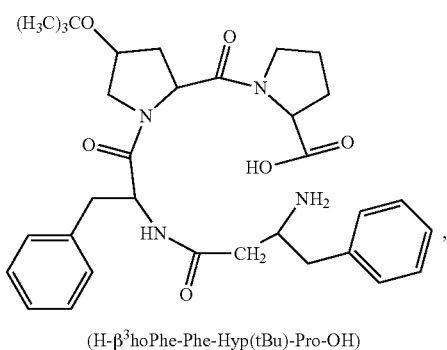
(H-β³hoPhe-Phe-Hyp(tBu)-Pro-OH)
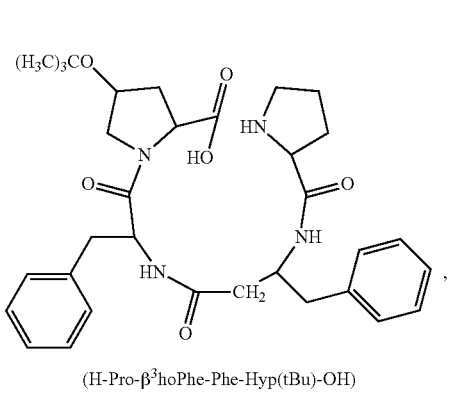
(H-Pro-β³hoPhe-Phe-Hyp(tBu)-OH)
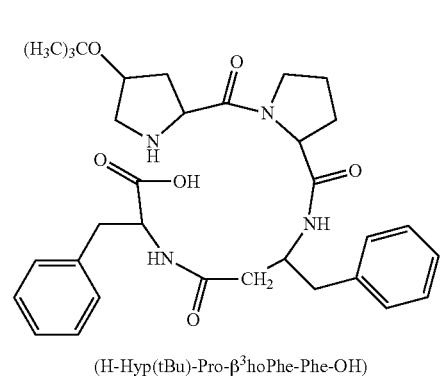
(H-Hyp(tBu)-Pro-β³hoPhe-Phe-OH)
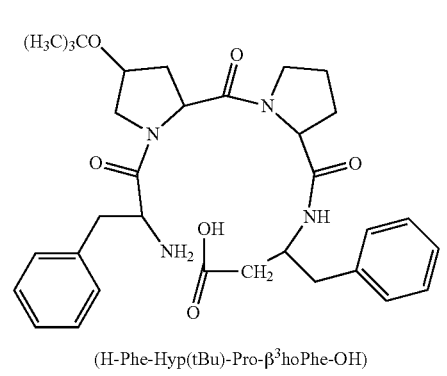
(H-Phe-Hyp(tBu)-Pro-β³hoPhe-OH)

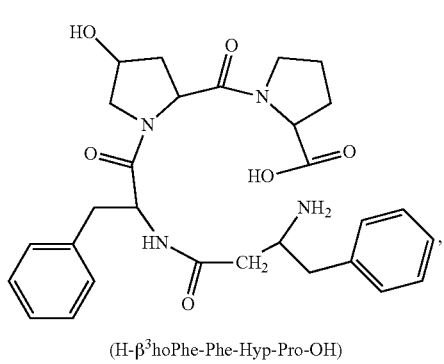
(H-β³hoPhe-Phe-Hyp-Pro-OH)
II-1-j
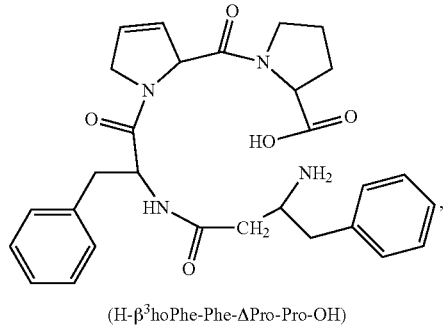
(H-β³hoPhe-Phe-ΔPro-Pro-OH)
II-1-k
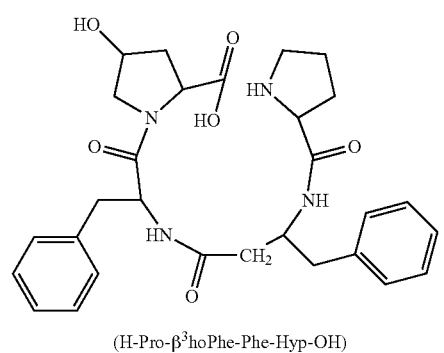
(H-Pro-β³hoPhe-Phe-Hyp-OH)
II-2-j
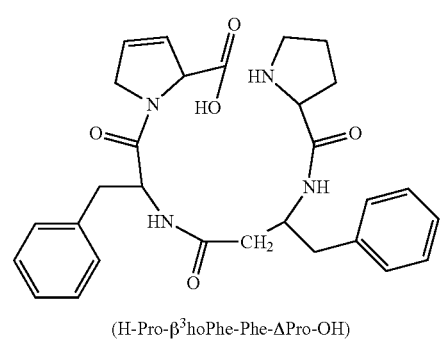
(H-Pro-β³hoPhe-Phe-ΔPro-OH)
II-2-k
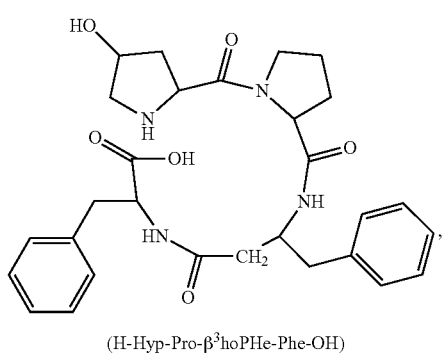
(H-Hyp-Pro-β³hoPHe-Phe-OH)
II-3-j
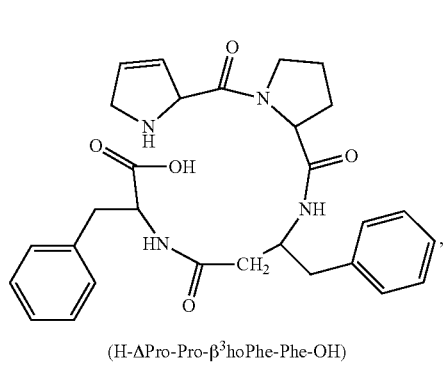
(H-ΔPro-Pro-β³hoPhe-Phe-OH)
II-3-k
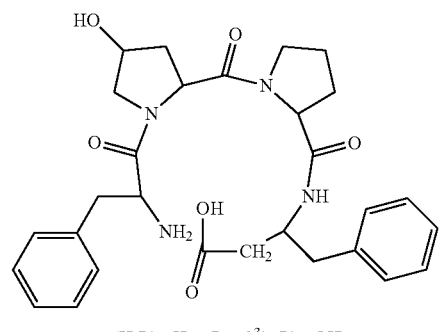
(H-Phe-Hyp-Pro-β³hoPhe-OH)
II-4-j
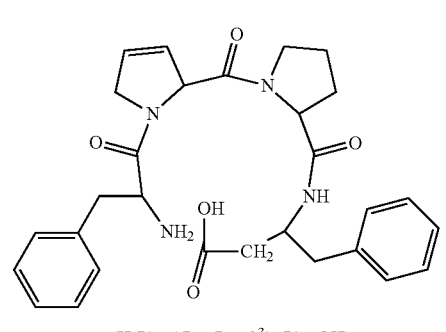
(H-Phe-ΔPro-Pro-β³hoPhe-OH)
II-4-k

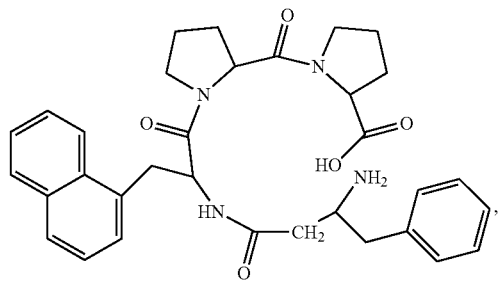
(H-β³hoPhe-1Nal-Pro-Pro-OH))
II-1-l
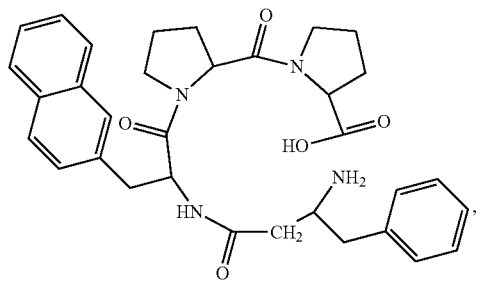
(H-β³hoPhe-2Nal-Pro-Pro-OH))
II-1-m
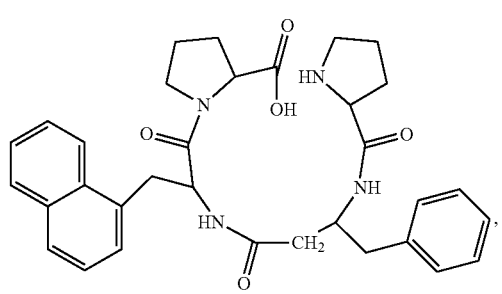
(H-Pro-β³hoPhe-1Nal-Pro-OH)
II-2-l
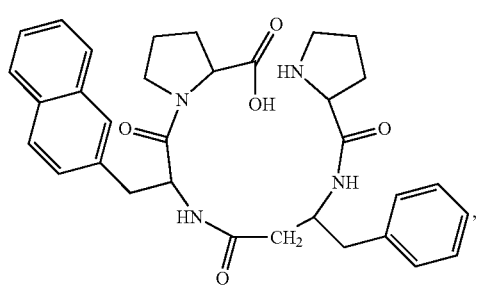
(H-Pro-β³hoPhe-2Nal-Pro-OH))
II-2-m
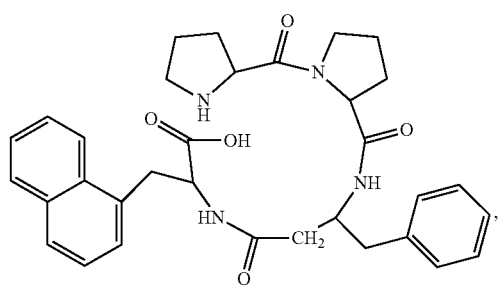
(H-Pro-Pro-β³hoPhe-1Nal-OH))
II-3-l
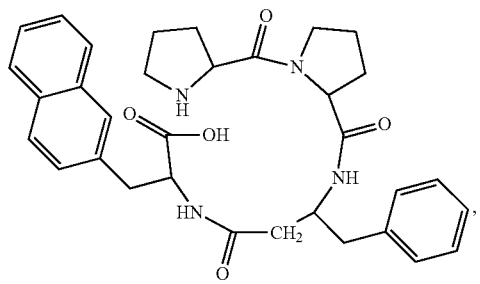
(H-Pro-Pro-β³hoPhe-2Nal-OH)
II-3-m
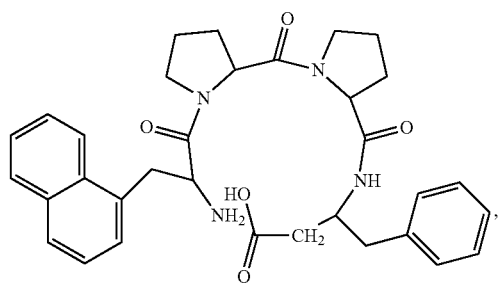
(H-1Nal-Pro-Pro-β³hoPhe-OH)
II-4-l
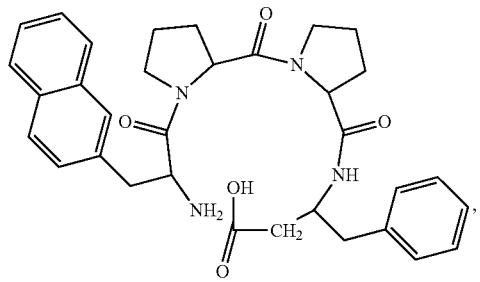
(H-2Nal-Pro-Pro-β³hoPhe-OH)
II-4-m II-1-n
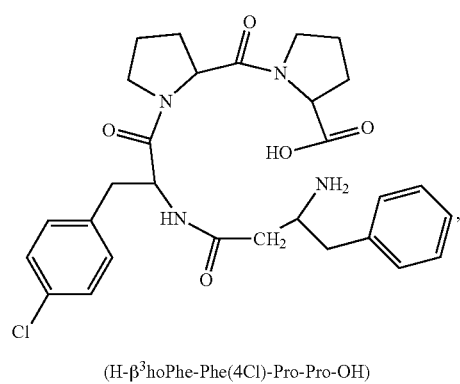
(H-β³hoPhe-Phe(4Cl)-Pro-Pro-OH)
II-2-n
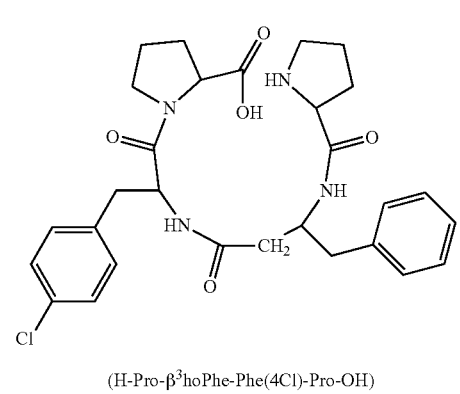
(H-Pro-β³hoPhe-Phe(4Cl)-Pro-OH)
II-3-n
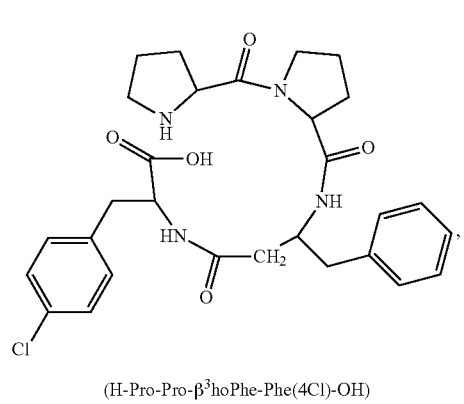
(H-Pro-Pro-β³hoPhe-Phe(4Cl)-OH)
II-4-n
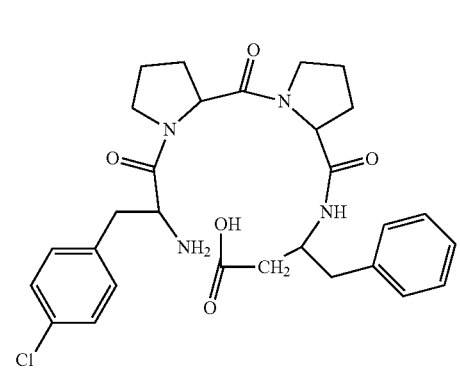
(H-Phe(4Cl)-Pro-Pro-β³hoPhe-OH)
II-1-o
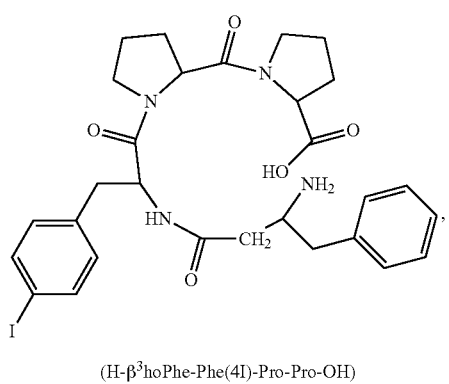
(H-β³hoPhe-Phe(4I)-Pro-Pro-OH)
II-2-o
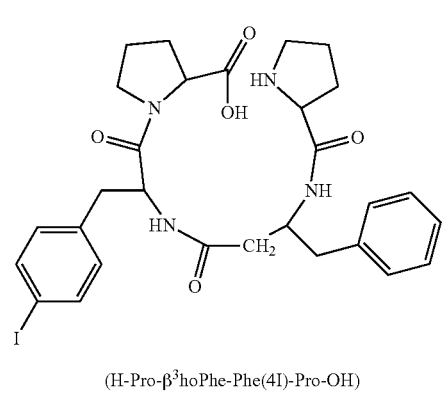
(H-Pro-β³hoPhe-Phe(4I)-Pro-OH)
II-3-o
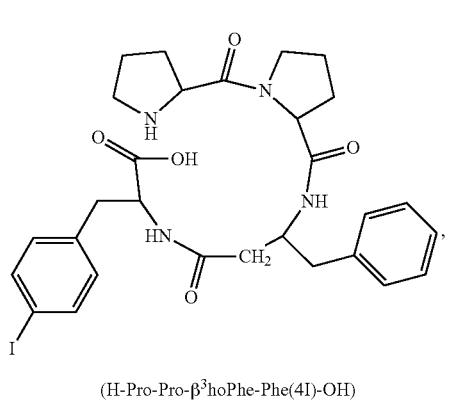
(H-Pro-Pro-β³hoPhe-Phe(4I)-OH)
II-4-o
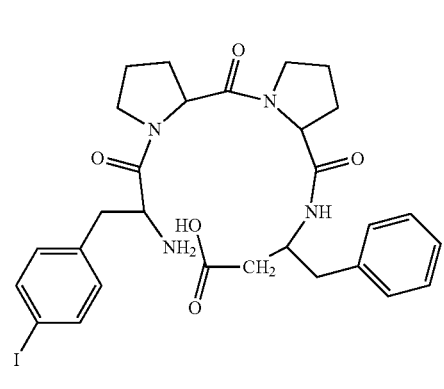
(H-Phe(4I)-Pro-Pro-β³hoPhe-OH)

II-1-p
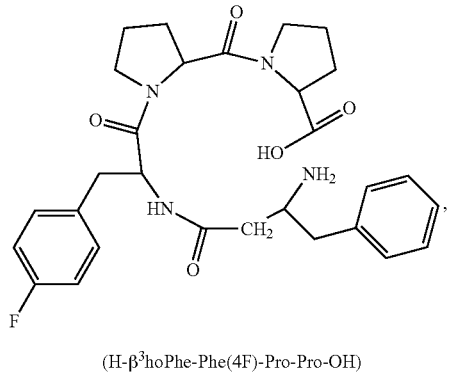
(H-β³hoPhe-Phe(4F)-Pro-Pro-OH)
II-2-p
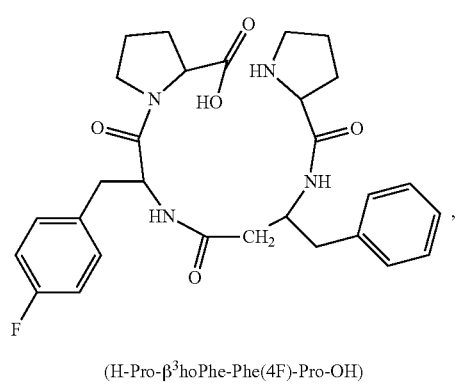
(H-Pro-β³hoPhe-Phe(4F)-Pro-OH)
II-3-p
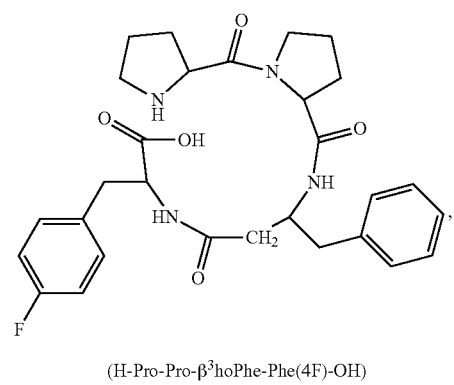
(H-Pro-Pro-β³hoPhe-Phe(4F)-OH)
II-4-p
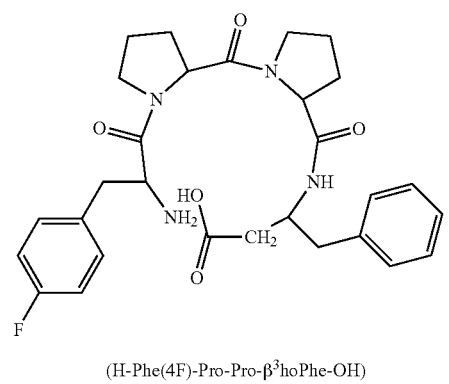
(H-Phe(4F)-Pro-Pro-β³hoPhe-OH)
II-1-q
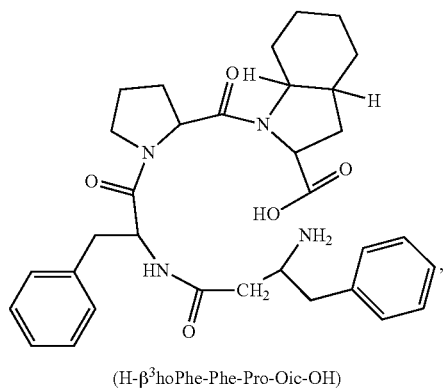
(H-β³hoPhe-Phe-Pro-Oic-OH)
II-2-q
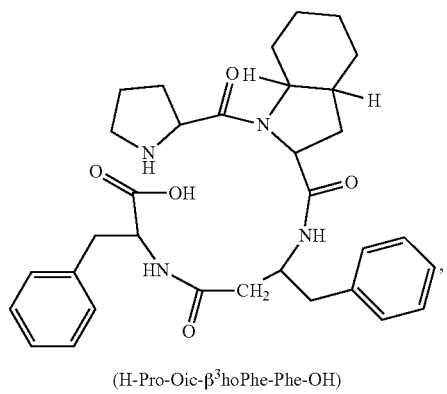
(H-Oic-β³hoPhe-Phe-Pro-OH)
II-3-q
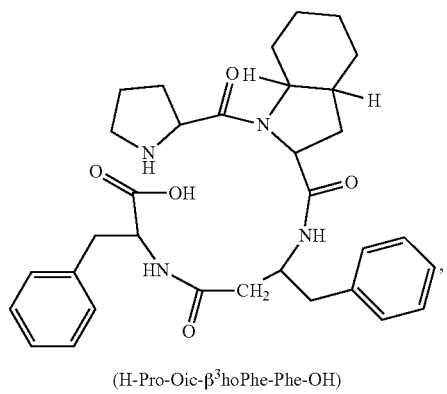
(H-Pro-Oic-β³hoPhe-Phe-OH)
II-4-q
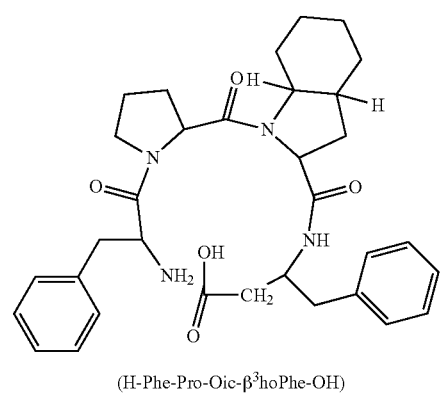
(H-Phe-Pro-Oic-β³hoPhe-OH)

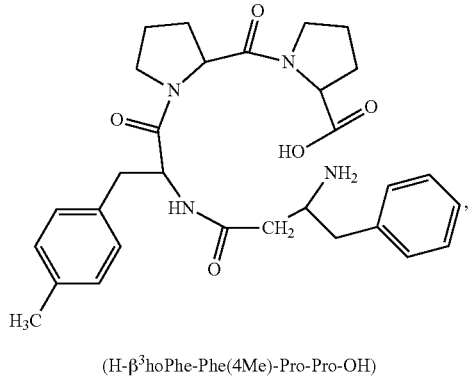
(H-β³hoPhe-Phe(4Me)-Pro-Pro-OH)  II-1-r
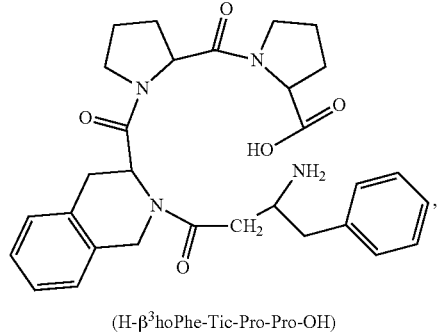
(H-β³hoPhe-Tic-Pro-Pro-OH)  II-1-s
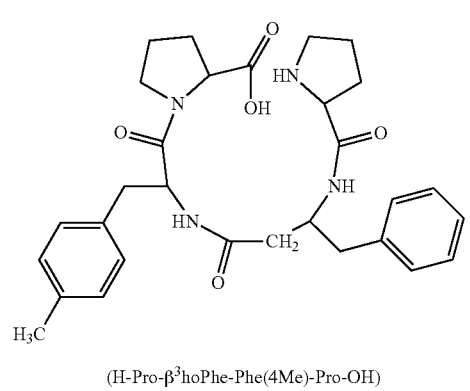
(H-Pro-β³hoPhe-Phe(4Me)-Pro-OH)  II-2-r
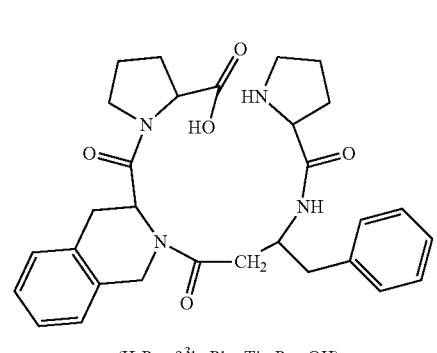
(H-Pro-β³hoPhe-Tic-Pro-OH)  II-2-s
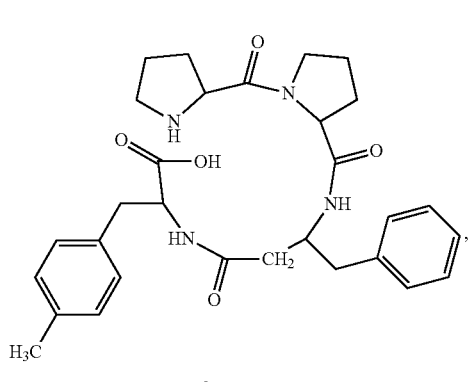
(H-Pro-Pro-β³hoPhe-Phe(4Me)-OH)  II-3-r
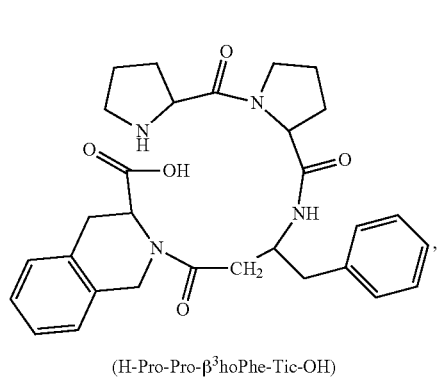
(H-Pro-Pro-β³hoPhe-Tic-OH)  II-3-s
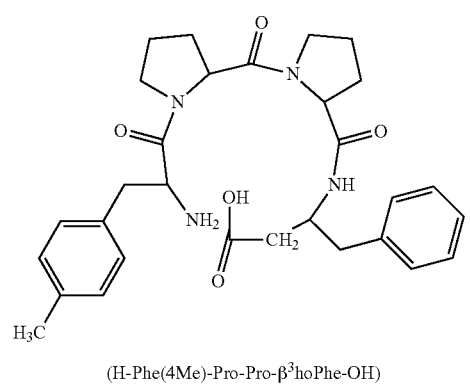
(H-Phe(4Me)-Pro-Pro-β³hoPhe-OH)  II-4-r
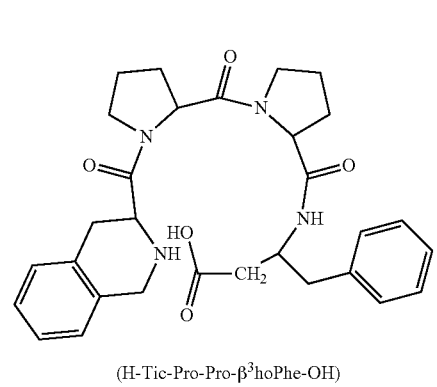
(H-Tic-Pro-Pro-β³hoPhe-OH)  II-4-s II-1-t
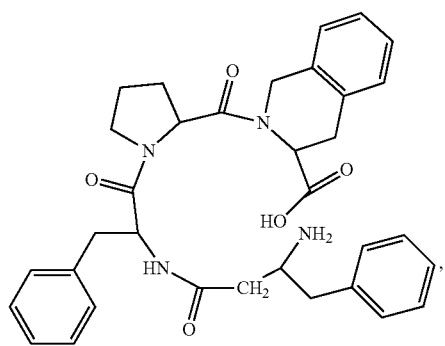
(H-β³hoPhe-Phe-Pro-Tic-OH)
II-2-t
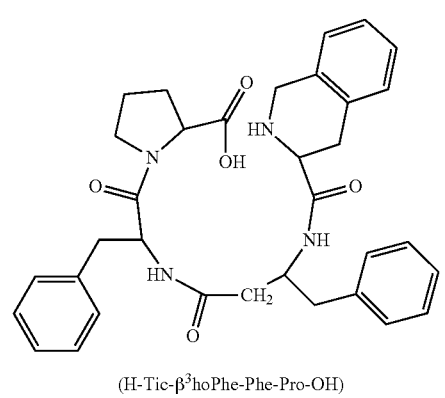
(H-Tic-β³hoPhe-Phe-Pro-OH)
II-3-t
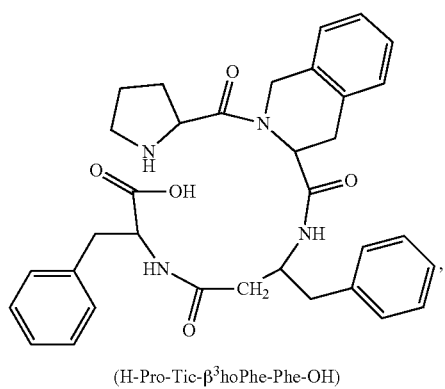
(H-Pro-Tic-β³hoPhe-Phe-OH)
II-4-t
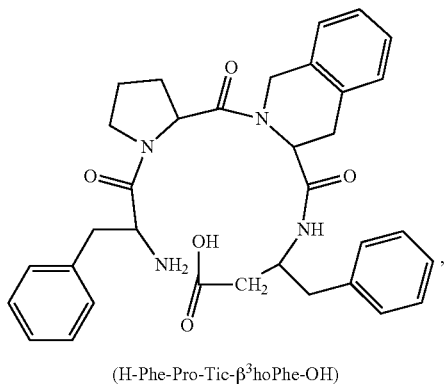
(H-Phe-Pro-Tic-β³hoPhe-OH)
II-1-u
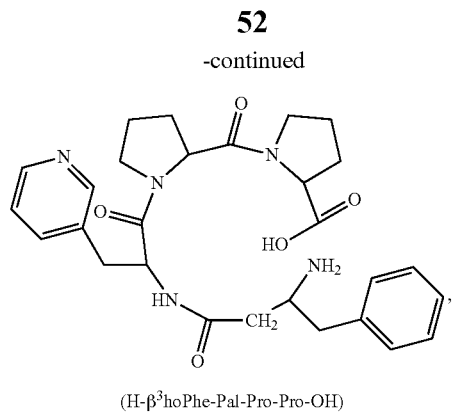
(H-β³hoPhe-Pal-Pro-Pro-OH)
II-2-u
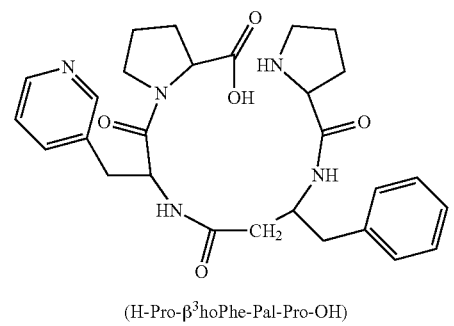
(H-Pro-β³hoPhe-Pal-Pro-OH)
II-3-u
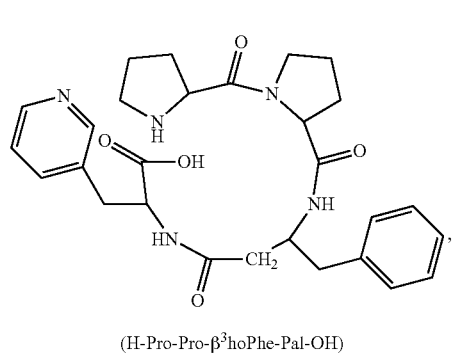
(H-Pro-Pro-β³hoPhe-Pal-OH)
II-4-u
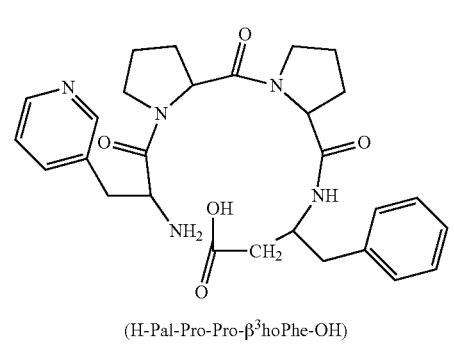
(H-Pal-Pro-Pro-β³hoPhe-OH)

53
-continued
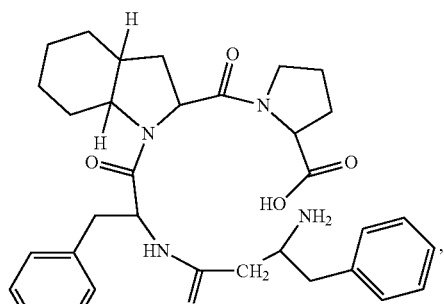
II-1-v
(H-β³hoPhe-Phe-Oic-Pro-OH)
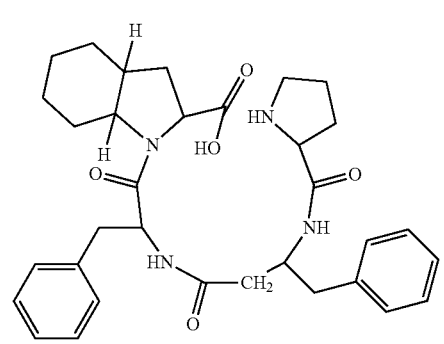
II-2-v
(H-Pro-β³hoPhe-Phe-Oic-OH)
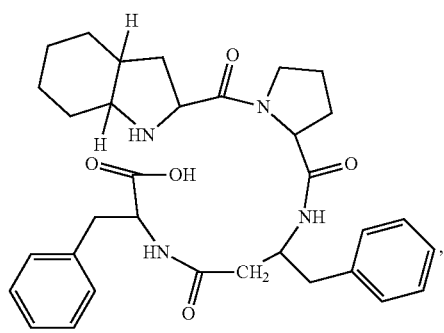
II-3-v
(H-Oic-Pro-β³hoPhe-Phe-OH)
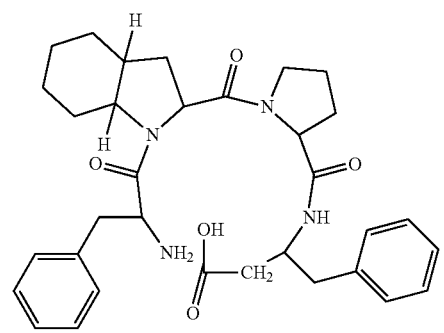
II-4-v
(H-Phe-Oic-Pro-β³hoPhe-OH)
54
-continued
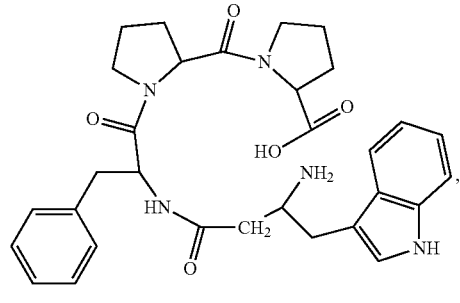
II-1-w
(H-β³hoTrp-Phe-Pro-Pro-OH)
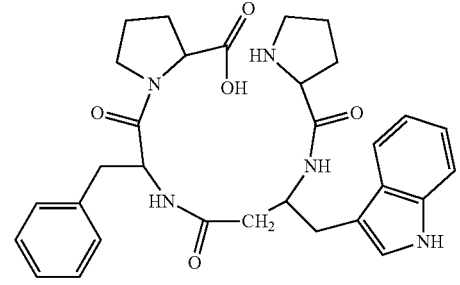
II-2-w
(H-Pro-β³hoTrp-Pho-Pro-OH)
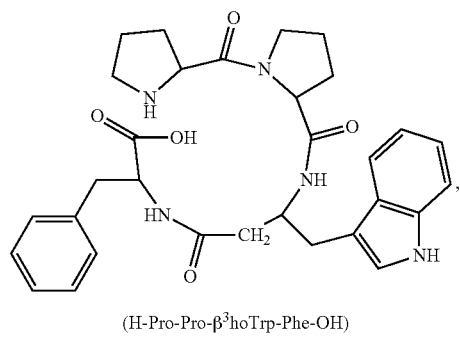
II-3-w
(H-Pro-Pro-β³hoTrp-Phe-OH)
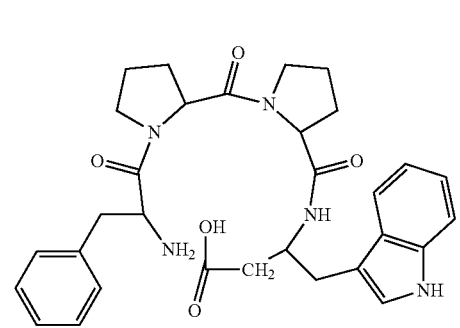
II-4-w
(H-Phe-Pro-Pro-β³hoTrp-OH)

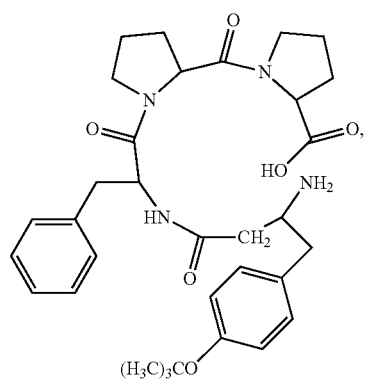
(H-β³hoTyr(tBu)-Phe-Pro-Pro-OH)  II-1-x
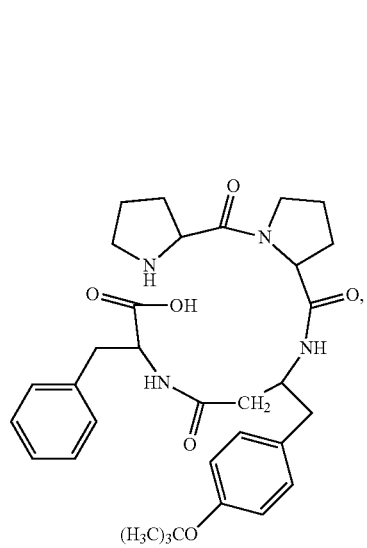
(H-Pro-β³hoTyr(tBu)-Pro-Pro-OH)  II-2-x
(H-Pro-Pro-β³hoTyr(tBu)-Phe-OH)  II-3-x
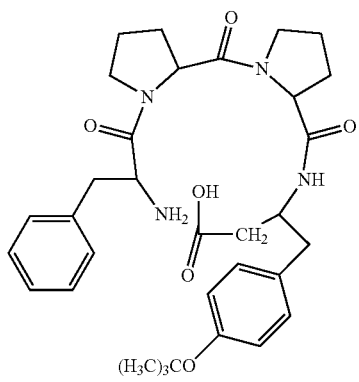
(H-Phe-Pro-Pro-β³hoTyr(tBu)-OH)  II-4-x
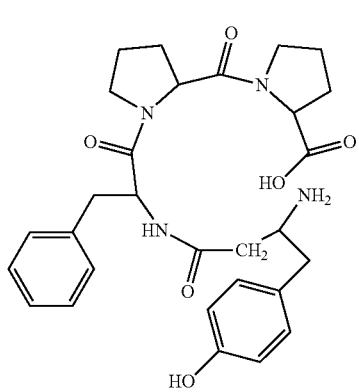
(H-β³hoTyr-Phe-Pro-Pro-OH)  II-1-y
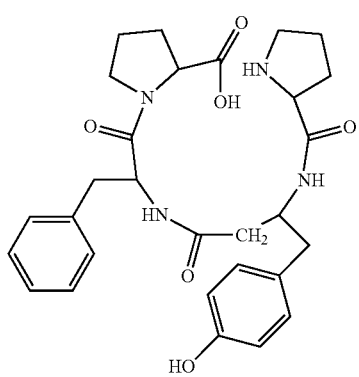
(H-Pro-β³hoTyr-Phe-Pro-OH)  II-2-y

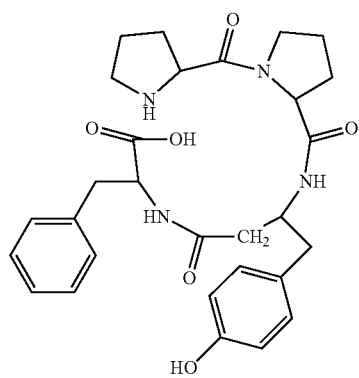
(H-Pro-Pro-β³hoTyr-Phe-OH)
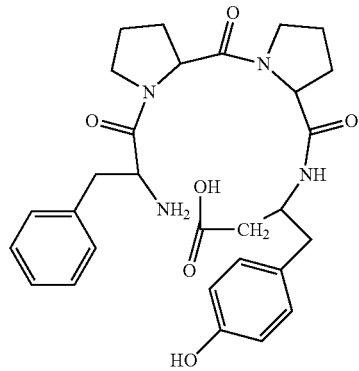
(H-Phe-Pro-Pro-β³hoTyr-OH)
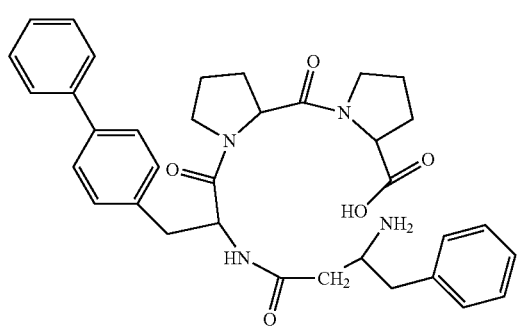
(H-β³hoPhe-Bip-Pro-Pro-OH)
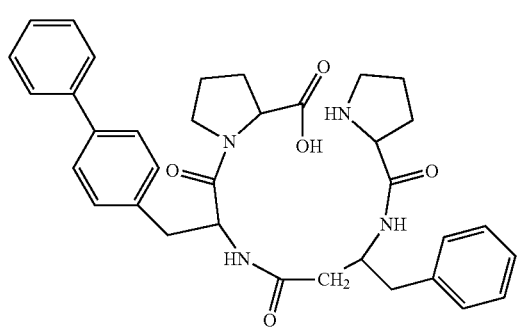
(H-Pro-β³hoPhe-Bip-Pro-OH)
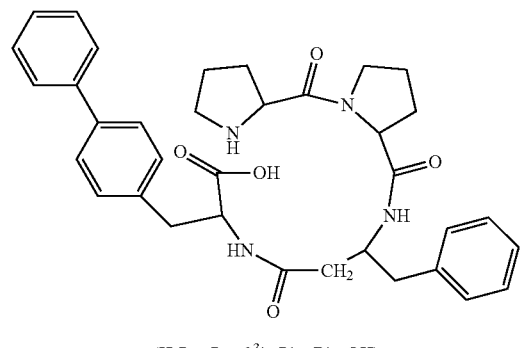
(H-Pro-Pro-β³hoPhe-Bip-OH)
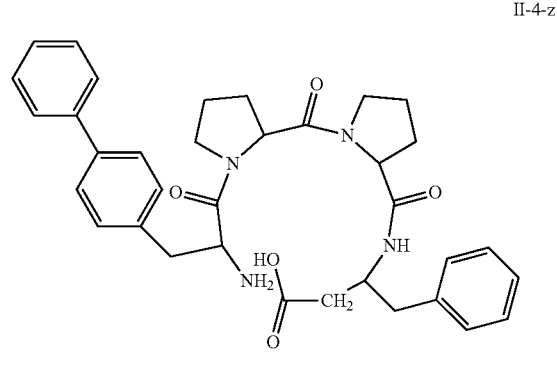
(H-Bip-Pro-Pro-β³hoPhe-OH)
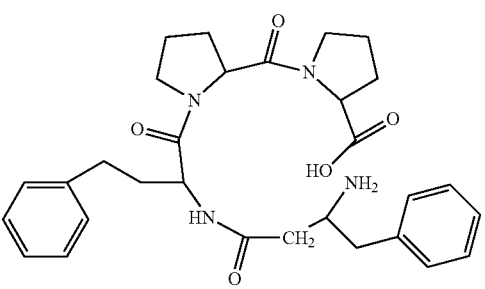
(H-β³hoPhe-hoPhe-Pro-Pro-OH)
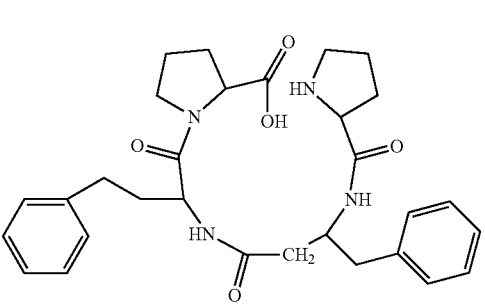
(H-Pro-β³hoPhe-hoPhe-Pro-OH)

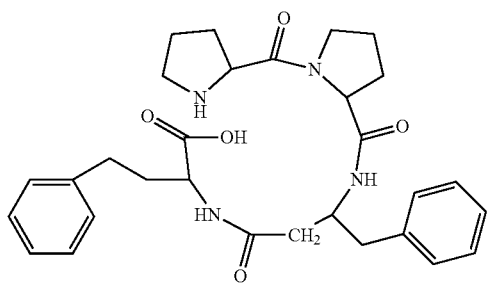
II-3-aa
(H-Pro-Pro-β³hoPhe-hoPhe-OH)
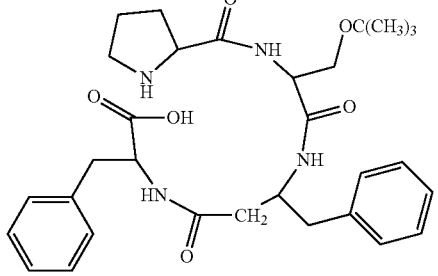
II-3-ab
(H-Pro-Ser(tBu)-β³hoPhe-Phe-OH)
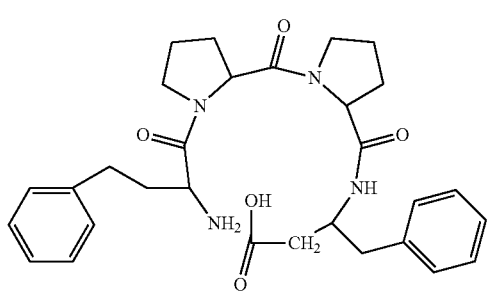
II-4-aa
(H-hoPhe-Pro-Pro-β³hoPhe-OH)
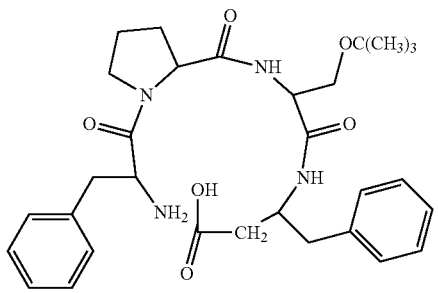
II-4-ab
(H-Phe-Pro-Ser(tBu)-β³hoPhe-OH)
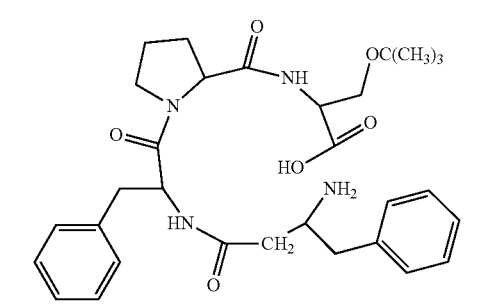
II-1-ab
(H-β³hoPhe-Phe-Pro-Ser(tBu)-OH)
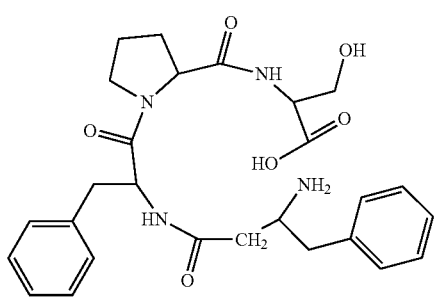
II-1-ac
(H-β³hoPhe-Phe-Pro-Ser-OH)
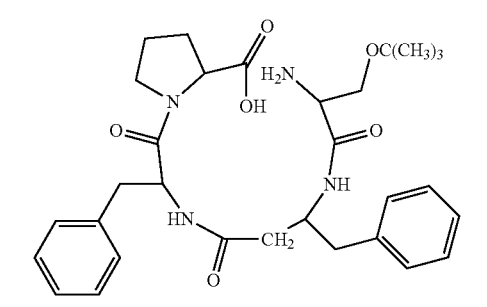
II-2-ab
(H-Ser(tBu)-β³hoPhe-Phe-Pro-OH)
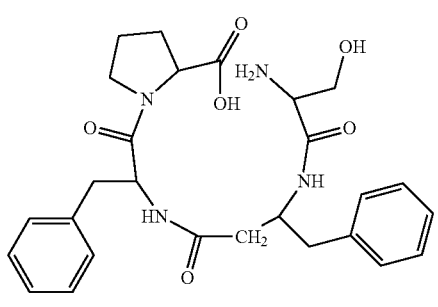
II-2-ac
(H-Ser-β³hoPhe-Phe-Pro-OH)

II-3-ac
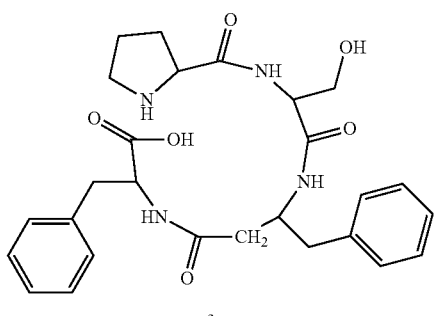
(H-Pro-Ser-β³hoPhe-Phe-OH)
II-4-ac
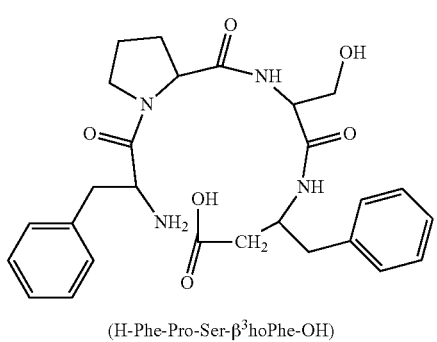
(H-Phe-Pro-Ser-β³hoPhe-OH)
II-1-ad
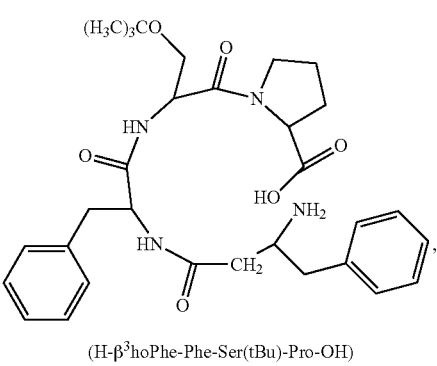
(H-β³hoPhe-Phe-Ser(tBu)-Pro-OH)
II-2-ad
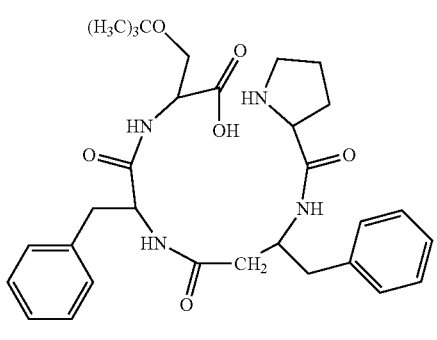
(H-Pro-β³hoPhe-Phe-Ser(tBu)-OH)
II-3-ad
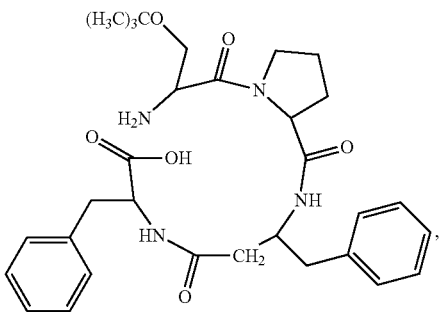
(H-Ser(tBu)-Pro-β³hoPhe-Phe-OH)
II-4-ad
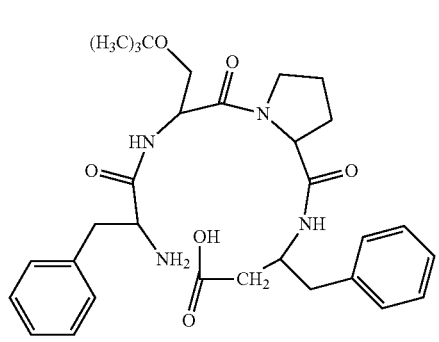
(H-Phe-Ser(tBu)-Pro-β³hoPhe-OH)
II-1-ae
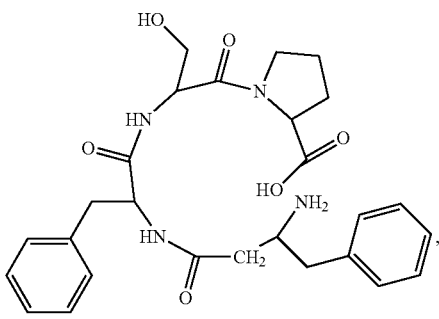
(H-β³hoPhe-Phe-Ser-Pro-OH)
II-2-ae
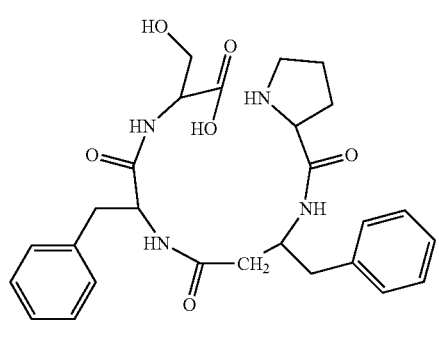
(H-Pro-β³hoPhe-Phe-Ser-OH)

-continued

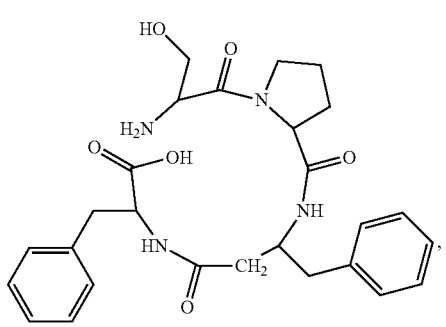

(H-Ser-Pro-β³hoPhe-Phe-OH)
II-3-ae

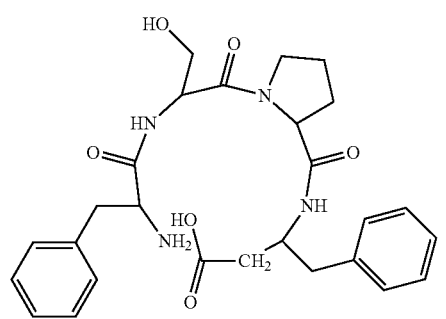

(H-Phe-Ser-Pro-β³hoPhe-OH)
II-4-ad

In some embodiments the compound is a compound of formula II-4-a. In some embodiments, the compound is a compound of formula II-1-a. In some embodiments, the compound is a compound of formula II-2-a. In some embodiments, the compound is a compound of formula II-3-a. In some embodiments, the compound is a compound of formula II-4-b. In some embodiments, the compound is a compound of formula II-1-b. In some embodiments, the compound is a compound of formula II-2-b. In some embodiments, the compound is a compound of formula II-3-b. In some embodiments, the compound is a compound of formula II-4-c. In some embodiments, the compound is a compound of formula II-1-c. In some embodiments, the compound is a compound of formula II-2-c. In some embodiments, the compound is a compound of formula II-3-c. In some embodiments, the compound is a compound of formula II-4-d. In some embodiments, the compound is a compound of formula II-1-d. In some embodiments, the compound is a compound of formula II-2-d. In some embodiments, the compound is a compound of formula II-3-d. In some embodiments, the compound is a compound of formula II-4-e. In some embodiments, the compound is a compound of formula II-1-e. In some embodiments, the compound is a compound of formula II-2-e. In some embodiments, the compound is a compound of formula II-3-e. In some embodiments, the compound is a compound of formula II-4-f. In some embodiments, the compound is a compound of formula II-1-f. In some embodiments, the compound is a compound of formula II-2-f. In some embodiments, the compound is a compound of formula II-3-f. In some embodiments, the compound is a compound of formula II-4-g. In some embodiments, the compound is compound of formula II-1-g. In some embodiments, the compound is compound of formula II-2-g. In some embodiments, the compound is compound of formula II-3-g. In some embodiments, the compound is a compound of formula II-4-h. In some embodiments, the compound is compound of formula II-1-h. In some embodiments, the compound is compound of formula II-2-h. In some embodiments, the compound is compound of formula II-3-h. In some embodiments, the compound is compound of formula II-1-i. In some embodiments, the compound is compound of formula II-2-i. In some embodiments, the compound is compound of formula II-3-i. In some embodiments, the compound is a compound of formula II-4-i. In some embodiments, the compound is compound of formula II-1-j. In some embodiments, the compound is compound of formula II-2-j. In some embodiments, the compound is compound of formula II-3-j. In some embodiments, the compound is a compound of formula II-4-j. In some embodiments, the compound is compound of formula II-1-k. In some embodiments, the compound is compound of formula II-2-k. In some embodiments, the compound is compound of formula II-3-k. In some embodiments, the compound is a compound of formula II-4-k. In some embodiments, the compound is compound of formula II-1-l. In some embodiments, the compound is compound of formula II-2-l. In some embodiments, the compound is compound of formula II-3-l. In some embodiments, the compound is a compound of formula II-4-l. In some embodiments, the compound is compound of formula II-1-m. In some embodiments, the compound is compound of formula II-2-m. In some embodiments, the compound is compound of formula II-3-m. In some embodiments, the compound is a compound of formula II-4-m. In some embodiments, the compound is compound of formula II-1-n. In some embodiments, the compound is compound of formula II-2-n. In some embodiments, the compound is compound of formula II-3-n. In some embodiments, the compound is a compound of formula II-4-n. In some embodiments, the compound is compound of formula II-1-o. In some embodiments, the compound is compound of formula II-2-o. In some embodiments, the compound is compound of formula II-3-o. In some embodiments, the compound is a compound of formula II-4-o. In some embodiments, the compound is compound of formula II-1-p. In some embodiments, the compound is compound of formula II-2-p. In some embodiments, the compound is compound of formula II-3-p. In some embodiments, the compound is a compound of formula II-4-p. In some embodiments, the compound is compound of formula II-1-q. In some embodiments, the compound is compound of formula II-2-q. In some embodiments, the compound is compound of formula II-3-q. In some embodiments, the compound is a compound of formula II-4-q. In some embodiments, the compound is compound of formula II-1-r. In some embodiments, the compound is compound of formula II-2-r. In some embodiments, the compound is compound of formula II-3-r. In some embodiments, the compound is a compound of formula II-4-r. In some embodiments, the compound is compound of formula II-1-s. In some embodiments, the compound is compound of formula II-2-s. In some embodiments, the compound is compound of formula II-3-s. In some embodiments, the compound is a compound of formula II-4-s. In some embodiments, the compound is compound of formula II-1-t. In some embodiments, the compound is compound of formula II-2-t. In some embodiments, the compound is compound of formula II-3-t. In some embodiments, the compound is a compound of formula II-4-t. In some embodiments, the compound is compound of formula II-1-u. In some embodiments, the compound is compound of formula II-2-u. In some embodiments, the compound is compound of formula II-3-u. In some embodiments, the compound is a compound of formula II-4-u. In some embodiments, the compound is compound of formula II-1-v. In some embodiments, the compound is compound of formula II-2-v. In some embodiments, the compound is compound of formula II-3-v. In some embodiments, the compound is a compound of formula II-4-v. In some embodiments, the compound is compound of formula II-1-w. In some embodiments, the compound is compound of formula II-2-w. In some embodiments, the compound is compound of formula II-3-w. In some embodiments, the compound is a compound of formula II-4-w. In some embodiments, the compound is compound of formula II-1-x. In some embodiments, the compound is compound of formula II-2-x. In some embodiments, the compound is compound of formula II-3-x. In some embodiments, the compound is a compound of formula II-4-x. In some embodiments, the compound is compound of formula II-1-y. In some embodiments, the compound is compound of formula II-2-y. In some embodiments, the compound is compound of formula II-3-y. In some embodiments, the compound is a compound of formula II-4-y. In some embodiments, the compound is compound of formula II-1-z. In some embodiments, the compound is compound of formula II-2-z. In some embodiments, the compound is compound of formula II-3-z. In some embodiments, the compound is a compound of formula II-4-z. In some embodiments, the compound is compound of formula II-1-aa. In some embodiments, the compound is compound of formula II-2-aa. In some embodiments, the compound is compound of formula II-3-aa. In some embodiments, the compound is a compound of formula II-4-aa. In some embodiments, the compound is compound of formula II-1-ab. In some embodiments, the compound is compound of formula II-2-ab. In some embodiments, the compound is compound of formula II-3-ab. In some embodiments, the compound is a compound of formula II-4-ab. In some embodiments, the compound is a compound of formula II-1-ac. In some embodiments, the compound is a compound of formula II-2-ac. In some embodiments, the compound is compound of formula II-3-ac. In some embodiments, the compound is a compound of formula II-4-ac. In some embodiments, the compound is compound of formula II-1-ad. In some embodiments, the compound is compound of formula II-2-ad. In some embodiments, the compound is compound of formula II-3-ad. In some embodiments, the compound is a compound of formula II-4-ad. In some embodiments, the compound is compound of formula II-1-ae. In some embodiments, the compound is compound of formula II-2-ae. In some embodiments, the compound is compound of formula II-3-ae. In some embodiments, the compound is a compound of formula II-4-ae.

In some embodiments the compound of formula II is selected from the group consisting of:

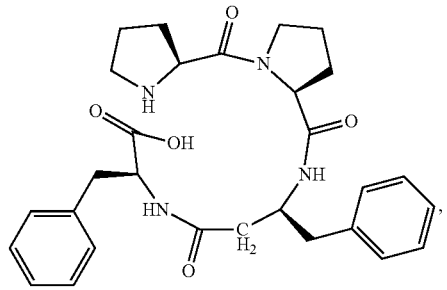

II-A-1

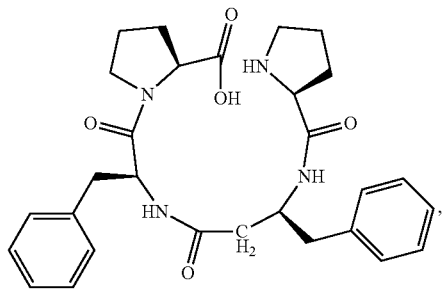

II-A-2

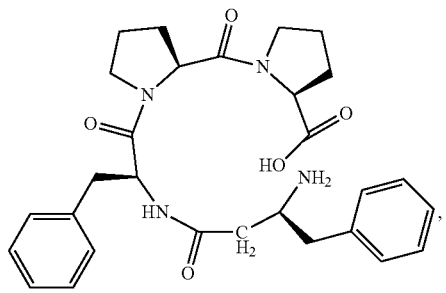

II-A-3

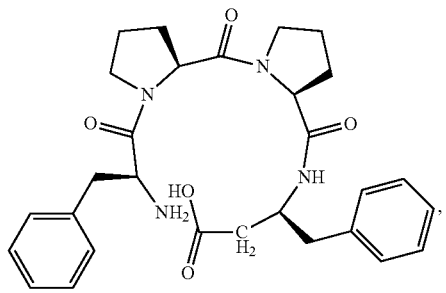

II-A-4

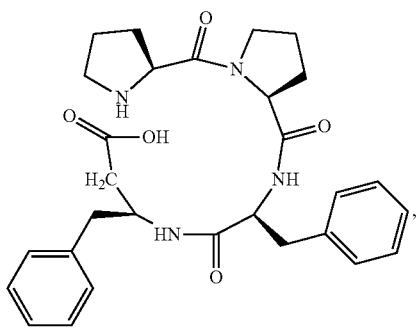

II-B-1

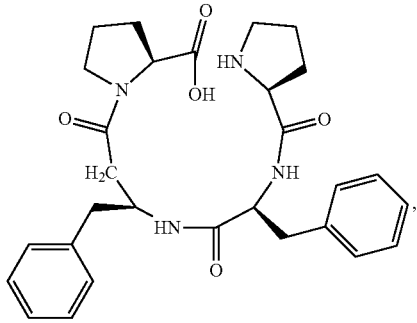

II-B-2

II-B-3
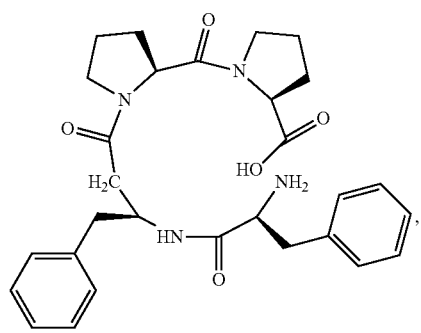
II-B-4
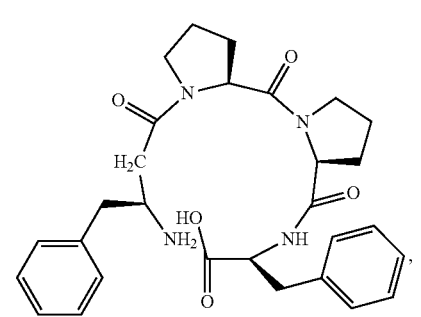
II-C-1
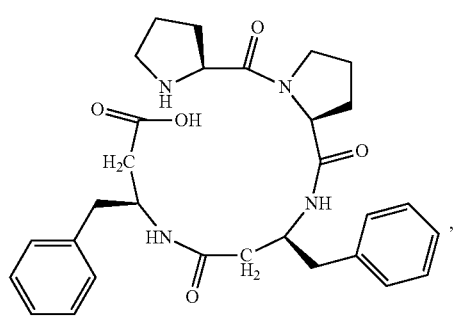
II-C-2
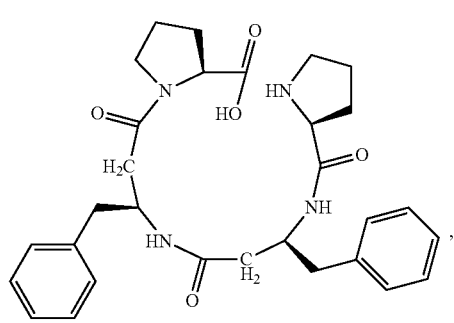
II-C-3
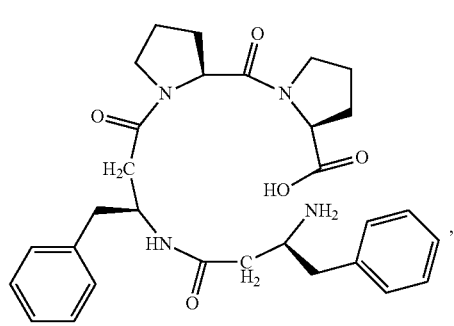
II-C-4
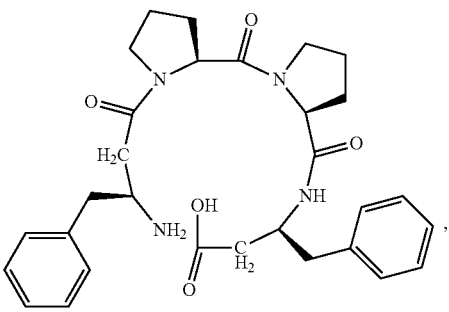
II-D-1
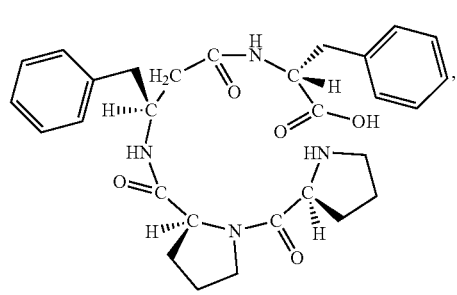
II-D-2
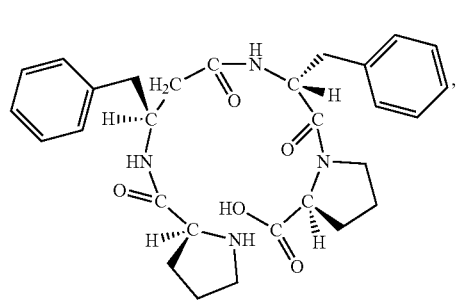
II-D-3
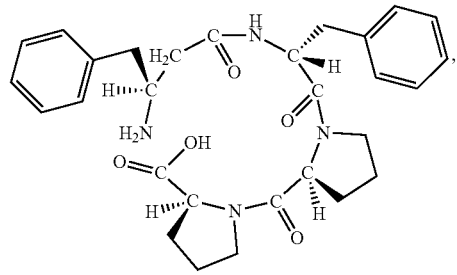
II-D-4
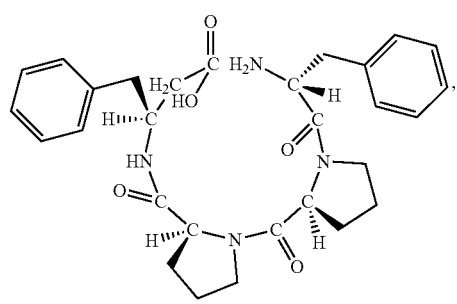

-continued
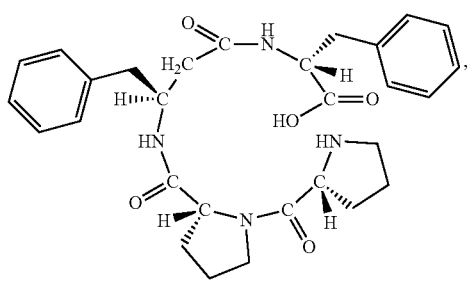
II-E-1
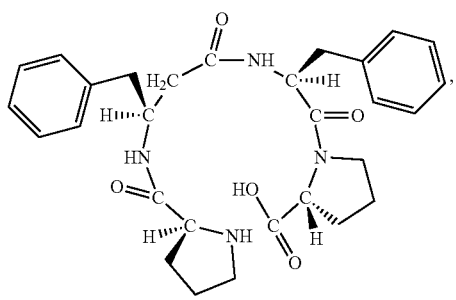
II-F-2
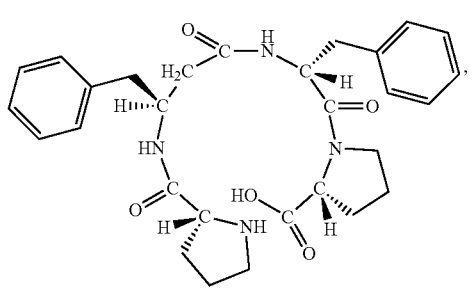
II-E-2
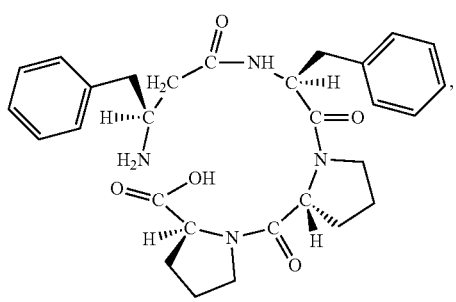
II-F-3
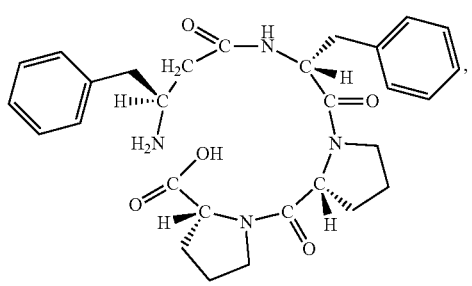
II-E-3
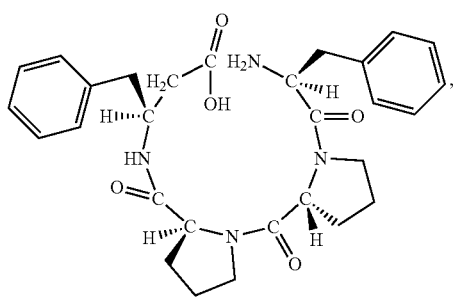
II-F-4
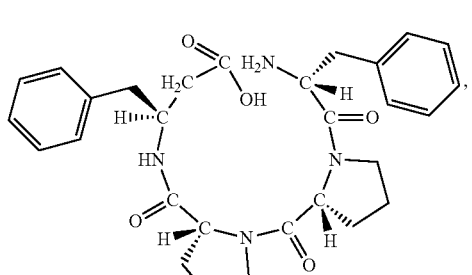
II-E-4
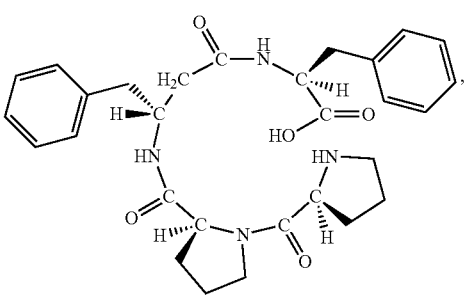
II-G-1
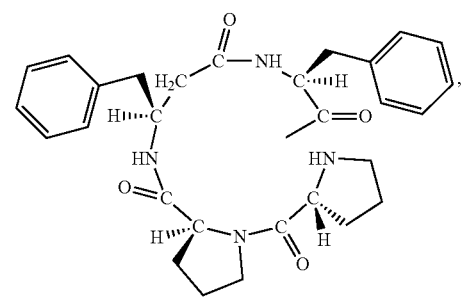
II-F-1
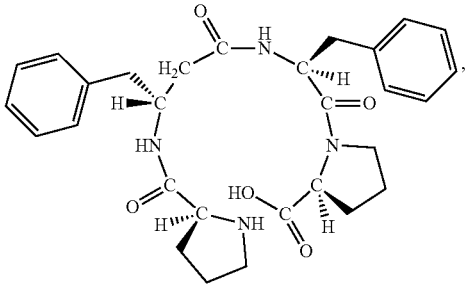
II-G-2

II-G-3
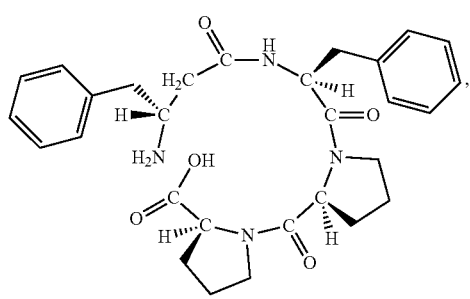
II-G-4
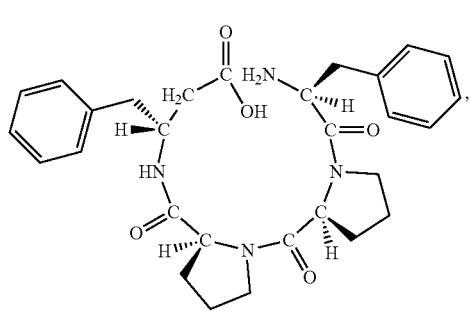
II-H-1
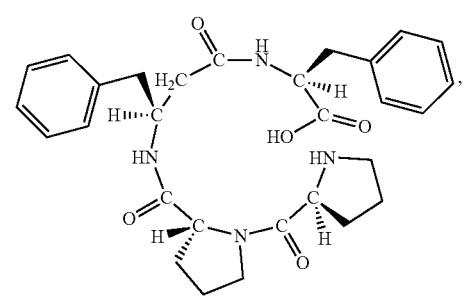
II-H-1
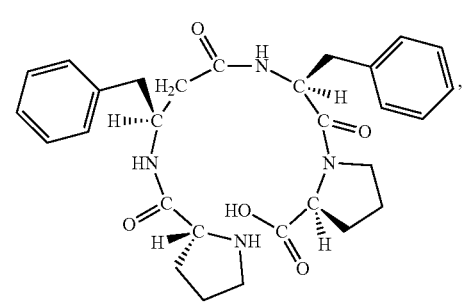
II-H-3
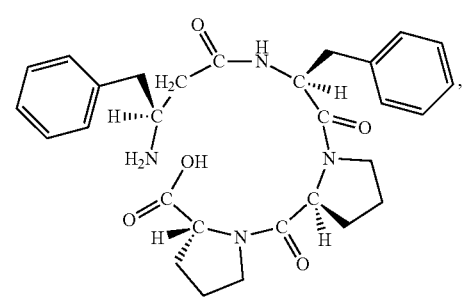
II-H-4
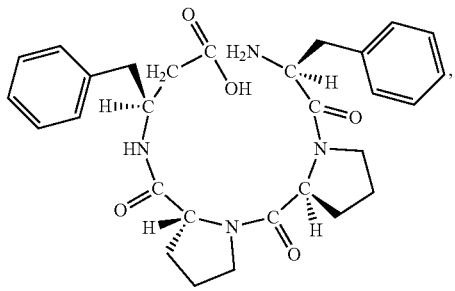
II-J-1
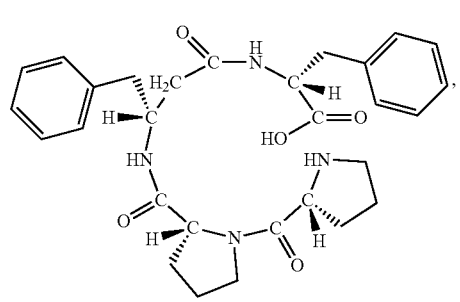
II-J-3
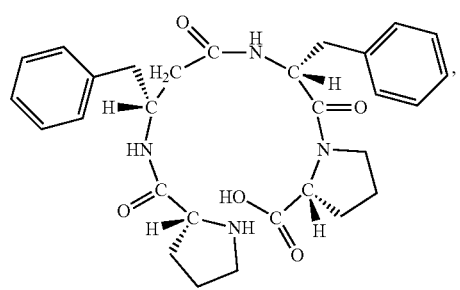
II-J-3
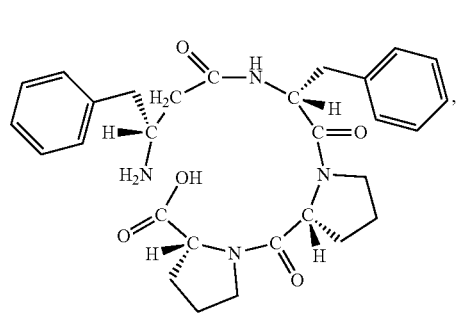
II-J-4
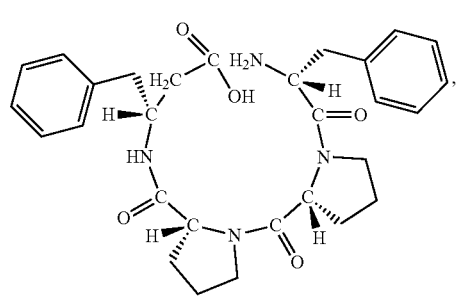

-continued
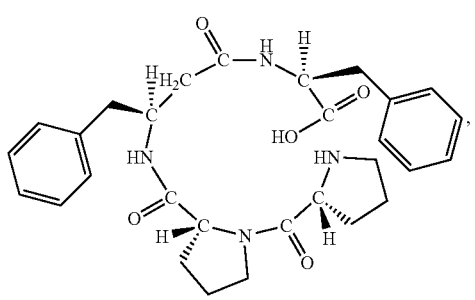
II-K-1
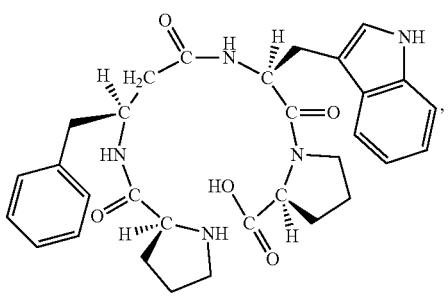
II-L-1
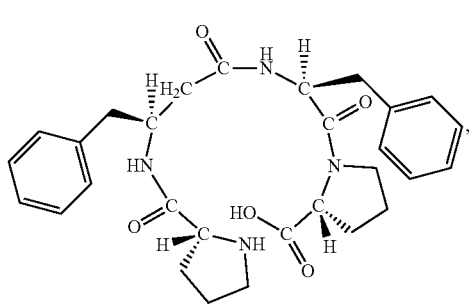
II-K-2
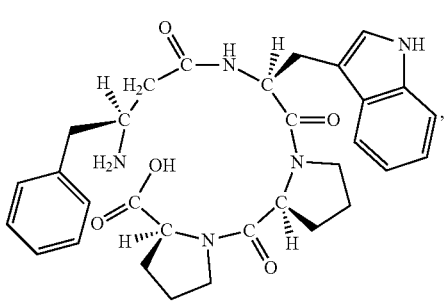
II-L-3
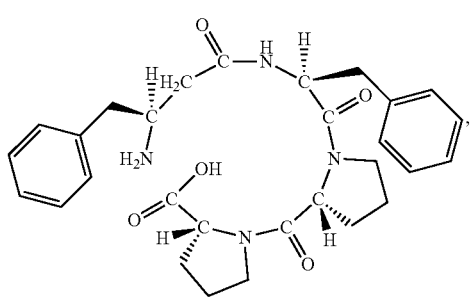
II-K-3
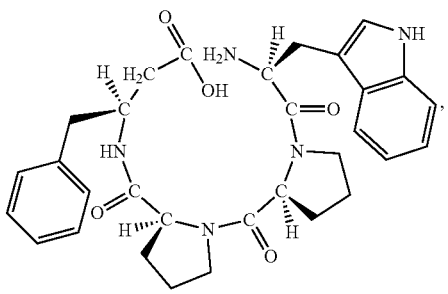
II-L-4
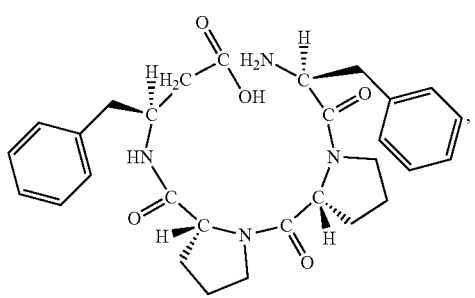
II-K-4
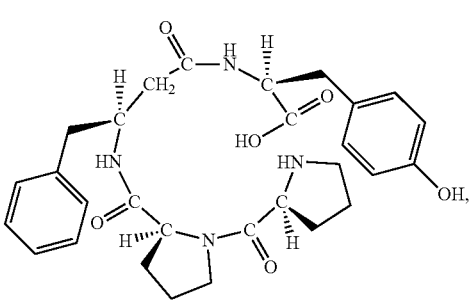
II-M-1
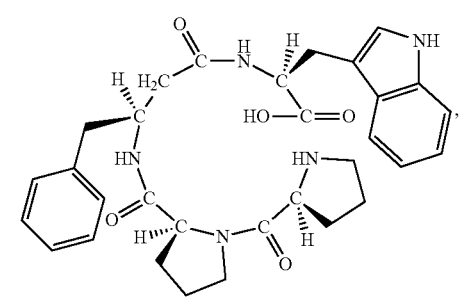
II-L-1
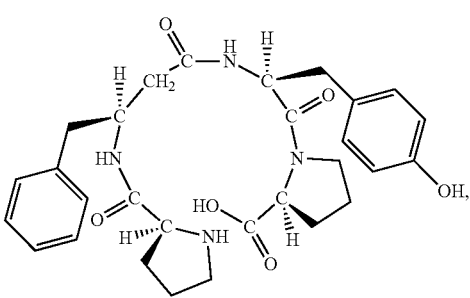
II-M-2

II-M-3
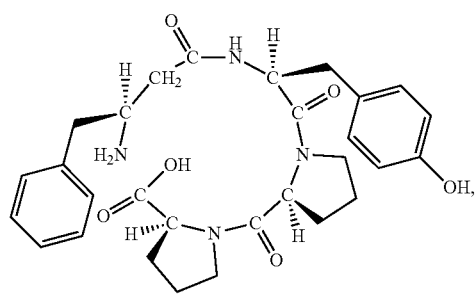
II-N-4
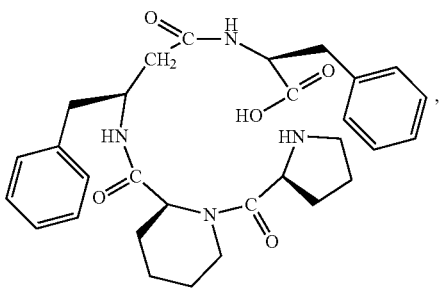
II-M-4
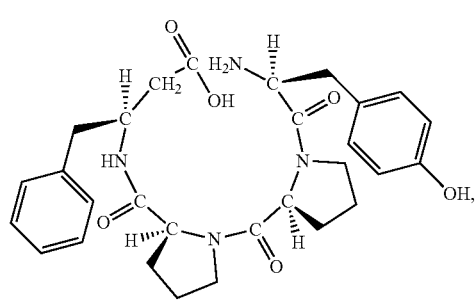
II-O-1
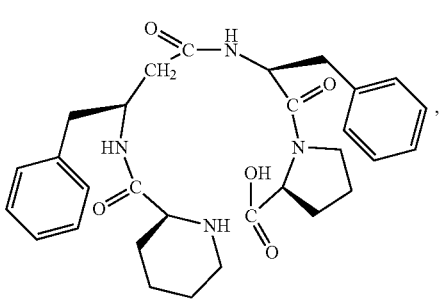
II-N-1
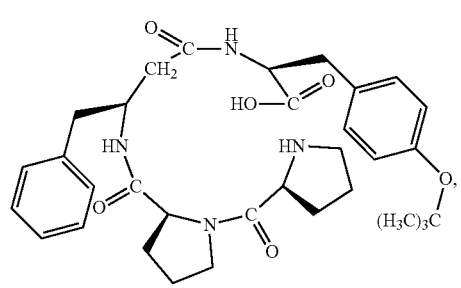
II-O-2
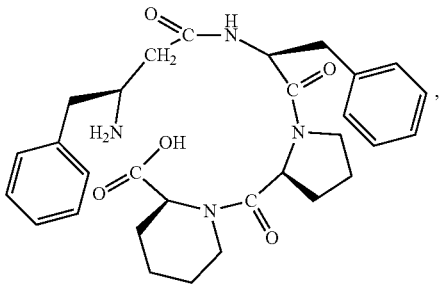
II-N-2
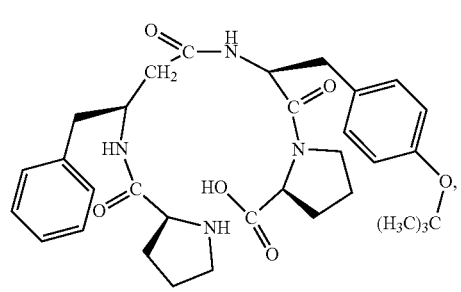
II-O-3
II-N-3
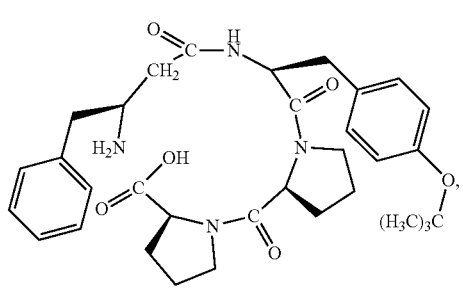
II-O-4
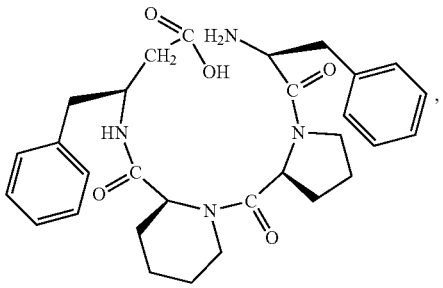

II-P-1
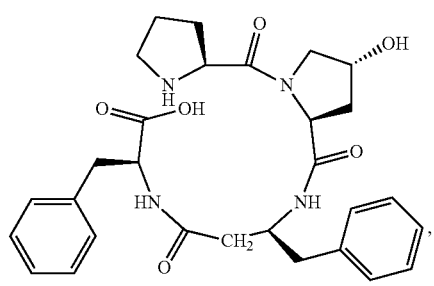
II-P-2
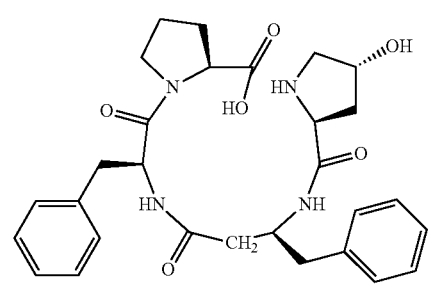
II-P-3
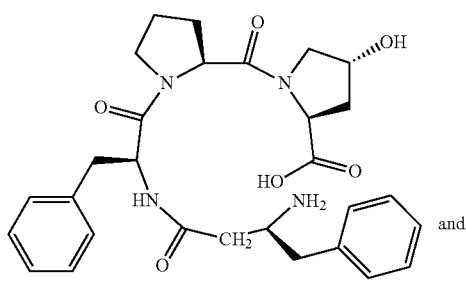
and
II-P-4
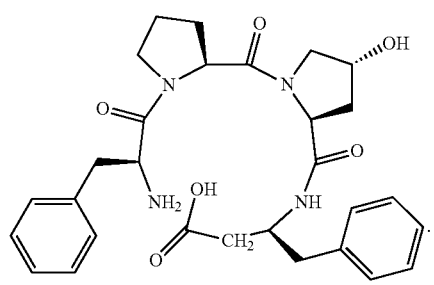
II-Q-1
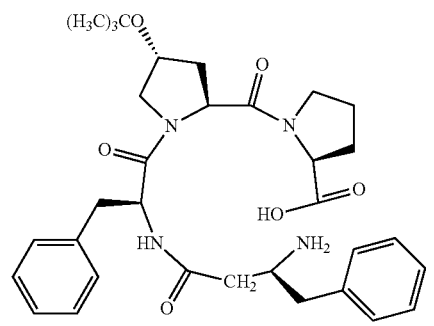
II-Q-2
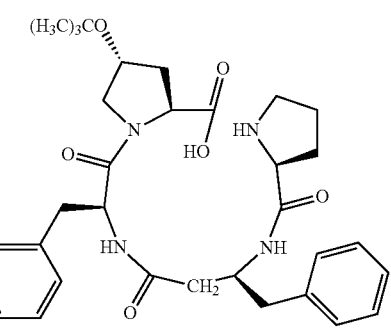
II-Q-3
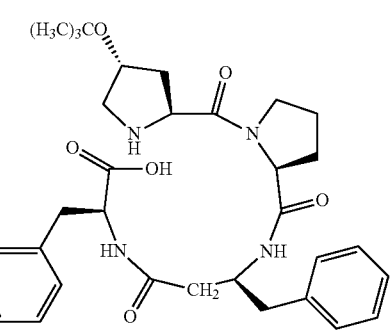
II-Q-4
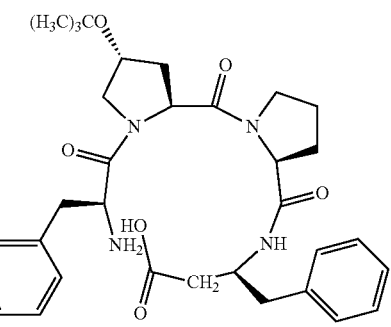
II-R-1
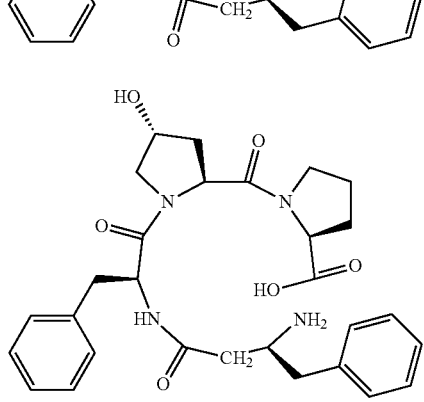
II-R-2
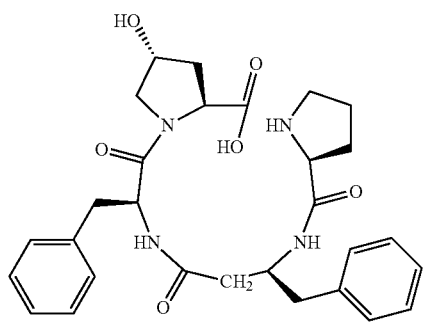

II-R-3
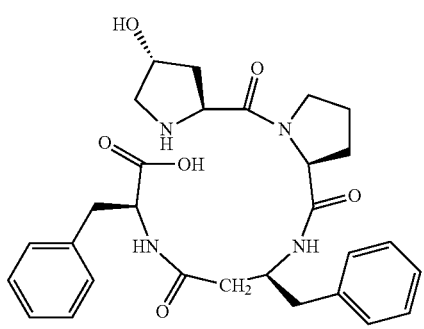
II-R-4
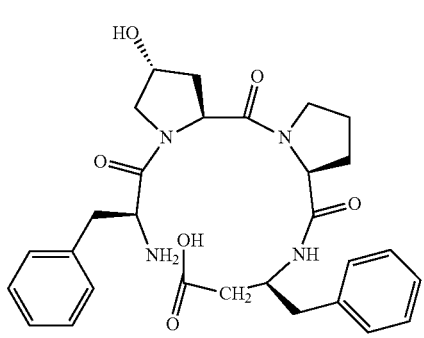
II-S-1
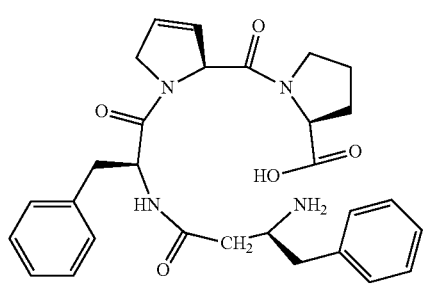
II-S-2
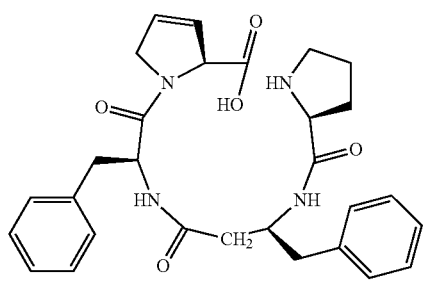
II-S-3
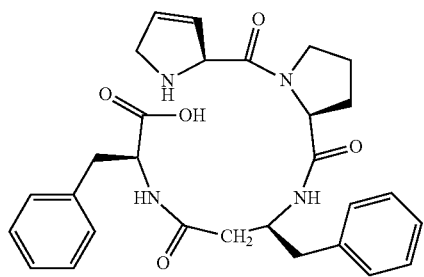
II-S-4
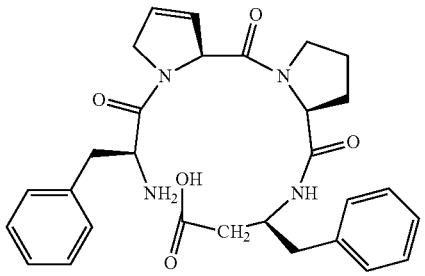
II-T-1
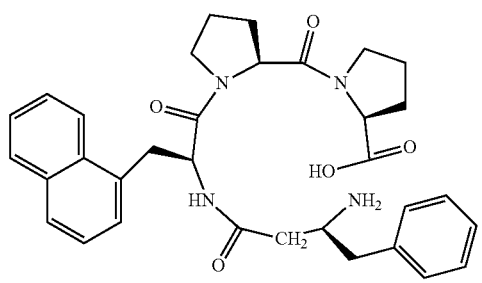
II-T-2
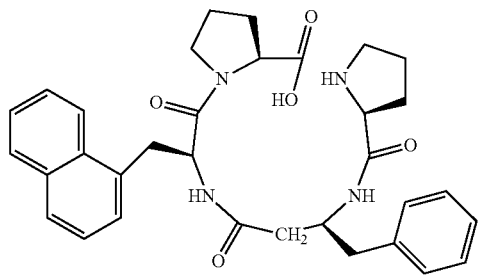
II-T-3
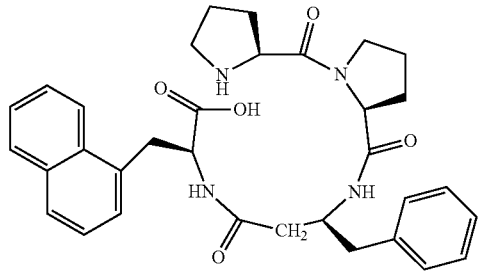
II-T-4
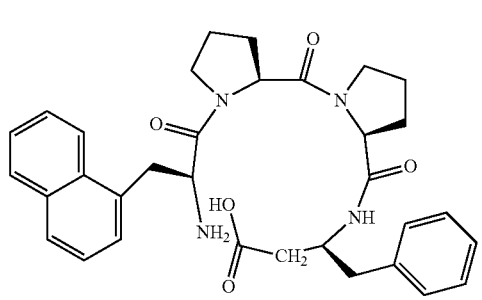

II-U-1
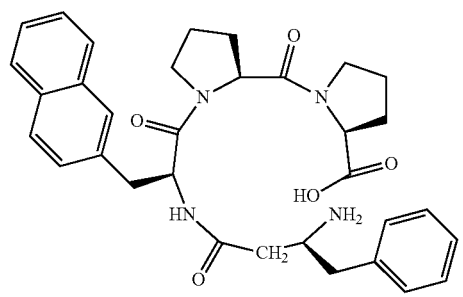
II-U-2
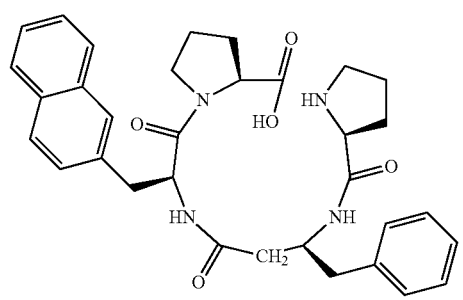
II-U-3
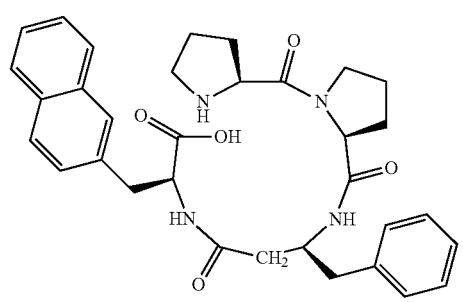
II-U-4
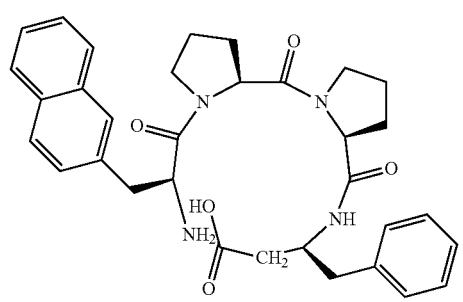
II-V-1
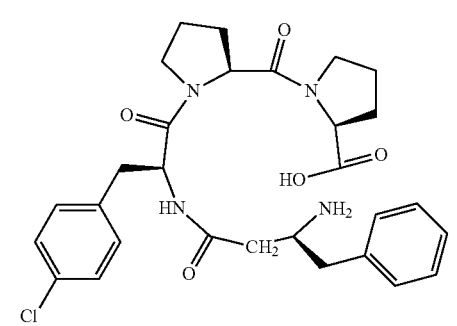
II-V-2
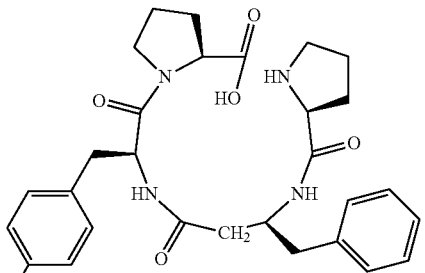
II-V-3
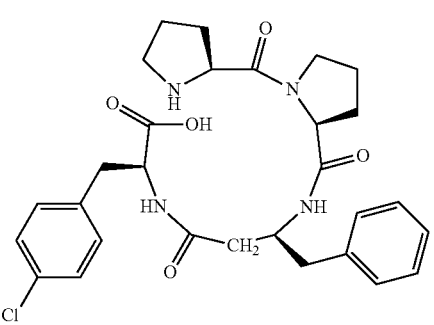
II-V-4
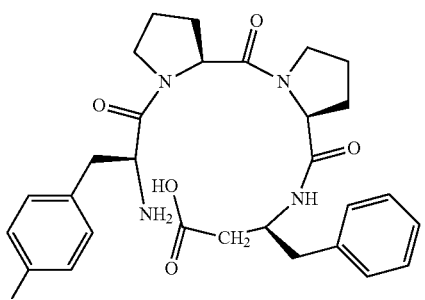
II-W-1
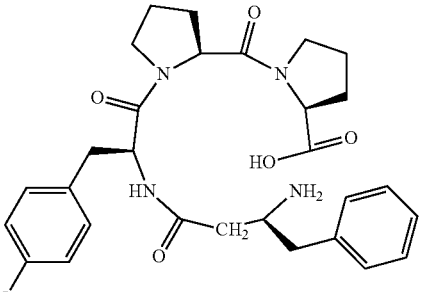
II-W-2
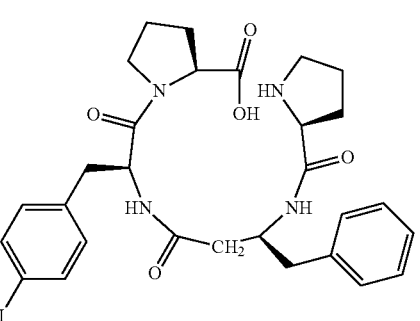

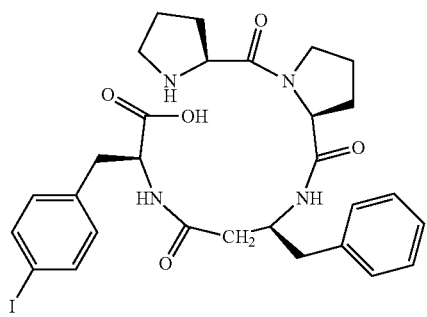
II-W-3
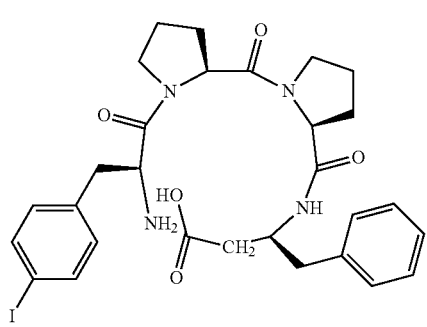
II-W-4
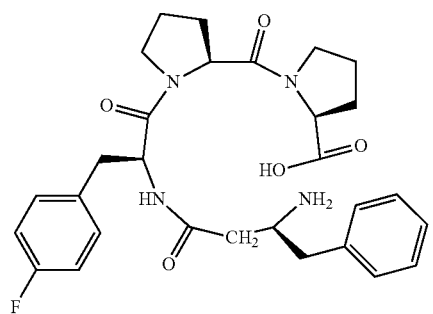
II-X-1
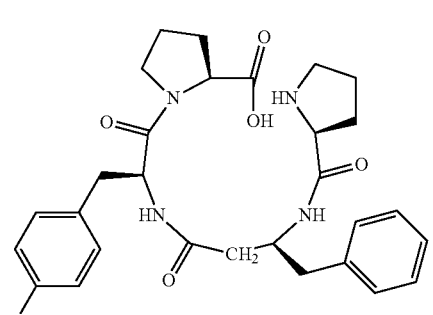
II-X-2
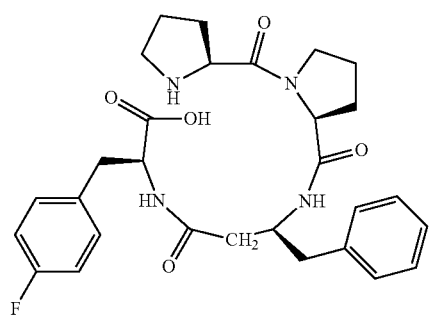
II-X-3
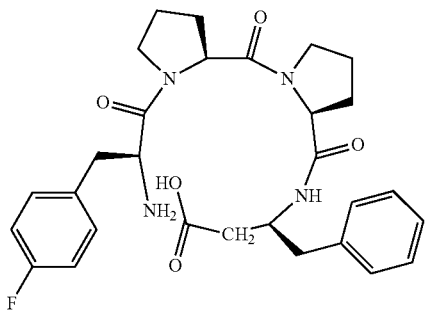
II-X-4
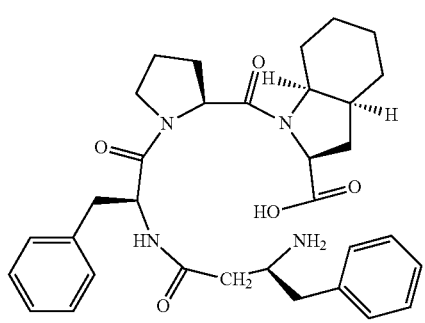
II-Y-1
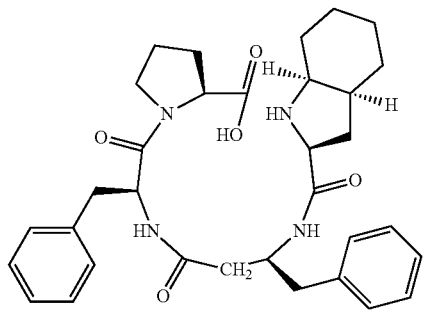
II-Y-2
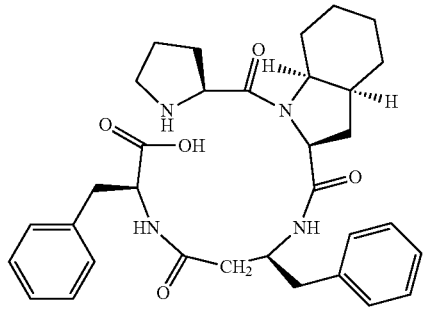
II-Y-3
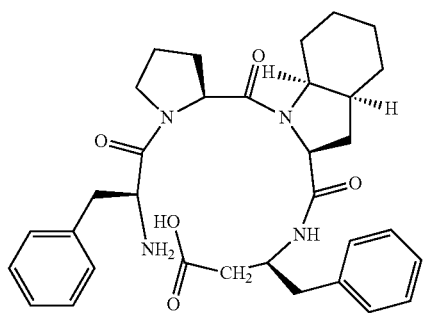
II-Y-4

II-Z-1
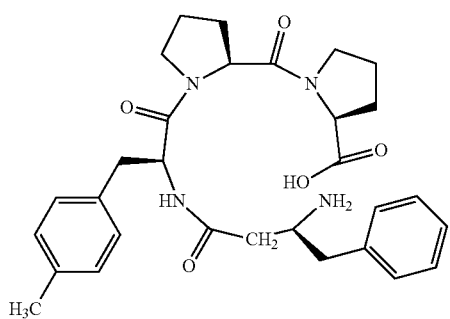
II-Z-2
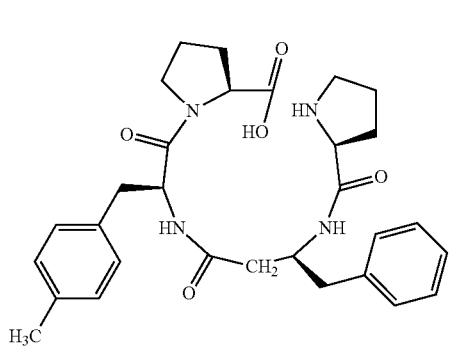
II-Z-3
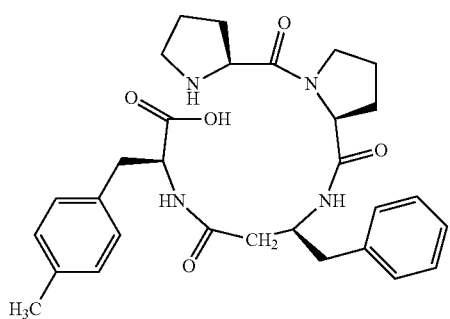
II-Z-4
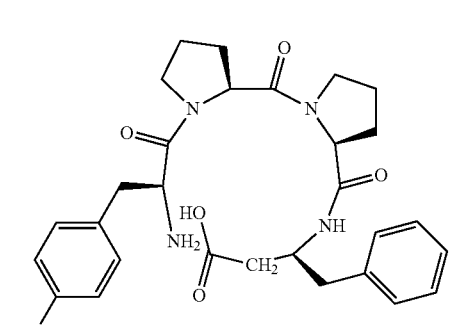
II-AA-1
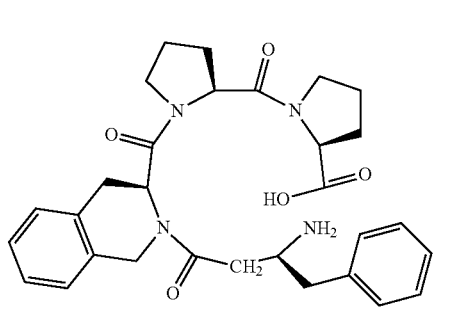
II-AA-2
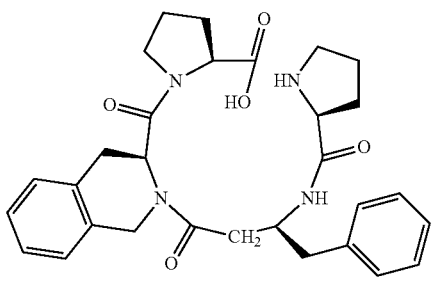
II-AA-3
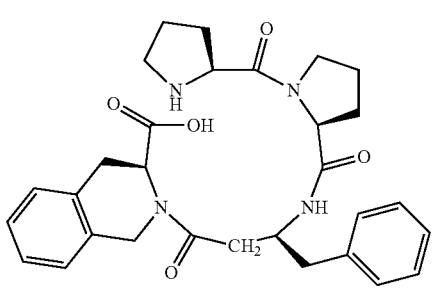
II-AA-4
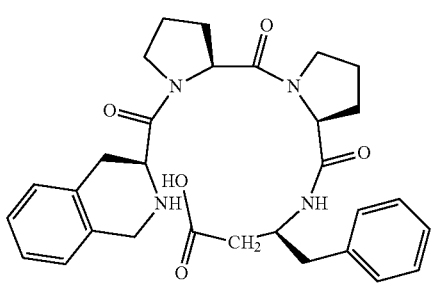
II-AB-1
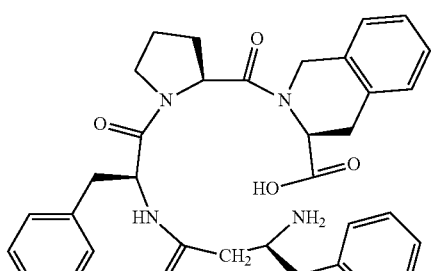
II-AB-2
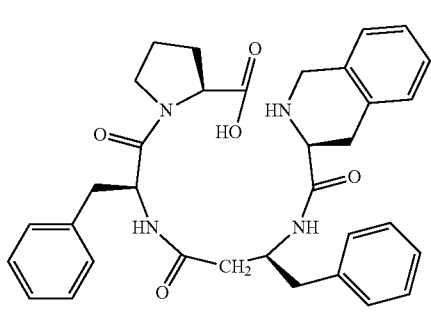

II-AB-3
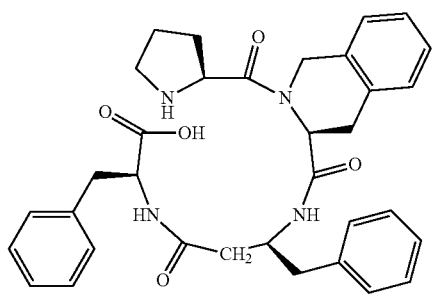
II-AB-4
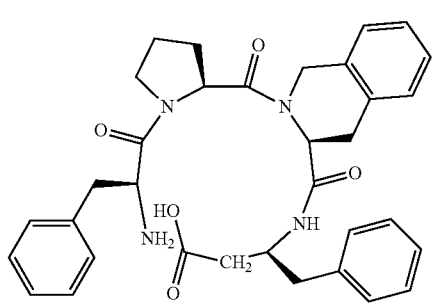
II-AC-1
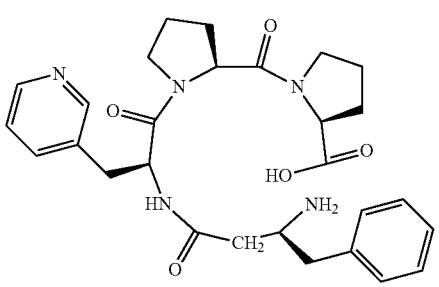
II-AC-2
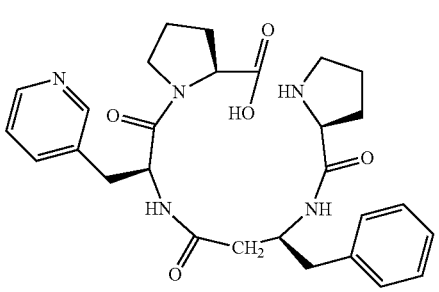
II-AC-3
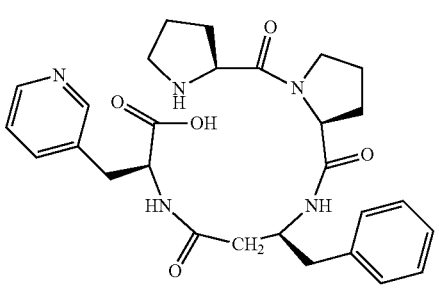
II-AC-4
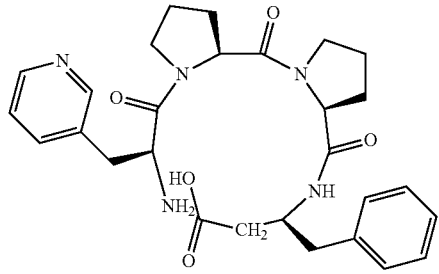
II-AD-1
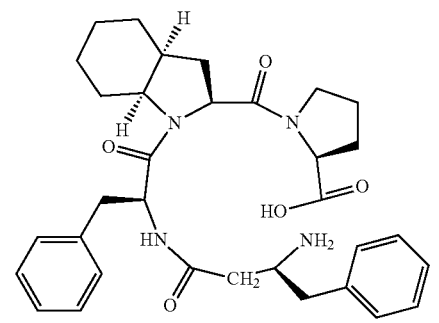
II-AD-2
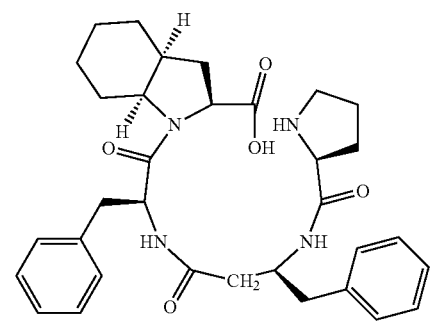
II-AD-3
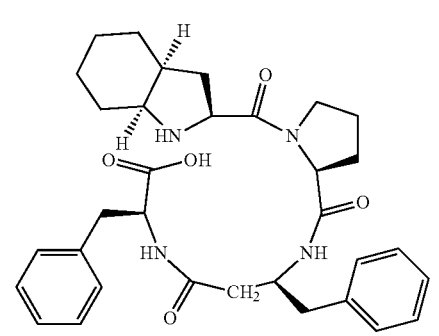
II-AD-4
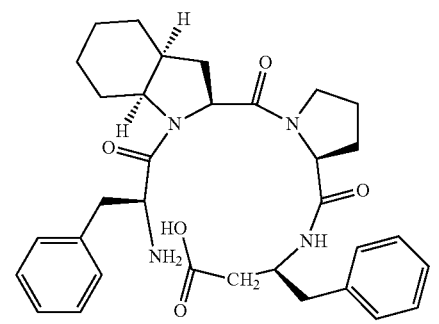

89
-continued
II-AE-1
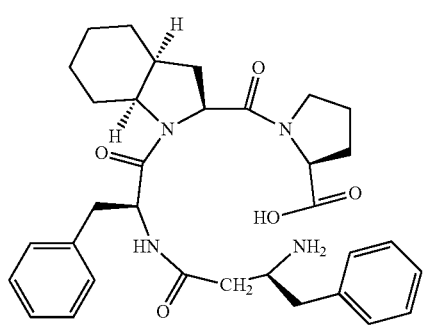
II-AE-2
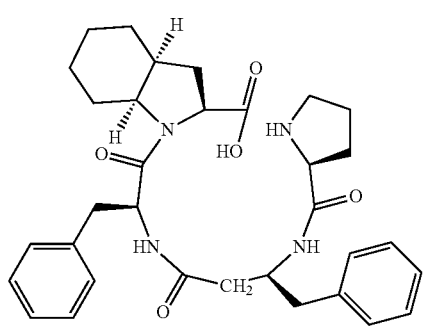
II-AE-3
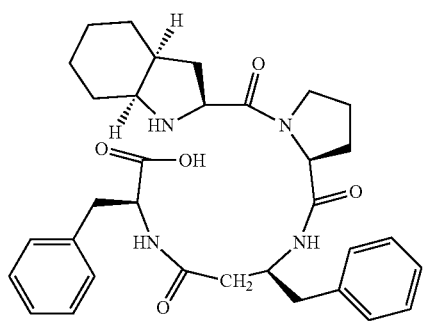
II-AE-4
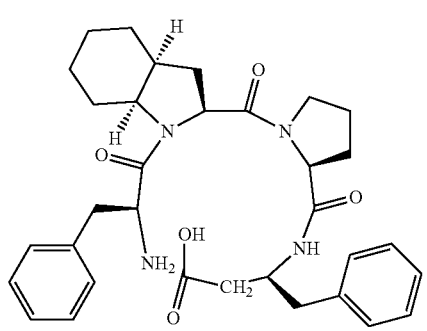
90
-continued
II-AF-1
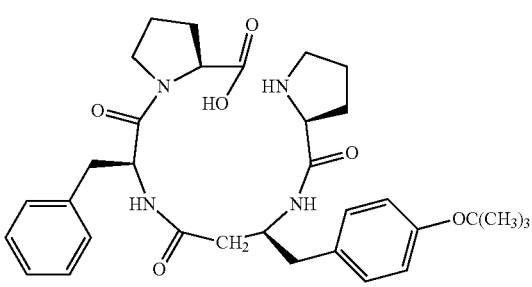
II-AF-2
II-AF-3
II-AF-4
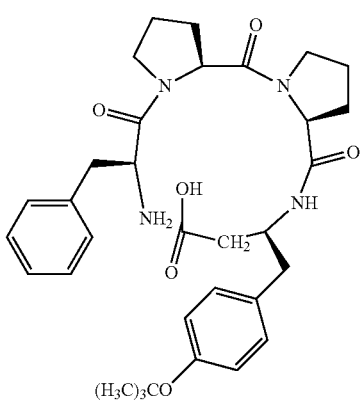

II-AG-1
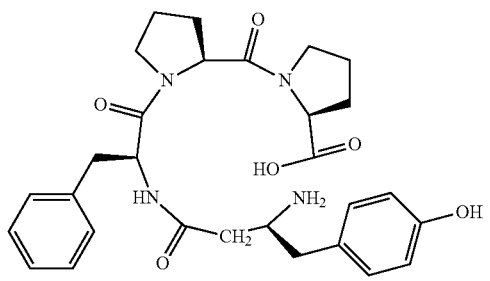
II-AG-2
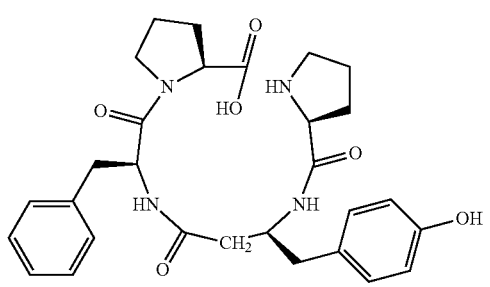
II-AG-3
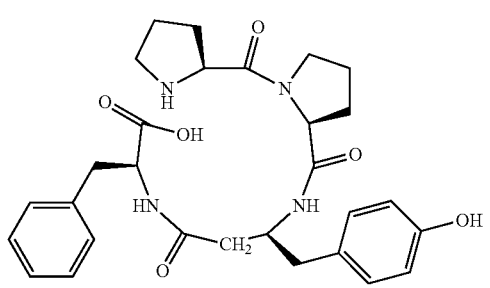
II-AG-4
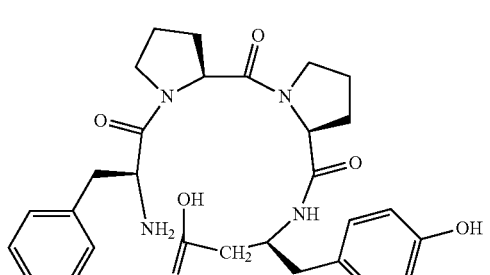
II-AH-1
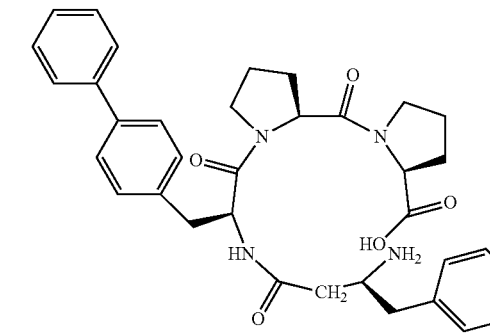
II-AH-2
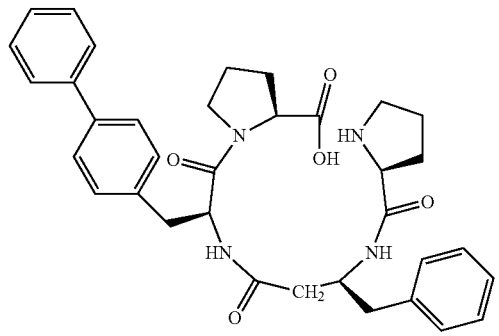
II-AH-3
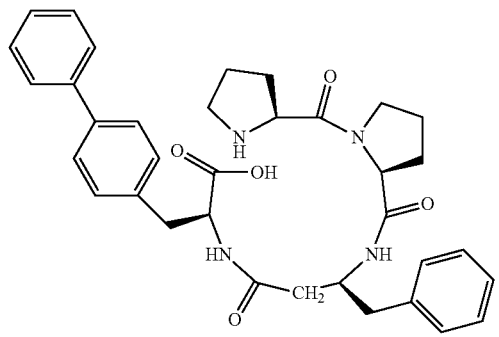
II-AH-4
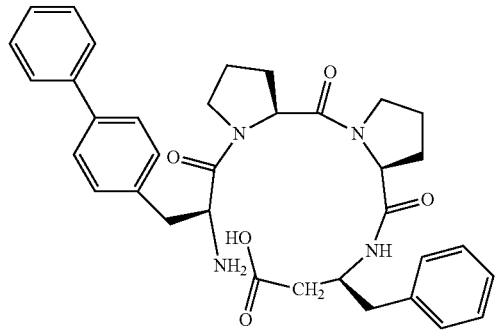
II-AI-1
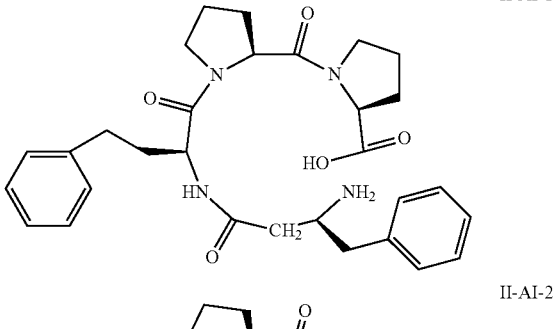
II-AI-2
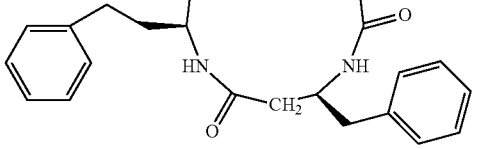

-continued
II-AJ-3
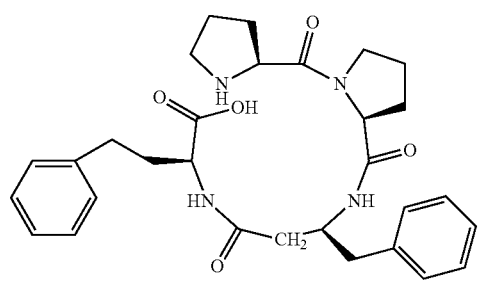
II-AI-4
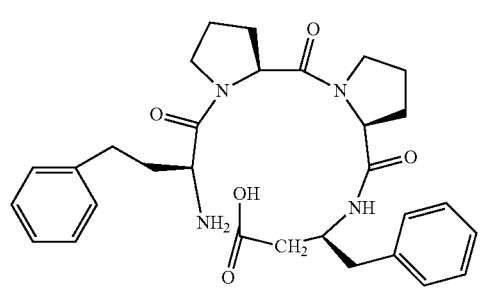
II-AJ-1
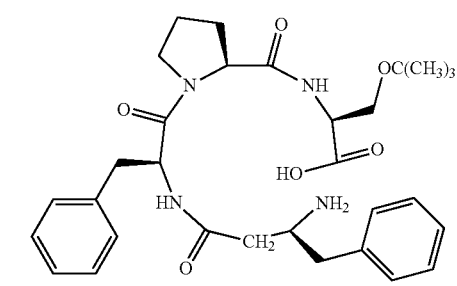
II-AJ-2
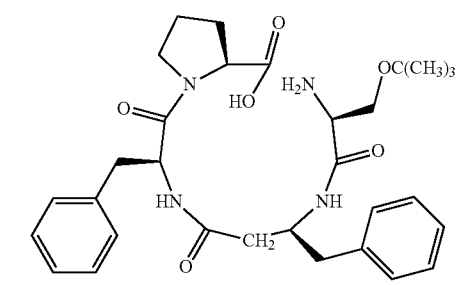
II-AJ-3
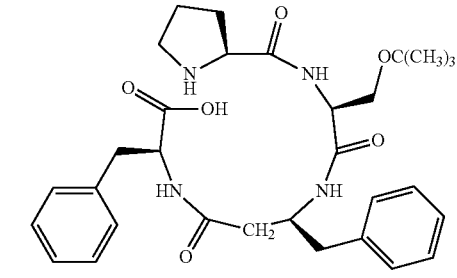
-continued
II-AJ-4
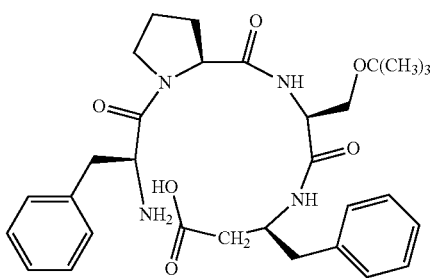
II-AK-1
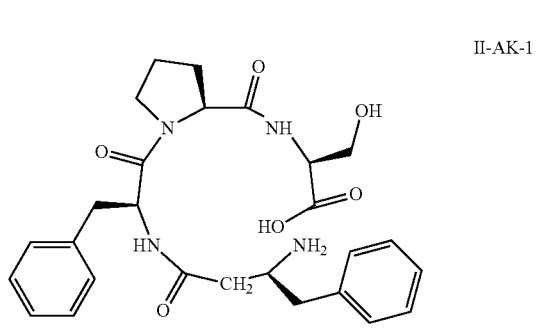
II-AK-2
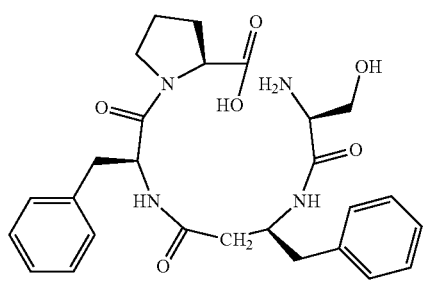
II-AK-3
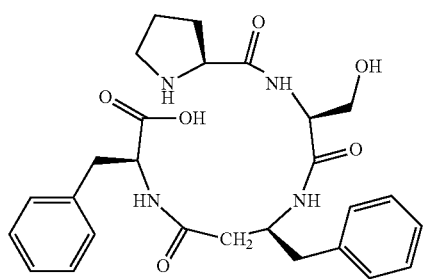
II-AK-4
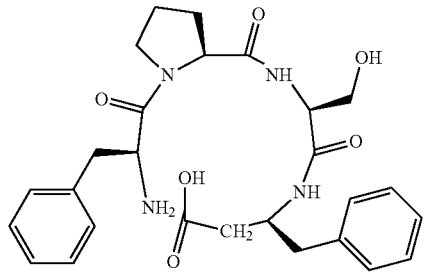

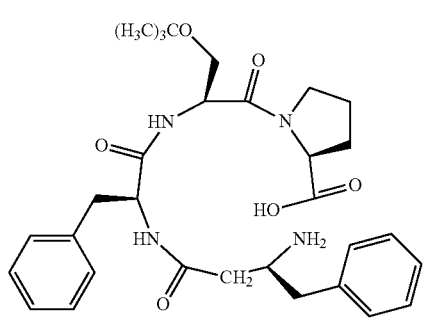

II-AL-1

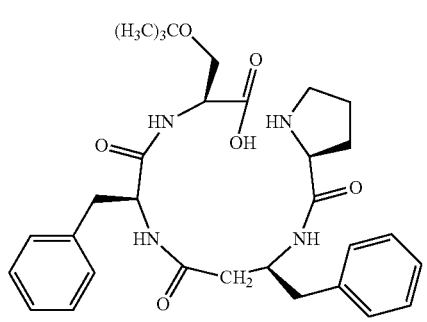

II-AL-2

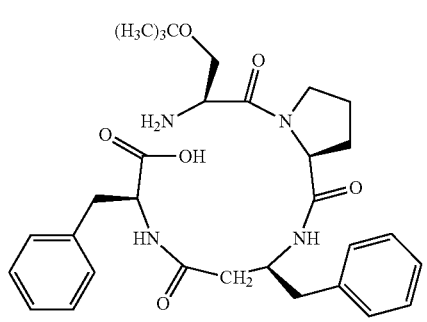

II-AL-3

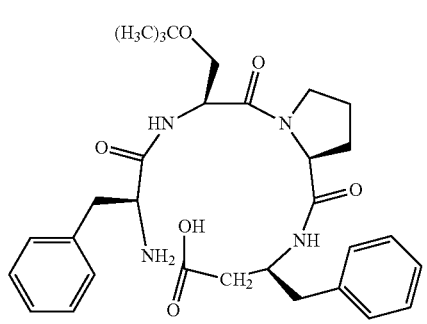

II-AL-4

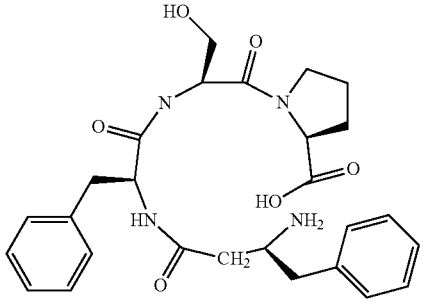

II-AM-1

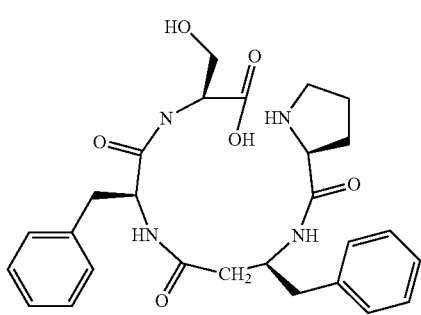

II-AM-2

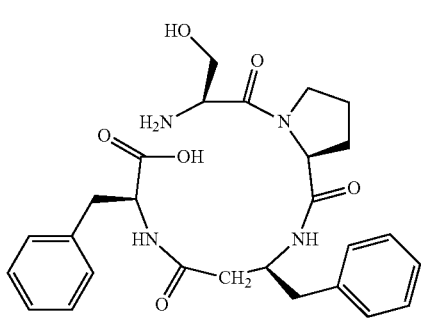

II-AM-3

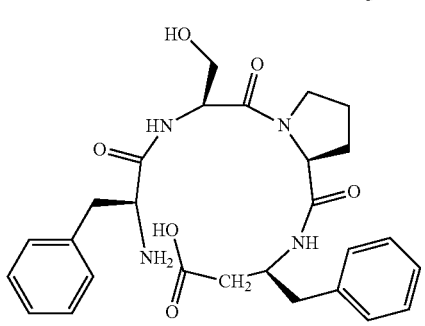

II-AM-4

In some embodiments, the compound is a compound of formula II-A-1. In some embodiments, the compound is a compound of formula II-A-2. In some embodiments, the compound is a compound of formula II-A-3. In some embodiments, the compound is a compound of formula II-A-4. In some embodiments, the compound is a compound of formula II-B-1. In some embodiments, the compound is a compound of formula II-B-2. In some embodiments, the compound is a compound of formula II-B-3. In some embodiments, the compound is a compound of formula II-B-4. In some embodiments, the compound is a compound of formula II-C-1. In some embodiments, the compound is a compound of formula II-C-2. In some embodiments, the compound is a compound of formula II-C-3. In some embodiments, the compound is a compound of formula II-C-4. In some embodiments, the compound is a compound of formula II-D-1. In some embodiments, the compound is a compound of formula II-D-2. In some embodiments, the compound is a compound of formula II-D-3. In some embodiments, the compound is a compound of formula II-D-4. In some embodiments, the compound is a compound of formula II-E-1. In some embodiments, the compound is a compound of formula II-E-2. In some embodiments, the compound is a compound of formula II-E-3. In some embodiments, the compound is a compound of formula II-E-4. In some embodiments, the compound is a compound of formula II-F-1. In some embodiments, the compound is a compound of formula II-F-2. In some embodiments, the compound is a compound of formula II-F-3. In some embodiments, the compound is a compound of formula II-F-4. In some embodiments, the compound is a compound of formula II-G-1. In some embodiments, the compound is a compound of formula II-G-2. In some embodiments, the compound is a compound of formula II-G-3. In some embodiments, the compound is a compound of formula II-G-4. In some embodiments, the compound is a compound of formula II-H-1. In some embodiments, the compound is a compound of formula II-H-2. In some embodiments, the compound is a compound of formula II-H-3. In some embodiments, the compound is a compound of formula II-H-4. In some embodiments, the compound is a compound of formula II-J-1. In some embodiments, the compound is a compound of formula II-J-2. In some embodiments, the compound is a compound of formula II-J-3. In some embodiments, the compound is a compound of formula II-J-4. In some embodiments, the compound is a compound of formula II-K-1. In some embodiments, the compound is a compound of formula II-K-2. In some embodiments, the compound is a compound of formula II-K-3. In some embodiments, the compound is a compound of formula II-K-4. In some embodiments, the compound is a compound of formula II-L-1. In some embodiments, the compound is a compound of formula II-L-2. In some embodiments, the compound is a compound of formula II-L-3. In some embodiments, the compound is a compound of formula II-L-4. In some embodiments, the compound is a compound of formula II-M-1. In some embodiments, the compound is a compound of formula II-M-2. In some embodiments, the compound is a compound of formula II-M-3. In some embodiments, the compound is a compound of formula II-M-4. In some embodiments, the compound is a compound of formula II-N-1. In some embodiments, the compound is a compound of formula II-N-2. In some embodiments, the compound is a compound of formula II-N-3. In some embodiments, the compound is a compound of formula II-N-4. In some embodiments, the compound is a compound of formula II-O-1. In some embodiments, the compound is a compound of formula II-O-2. In some embodiments, the compound is a compound of formula II-O-3. In some embodiments, the compound is a compound of formula II-O-4. In some embodiments, the compound is a compound of formula II-P-1. In some embodiments, the compound is a compound of formula II-P-2. In some embodiments, the compound is a compound of formula II-P-3. In some embodiments, the compound is a compound of formula II-P-4. In some embodiments the compound is a compound of formula II-Q-1. In some embodiments the compound is a compound of formula II-Q-2. In some embodiments the compound is a compound of formula II-Q-3. In some embodiments the compound is a compound of formula II-Q-4. In some embodiments the compound is a compound of formula II-R-1. In some embodiments the compound is a compound of formula II-R-2. In some embodiments the compound is a compound of formula II-R-3. In some embodiments the compound is a compound of formula II-R-4. In some embodiments the compound is a compound of formula II-S-1. In some embodiments the compound is a compound of formula II-T-2. In some embodiments the compound is a compound of formula II-S-3. In some embodiments the compound is a compound of formula II-S-4. In some embodiments the compound is a compound of formula II-T-1. In some embodiments the compound is a compound of formula II-T-2. In some embodiments the compound is a compound of formula II-T-3. In some embodiments the compound is a compound of formula II-T-4. In some embodiments the compound is a compound of formula II-U-1. In some embodiments the compound is a compound of formula II-U-2. In some embodiments the compound is a compound of formula II-U-3. In some embodiments the compound is a compound of formula II-U-4. In some embodiments the compound is a compound of formula II-V-1. In some embodiments the compound is a compound of formula II-V-2. In some embodiments the compound is a compound of formula II-V-3. In some embodiments the compound is a compound of formula II-V-4. In some embodiments the compound is a compound of formula II-W-1. In some embodiments the compound is a compound of formula II-W-2. In some embodiments the compound is a compound of formula II-W-3. In some embodiments the compound is a compound of formula II-W-4. In some embodiments the compound is a compound of formula II-X-1. In some embodiments the compound is a compound of formula II-X-2. In some embodiments the compound is a compound of formula II-X-3. In some embodiments the compound is a compound of formula II-X-4. In some embodiments the compound is a compound of formula II-Y-1. In some embodiments the compound is a compound of formula II-Y-2. In some embodiments the compound is a compound of formula II-Y-3. In some embodiments the compound is a compound of formula II-Y-4. In some embodiments the compound is a compound of formula II-Z-1. In some embodiments the compound is a compound of formula II-Z-2. In some embodiments the compound is a compound of formula II-Z-3. In some embodiments the compound is a compound of formula II-Z-4. In some embodiments the compound is a compound of formula II-AA-1. In some embodiments the compound is a compound of formula II-AA-2. In some embodiments the compound is a compound of formula II-AA-3. In some embodiments the compound is a compound of formula II-AA-4. In some embodiments the compound is a compound of formula II-AB-1. In some embodiments the compound is a compound of formula II-AB-2. In some embodiments the compound is a compound of formula II-AB-3. In some embodiments the compound is a compound of formula II-AB-4. In some embodiments the compound is a compound of formula II-AC-1. In some embodiments the compound is a compound of formula II-AC-2. In some embodiments the compound is a compound of formula II-AC-3. In some embodiments the compound is a compound of formula II-AC-4. In some embodiments the compound is a compound of formula II-AD-1. In some embodiments the compound is a compound of formula II-AD-2. In some embodiments the compound is a compound of formula II-AD-3. In some embodiments the compound is a compound of formula II-AD-4. In some embodiments the compound is a compound of formula II-AE-1. In some embodiments the compound is a compound of formula II-AE-2. In some embodiments the compound is a compound of formula II-AE-3. In some embodiments the compound is a compound of formula II-AE-4. In some embodiments the compound is a compound of formula II-AF-1. In some embodiments the compound is a compound of formula II-AF-2. In some embodiments the compound is a compound of formula II-AF-3. In some embodiments the compound is a compound of formula II-AF-4. In some embodiments the compound is a compound of formula II-AG-1. In some embodiments the compound is a compound of formula II-AG-2. In some embodiments the compound is a compound of formula II-AG-3. In some embodiments the compound is a compound of formula II-AG-4. In some embodiments the compound is a compound of formula II-AH-1. In some embodiments the compound is a compound of formula II-AH-2. In some embodiments the compound is a compound of formula II-AH-3. In some embodiments the compound is a compound of formula II-AH-4. In some embodiments the compound is a compound of formula II-AI-1. In some embodiments the compound is a compound of formula II-AI-2. In some embodiments the compound is a compound of formula II-AI-3. In some embodiments the compound is a compound of formula II-AI-4. In some embodiments the compound is a compound of formula II-AJ-1. In some embodiments the compound is a compound of formula II-AJ-2. In some embodiments the compound is a compound of formula II-AJ-3. In some embodiments the compound is a compound of formula II-AJ-4. In some embodiments the compound is a compound of formula II-AK-1. In some embodiments the compound is a compound of formula II-AK-2. In some embodiments the compound is a compound of formula II-AK-3. In some embodiments the compound is a compound of formula II-AK-4. In some embodiments the compound is a compound of formula II-AL-1. In some embodiments the compound is a compound of formula II-AL-2. In some embodiments the compound is a compound of formula II-AL-3. In some embodiments the compound is a compound of formula II-AL-4. In some embodiments the compound is a compound of formula II-AM-1. In some embodiments the compound is a compound of formula II-AM-2. In some embodiments the compound is a compound of formula II-AM-3. In some embodiments the compound is a compound of formula II-AM-4.

DETAILED DESCRIPTION

It has been found that compounds of formula I exhibit immunosuppressive and/or antiinflammatory activity, while at the same time exhibiting less toxicity, than some known compounds. Thus compounds of formula I may be useful as immunosuppressive and/or antiinflammatory agents. As used herein, the term "immune-mediated" refers to a disease or condition in which the body's immune system overreacts and/or attacks the body.

Throughout this specification the terms and substituents retain their definitions.

"Alkyl" is intended to include linear, branched, or cyclic saturated hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. The term "carbocycle" is intended to include ring systems consisting entirely of carbon but of any oxidation state. Thus ($C_3$-$C_{10}$) carbocycle refers to such systems as cyclopropane, benzene and cyclohexene; ($C_8$-$C_{12}$) carbopolycycle refers to such systems as norbornane, decalin, indane and naphthalene.

Alkoxy or alkoxyl refers to groups of from 1 to 8 carbon atoms of a straight, branched, cyclic configuration and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl means 6-membered aromatic ring; a bicyclic 9- or 10-membered aromatic ring system; or a tricyclic 13- or 14-membered aromatic ring system. The aromatic 6- to 14-membered carbocyclic rings include, e.g., benzene, naphthalene, indane, tetralin, and fluorene.

Heteroaryl mean a 5- or 6-membered heteroaromatic ring containing 1-3 heteroatoms selected from O, N, or S; a bicyclic 9- or 10-membered heteroaromatic ring system containing 1-3 heteroatoms selected from O, N, or S; or a tricyclic 13- or 14-membered heteroaromatic ring system containing 1-3 heteroatoms selected from O, N, or S. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Substituted alkyl, aryl, cycloalkyl, heterocyclyl etc. refer to alkyl, aryl, cycloalkyl, or heterocyclyl wherein up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The following abbreviations and terms have the indicated meanings throughout:
Bip=3-(4-biphenylyl)alanine
Boc=t-butyloxy carbonyl
c-=cyclo
DCM=dichloromethane=methylene chloride=$CH_2Cl_2$
DEX=dexamethasone
DIEA=N,N-diisopropylethyl amine
DIPEA=N,N-diisopropylethyl amine
DMF=N,N-dimethylformamide
Δpro=3,4-dehydroproline
Fmoc=9-fluorenylmethoxycarbonyl
HATU=O-(7-Azabenzotriazol-1-yl)-1,1,3,3-tetramethyluronium hexafluorophosphate
HBTU=O-(benzotriazol-1-yl)-1,1,3,3-tetramethyluronium hexafluorophosphate
HOAc=acetic acid
HOAt=1-hydroxy-7-azabenzotriazole
HOBt=1-hydroxybenzotriazole
hoPhe=2-amino-4-phenylbutanoic acid
Hyp=4-hydroxyproline
Hyp(tBu)=4-t-butoxyproline
Me=methyl
1Nal=3-(1-naphthyl)alanine
2Nal=3-(2-naphthyl)alanine
Oic=Octahydro-1H-indole-2-carboxylic acid
3Pal=(3-pyridyl)alanine
Pip=Pipecolic acid
Phe=phenylalanine
Phe(4Cl)=3-(4-chlorophenyl)alanine
Phe(4F)=3-(4-fluorophenyl)alanine
Phe(4I)=3-(4-iodophenyl)alanine
Phe(4Me)=3-(4-methylphenyl)alanine
Pro=proline
PyBOP=O-(benzotriazol-1-yl)-trispyrrolidinephosphonium hexafluorophosphate
rt=room temperature
Ser(tBu)=O-t-Butyl Serine
TBTU=O-(benzotriazol-1-yl)-1,1,3,3-tetramethyluronium tetrafluoroborate
TFA=trifluoroacetic acid
Tic=1,2,3,4-tetrahydroisoquinoline-3-carboxylic acid
t-Hyp=trans-4-hydroxyproline
Trp=tryptophan
Tyr=tyrosine
Tyr(tBu)=(O-tert-butyl) tyrosine Furthermore, a comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In addition, with respect to non-naturally occurring amino acids in which an additional methylene group is present in the backbone, the notation "$\beta^3$-Ho-" (or "beta 3-homo-") is used herein to refer to an amino acid having an extra methylene (—$CH_2$—) in the backbone between the side-chain bearing carbon atom and the terminal carbon atom; the notation "$\beta^2$-Ho-" (or "beta 2-homo-") is used herein to refer to an amino acid having an extra methylene in the backbone between the side-chain bearing carbon atom and the terminal nitrogen atom.

Embodiments of the present invention include compounds of formula I in the form of salts, in particular acid addition salts. Suitable salts include those formed with both organic and inorganic acids. Such acid addition salts will normally be pharmaceutically acceptable, although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of formula I can be made by reacting the appropriate compound in the form of the free base with the appropriate acid.

The compounds of formula I in accordance with the embodiments of the invention are cyclic tetrapeptides. The synthesis of these peptides may be accomplished by cyclizing corresponding linear peptides that are themselves synthesized using methodologies known in the art; see, for example, Merrifield, J. Am. Chem. Soc., 85:2149 (1964); Houghten, Proc. Natl. Acad. Sci. USA, 82:5132 (1985); Kelley & Winkler in *Genetic Engineering Principles and Methods*, Setlow, J. K, ed., Plenum Press, N.Y., vol. 12, pp 1-19 (1990); Stewart & Young, *Solid Phase Peptide Synthesis*, Pierce Chemical Co., Rockford, Ill. (1984); Mergler et al. (1988) Tetrahedron Letters 29:4005-4008; Mergler et al. (1988) Tetrahedron Letters 29:4009-4012; Kamber et al. (eds), *Peptides, Chemistry and Biology*, ESCOM, Leiden (1992) pp. 525-526; Riniker et al. (1993) Tetrahedron Letters 49:9307-9320; Lloyd-Williams et al. (1993) Tetrahedron Letters 49:11065-11133; Andersson et al. (2000) Biopolymers 55:227-250; Bray, Nature Reviews 2:587-593 (2003), U.S. Pat. Nos. 4,105,603, 3,972,859, 3,842,067, 3,862,925, 6,015,881, 6,197,927, and 7,439,222. Such synthesis may be accomplished via liquid-phase or solid-phase synthesis, or by a combination of both, as is known in the art.

Liquid phase methods (often referred to as solution phase methods) of synthesis carry out all reactions in a homogeneous phase. Successive amino acids are coupled in solution until the desired peptide material is formed. During synthesis, successive intermediate peptides are purified by precipitation and/or washes.

In solid phase peptide synthesis (SPPS), a first amino acid or peptide group is bound to an insoluble support, such as a resin. Successive amino acids or peptide groups are added to the first amino acid or peptide group until the peptide material of interest is formed. The product of solid phase synthesis is thus a peptide bound to an insoluble support. Peptides synthesized via SPPS techniques are then cleaved from the resin, and the cleaved peptide is isolated.

More specifically, solid phase synthesis begins at the carboxy terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g. a polyamide or polystyrene resin) as shown in FIGS. 1-1 and 1-2, on pages 2 and 4 of Stewart & Young, supra. In some cases, the C-terminal amino acid is coupled to a polystyrene resin to form a benzyl ester. A macromolecular support is selected such that the peptide anchor link is stable under the conditions used to deprotect the a-amino group of the blocked amino acids in peptide synthesis. If a base-labile a-protecting group is used, then it is desirable to use an acid-labile link between the peptide and the solid support. For example, an acid-labile ether resin is effective for base-labile Fmoc-amino acid peptide synthesis as described on page 16 of Stewart & Young, supra. Alternatively, a peptide anchor link and a-protecting group that are differentially labile to acidolysis can be used. For example, an aminomethyl resin such as the phenylacetamidomethyl (Pam) resin works well in conjunction with Boc-amino acid peptide synthesis as described on pages 11-12 of Stewart & Young, supra. Guiller et al., Chem Rev. 2000, 100, 2091-2157, reviewed linkers and cleavage strategies in solid-phase organic synthesis and combinatorial chemistry, including peptide synthesis.

After the initial amino acid is coupled to an inert solid support, the a-amino protecting group of the initial amino acid is removed with, for example, trifluoroacetic acid (TFA) in methylene chloride and neutralizing in, for example, triethylamine (TEA). Following deprotection of the initial amino acid's a-amino group, the next a-amino and sidechain protected amino acid in the synthesis is added. The remaining a-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino] phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the a-amino group on an amino acid or peptide fragment while the C-terminal carboxy group of the amino acid or peptide fragment reacts with the free N-terminal amino group of the growing solid phase polypeptide chain, followed by the selective removal of the a-amino protecting group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

a- and w-amino side chains can be protected, for example, with benzyloxycarbonyl (abbreviated Z), isonicotinyloxycarbonyl (iNoc), o-chlorobenzyloxycarbonyl [Z(2Cl) or 2-Cl—Z], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxy-carbonyl (Adoc), 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl (Pht), formyl (For), 2-nitrophenylsulphenyl (Nps), diphenylphosphinothioyl (Ppt), and dimethylphosphinothioyl (Mpt) groups, and the like. Additional examples of side chain protecting groups include acetyl (Ac), benzoyl (Bz), tert butyl (t-Bu), triphenylmethyl (trityl, Trt), tetrahydropyranyl, benzyl (Bzl), 2,6-dichlorobenzyl, nitro, p-toluenesulfonyl (Tos), xanthyl (Xan), benzyl, methyl, ethyl, and t-butyl ester, and aromatic or aliphatic urethan-type protecting groups, photolabile groups such as nitro veratryl oxycarbonyl (Nvoc), and fluoride labile groups such as trimethylsilylethyloxycarbonyl (TEOC).

Examples of amino terminal protecting groups (also referred to herein as N-terminal protecting groups) include: (1) acyl-type protecting groups, such as formyl, acrylyl (Acr), benzoyl (Bz) and acetyl (Ac); (2) aromatic urethan-type protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenylmethyloxycarbonyl (Fmoc), 2-(4-biphenylyl)-propyl(2)oxycarbonyl (Bpoc), 2-phyenlpropyl (2)-oxycarbonyl (Poc), and t-butyloxycarbonyl (Boc).

Protective groups for the carboxy functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

While it may be possible for the compounds of formula I to be administered as the raw chemical, it is preferable to present them as a pharmaceutical composition. According to a further aspect, there are provided in accordance with embodiments of the present invention a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Methods for making such formulations include the step of bringing into association a compound of formula I or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations in accordance with embodiments of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations in accordance with embodiments of this invention may include other agents conventional in the art having regard to the type of formulation in question, for example those suitable for oral administration may include flavoring agents.

As stated, in accordance with embodiments of the invention, compounds in accordance with embodiments of the invention may be used for the treatment or prevention of certain diseases or conditions. The term "preventing" as used herein refers to administering a medicament beforehand to forestall or obtund an attack. The person of ordinary skill in the medical art (to which the present method of use claims are directed) recognizes that the term "prevent" is not an absolute term. In the medical art it is understood to refer to the prophylactic administration of a drug to substantially diminish the likelihood or seriousness of a condition, and this is the sense intended in applicants' claims. The reader's attention is directed to the Physician's Desk Reference, a standard text in the field, in which the term "prevent" occurs hundreds of times. No person of skill in the medical art construes the term in an absolute sense. Similarly, where it is stated that compounds in accordance with embodiments of the invention may be used to suppress an immune response, "suppress" will be understood to include reducing the degree of the response, and not necessarily absolutely preventing the response.

It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a composition aspect, is all compounds of formulae I and II, except those that are in the public's possession.

Embodiments of the invention will be better understood with reference to the figures, in which.

Figure 4:
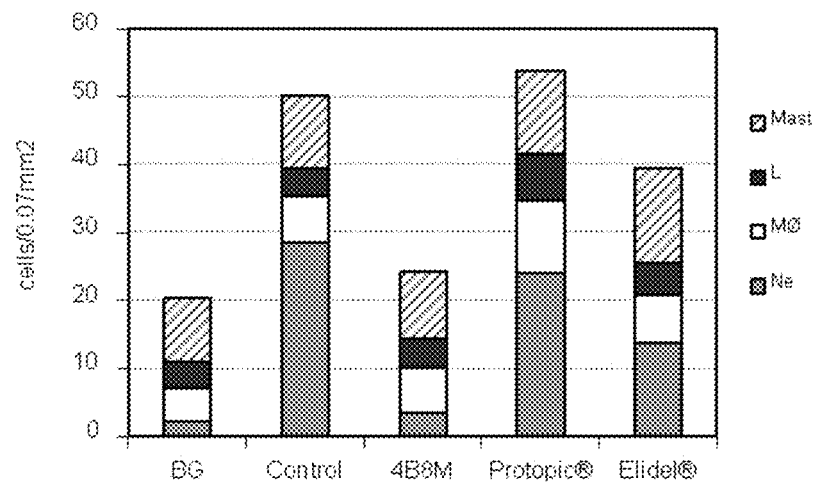
Figure 5:
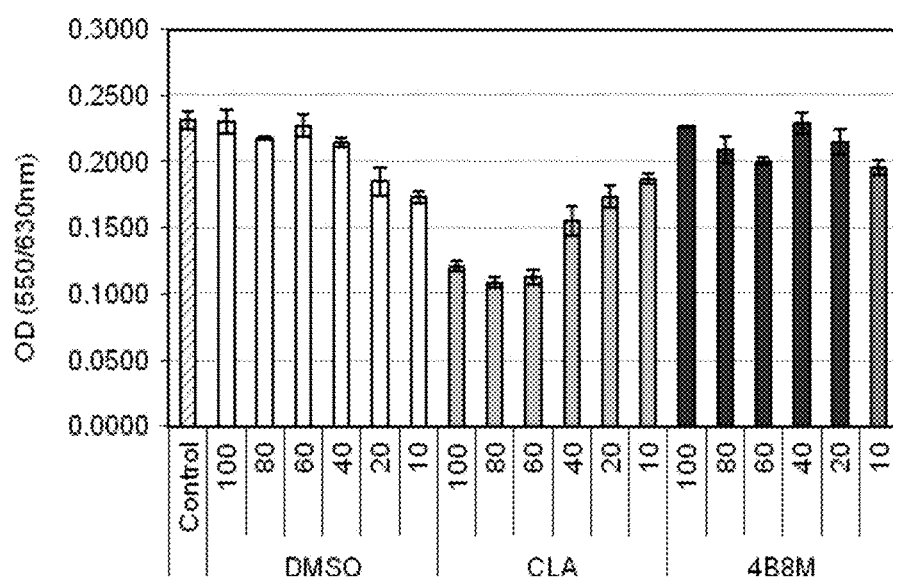
Figure 6:
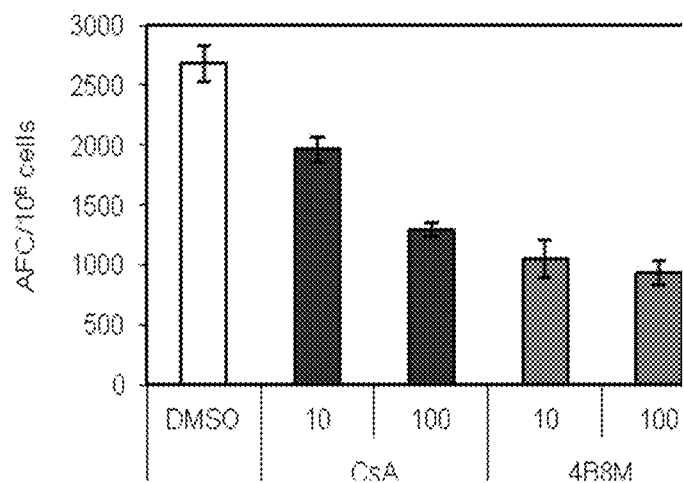
Figure 7:
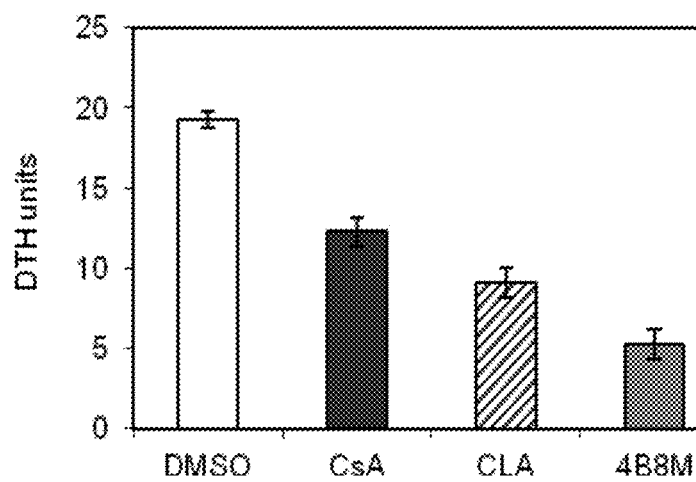
Figure 10A:
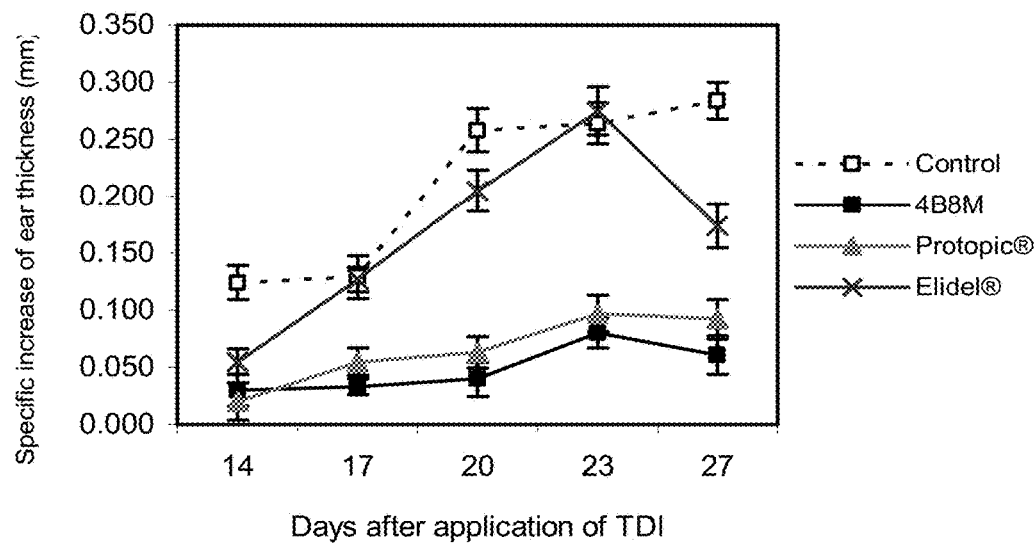
Figure 10B:
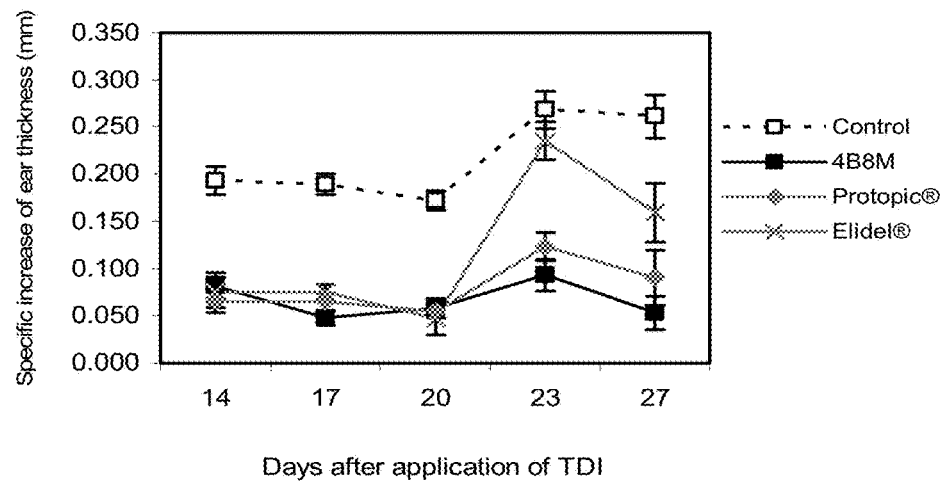
Figure 11:
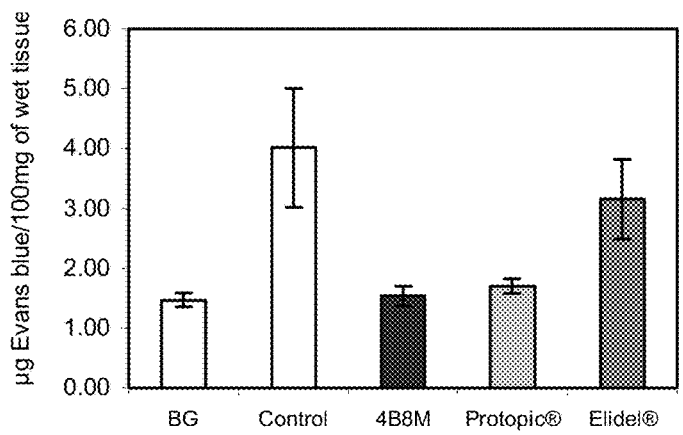
Figure 12:
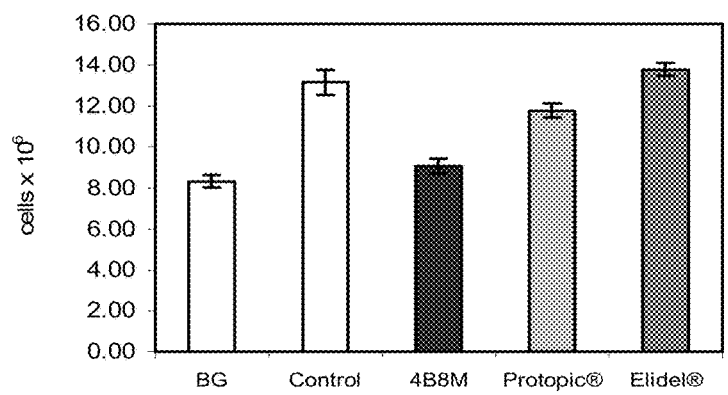
Figure 13:
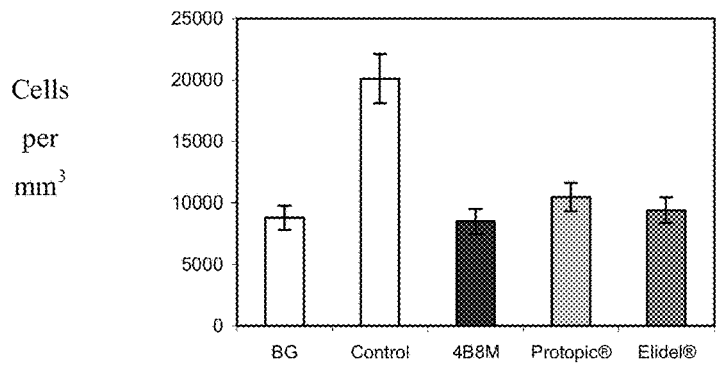
Figure 14:
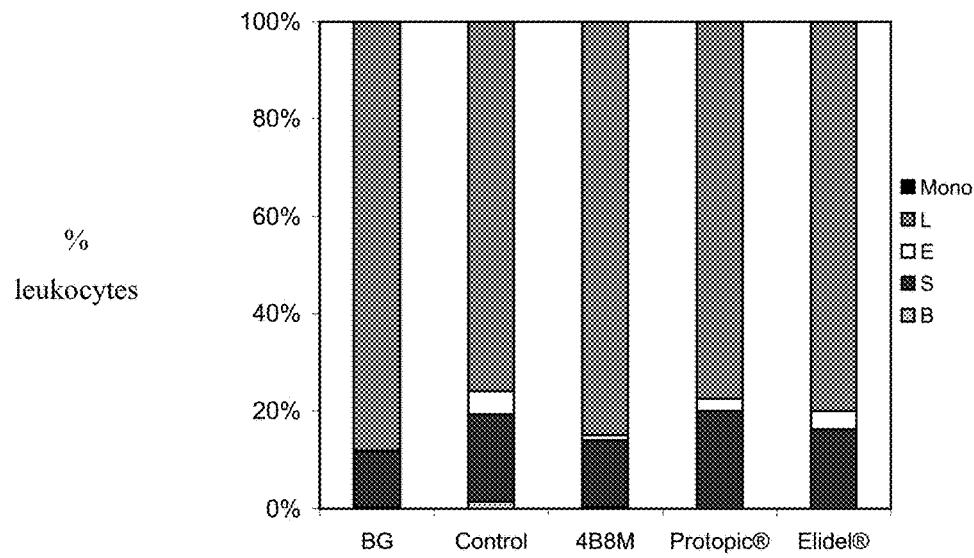
Figure 15:
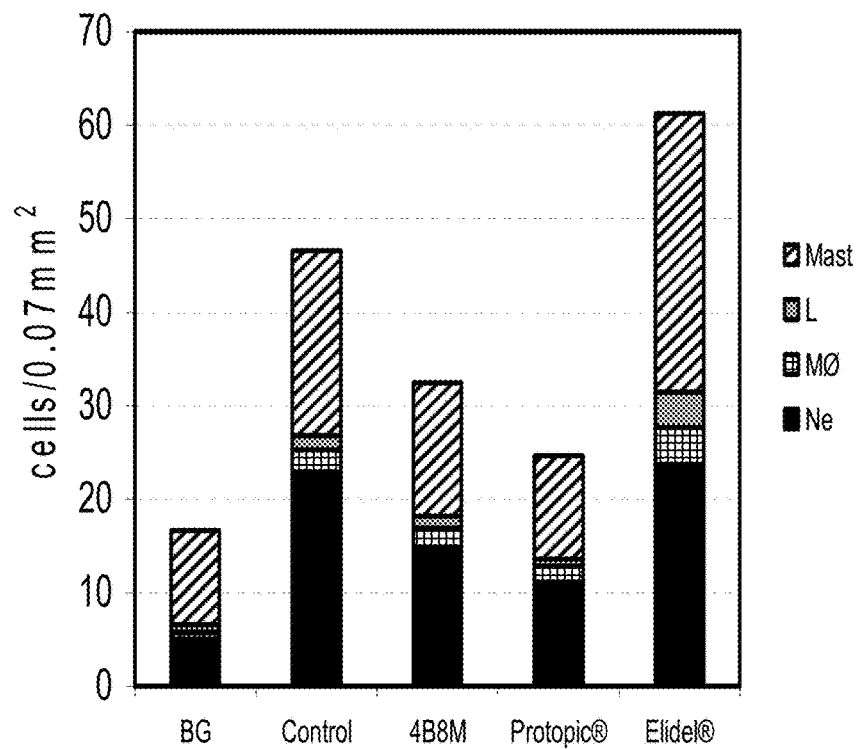
Figure 16A:
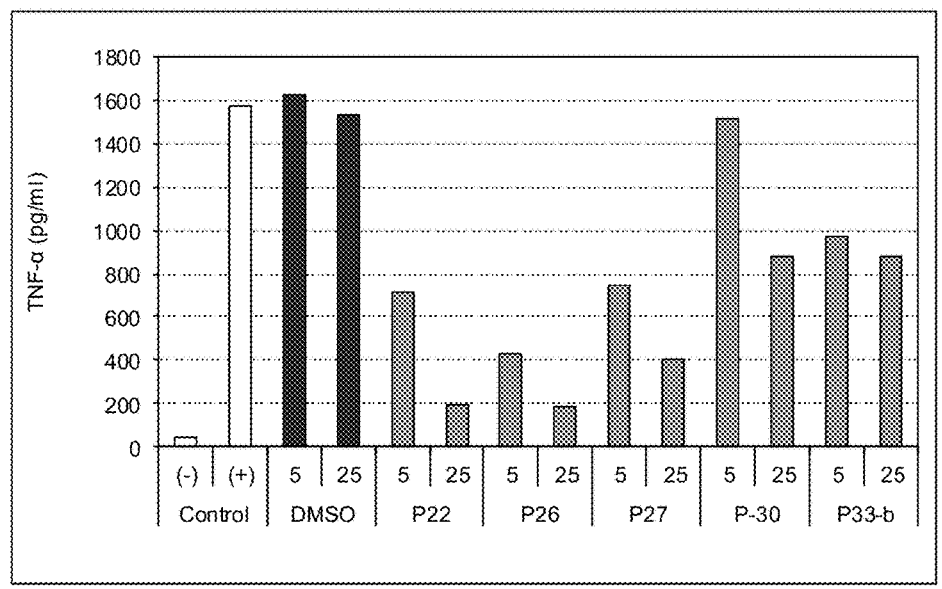
Figure 16B:
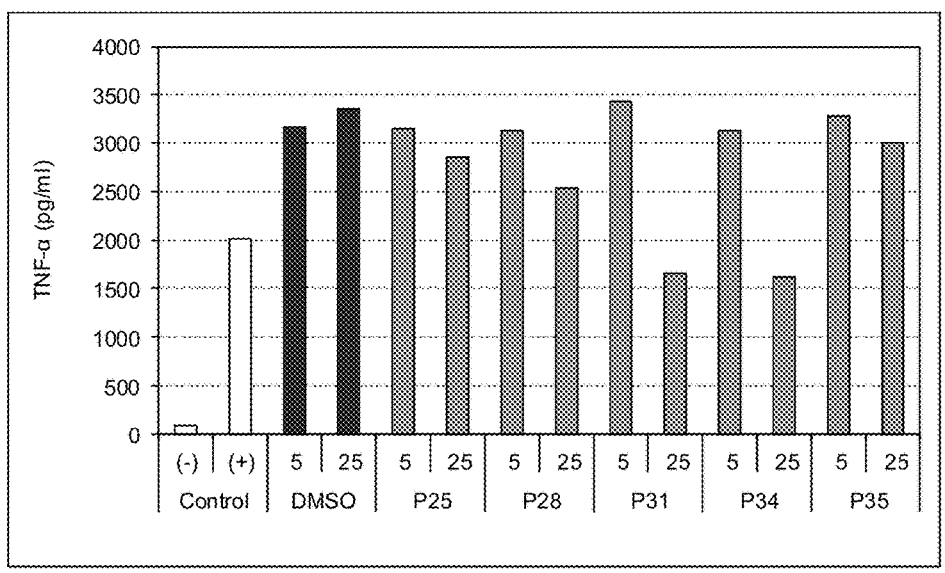
Figure 16C:
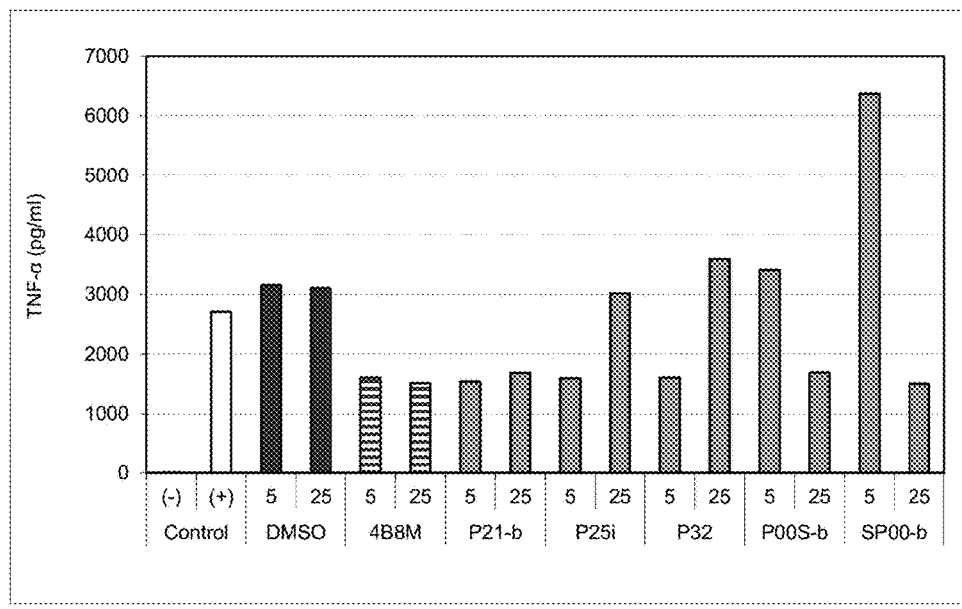
Figure 16D:
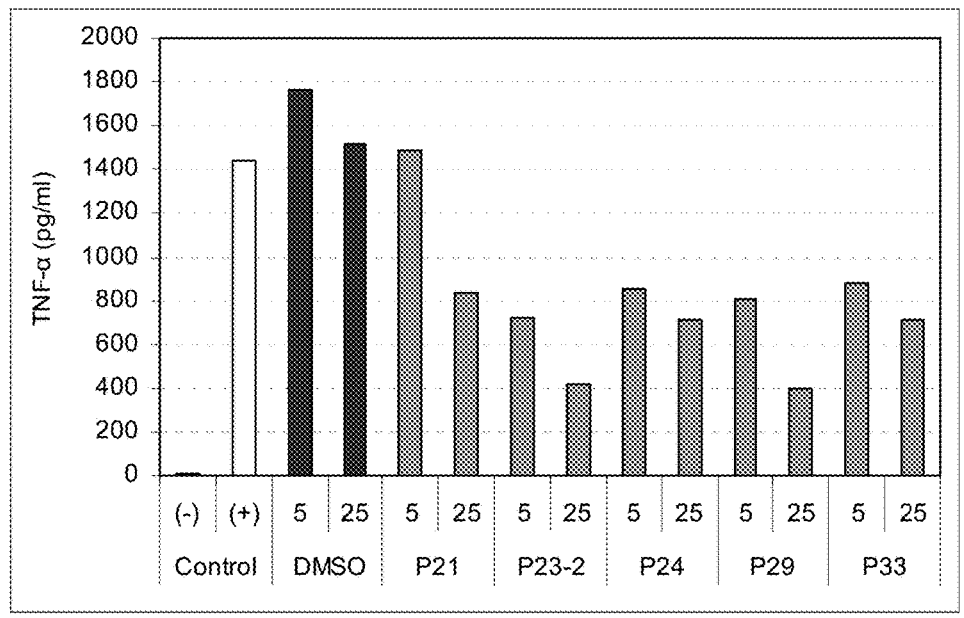

FIG. 4 presents number and participation of cell types in the draining lymph nodes registered in the experiment described in Example 2;

FIG. 5 presents toxicity of the compound of formula I-A against mononuclear cells from human blood in as described in Example 3;

FIG. 6 presents effects of the intraperitoneal administration of the compound of formula I-A on the humoral immune response of mice to sheep erythrocytes as described in Example 4;

FIG. 7 shows effects of the intraperitoneal administration of the compound of formula I-A on the cellular immune response to ovalbumin as described in Example 5;

FIGS. 8A, 8B, 8C, 8D, 8E and 8F show the effects of peptides in accordance with embodiments of the invention on PMBC survival in vitro;

FIGS. 9A, 9B, 9C, 9D, 9E and 9F show the effects of peptides in accordance with embodiments of the invention on PHA-induced PBMC proliferation in vitro;

FIGS. 10A and 10B show the effects of several compounds on changes in ear thickness in response to antigenic challenge, as described in Example 7;

FIG. 11 shows the permeability of capillary blood vessels in the Evans blue test, as described in Example 7;

FIG. 12 shows the total number of cells in the draining lymph nodes, as described in Example 7;

FIG. 13 shows the effects of the compounds on the numbers of circulating leukocytes, as described in Example 7;

FIG. 14 which shows the types of leukocytes present in different cases, as described in Example 7;

FIG. 15 provides morphometric data on the number and composition of cells in mouse auricles, as described in Example 7;

FIGS. 16A-16D graph the effects of some of the peptides on LPS-induced TNF-α production in whole blood cell cultures;

FIGS. 17 A-C graph antigen-specific increase of the foot pad thickness; and

Figure 18A:
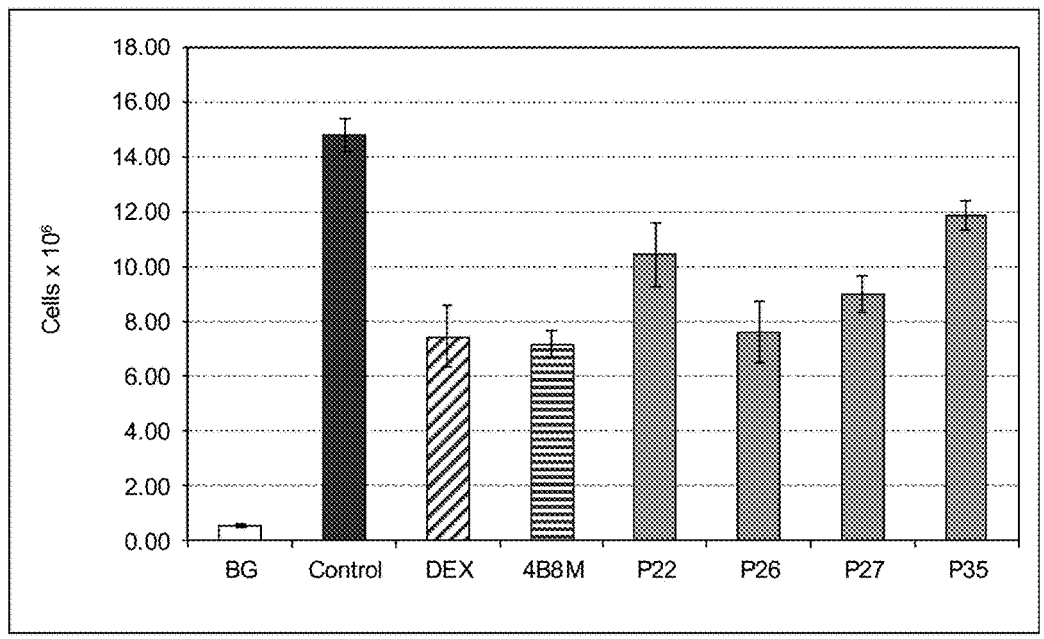
Figure 18B:
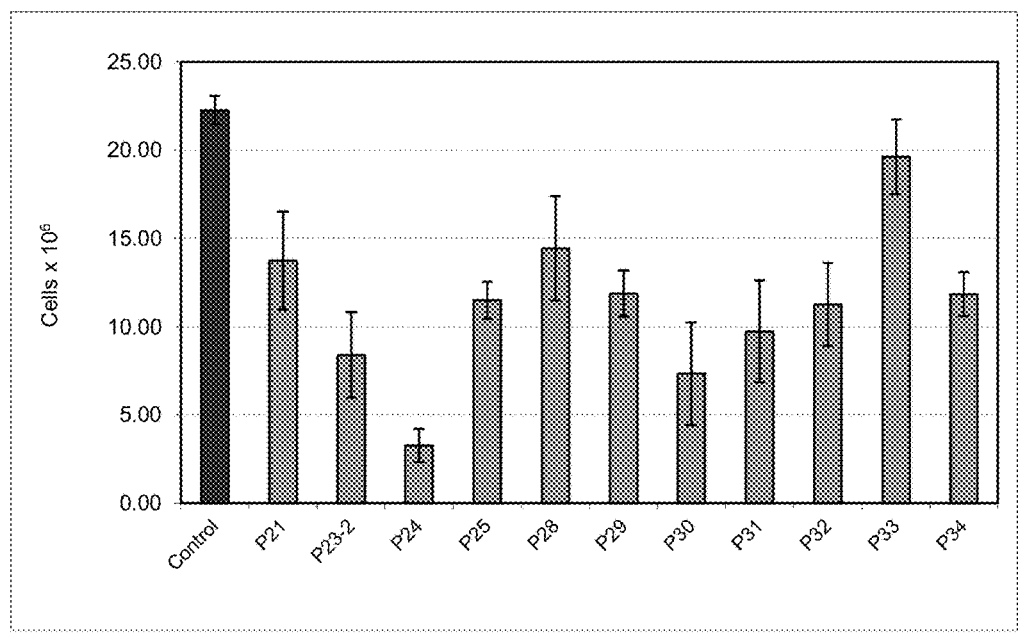

FIGS. 18A-B graph results of the carrageenan air-pouch test on some peptides.

EXAMPLE 1. SYNTHESIS OF CYCLIC TETRAPEPTIDES

Cyclic tetrapeptides according to embodiments of the invention can be synthesized by the use of known peptide synthesis methods, such as solution-phase or solid-phase methods. In general the synthesis involves two consecutive steps: (1) synthesis of a linear tetrapeptide and (2) cyclization to yield the cyclic tetrapeptide. The linear tetrapeptide may be prepared in protected form and then deprotected prior to cyclization.

To illustrate, the synthesis of linear tetrapeptides on a solid support (Fmoc-L-phenylalanine attached to a Wang-type resin, or either L-beta-3-homophenylalanine or L-proline attached to a 2-chloro trityl resin) was conducted according to the following protocol:
1. The resin was swelled in dimethylformamide (DMF) (0.25 mmol, 10 ml/g resin) for 15 min.
2. The Fmoc group was removed with a 20% solution of piperidine in DMF (2×20 min).
3. The resin was washed with DMF (3×2 min)
4. The resin was washed with methanol (MeOH) (3×2 min)
5. The resin was washed with dichloromethane (DCM) (3×2 min)
6. Amino acid or peptide amino groups on the resin were acylated by shaking with a mixture of Fmoc-protected amino acid (4 eq), HBTU or TBTU (4 eq) and DIPEA (4 eq) dissolved in anhydrous DMF (4 ml/mmol), for 20 hours.
7. The resin was washed with DCM (3×2 min)
8. The resin was washed with MeOH (3×2 min)
9. The resin was washed with DCM (3×2 min)
10. The Kaiser test (for all amino acids except proline) was used to estimate if all amino groups were acylated.

If the result of the Kaiser test was negative, the resin was washed with DMF (1×2 min.) and a new coupling cycle started from point 2 of the protocol. If the result of the Kaiser test was positive, acylation was repeated with half the amount of the reagent used for the first coupling. In the case of acylation of proline, the Kaiser test is not sensitive enough to determine the degree of acylation, and for that reason in the case of proline the coupling procedure was repeated with the half amount of reagents. In the case of repeated acylation, the following washings were carried out:
7A. Washing with DCM (3×2 min)
8A. Washing with MeOH (3×2 min)
9A. Washing with DCM (3×2 min)

After the last coupling the resin was washed according to points 3-5 of the protocol. The Fmoc group was removed from the peptide as described in point 2, and the resin was washed again with DMF, MeOH and DCM as in points 3-5. Before the cleavage of the peptide from the polymeric support, the resin was dried overnight in a desiccator over KOH pellets under reduced pressure at room temperature.

Peptides were cleaved from the dried, Wang-type resin with a mixture of trifluoroacetic acid/water/triisopropylsilane 95:2.5:2.5 (v/v/v; 10 ml/1 g of peptidyl-resin). The solution obtained was partially evaporated at room temperature under reduced pressure and peptide was precipitated with 10 volumes of ether. After being filtered off, the crude peptide was dissolved in 0.05 M aqueous HCl and evaporated to dryness. The residue was dissolved in water and lyophilized.

Peptides were cleaved from 2-Cl-trityl resin by treatment with a 1:3:1 mixture of acetic acid/dichloromethane/trifluorethanol (v/v/v; 10 ml/1 g of peptidyl-resin). The resulting cleavage solution plus collected washings were filtered, evaporated to dryness at ambient temperature and reduced pressure, and the residue dissolved in a minimal volume of DCM, diluted with 20 volumes of hexane and re-evaporated (twice). Crude detached peptide was dissolved in water and lyophilized.

After lyophilized peptide was dried in a desiccator under vacuum over KOH and $P_2O_5$, it was ready for cyclisation.

In a typical synthesis following the above protocol, starting with Fmoc-Phe attached to the Wang resin (278 mg, 0.2 mmol, 0.72 mmol/g) and after sequential coupling of Fmoc-L-3-homoPhe-OH, Fmoc-Pro-OH and again Fmoc-Pro-OH, the yield after lyophylization was 91 mg (82%) of crude linear peptide with a purity of 94% (HPLC).

Crude peptides were cyclized in DCM solution (peptide concentration $2 \times 10^{-4}$ millimoles/Liter) with the aid of PyBOP/HOAt/2,4,6-collidine (3:3:5), with disappearance of linear precursors being traced by injecting samples of reaction solutions on an analytical reverse-phase (RP) HPLC column. At the end of the cyclization, the solution was evaporated to dryness under reduced pressure and the residue was partitioned between ethyl acetate (1000 ml of solvent per 1 millimole of peptide and 0.5 N HCl in water (100 ml of solution per 1 millimole of peptide). Organic phase was washed consecutively with 0.5 N HCl in water (2×), water (1×), 1M $NaHCO_3$ (3×) and water (1×). Organic solvent was removed under reduced pressure and the residual solid was dissolved in dioxane and freeze-dried. The crude product was purified on a preparative Vydac $C_{18}$ or Kromasil $C_8$ reversed-phase column (250 mm/22 mm, 100A, 10m) using an elution gradient of solvent B (0.038% TFA in 82% acetonitrile/water) in solvent A (0.05% TFA in water).

As an example of a cyclization reaction, a solution of H-Pro-Pro-$\beta^3$-hPhe-Phe-OH x HCl (55.7 mg, 0.1 mmol) in 500 ml DCM was treated with PyBOP (157 mg, 0.3 mmol) and HOAt (40 mg, 0.3 mmol) in the presence of 2,4,6-collidine (67.5 µL, 0.5 mmol), yielding after work-up and purification 13.5 mg (27%) of the cyclic tetrapeptide with purity 99% as determined by HPLC.

In this manner, compounds of formulae I-A through I-AM were synthesized. The following Tables 1A and 1B provide some data for the compounds of formulae I-A through I-P and I-Q through I-AM, respectively.

TABLE 1A

| | | HPLC (Vydac $C_{18}$ 250 × 4.6 mm, 5 µm, 300 A, 1 mL/min, 45-75% B in 15 min. A: 0.05% TFA/water, B: 0.038% TFA/82% Acetonitrile/water) | |
|---|---|---|---|
| No. | MS (MH$^+$)/MW calculated | $t_R$(min) | Purity (%, λ 214 nm) |
| I-A | 503.45/502.6 | 4.79 | 99.35 |
| I-B | 503.47/502.6 | 5.96 | 99.00 |
| I-C | 517.49/516.6 | 5.26 | 99.00 |
| I-D | 503.25/502.6 | 5.10 | 98.12 |
| I-E | 503.20/502.6 | 5.83 | 97.15 |
| I-F | 503.25/502.6 | 6.70 | 99.08 |
| I-G | 503.25/502.6 | 5.87 | 98.71 |
| I-H | 503.26/502.6 | 6.23 | 98.79 |
| I-J | 503.30/502.6 | 4.80 | 100.0 |
| I-K | 503.27/502.6 | 4.65 | 97.44 |
| I-L | 542.1/541.6 | 4.72 | 99.47 |
| I-M | 519.3/518.6 | 5.81 | 100.0 |
| I-N | 575.3/574.7 | 7.25 | 98.43 |
| I-O | 517.3/516.6 | 6.52 | 97.05 |
| I-P | MS + Na$^+$ = 541.47, MS + K$^+$ = 557.44/518.25 | 9.15 (C-8 Kromasil col., gradient 40-80% B in 15 min) | 99.00 |

TABLE 1B

Stationary phase: Kromasil column C8, 5 μm, 300 Å; Solution A: 0.05% aqueous trifluoroacetic acid (TFA), Solution B: 0.038% TFA in mixture acetonitrile-water 84:16. Linear gradient as indicated as % Solution B during 15 min.

| No. | Molecular mass g per mol/mass found MS + H | HPLC method* | Retention time [min] | Purity [%, $\lambda$ = 220 nm] |
|---|---|---|---|---|
| I-Q | 574.7/575.51 | 30-70 | 13.3 | 99 |
| I-R | 518.6/519.3 | 20-60 | 9.9 | 99 |
| I-S | 500.6/501.32 | 20-60 | 13.2 | 99 |
| I-T | 552.7/553.34 | 30-70 | 12.3 | >99 |
| I-U | 552.7/533.38 | 30-70 | 12.6 | >99 |
| I-V | 537.1/537.34 | 30-70 | 11.8 | >99 |
| I-W | 628.5/629.25 | 30-70 | 12.9 | >99 |
| I-X | 520.6/521.28 | 30-70 | 9.6 | >99 |
| I-Y | 556.7/557.41 | 40-80 | 10.9 | >99 |
| I-Z | 516.6/517.31 | 20-60 | 14.6 | >99 |
| I-AA | 514.6/515.42 | 30-70 | 10.0 | >99 |
| I-AB | 564.7/565.14 | 30-70 | 13.7 | >99 |
| I-AC | 503.6/504.29 | 10-50 | 11.2 | 99 |
| I-AD | 556.7/557.40 | 30-70 | 13.7 | >99 |
| I-AE | 541.6/542.40 | 30-70 | 9.3 | 99 |
| I-AF | 574.7/575.35 | 30-70 | 12.3 | >99 |
| I-AG | 518.6/537.3 | 20-60 | 7.8 | 99 |
| I-AH | 578.7/579.49 | 40-60 | 14.3 | >99 |
| I-AI | 516.6/517.39 | 20-60 | 14.2 | >99 |
| I-AJ | 548.7/587.29[b] | 40-80 | 9.8 | 99 |
| I-AK | 492.6/493.37 | 30-70 | 6.8 | 99 |
| I-AL | 548.7/571.28[c], 587.25[b] | 40-80 | 8.8 | 99 |
| I-AM | 492.6/493.36 | 30-70 | 7.0 | 97 |

[b]Mass is MS + K$^+$;
[c]Mass is MS + Na$^+$

EXAMPLE 2. THERAPEUTIC EFFICACY OF THE PEPTIDE AS A 0.1% OINTMENT IN THE MODEL OF CONTACT SENSITIVITY TO OXAZOLONE IN BALB/C MICE

The aim of this experiment was to verify the therapeutic action of compound I-A and its toxicity in a generally accepted animal model. In the experiment described below, the compound of formula I-A was applied as a therapeutic preparation in the form of 0.1% wt/wt ointment based on a commonly used pharmaceutical vehicle, namely an ointment composed of 50% vaseline and 50% lanoline. The usefulness of the preparation in reduction of the effector phase of the contact sensitivity to oxazolone in mice, in comparison with reference preparations such as tacrolimus (Protopic®) and pimecrolimus (Elidel®), widely used for treatment of skin diseases, was studied.

Materials and Methods

Mice: BALB/c female mice, 8-10 week-old, delivered by the Institute of Laboratory Medicine, Łódź, Poland, were used for the study. The mice were fed a commercial, pelleted food and water ad libitum. The local ethics committee approved the study.

Reagents: Water-in-oil cream and ointment were delivered by Nepentes. Cyclic tetrapeptide (compound I-A) was synthesized as described above. Protopic® (tacrolimus) was purchased from Astellas, Ireland; Elidel® (pimecrolimus) was purchased from Novartis; Hydrocortisonum® (hydrocortisone) was purchased from Aflofarm Farmacja Polska, Poland. DMSO was obtained from Fluka; oxazolone, acetone, Evans blue, Giemsa, May-Grünwald, and formalin were from Sigma.

Contact Sensitivity to Oxazolone:

The test was performed according to Noonan et al. (*Int. Arch. Allergy Appl. Immunol.*, 1978, 56, 523-532), with some modifications. Mice were shaved on the abdomen (2×2 cm area) and after 24 h 100 μl of 0.5% oxazolone in acetone was applied to the shaved area. The contact sensitivity reaction was elicited 5 days later by application of 50 μl of 1% oxazolone in acetone on both sides of the ears. Ear edema was measured 48 h later using a spring caliper. The results were presented as antigen-specific increase of ear thickness (i.e. the background (BG) ear thickness of mice was subtracted from the measured thickness).

Application of Compounds:

In the experiment shown, the compound of formula I-A was applied topically as a 0.1% ointment on both sides of the ears (total volume of 50 μl per ear), at 24 h and 26 h after elicitation of the reaction with the second dose of oxazolone. Reference compounds were used in a similar fashion in the form of commercially available preparations.

Determination of Lymph Node Cell Numbers:

Superficial parotid, mandibular and accessory mandibular lymph nodes were isolated, homogenized by pressing against a stainless screen into phosphate buffered solution (PBS), washed twice and re-suspended in PBS containing 0.2% Trypan blue. The total and nonviable cell numbers were determined using a light microscope and Bürker's hemocytometer. Mice treated only with the eliciting dose of antigen served as a background control.

Determination of Circulating Leukocyte Number and Blood Picture:

Mice were subjected to halothane anesthesia and bled from the retro-orbital plexus, followed by cervical dislocation. The number of blood leukocytes was determined by dilution of blood in Turk's solution and counting the cells in a hemocytometer. Blood smears were prepared on microscope glass, dried and stained with Giemsa and May-Grünwald reagents. The smears were subsequently reviewed histologically. The circulating leukocyte numbers were presented per 1 mm$^3$ and the blood cell compositions as a percentage of a given cell type. Mice treated only with the eliciting dose of antigen served as a background control.

Histological Analysis:

The auricles were fixed in 4% formalin solution for 48 h, washed for 24 h, dehydrated in an alcohol series and embedded in paraffin. The paraffin blocks were sliced in a Micron HM310 microtome into 6 μm sections. The sections were stained with haematoxylin and eosin and with toluidine blue. The histological analysis was performed in a Nikon Eclipse 801 light microscope. On the histological slides containing cross-sections of auricles, the morphometric estimations of neutrophils, macrophages, lymphocytes and mast cells in the perivascular and subepithelial connective tissue were performed. The cells were counted on the area of 0.07 mm$^2$ at 400× magnification. Morphometric analysis was done with the aid of imagine software NIS-Elements (Nikon). For every examined group, 25 enumerations of neutrophils, macrophages, lymphocytes and mast cells were carried out.

Statistics:

The results are presented as mean values ±standard error (SE). Brown-Forsyth's test was used to determine the homogeneity of variance between groups. When the variance was homogenous, analysis of variance (one-way ANOVA) was applied, followed by post hoc comparisons with the Tukey's test to estimate the significance of the differences between groups. Nonparametric data were evaluated with the Kruskal-Wallis' analysis of variance, as indicated in the text.

Significance was determined at p<0.05. Statistical analysis was performed using STATISTICA 7 for Windows. The statistical analysis applies to all data shown in this description.

Figure 1:
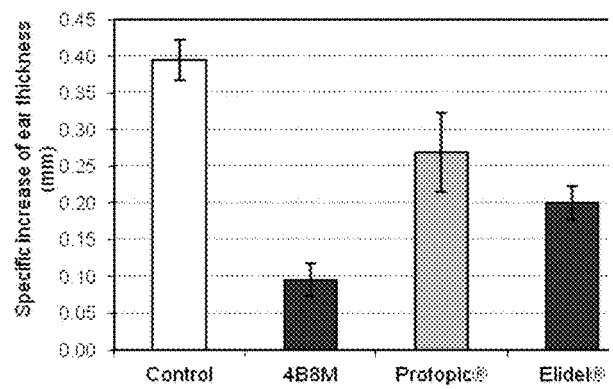
FIG. 1 shows antigen-specific increase of the ear thickness derived from the experiment described in Example 2.

Results:

The data included in FIG. 1 show the therapeutic efficacy of compound of formula I-A (labeled "4B8M" in FIG. 1 and subsequent figures) and the reference preparations in mice with fully developed contact sensitivity reaction to oxazolone. The preparations were applied topically as described in the Methods. FIG. 1 presents only antigen-specific increases of the ear thickness (as a result of subtracting background values measured in non-sensitized mice which were given only the eliciting dose of antigen). Compound I-A caused about 80% inhibition of the ear edema; Protopic® and Elidel® respectively caused about 30% and 50% inhibition.

Figure 2:
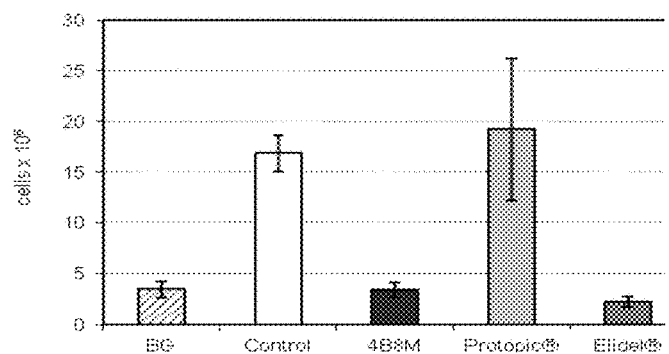
FIG. 2 shows total numbers of cells in the parotid lymph nodes observed in the experiment described in Example 2.

The intensity of inflammatory processes in the ears should correlate with cell numbers in the draining lymph nodes. Therefore, inhibition of inflammation should be associated with a decrease of cell number in the draining lymph nodes. FIG. 2 shows that both the compound of formula I-A as well as Elidel® decreased the numbers of lymphocytes in the draining lymph nodes to the level registered in non-sensitized mice. However, in mice treated with Protopic® the number of lymph node cells was similar to that in untreated mice.

Figure 3:
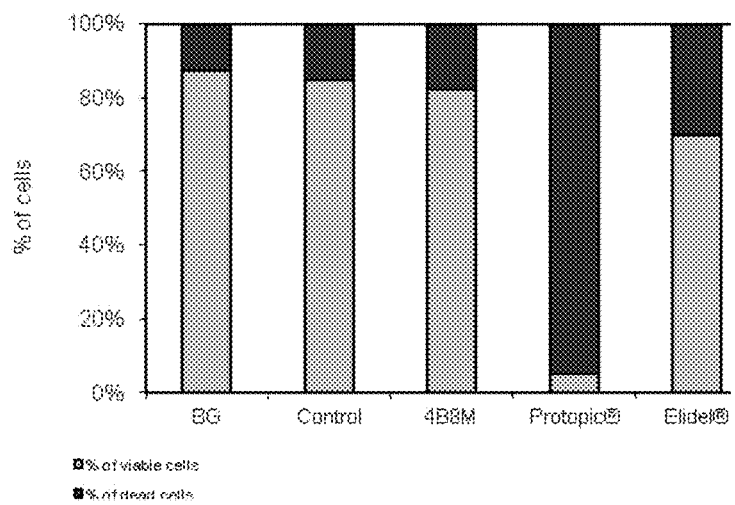
FIG. 3 shows the content of viable and dead cells in the parotid lymph nodes described in Example 2.

FIG. 3 shows the proportions of viable and dead cells in the draining lymph nodes, expressed in percentages. The compound of formula I-A exhibits a negligible toxic effect as compared to the control, non-treated mice. A higher toxic effect is caused by Elidel®, and Protopic® is exceptionally toxic with regard to lymph node cells.

Complementary information regarding the therapeutic efficacy of the preparations may be derived from histological analysis of the cell number and composition in the inflamed auricles. FIG. 4 depicts the numbers and participation of basic cell types involved in the local inflammatory process. In FIG. 4, Mast=mastocytes, L=lymphocytes, MO=macrophages, Ne=neutrophils. The auricles from untreated mice (K+) are characterized by a high infiltration of neutrophils. Application of the compound of formula I-A almost entirely reversed the changes observed in control mice (normalization of neutrophil number with some increase in the macrophage content). Protopic®, in turn, caused some changes in the proportion of respective cell types with no reduction of the total cell infiltrate. Elidel® caused a moderate diminution of the total cell number.

EXAMPLE 3. THE TOXICITY OF COMPOUND I-A VERSUS THAT OF CYCLOLINOPEPTIDE AGAINST HUMAN BLOOD MONONUCLEAR CELLS

For evaluation of toxicity of the compound of formula I-A, human peripheral mononuclear blood cells (PBMC) were chosen. This fraction consists of approximately 80% lymphocytes and 20% monocytes. As a reference compound, cyclolinopeptide (CLA) was selected since the compound of formula I-A shares a part of the sequence of CLA. CLA exhibits immunosuppressive properties comparable to that of cyclosporine A, but is less toxic.

Materials and Methods

The Cytotoxic Test:

Venous blood from a single donor was taken into heparinized syringes, diluted twice with phosphate buffered saline (PBS) and applied onto Lymphoprep® (Polfa, Kutno, Poland) (density of 1.077 g/ml). After centrifugation at 1200×g for 20 min, the mononuclear cells from the interphase were harvested and washed 3 times with PBS. The cells were re-suspended in a standard culture medium consisting of RPMI-1640 medium, L-glutamine, sodium pyruvate, 2-mercaptoethanol, 100 μg/ml each of streptomycin and penicillin, and 10% fetal calf serum. The cells were distributed to in 96-well flat-bottom culture plates at density of $2 \times 10^5/100$ μl. The compounds (formula I-A and CLA) were initially dissolved in DMSO (5 mg/500 μl) and subsequently in the culture medium. DMSO, appropriately diluted with the culture medium, was used as a control. After 24 h incubation in a cell culture incubator, cell viability was determined by a colorimetric method (Hansen et al., *J Immunol Methods,* 1989, 119, 203-210).

The results are shown in FIG. 5, presented as mean optical density values from quadruplicate wells (cell cultures)+SE. As can be seen in FIG. 5, the compound of formula I-A (listed as "4B8M") did not show appreciable toxicity in the concentration range of 10 to 100 μg/ml. CLA, on the other hand, showed a statistically significant cytotoxic effect at 40 μg/ml.

EXAMPLE 4. EFFECT OF PEPTIDE ON THE HUMORAL IMMUNE RESPONSE TO SRBC IN VIVO

CBA female mice, 8-12 weeks old, were delivered by The Institute of Laboratory Medicine, Lodz, Poland. The mice had free access to water and pelleted food. The local ethics committee approved the study. Sheep erythrocytes (SRBC) were delivered by Wroclaw University of Life and Environmental Sciences, Poland, and maintained on RPMI-1640 medium.

The Primary Humoral Immune Response to SRBC In Vivo:

Mice were immunized with 0.2 ml of 5% SRBC suspension (0.5 ml of SRBC pellet re-suspended to a volume of 10 ml of 0.9% NaCl), intraperitonelly. After 4 days the number of antibody-forming cells (AFC) in the spleens was determined using an assay of local hemolysis in agar gel (per Mishell et al., *J Exp Med,* 1967, 126, 423-442). The results are presented in FIG. 6 as a mean value of 5 mice ±standard error and expressed as AFC number per $10^6$ of viable splenocytes.

Mice were immunized with SRBC as described above and after 2 h were given 10 or 100 μg of the compound of formula I-A. Cyclosporin A (CsA) served as a reference drug. The number of antibody-forming cells to SRBC was measured after 4 days. As shown in FIG. 6, the compound of formula I-A was more inhibitory at both doses than CsA.

EXAMPLE 5. EFFECT OF PEPTIDE ON THE CELLULAR IMMUNE RESPONSE IN VIVO TO OVALBUMIN

Male CBA mice 8-12 weeks old were delivered by The Institute of Laboratory Medicine, Lodz, Poland. The mice had free access to water and pelleted food. Ovoalbumin was from Sigma and the adjuvants from Difco.

Delayed Type Hypersensitivity (DTH) Test:

Mice were sensitized subcutaneously with 5 μg of ovalbumin (OVA) emulsified in Freund's complete adjuvant in the tail base. After 4 days the mice were challenged with 50 μg of OVA in Freund's incomplete adjuvant in the hind footpads. Following the next 24 hours, the footpad thickness was measured using a caliper. Controls (background response mice) were not sensitized but received the challenging dose of OVA. The compound of formula I-A and the reference compound were administered to mice in two 100 µg intraperitoneal doses, 2 h before and 24 h after the sensitizing dose of antigen. The results, presented in FIG. 7 as a mean value of antigen-specific increase of footpad thickness measured in 5 mice and expressed in DTH units (one DTH unit=$10^{-2}$ cm) ±standard error, show that the compound of formula I-A, given in two doses, 2 h and 24 h after immunization, inhibited the delayed-type hypersensitivity reaction to OVA. That suppressive action was stronger than those of CLA and CsA.

EXAMPLE 6

Cyclic tetrapeptides were tested in vitro for their effects on phytohemagglutinin A (PHA)-induced proliferation of human peripheral blood mononuclear cells (PBMC) and for lipopolysaccharide (LPS)-induced production of tumor necrosis factor alpha (TNF-α) production by whole blood cell cultures at 1-100 µg/ml concentration range. Compounds were also tested for cell toxicity at 1-100 µg/ml concentration range against human PBMC.

Materials and Methods:

Reagents:

RPMI-1640 medium (Cibi/Life Technologies, UK), fetal calf serum (FCS, Gibco), DMSO, phytohemagglutinin A (PHA), lipopolysaccharide (LPS) from E. coli strain O111: B4 (Sigma), 93-[4,5-dimethylthiazol-2-yl]-2,5-diphenyltetrazolium bromide (MTT), SDS and DMF (Sigma). The culture medium consisted of RPMI-1640, 10% addition of FCS, L-glutamine, sodium pyruvate, 2-mercaptoetanol and antibiotics (streptomycin and penicillin). Cyclic tetrapeptides were initially dissolved in DMSO (5 mg/ml), the dissolved in the culture medium to the desired concentration.

Isolation of PBMC:

Venous blood was taken from a single donor (a male, 62-years old) into heparinized syringes and diluted twice with phosphate-buffered saline (PBS). PBMC were isolated by centrifugation on Ficoll-uropoline gradient (density 1.077 g/ml) (Lymphoprep; PAA Laboratories), at 800×g for 20 min at 4° C. The interphase cells, consisting of lymphocytes (20%) and monocytes (80%) were then washed three times with Hanks' medium and re-suspended in the culture medium at density of $2 \times 10^6$ cells/ml.

The Proliferative Response of PBMC to PHA:

The isolated PBMC were distributed into 96-well flat-bottom plates in 100 µl aliquots ($2 \times 10^5$ cells/well). PHA was used at concentration of 5 µg/ml. The compounds were tested at concentrations of 1, 10 and 100 µg/ml. DMSO at appropriate dilutions served as control. After a four-day incubation in a cell culture incubator, the proliferative response of cells was determined by the colorimetric MTT method (Hansen et al., J. Immunol. Methods, 1989, pp. 203-210). The data are presented as a mean OD value from quadriplicate wells ±standard error (SE). The cultures "Control (−)" contained no mitogen (PHA). The cultures "Control (PHA)" contained PHA but not cyclic tetrapeptides.

Toxicity Test:

PBMC, at a density of $2 \times 10^5/100$ µl/well ($3 \times 10^5/100$ µl/well for peptides I-Q through I-AM), re-suspended in the culture medium, were cultured for 24 h in a cell culture incubator with the cyclic tetrapeptides at concentrations of 1, 10 and 100 µg/ml concentrations. Appropriate dilutions of DMSO in RPMI 1640 medium were used as controls. Cell survival was determined by the MTT colorimetric method (Hansen et al., J. Immunol. Methods, 1989, pp. 203-210). The data are presented as a mean OD value from quadriplicate wells ±standard error (SE). The cultures "Control (−)" contained only cells in the culture medium.

Induction of TNF-Alpha Production and Determination of TNF Alpha Activity (Per Espevik et al., J. Immunol. Methods, 95 (1986):99-103):

Human whole blood was diluted 10-fold with RPMI-1640 medium and distributed to 24-well culture plates in 1 ml aliquots. LPS was added to the culture at a concentration of 1 µg/ml. The studied peptides were used at concentrations of 1, 10 and 100 µg/ml. After overnight incubation, the supernatants were harvested and frozen at −20° C. until cytokine determination. TNF-α activity was determined using a bioassay. Briefly, WEHI 164.13 cells (ATCC CRL 1751) were seeded at a concentration of $2 \times 10^4$ cells/well in quadriplicate. Increasing dilutions of the assayed supernatant were mixed with the target cells in the presence of actinomycin D (1 µg/ml). After 20 h of incubation, MTT was added into the wells, and the cultures were incubated for an additional 4 h. Next, a lysing buffer (20% SDS with 50% DMF, pH 4.7) was added and the optical density at 550 nm with the reference wavelength of 630 nm in a Dynatech 5000 spectrophotometer was measured after 24 h. The detection limit of the assay was about 2.5 pg/ml. One unit of TNF-α activity was defined as an inverse of supernatant dilution where 50% cell death took place. The cultures labeled "Control (−)" contained no LPS. The cultures labeled "Control (LPS)" contained LPS and none of the studied compounds. Statistical analysis was not applied since the data derive from single cultures (wells).

Colorimetric MTT Assay for Cell Growth and Kill:

The assay was performed per Hansen et al., J. Immunol. Methods, 1989, 119 pp. 203-210. Briefly, 25 µl of MTT (5 mg/ml) stock solution was added per well at the end of cell incubation and the plates were incubated for 3 h in a cell culture incubator. Then, 100 µl of the extraction buffer (20% SDS with 50% DMF, pH 4.7) was added. After additional overnight incubation, the optical density was measured at 550 nm (Dynatech 5000).

Statistical Analysis:

Where applicable, results are presented as mean values ±standard error (SE). Brown-Forsyth's test was used to determine the homogeneity of variance between groups. When the variance was homogenous, analysis of variance (one-way ANOVA) was applied, followed by post hoc comparisons with the Tukey's test to estimate the significance of the differences between groups. Significance was determined at P<0.05. Statistical analysis was performed using STATISTICA 6.1 for Windows.

Results

Effects of the Compounds on Survival of PBMC:

The effects of the peptides on PMBC survival in 24h culture are presented in FIGS. 8A, 8B, 8C, 8D, 8E and 8F. Peptide 4B8M (compound I-A) was included as a reference compound. Appropriate dilutions of DMSO were added to control cultures. The results showed no signs of toxicity of the compounds in the studied concentration range. In the figures, P01=compound I-D, P02=compound I-E, P03=compound I-F, P04=compound I-G, P05=compound I-H, P06=compound I-J, P07=compound I-K, P08=compound I-L, P10a=compound I-M, P10b=compound I-N, P11=compound I-O, P21=compound I-R, P-21b=compound I-Q, P22=compound I-S, P23-2=compound I-U, P24=compound I-V, P25=compound I-X, P25-i=compound I-W, P26=compound I-Y, P27=compound I-Z, P28=compound I-AA, P29=compound I-AB, P30=compound I-AC, P31=compound I-AD, P32=compound I-AE, P33=compound I-AG, P33-b=compound I-AF, P34=compound I-AH, P35=compound I-AI, P00S-b=compound I-AJ, SP00-b=compound I-AL. (Due to incomplete solubility in the aqueous culture medium, the following compounds were not tested for toxicity toward PBMC in vitro: P21-b, P25, P25-i, P32, P34, P35, and P00Sb).

Figure 8A:
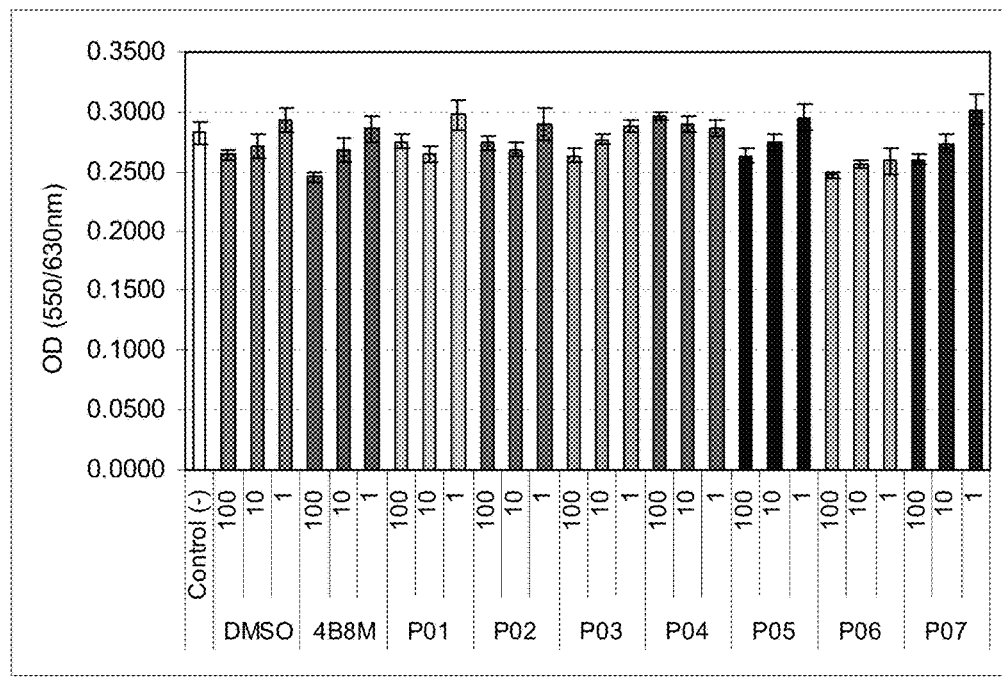
Figure 8B:
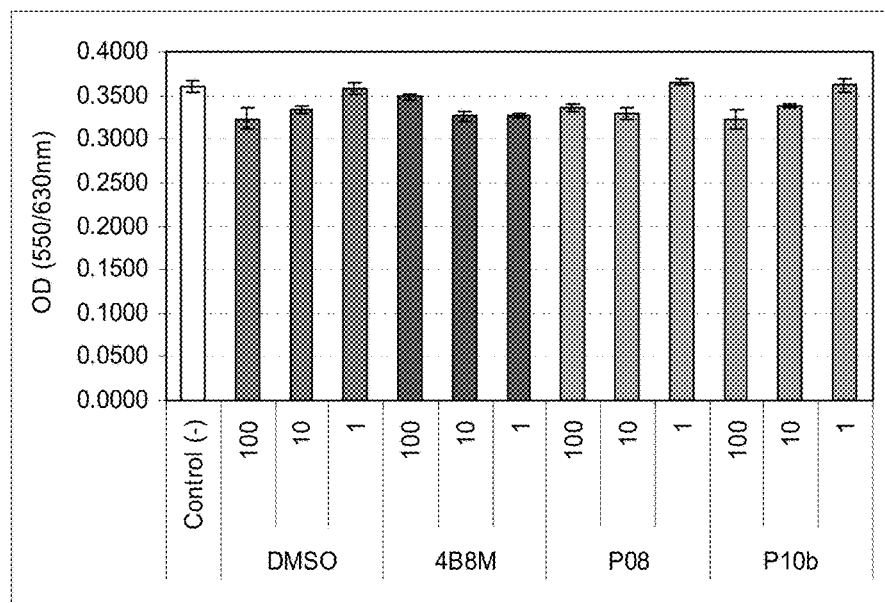
Figure 8C:
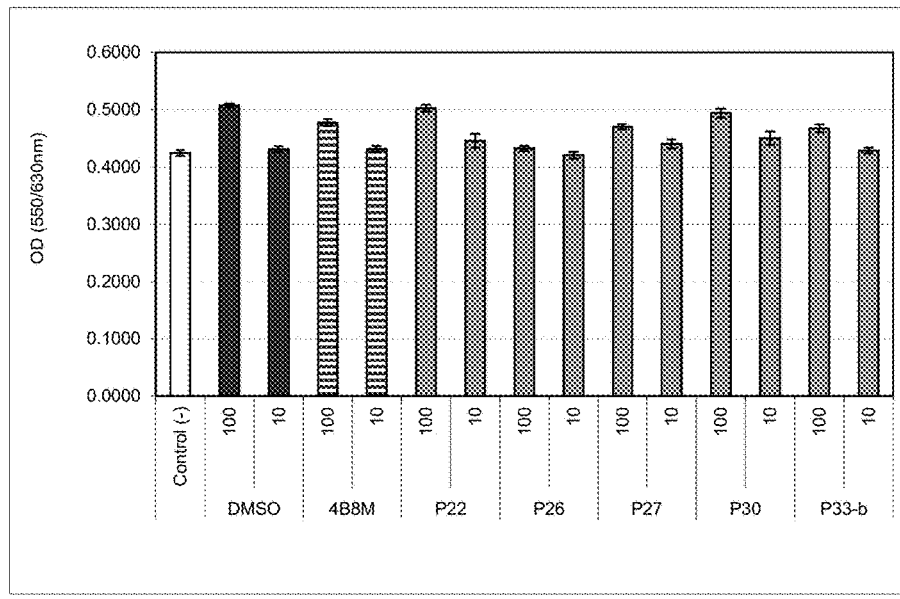
Figure 8D:
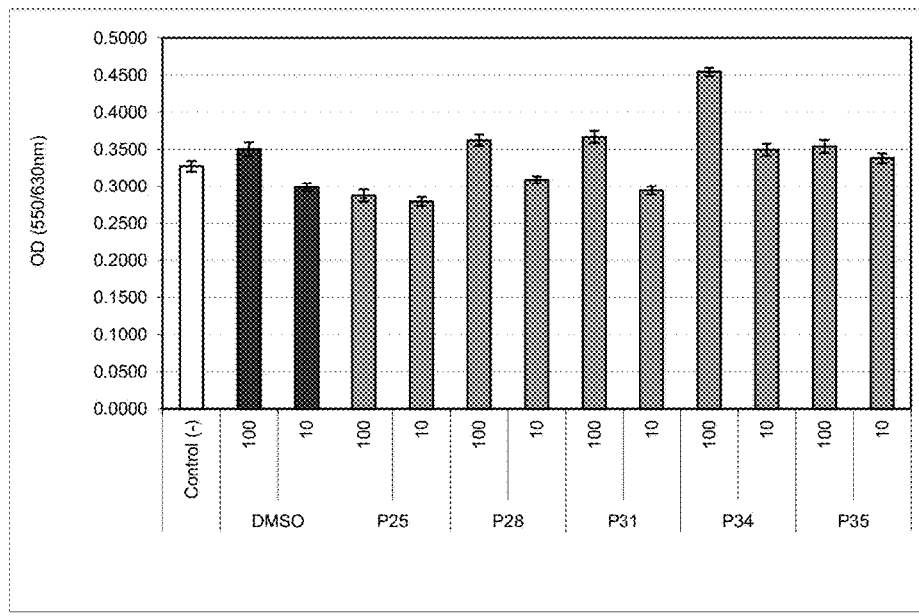
Figure 8E:
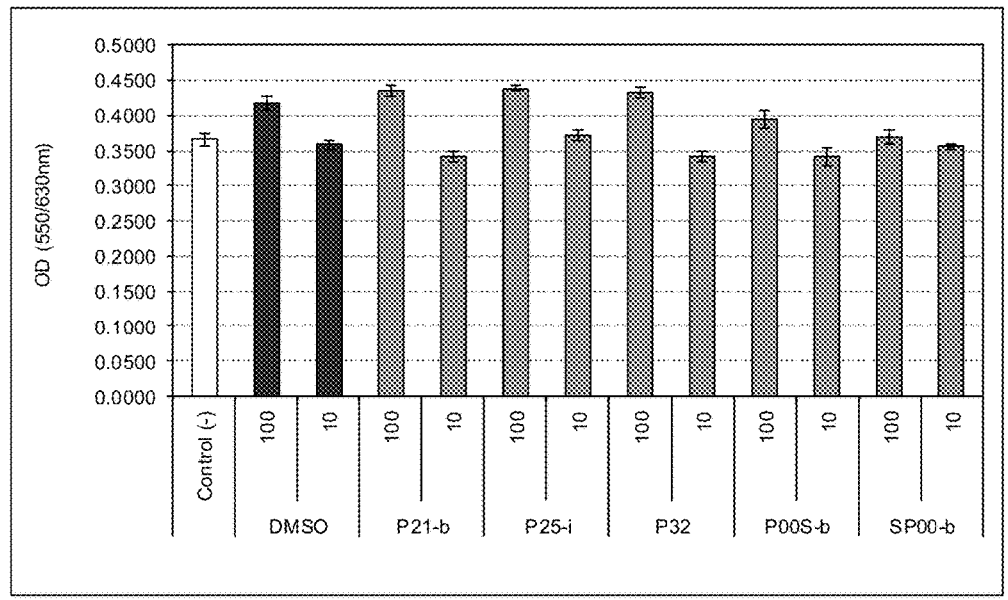
Figure 8F:
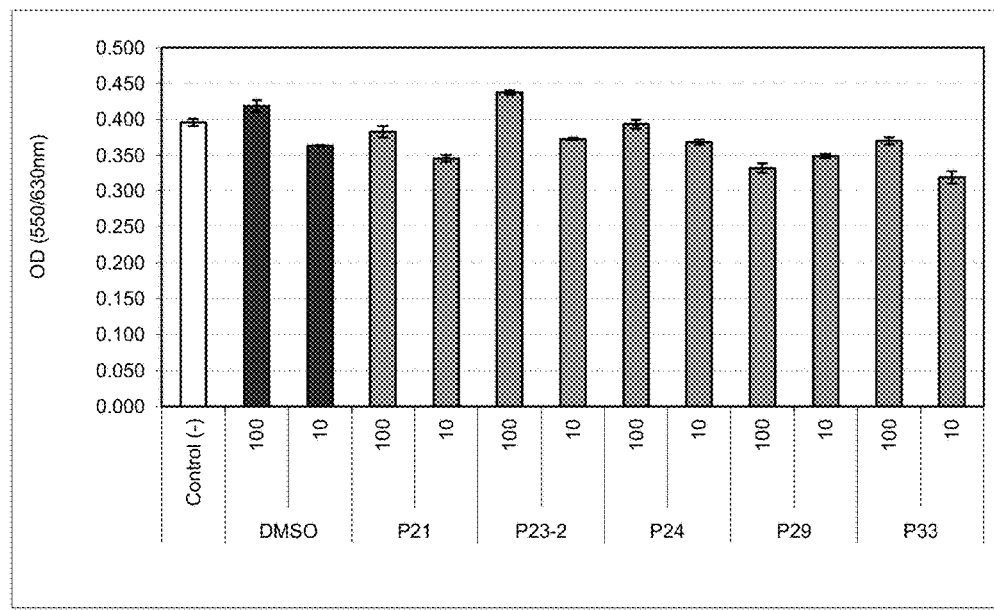

FIGS. 8A, 8B, 8C, 8D and 8E show the effects of the tested peptides on the survival of PBMC. FIG. 8A: Statistics (all comparisons vs. DMSO at appropriate dilutions): 100 µg/ml: 4B8M NS (P=0.9999); P01 NS (P=1.0000); P02 NS (P=1.0000); P03 NS (P=1.0000); P04 NS (P=0.9047); P05 NS (P=1.0000); P06 NS (P=0.9999); P07 NS (P=1.0000); 10 µg/ml: 4B8M NS (P=1.0000); P01 NS (P=1.0000); P02 NS (P=1.0000); P03 NS (P=1.0000); P04 NS (P=0.9999); P05 NS (P=1.0000); P06 NS (P=1.0000); P07 NS (P=1.0000); 1 µg/ml: 4B8M NS (P=1.0000); P01 NS (P=1.0000); P02 NS (P=1.0000); P03 NS (P=1.0000); P04 NS (P=1.0000); P05 NS (P=1.0000); P06 NS (P=0.8253); P07 NS (P=1.0000) (ANOVA). FIG. 8B: Statistics (all comparisons vs. DMSO at appropriate dilutions): 100 µg/ml: 4B8M NS (P=0.0669); P08 NS (P=0.9957); P10b NS (P=1.0000); 10 µg/ml: 4B8M NS (P=0.9999); P08 NS (P=1.0000); P10b NS (P=1.0000); 1 µg/ml: 4B8M NS (P=0.3176); P08 NS (P=0.9999); P10b NS (P=1.0000) (ANOVA). FIG. 8C: Statistics: Control(−) vs DMSO 100 P=0.0001; Control (−) vs DMSO 10 NS (P=0.9999); 100 µg/ml, DMSO vs peptides: 4B8M NS (P=0.1700); P22 NS (P=1.0000); P26 P=0.0001; P27 P=0.0236; P30 NS (P=0.9882); P33-b P=0.0090; 10 µg/ml, DMSO vs peptides: 4B8M NS (P=1.0000); P22 NS (P=0.9753); P26 NS (P=0.9992); P27 NS (P=0.9997); P30 NS (P=0.8178); P33-b NS (P=1.0000) (ANOVA). FIG. 8D: Statistics: Control(−) vs DMSO 100 NS (P=0.6584); Control (−) vs DMSO 10 NS (P=0.3032); 100 µg/ml, DMSO vs peptides: P25 P=0.0001; P28 NS (P=0.9978); P31 NS (P=0.9531); P34 P=0.0001; P35 NS (P=1.0000); 10 µg/ml, DMSO vs peptides: P25 NS (P=0.8597); P28 NS (P=0.9997); P31 NS (P=1.0000); P34 P=0.0005; P35 P=0.0222 (ANOVA). FIG. 8E: Statistics: Control(−) vs DMSO 100 P=0.0201; Control(−) vs DMSO 10 NS (P=0.9999); 100 µg/ml, DMSO vs peptides: P21-b NS (P=0.9185); P25-i NS (P=0.9602); P32 NS (P=0.9984); P00S-b NS (P=0.9250); SP00-b P=0.0466; 10 µg/ml, DMSO vs peptides: P21-b NS (P=0.9976); P25-i NS (P=0.9992); P32 NS (P=0.9954); P00S-b NS (P=0.9962); SP00-b (P=1.0000) (ANOVA). FIG. 8F: Statistics: Control(−) vs DMSO 100 NS (P=0.2153); Control(−) vs DMSO 10 P=0.0076; 100 µg/ml, DMSO vs peptides: P21 P=0.0019; P23-2 NS (P=0.4949); P24 NS (P=0.1122); P29 P=0.0001; P33 P=0.0001; 10 µg/ml, DMSO vs peptides: P21 NS (P=0.6250); P23-2 NS (P=0.9972); P24 NS (P=0.9999); P29 NS (P=0.8876); P33 (P=0.0001) (ANOVA).

Effects of the Peptides on PHA-Induced PMBC Proliferation:

The effects of the peptides on the proliferative response of PMBC are presented in FIGS. 9A, 9B, 9C, 9D, 9E and 9F. Peptide 4B8M was included as a reference compound. Appropriate dilutions of DMSO were added to control cultures.

Figure 9A:
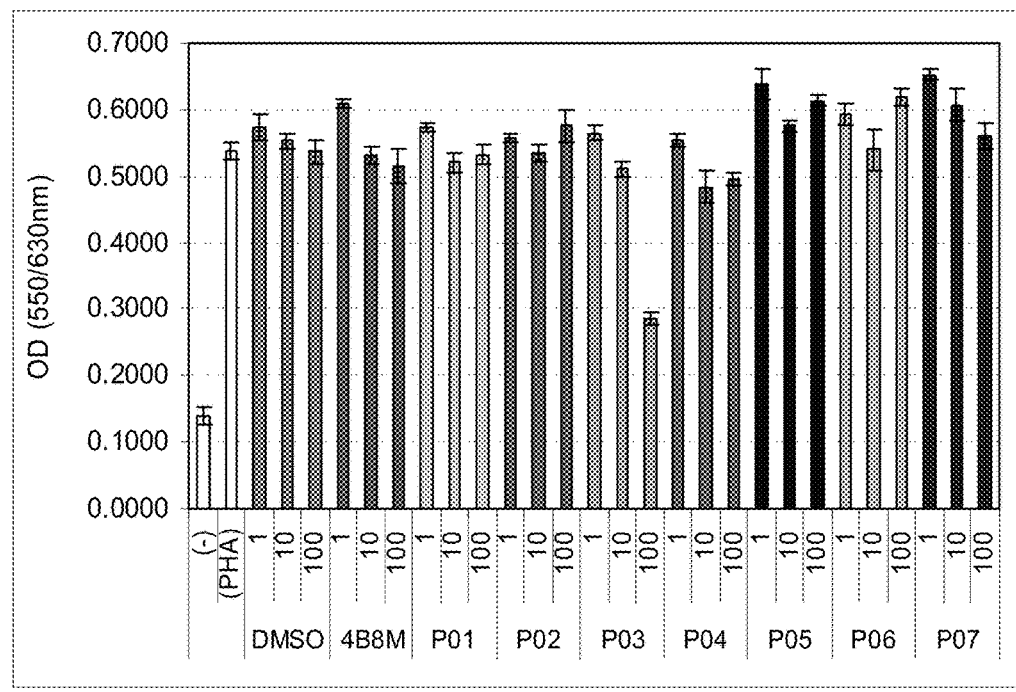

FIG. 9A: Effects of the peptides on PHA-induced PBMC proliferation: Statistics (all comparisons vs. DMSO at appropriate dilutions): 1 µg/ml: 4B8M NS (P=0.9995); P01 NS (P=1.0000); P02 NS (P=1.0000); P03 NS (P=1.0000); P04 NS (P=0.9047); P05 NS (P=0.5198); P06 NS (P=1.0000); P07 NS (P=0.1445); 10 µg/ml: 4B8M NS (P=1.0000); P01 NS (P=0.9999); P02 NS (P=1.0000); P03 NS (P=0.9930); P04 NS (P=0.4297); P05 NS (P=1.0000); P06 NS (P=1.0000); P07 NS (P=0.8647); 100 µg/ml: 4B8M NS (P=1.0000); P01 NS (P=1.0000); P02 NS (P=0.9982); P03 P=0.0001; P04 NS (P=0.9970); P05 NS (P=0.2037); P06 NS (P=0.1257); P07 NS (P=1.0000) (ANOVA).

Figure 9B:
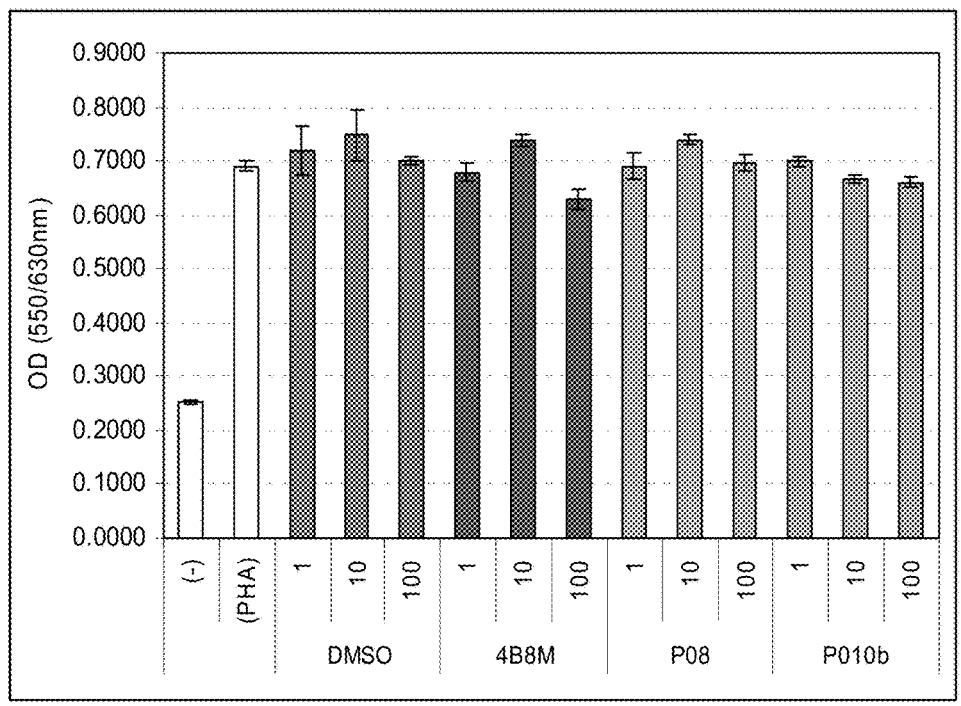

FIG. 9B: Effects of the peptides on PHA-induced PBMC proliferation: Statistics (all comparisons vs. DMSO at appropriate dilutions): 1 µg/ml: 4B8M NS (P=0.9919); P08 NS (P=0.9999); P10b NS (P=1.0000); 10 µg/ml: 4B8M NS (P=1.0000); P08 NS (P=1.0000); P10b NS (P=0.2763); 100 µg/ml: 4B8M NS (P=0.4941); P08 NS (P=1.0000); P10b NS (P=0.9933) (ANOVA).

Figure 9C:
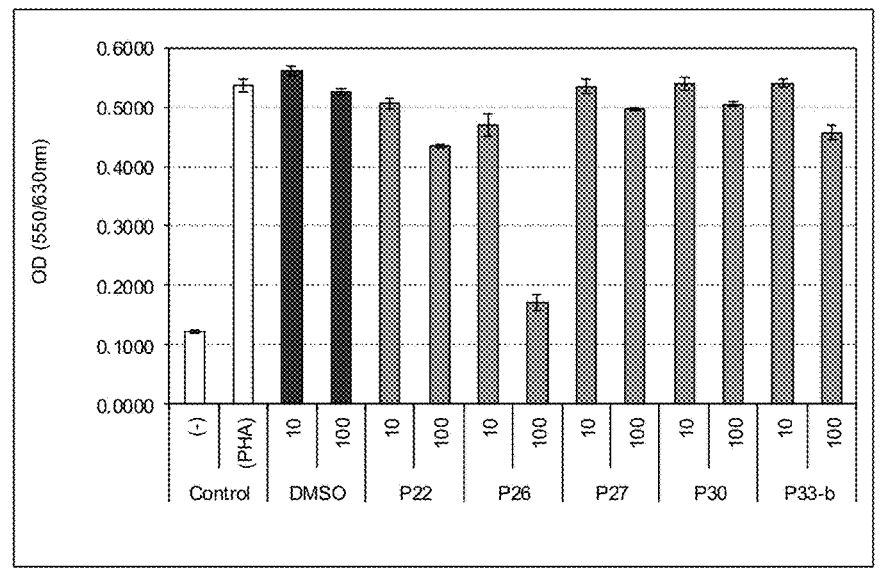

FIG. 9C: Effects of the peptides on PHA-induced PBMC proliferation: Statistics (all comparisons vs. DMSO at appropriate dilutions): Control(−) vs Control(PHA) P=0.0001; Control(PHA) vs DMSO 10 NS (P=0.9407); Control(PHA) vs DMSO 100 NS (P=0.9999); 10 µg/ml, DMSO vs peptides: P22 P=0.0275; P26 P=0.0001; P27 NS (P=0.9121); P30 NS (P=0.9850); P33-b NS (P=0.9850); 100 µg/ml, DMSO vs peptides: P22 P=0.0001; P26 P=0.0001; P27 NS (P=0.8195); P30 NS (P=0.9871); P33-b P=0.0010 (ANOVA).

Figure 9D:
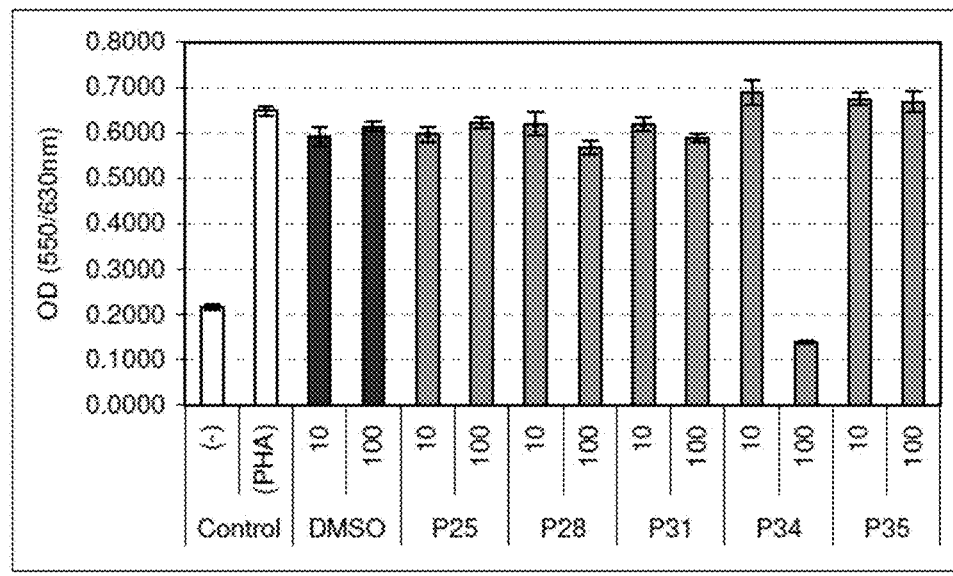

FIG. 9D: Effects of the peptides on PHA-induced PBMC proliferation: Statistics (all comparisons vs. DMSO at appropriate dilutions): Control(−) vs Control(PHA) P=0.0151; Control(PHA) vs DMSO 10 NS (P=1.0000); Control(PHA) vs DMSO 100 NS (P=1.0000); 10 µg/ml, DMSO vs peptides: all comparisons NS (P=1.0000); 100 µg/ml, DMSO vs peptides: P25 NS (P=1.0000); P28 NS (P=1.0000); P31 NS (P=1.0000); P34 S (P=0.001861); P35 NS (P=1.0000) (ANOVA of Kruskal-Wallis).

Figure 9E:
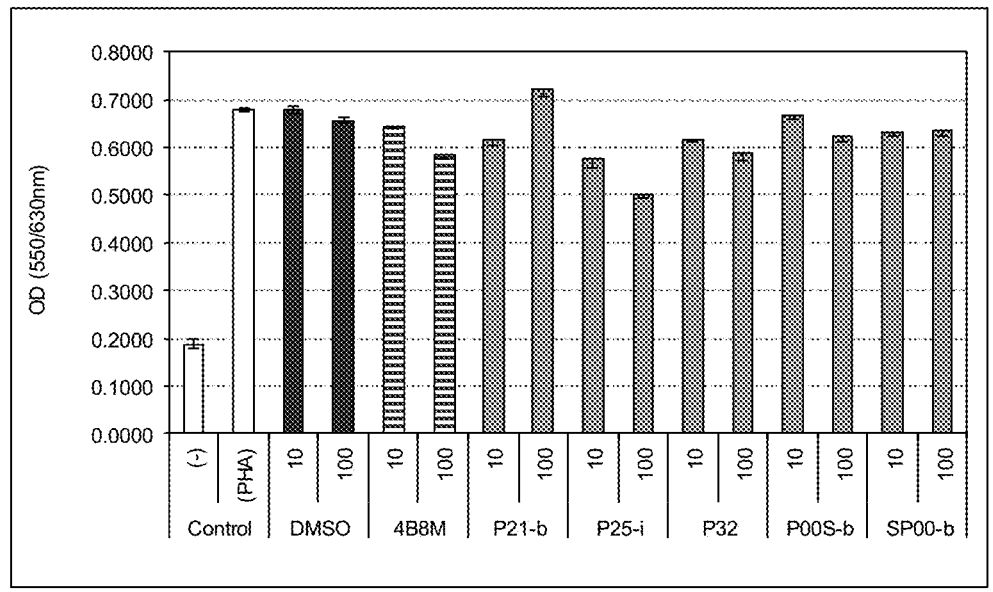

FIG. 9E: Effects of the peptides on PHA-induced PBMC proliferation: Statistics (all comparisons vs. DMSO at appropriate dilutions): Statistics: Control(−) vs Control (PHA) P=0.0001; Control(PHA) vs DMSO 10 NS (P=1.0000); Control(PHA) vs DMSO 100 NS (P=0.9778); 10 µg/ml, DMSO vs peptides: 4B8M NS (P=0.7530); P21-b P=0.0141; P25-i P=0.0001; P32 P=0.0127; P00S-b NS (P=1.0000); SP00-b NS (P=0.2258); 100 µg/ml, DMSO vs peptides: 4B8M P=0.0016; P21-b P=0.0056; P25-i P=0.0001; P32 P=0.0023; P00S-b NS (P=0.7035); SP00-b (P=0.9976) (ANOVA).

Figure 9F:
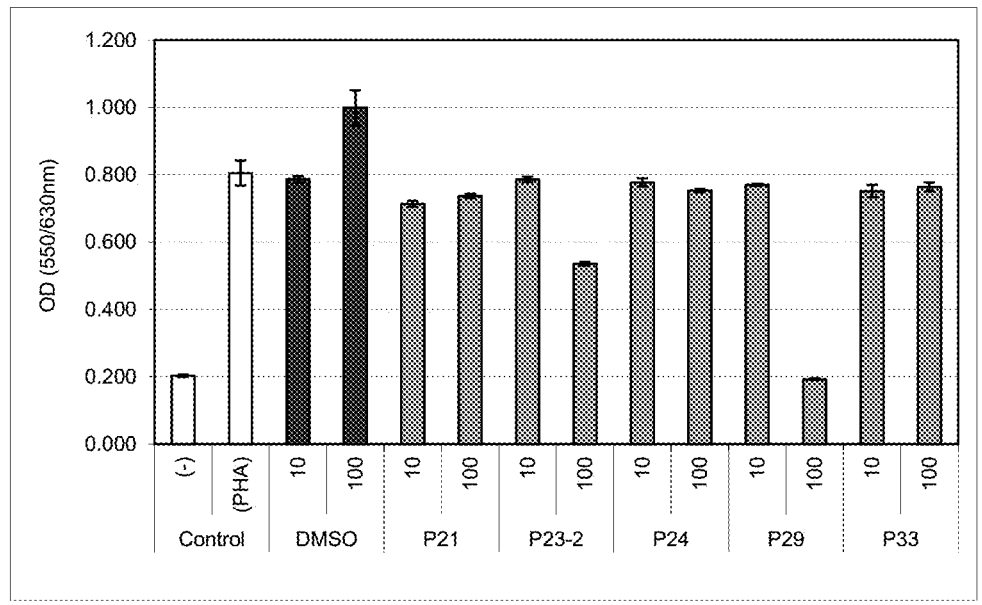

FIG. 9F: Effects of the peptides on PHA-induced PBMC proliferation: Statistics (all comparisons vs. DMSO at appropriate dilutions): Control(−) vs Control(PHA) NS (P=0.1468); Control(PHA) vs DMSO 10 NS (P=1.0000); Control(PHA) vs DMSO 100 NS (P=1.0000); 10 µg/ml, DMSO vs peptides: P21 NS (P=0.7122); P23-2 NS (P=1.0000); P24 NS (P=1.0000); P29 NS (P=1.0000); P33 NS (P=1.0000); 100 µg/ml, DMSO vs peptides: P21 P=0.0436; P23-2 P=0.0002; P24 NS (P=0.4681); P29 P=0.0001; P33 (P=1.0000) (ANOVA of Kruskal-Wallis).

Effects of the Peptides on LPS-Induced TNF-α Production in Whole Blood Cell Cultures:

The effects of some of the peptides on LPS-induced TNF-α production in whole blood cell cultures are presented in Tables 2A and 2B; additional results are presented in FIGS. 16A, 16B, 16C and 16D. Peptide 4B8M was included as a reference compound. Appropriate dilutions of DMSO were added to control cultures.

TABLE 2A

Effects of peptides on LPS-induced TNF-α production

| Compound | Compound concentration (μg/ml) | TNF-α (pg/ml) | % inhibition vs. DMSO |
|---|---|---|---|
| Control (−) | — | 92 | — |
| Control (LPS) | — | 6668 | — |
| DMSO Only | 1 | 8167 | — |
|  | 10 | 8006 | — |
|  | 100 | 196 | — |
| 4B8M | 1 | 7364 | 9.8 |
| (compound I-A) | 10 | 7176 | 10.4 |
|  | 100 | 178 | 9.2 |
| P01 | 1 | 7016 | 14.1 |
| (compound I-D) | 10 | 5757 | 28.1 |
|  | 100 | 141 | 28.1 |
| P02 | 1 | 6614 | 19.0 |
| (compound I-E) | 10 | 6346 | 20.7 |
|  | 100 | 176 | 10.2 |
| P03 | 1 | 6052 | 25.9 |
| (compound I-F) | 10 | 5222 | 34.8 |
|  | 100 | 76 | 61.2 |
| P04 | 1 | 5463 | 33.1 |
| (compound I-G) | 10 | 5302 | 33.8 |
|  | 100 | 58 | 70.4 |
| P05 | 1 | 7123 | 12.8 |
| (compound I-H) | 10 | 7203 | 10.0 |
|  | 100 | 110 | 43.9 |
| P06 | 1 | 8033 | 1.6 |
| (compound I-J) | 10 | 7658 | 4.4 |
|  | 100 | 203 | 0.0 |
| P07 | 1 | 6453 | 21.0 |
| (compound I-L) | 10 | 7284 | 9.0 |
|  | 100 | 163 | 16.8 |

TABLE 2B

Effects of the peptides on LPS-induced TNF alpha production

| Compound | compound concentration (μg/ml) | TNF alpha (pg/ml) | % of inhibition vs. DMSO |
|---|---|---|---|
| Control (−) | — | 223 | — |
| Control (LPS) | — | 4260 | — |
| DMSO Only | 1 | 4550 | — |
|  | 10 | 4351 | — |
|  | 100 | 854 | — |
| 4B8M | 1 | 4097 | 10.0 |
| (compound I-A) | 10 | 4416 | — |
|  | 100 | 979 | — |
| P08 | 1 | 4039 | 11.2 |
| (compound I-M) | 10 | 3363 | 22.7 |
|  | 100 | 269 | 68.5 |
| P10b | 1 | 3792 | 16.7 |
| (compound I-O) | 10 | 3739 | 14.0 |
|  | 100 | 282 | 67.0 |

EXAMPLE 7. INHIBITORY EFFECT OF COMPOUND I-A ON TOLUENE DIISOCYANATE-INDUCED EAR INFLAMMATION IN MICE

The efficacy of the compound I-A in suppressing ear inflammation in BALB/c mice which was induced with toluene diisocyanate (TDI). Commercially available Protopic® (tacrolimus) and Elidel® (pimecrolimus) served as reference drugs.

Materials and Methods

Mice:

BALB/c female mice, 8-10 weeks old, were delivered by the Institute of Laboratory Medicine, Łódź, Poland. The mice were fed a commercial, pelleted food and water ad libitum. The local ethics committee approved the study.

Reagents.

Compound I-A was synthesized as described above; Protopic® (tacrolimus) was from Astellas, Ireland; Elidel® (pimecrolimus) from Novartis; DMSO from Fluka; TDI, acetone, Evans blue, Trypan blue, Giemsa, May-Grünwald, haematoxylin, eosin, toluidine blue and formalin were from Sigma.

Immune Response to TDI.

The test was performed according to Yamamoto, *Eur. J. Pharmacol.*, 2006, 550, 166-172, with minor modifications. Mice were shaved on the abdomen (2×2 cm area) and after 24 h 100 μl of 3% TDI in acetone was applied through 3 consecutive days. After 14 days the reaction was elicited by application of 50 μl of 0.3% TDI on both sides of the ears. The procedure was repeated 5 times every 3 days. Ear thickness was measured using a spring caliper (Mitutoyo) 5 h and 24 h after each challenge with TDI.

Application of Compounds.

Compound I-A was applied topically in the form of 0.1% ointment on both sides of the ears (total volume of 100 μl-50 μl per ear), one hour after each challenge with TDI. The reference drugs were applied in a similar way.

Determination of Lymph Node Cell Numbers.

Superficial parotid, mandibular and accessory mandibular lymph nodes were isolated, homogenized by pressing against a stainless screen into PBS, washed 2× with PBS and re-suspended in PBS containing 0.2% Trypan blue. The total and nonviable cell numbers were counted using a light microscope and Bürker's hemocytometer.

Determination of Circulating Leukocyte Number and Blood Picture.

Mice were subjected to halothane anesthesia and bled from the retro-orbital plexus, followed by the cervical dislocation. The number of blood leukocytes was determined by dilution of blood in Turk's solution and counting the cells in a hemocytometer. Blood smears were prepared on microscope glass, dried and stained with Giemsa and May-Grünwald reagents. The smears were subsequently reviewed histologically. The cell numbers were presented per 1 μl and the blood cell compositions as a percentage of a given cell type.

Evans Blue Test.

Mice were given 1 mg of Evans blue in 0.2 ml of 0.9% NaCl, intravenously. After 30 min mice were sacrificed, the ears were cut off, weighed and immersed in 50 μl of 1M KOH for 18 h at 37° C. The dye was extracted from the ears using 450 μl of 0.2 M phosphate acid and acetone (5:13 ratio). The samples were centrifuged at 3,000 rpm for 15 min. The optical densities (OD) of the supernatants were measured at 630 nm. The amount of Evans blue (g/ml) was determined based on a standard curve. The results were presented as the amount of Evans blue per 100 mg of wet tissue. Mice treated only with the eliciting dose of antigen served as a background control.

Histological Analysis.

The auricles were fixed in 4% formalin solution for 48 h, washed for 24 h, dehydrated in an alcohol series and embedded in paraffin. The paraffin blocks were sliced in a Micron HM310 microtome into 6 m sections. The sections were stained with haematoxylin and eosin and with toluidine blue. Histological analysis was performed using a Nikon Eclipse 801light microscope. Morphometric estimations of neutrophils, macrophages, lymphocytes and mast cells in the perivascular and subepithelial connective tissue were performed on the histological slides containing cross-sections of auricles. Cells were counted on an area of 0.07 mm² at 400× magnification. Morphometric analysis was performed using an imagine software NIS-Elements (Nikon). For every preparation examined, 25 enumerations of neutrophils, macrophages, lymphocytes and mast cells were carried out.

Statistics.

The results in FIGS. 10A and 10B are presented as mean values ±standard error (SE). Brown-Forsyth's test was used to determine the homogeneity of variance between the groups. When the variance was homogenous, analysis of variance (one-way ANOVA) was applied, followed by post hoc comparisons with the Tukey's test to estimate the significance of the differences between groups. Nonparametric data were evaluated with the Kruskal-Wallis' analysis of variance, as indicated in the text. Significance was determined at P<0.05. Statistical analysis was performed using STATISTICA 7 for Windows.

Results

Effects of the Compounds on the Ear Thickness.

The humoral immune response to TDI was elicited as described in the Methods. Mice were treated topically with the tetrapeptide (formula I-A, labeled 4B8M in FIGS. 10A and 10B) and the reference compounds one hour after each challenge with antigen. The effects of the treatments are presented in FIGS. 10A and 10B, which show ear thickness measure 5 h (FIG. 10A) and 24 h (FIG. 10B) after administration on the day of the test indicated in the figure. Control responses to TDI gradually elevated after each antigen challenge (best seen in the 5 h measurement). The results showed differentiated efficacy of the compounds in reducing the ear swelling.

FIG. 10A: Day 14: Control vs 4B8M P=0.0005; Control vs Protopic® P=0.0002; Control vs Elidel® P=0.0152; 4B8M vs Protopic® NS; 4B8M vs Elidel® NS; Day 17: Control vs 4B8M P=0.0001; Control vs Protopic® P=0.0001; Control vs Elidel® P=0.0377; 4B8M vs Protopic® NS; 4B8M vs Elidel® P=0.0002; Day 20: Control vs 4B8M P=0.0001; Control vs Protopic® P=0.0001; Control vs Elidel® NS; 4B8M vs Protopic® NS; 4B8M vs Elidel® P=0.0001; Day 23: Control vs 4B8M P=0.0001; Control vs Protopic® P=0.0001; Control vs Elidel® NS; 4B8M vs Protopic® NS; 4B8M vs Elidel® P=0.0001; Day 27: Control vs 4B8M P=0.0001; Control vs Protopic® P=0.0001; Control vs Elidel® P=0.0001; 4B8M vs Protopic® NS; 4B8M vs Elidel® P=0.0001 (ANOVA). FIG. 10B: Day 14: Control vs 4B8M P=0.0001; Control vs Protopic® P=0.0001; Control vs Elidel® P=0.0004; 4B8M vs Protopic® NS; 4B8M vs Elidel® NS; Day 17: Control vs 4B8M P=0.0001; Control vs Protopic® P=0.0023; Control vs Elidel® P=0.0004; 4B8M vs Protopic® NS; 4B8M vs Elidel® NS; Day 20: Control vs 4B8M P=0.0006; Control vs Protopic® P=0.0003; Control vs Elidel® P=0.0156; 4B8M vs Protopic® NS; 4B8M vs Elidel® NS; Day 23: Control vs 4B8M P=0.0001; Control vs Protopic® P=0.0001; Control vs Elidel® P=0.0039; 4B8M vs Protopic® NS; 4B8M vs Elidel® P=0.0027; Day 27: Control vs 4B8M P=0.0001; Control vs Protopic® P=0.0001; Control vs Elidel® P=0.0023; 4B8M vs Protopic® NS; 4B8M vs Elidel® P=0.0016 (ANOVA).

Effects of the Compounds on Permeability of Skin Vessels:

The permeability of capillary blood vessels is presented in FIG. 11, which shows the permeability of capillary blood vessels in the Evans blue test. The procedure, as described above, was performed 24 h after the fifth challenge with TDI (on day 28). As shown in the FIG. 11, the rates of blood vessel permeability were strictly correlated with the effects of the compounds on ear thickness in the respective mouse groups. Statistics: BG vs Control P=0.0248; Control vs 4B8M (I-A) P=0.030; Control vs Protopic® NS; Control vs Elidel® NS; 4B8M (I-A) vs Protopic® NS; 4B8M (I-A) vs Elidel® NS (ANOVA).

Effects of the Compounds on Number of Cells in Draining Lymph Nodes:

FIG. 12 shows the total number of cells in the draining lymph nodes. As shown in FIG. 12, the treatment of mice with compound I-A resulted in a reduction of the lymph node cell numbers almost to the background levels (non-sensitized mice). Statistics: BG vs Control P=0.0001; Control vs 4B8M (I-A) P=0.0001; Control vs Protopic® NS; Control vs Elidel® NS; 4B8M (I-A) vs Protopic® P=0.0183; 4B8M (I-A) vs Elidel® P=0.0001 (ANOVA of Kruskal-Wallis).

Effects of the Compounds on the Numbers of Circulating Leukocytes.

FIG. 13 shows the effects of the compounds on the numbers of circulating leukocytes; the application of the studied preparations lowered the numbers of circulating leukocytes to the levels observed in control, unsensitized mice. Statistics: BG vs Control P=0.0001; Control vs 4B8M (I-A) P=0.0001; Control vs Protopic® P=0.0001; Control vs Elidel® P=0.0001; 4B8M (I-A) vs Protopic® NS; 4B8M (I-A) vs Elidel® NS (ANOVA).

Effects of compounds on blood cell composition: The blood composition in control mice with fully developed reaction to TDI was characterized by an increased content of neutrophils and eosinophils compared to control, background mice (FIG. 14, which shows a breakdown of the types of leukocytes in each case). The blood picture was normalized upon application of 4B8M (I-A) (a reduction of neutrophil and eosinophil contents) but not following administration of Protopic® or Elidel®. Statistics: Bands (B): BG vs Control NS; Control vs 4B8M (I-A) NS; Control vs Protopic® P=0.0500; Control vs Elidel® P=0.0500; 4B8M (I-A) vs Protopic® NS; 4B8M vs Elidel® NS (ANOVA of Kruskal-Wallis); Segments (S): BG vs Control P=0.0131; Control vs 4B8M (I-A) NS; Control vs Protopic® NS; Control vs Elidel® NS; 4B8M (I-A) vs Protopic® P=0.0163; 4B8M (I-A) vs Elidel® NS (ANOVA of Kruskal-Wallis); Eosinophils (E): BG vs Control P=0.0001; Control vs 4B8M (I-A) P=0.0001; Control vs Protopic® NS; Control vs Elidel® NS; 4B8M (I-A) vs Protopic® NS; 4B8M vs Elidel® P=0.0146 (ANOVA of Kruskal-Wallis); Lymphocytes (L): BG vs Control P=0.0001; Control vs 4B8M (I-A) P=0.0043; Control vs Protopic® NS; Control vs Elidel® NS; 4B8M (I-A) vs Protopic® P=0.0345; 4B8M (I-A) vs Elidel® NS (ANOVA of Kruskal-Wallis).

The Effects of the Compounds on Cell Composition in the Auricles:

FIG. 15 provides morphometric data on the number and composition of cells in the auricles. The composition of cell types within the auricles differed among the studied mouse groups is presented in FIG. 15. The predominant, residing cell types in control non-sensitized mice are mastocytes and neutrofils (10 and 5 cells per the analyzed area, respectively). In sensitized, control mice, untreated with the therapeutics, the number of mastocytes increased twofold and neutrophils almost 5-fold (20 and 23 cells, respectively). Protopic® and Compound I-A were effective in reducing the cell numbers to 14 and 14.8. Statistics: Ne (neutrophils): BG vs Control P=0.0001; Control vs 4B8M (I-A) P=0.0151; Control vs Protopic® P=0.0001; Control vs Elidel® NS; 4B8M vs Protopic® NS; 4B8M (I-A) vs Elidel® P=0.0003 (ANOVA of Kruskal-Wallis); MØ (macrophages): BG vs Control P=0.0144; Control vs 4B8M (I-A) NS; Control vs Protopic® NS; Control vs Elidel® P=0.0255; 4B8M vs Protopic® NS; 4B8M (I-A) vs Elidel® P=0.0031 (ANOVA of Kruskal-Wallis); L (lymphocytes): BG vs Control NS; Control vs 4B8M (I-A) NS; Control vs Protopic® NS; Control vs Elidel® P=0.0023; 4B8M vs Protopic® NS; 4B8M (I-A) vs Elidel® P=0.0001 (Anova of Kruskal-Wallis); Mast (mastocytes): BG vs Control P=0.0001; Control vs 4B8M (I-A) NS; Control vs Protopic® P=0.0001; Control vs Elidel® NS; 4B8M (I-A) vs Protopic® NS; 4B8M (I-A) vs Elidel® P=0.0001 (ANOVA of Kruskal-Wallis).

EXAMPLE 8—IN VITRO TESTS OF COMPOUNDS I-B AND I-C

Methods

Proliferative Response of Splenocytes to Concanavalin a (ConA):

Spleens were pressed against a plastic screen into 0.83% $NH_4Cl$ solution to lyse erythrocytes (5 min incubation at room temperature). The cells were then washed twice with Hanks' medium, passed through glass wool column to remove debris, and re-suspended in the culture medium, referred to below as the "culture medium", consisting of RPMI-1640, supplemented with 10% of fetal calf serum, L-glutamine, sodium pyruvate, 2-mercaptoethanol, streptomycin and penicillin (100 µg/ml). The cells were then distributed into 96-well flat-bottom tissue culture plates (Nunc) at a density of $2\times10^5$ cells/100 µl/well. Con A (2.5 µg/ml) was added to induce cell proliferation. The compounds were added to the cultures at doses of 1-100 µg/ml. After a three-day incubation, cell proliferation was determined using the colorimetric MTT method (Hansen M B, *J Immunol Methods*, 1989, 119, 203-210). The results were presented as the mean optical density (OD) at 550 nm ±SE from quadriplicate determinations (wells).

Secondary Humoral Immune Response In Vitro to Sheep Erythrocytes (SRBC):

Mice were sensitized intraperitoneally with 0.2 ml of 5% (v/v) SRBC suspension. After four days spleens from these mice were isolated and single cell suspensions prepared by homogenization in PBS solution. After washing the cells in PBS by centrifugation, the cells were re-suspended in the culture medium at a density of $5\times10^6$ cells/ml. The cells were subsequently distributed to 24-well culture plates in 1 ml aliquots and 0.05 ml of 0.005% SRBC was added as the antigen to each well. The compounds were added to the cultures at the beginning of the four-day incubation period at concentration ranges of 1-100 µg/ml. The number of antibody-forming cells (AFC) in the cultures was determined using a method of local hemolysis in agar gel according to Mishell et al., *J Exp Med*, 1967, 126, 423-442.

Toxicity Test:

Splenocytes, at a density of $2\times10^5$ cells/100 µl/well, re-suspended in the culture medium, were cultured for 24 h in a cell culture incubator with the compounds (1-100 µg/ml). Cell survival was determined by MTT colorimetric method. The results were presented as mean optical density (OD) at 550 nm from 4 wells. The viability of cells in respective compound concentrations was compared to appropriate DMSO control groups (100% survival), corresponding to respective compound concentrations.

Results

At 50-100 µg/ml concentrations, compound I-C showed a strong inhibitory effect on concanavalin A-induced mouse splenocyte proliferation. At 100 µg/m, this compound showed 70% toxicity to splenocytes. At 10 µg/m and 100 µg/m, compound I-C showed 33% and 80% suppression, respectively, in the model of in vitro humoral immune response to SRBC in mouse splenocyte cultures. In the model of delayed type hypersensitivity to ovalbumin, compound I-C showed 26.9% inhibition at the dose of 100 µg, compared to 72.7% inhibition by compound I-A.

At 100 µg/ml concentration, compound I-B demonstrated a weak antiproliferative effect on concanavalin A-induced splenocyte proliferation; no such effect was observed at lower concentrations. Compound I-B had 30% toxicity at this concentration.

EXAMPLE 9—CARRAGEENAN-INDUCED FOOT-PAD EDEMA TEST AND CARRAGEENAN AIR-POUCH TEST

Figure 17A:
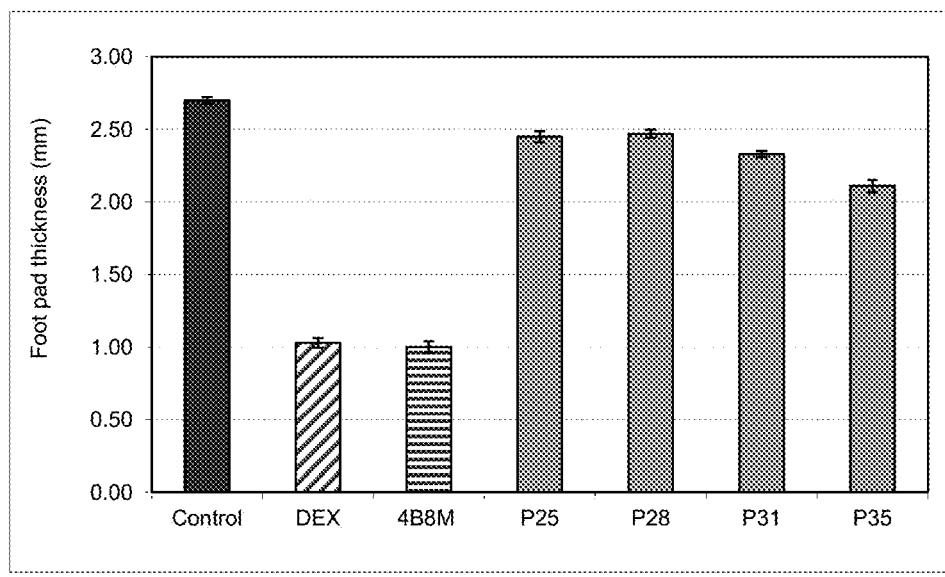
Figure 17B:
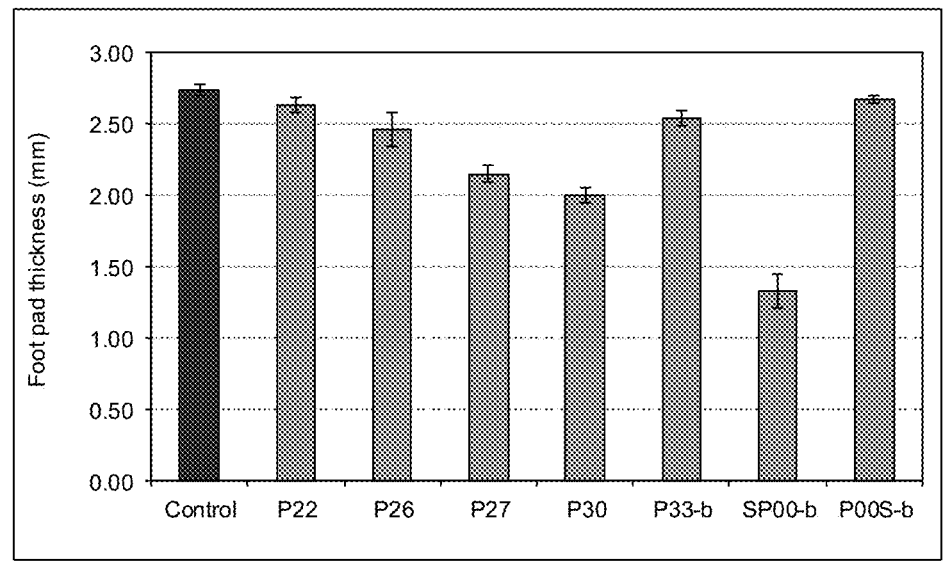
Figure 17C:
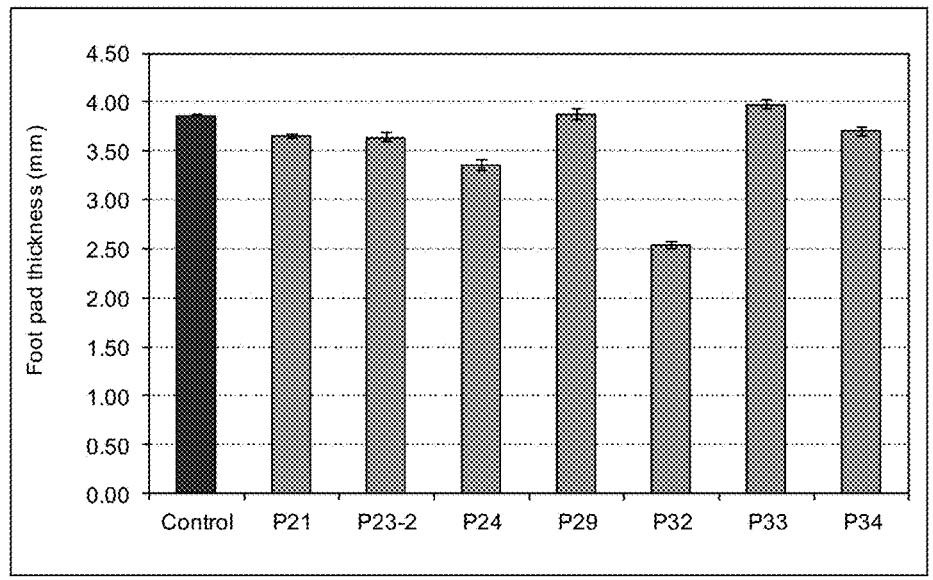

Carrageenan-Induced Foot-Pad Edema Test:

In this and the air-pouch test, 1.5 mg peptide was dissolved in 300 µl of DMSO, then in 0.9% NaCl to achieve the desired dose (250 µg/0.2 ml or 100 µg/0.2 ml). Carrageenan (Sigma) was dissolved in 0.9% aqueous NaCl (overnight). 50 µl of 2% carrageenan solution was injected intradermally into hind foot pads. The peptides were given in a single 250 µg dose (0.2 ml) per mouse intraperitoneally (i.p.), 30 min before carrageenan administration. Dexamethasone (DEX) (Dexaven, Polfa, Poland), a reference drug, was given i.p. in dose 25 µg per mouse. Control mice were administered i.p. appropriately diluted solvent (DMSO in aqueous NaCl) instead of peptides. The foot pads of "background" (BG) mice were injected with 50 µl of 0.9% aqueous NaCl. Foot pad edema was measured with a spring caliper, 2 h, 3 h and 4 h after administration of carrageenan. The results are presented in FIGS. 17A, 17B and 17C as mean values of the antigen-specific increase of the foot pad thickness measured in 5 mice in each experimental group and expressed in mm ±SE (only results from measurements 4 h following administration of carrageenan are presented in figures). Statistics: FIG. 17A: Control vs: DEX P=0.0001; 4B8M P=0.0001; P25 NS (P=1.0000); P28 NS (P=1.0000); P31 NS (P=0.0528); P35 P=0.0008 (ANOVA of Kruskal-Wallis); FIG. 17B: Statistics: Control vs: P22 NS (P=1.0000); P26 NS (P=1.0000); P27 P=0.0050; P30 P=0.0004; P33-b NS (P=1.0000); SP00-b P=0.0001; P00S-b NS (P=1.0000) (ANOVA of Kruskal-Wallis); FIG. 17C: Statistics: Control vs: P21 P=0.0147; P23-2 P=0.0083; P24 P=0.0001; P29 NS (P=0.9999); P32 P=0.0001; P33 NS (P=0.6806); P34 NS (P=0.1920) (ANOVA).

Carrageenan Air-Pouch Test:

Air pouches were formed by subdermal injection into the dorsal region (in a halothane anesthesia) of 5 $cm^3$ of air (needle 23G x 11/4, 5 ml syringe). On day 3 the air pouches were given an additional 2 ml of air and an inflammatory process was elicited by an intra-pouch injection of 1% of carrageenan in 0.5 ml of 0.9% aqueous NaCl. The peptides were given i.p. at a dose of 100 µg one hour before carrageenan injection into the air pouch. The mice from the "background" (BG) group were given 0.9% aqueous NaCl i.p. and 0.9% aqueous NaCl into the air pouches. Control mice were given appropriately diluted DMSO i.p. and carrageenan into the air pouches. 24 h after carrageenan injection, the mice were sacrificed by cervical dislocation, the air pouches were supplemented with 1 ml of 0.9% aqueous NaCl and the exudates from the air pouches were aspirated using a syringe. The exudates were diluted with 0.9% aqueous NaCl and the cells were counted in a Bürker hemocytometer. Data are presented in FIGS. 18A and 18B as the mean values from 10 mice/group (cell number×10$^6$ per mouse) ±SE. Then the cells were centrifuged and 0.1 ml of the supernatant was saved for TNF-α determination (see Determination of TNF-α activity, above). The cell pellets were used to perform smears on microscopic glasses, which were stained with Giemsa and May-Grünwald reagents for evaluation of mast cell degranulation. Cell analysis was performed by a histologist using a light microscope and 1000× magnification. The content of intact and degranulated mast cells is given in percentage (mean values from 10 mice/group) ±SE. Statistics: FIG. 18A: BG vs Control P=0.0000; Control vs: DEX P=0.0034; 4B8M P=0.0005; P22 NS (P=0.7275); P26 P=0.0032; P27 NS (P=0.0659); P35 NS (P=1.0000) (ANOVA of Kruskal-Wallis); FIG. 18B: Control vs: P21 NS (P=0.322); P23-2 P=0.0020; P24 P=0.0001; P25 P=0.0418; P28 NS (P=0.3502); P29 NS (P=0.0582); P30 P=0.0006; P31 P=0.0078; P32 P=0.0340; P33 NS (P=0.9993); P34 NS (p=0.0566) (ANOVA).

Although the foregoing invention has been described in some detail for purposes of illustration, it will be readily apparent to one skilled in the art that changes and modifications may be made without departing from the scope of the invention described herein.

What is claimed is:

1. A method of treating an immune-mediated disease selected from psoriasis and dermatitis, comprising administering to a patient in need thereof an efficacious amount of a compound of formula I:

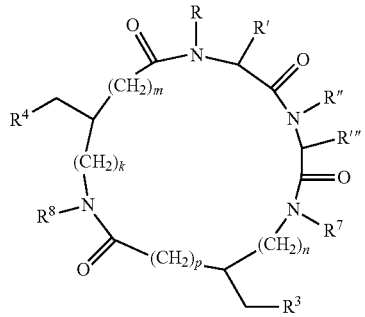

I wherein
k, m, n and p are each independently 0, 1 or 2, provided that at least one of k, m, n and p is not zero;
R is selected from H and $C_{1-3}$ alkyl and R' is selected from H and optionally substituted $C_{1-3}$ alkyl, or, when taken together, R and R', together with the peptide backbone atoms to which they are attached, form an optionally substituted 5- or 6-membered ring or an optionally substituted 9- or 10-membered bicyclic ring, said 5- or 6-membered ring or said 9- or 10-membered bicyclic ring being saturated or unsaturated;
R" is selected from H and $C_{1-3}$ alkyl and R'" is selected from H and optionally substituted $C_{1-3}$ alkyl, or, when taken together, R" and R'", together with the peptide backbone atoms to which they are attached, form an optionally substituted 5- or 6-membered ring or an optionally substituted 9- or 10-membered bicyclic ring, said 5- or 6-membered ring or said 9- or 10-membered bicyclic ring being saturated or unsaturated;
$R^7$ and $R^8$ are each H; and
$R^3$ and $R^4$ are each independently selected from aryl ($C_y$alkyl), substituted aryl($C_y$alkyl), heteroaryl-($C_y$alkyl) and substituted heteroaryl($C_y$alkyl), wherein y is 0, 1 or 2; or $R^3$ may be taken together with $R^7$ and the intervening carbon and nitrogen atoms to form a 5- or 6-membered ring or a 9- or 10-membered cyclic ring, which 5- or 6-membered ring or a 9- or 10-membered bicyclic ring may contain unsaturation, and $R^4$ may taken together with $R^8$ and the intervening carbon and nitrogen atoms to form a 5- or 6-membered ring or a 9- or 10-membered bicyclic ring, which 5- or 6-membered ring or a 9- or 10-membered bicyclic ring may be contain unsaturation;

or a pharmaceutically acceptable salt thereof.

2. The method according to claim 1 wherein the compound is selected from the group consisting of:

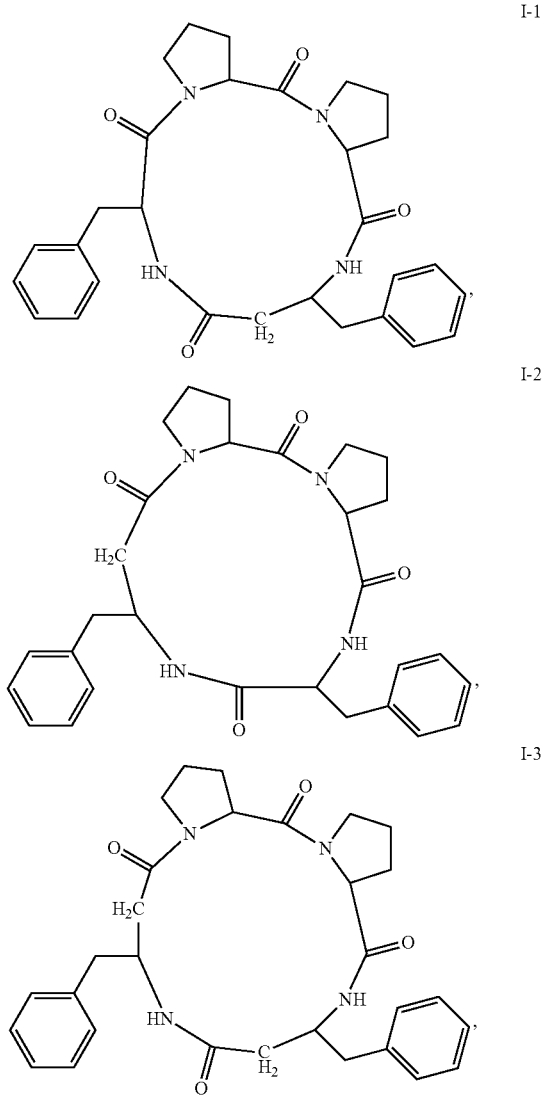

I-4
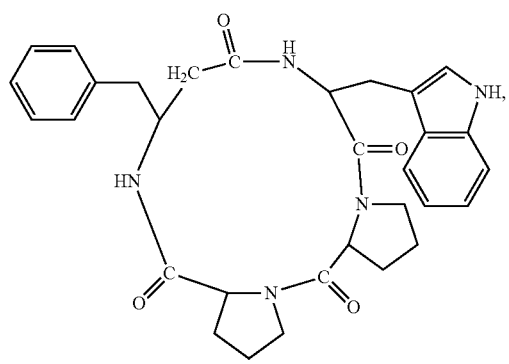
I-8
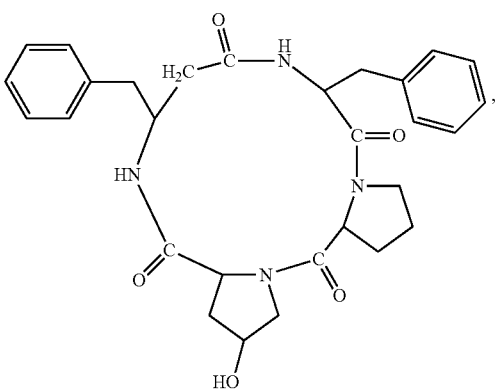
I-5
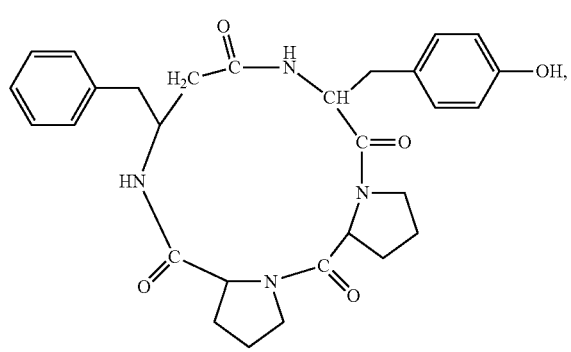
I-9
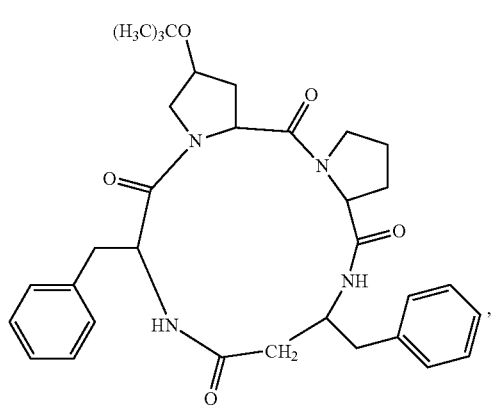
I-6
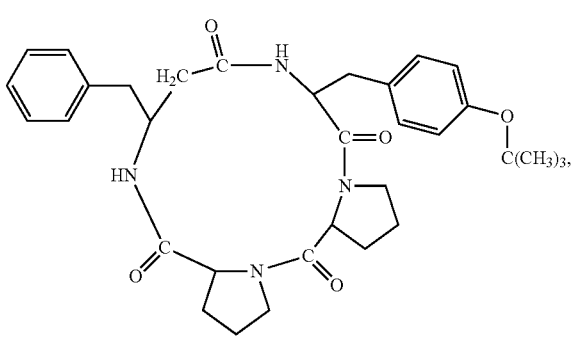
I-10
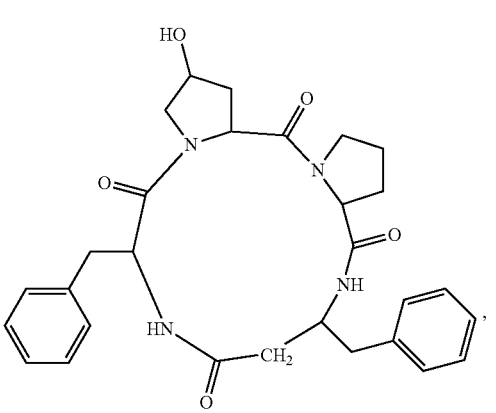
I-7
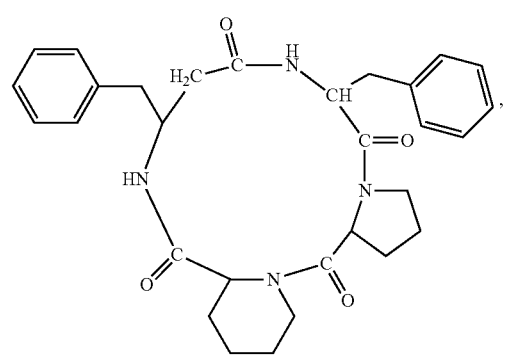
I-11
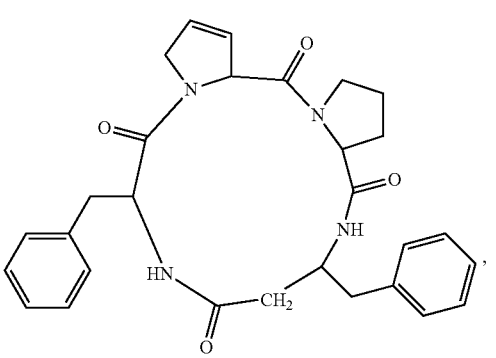

I-12
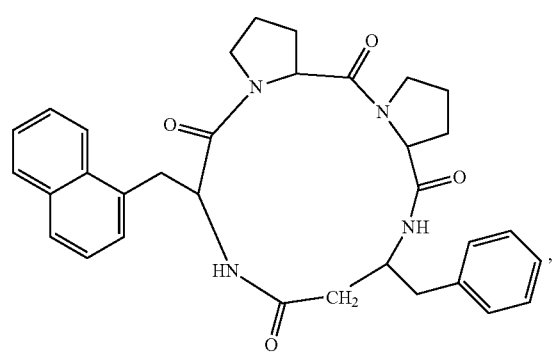
I-13
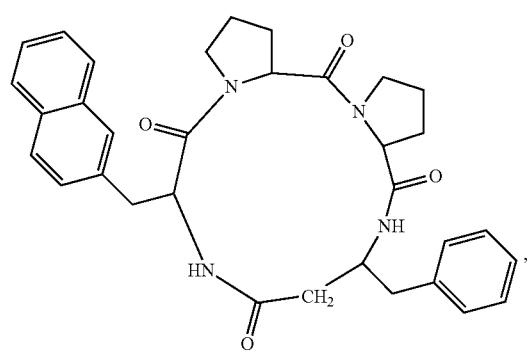
I-14
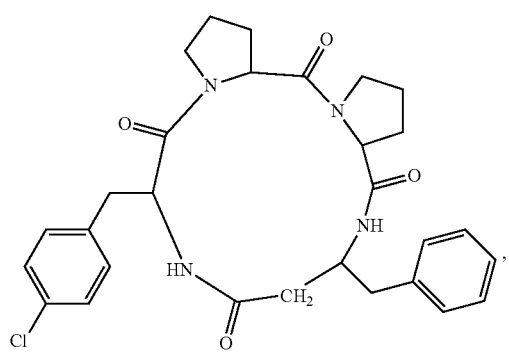
I-15
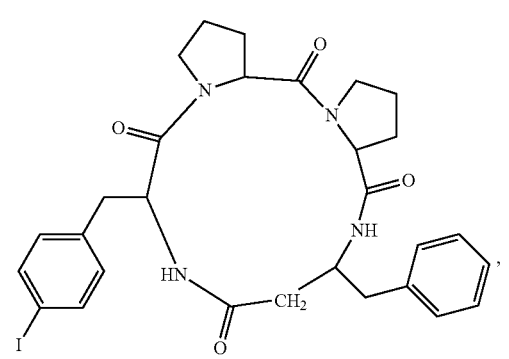
I-16
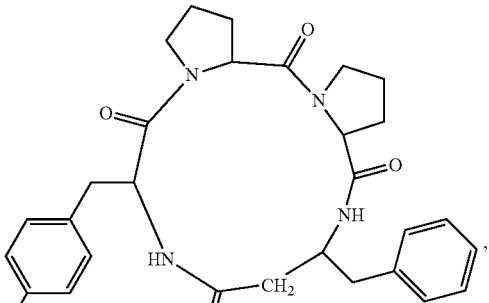
I-17
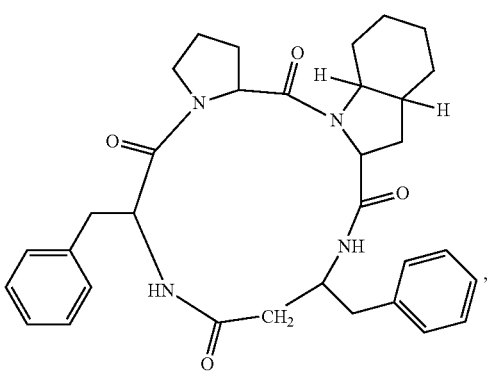
I-18
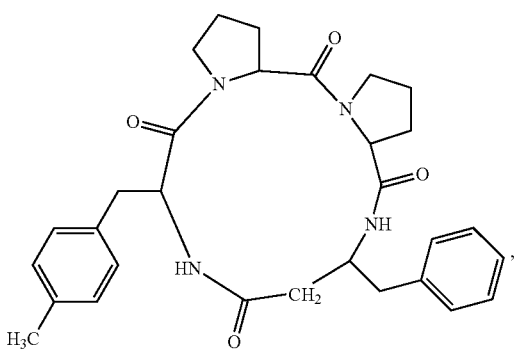
I-19
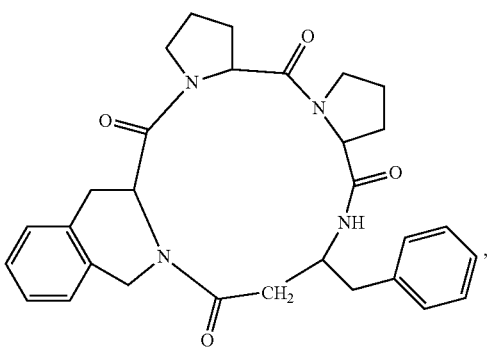

-continued
I-20
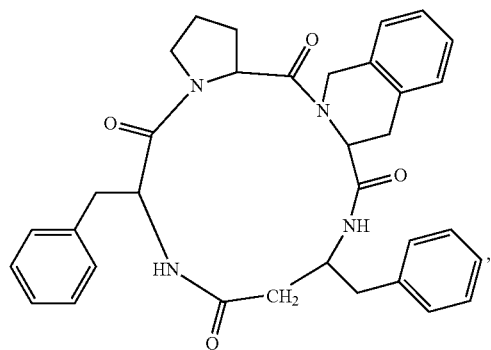
I-21
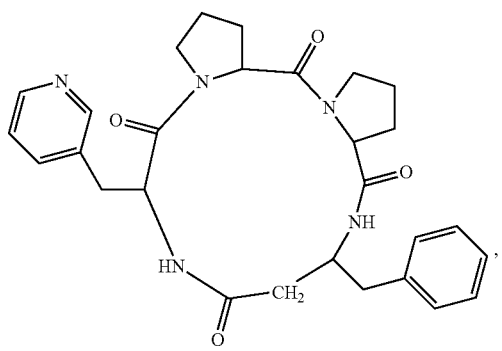
I-22
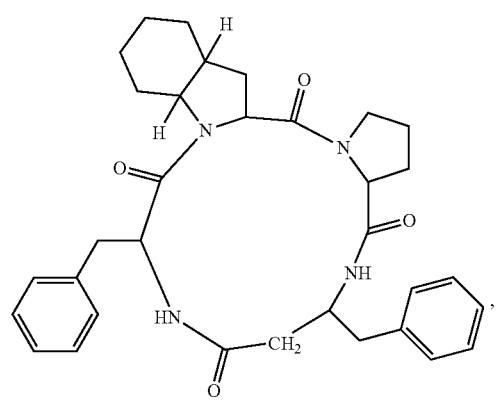
I-23
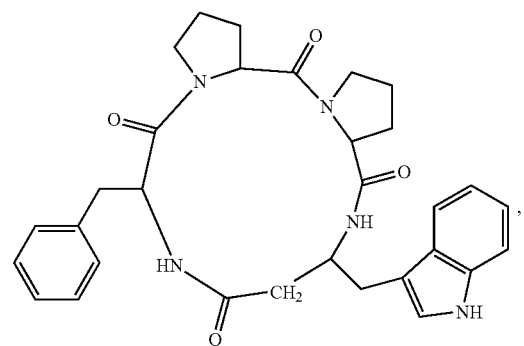
-continued
I-24
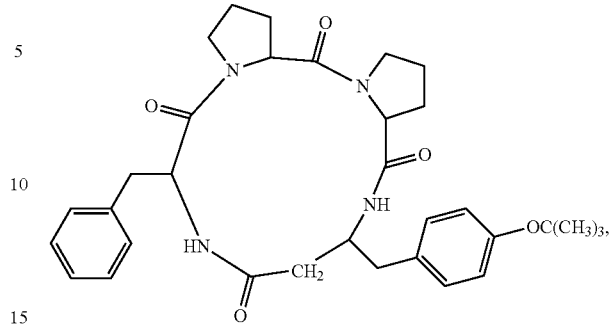
I-25
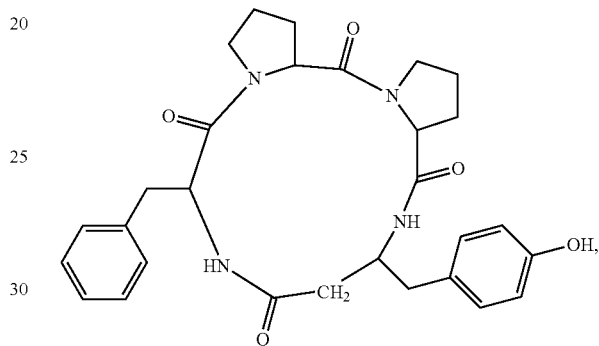
I-26
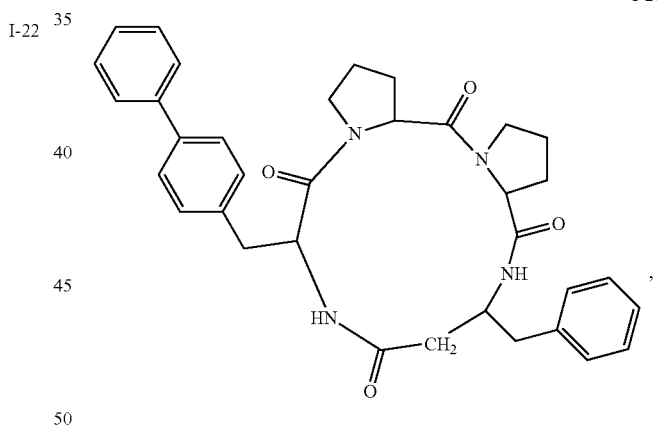
I-27
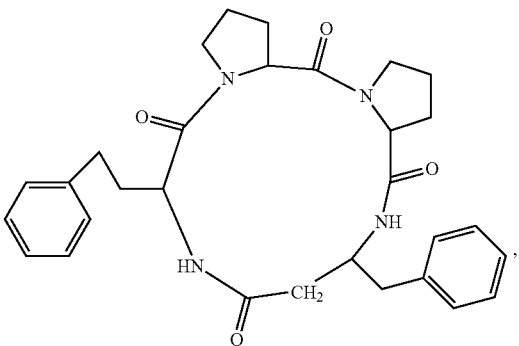

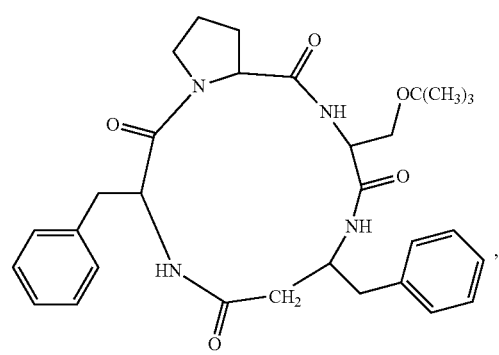
I-28
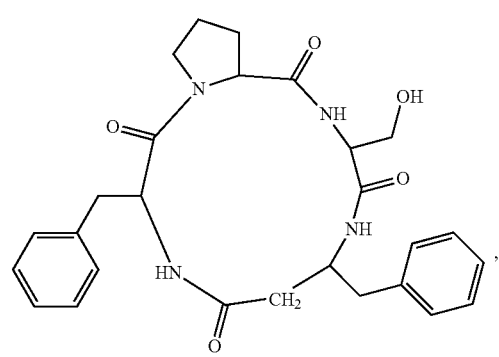
I-29
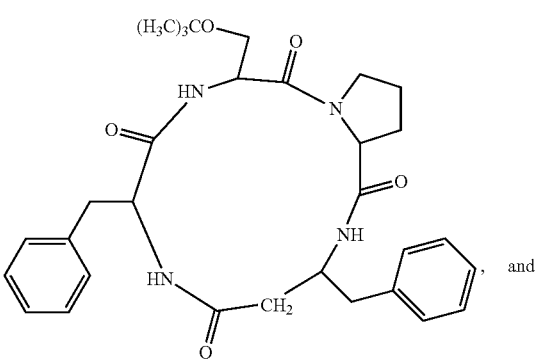
I-30
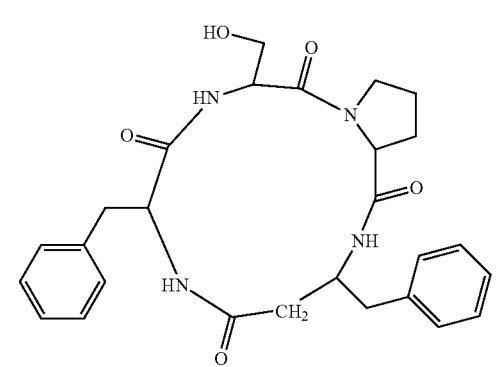
I-31
or a pharmaceutically acceptable salt thereof.
3. The method according to claim 2 where the compound is of formula I-1, or a pharmaceutically acceptable salt thereof.
4. The method according to claim 2 wherein the compound is selected from the group consisting of:
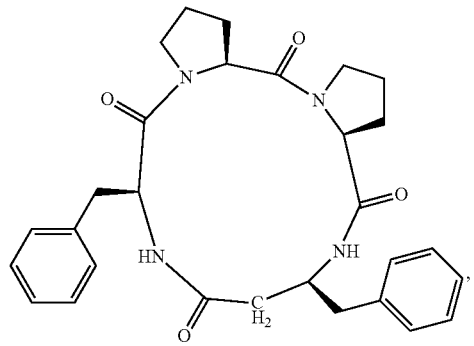
I-A
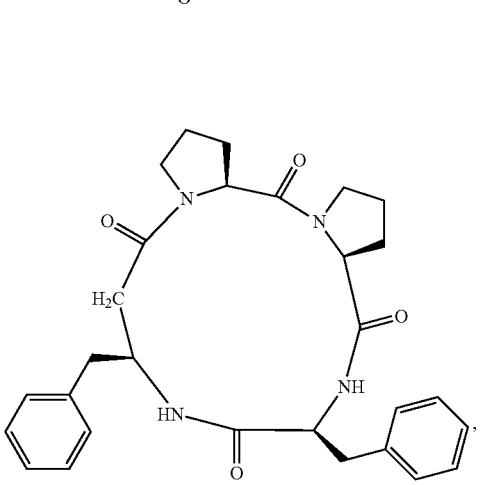
I-B
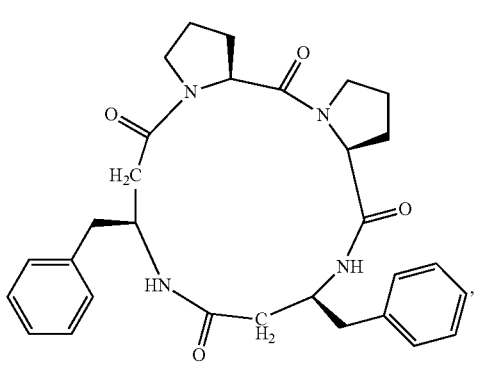
I-C
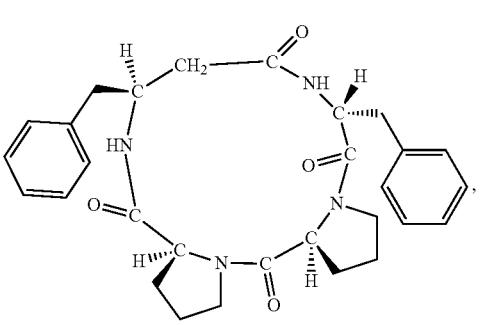
I-D I-E
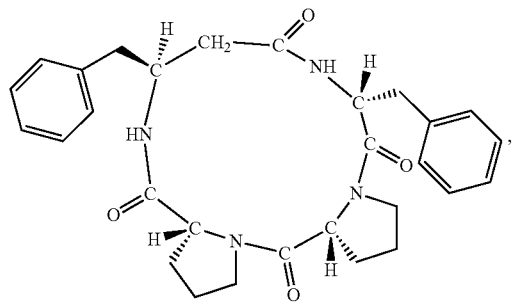
I-F
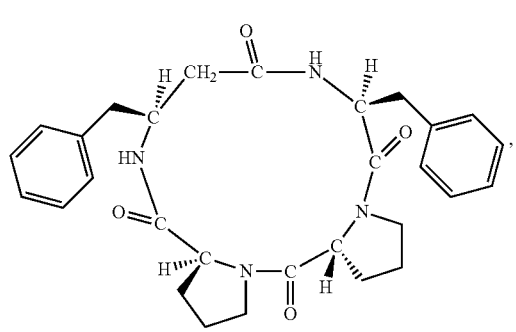
I-G
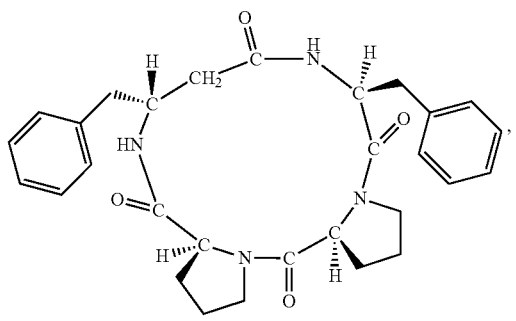
I-H
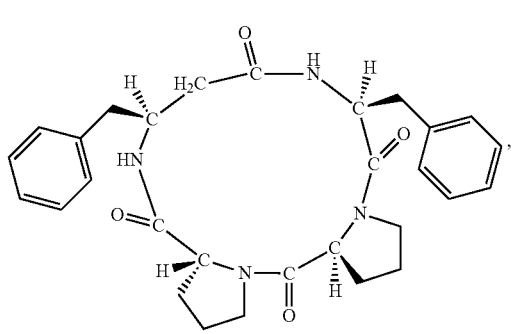
I-J
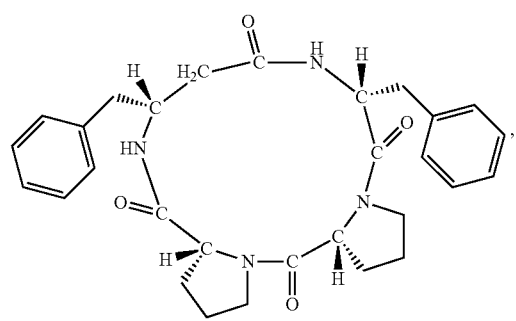
I-K
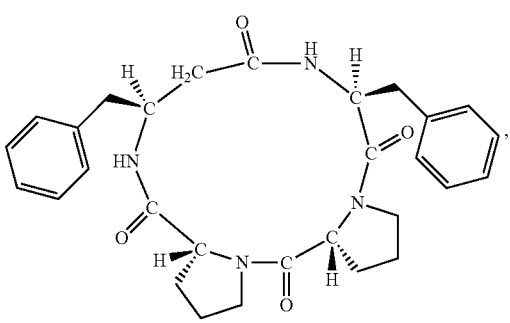
I-L
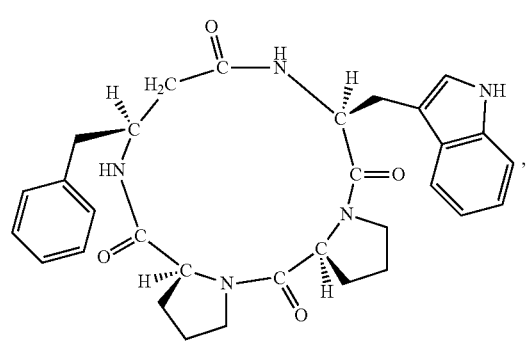
I-M
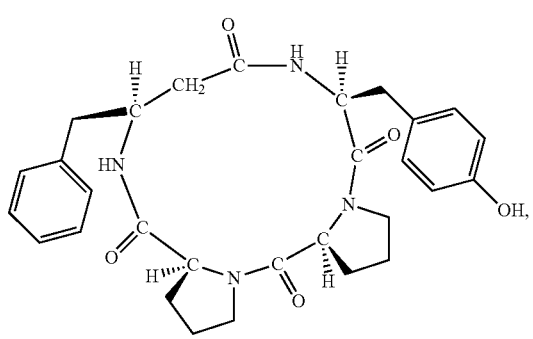
I-N
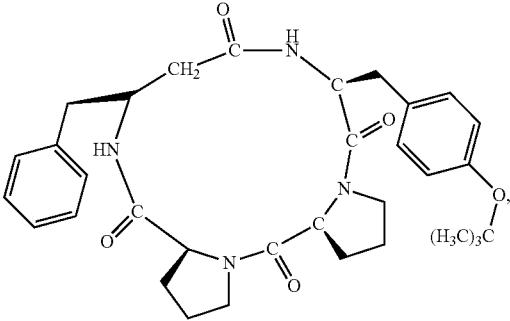

I-O
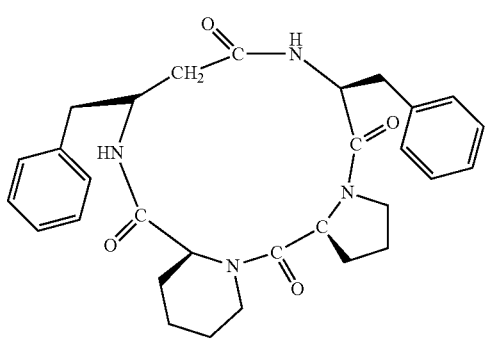
I-P
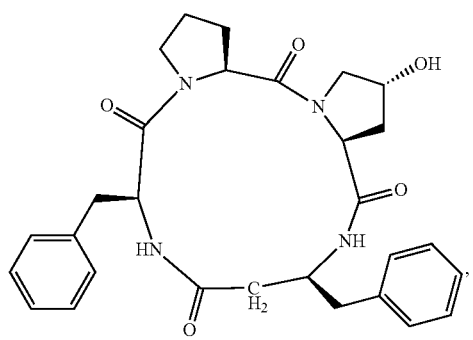
I-Q
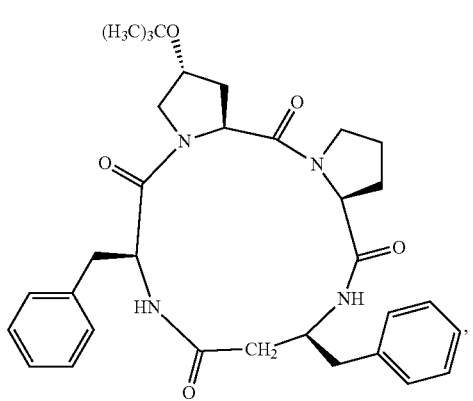
I-R
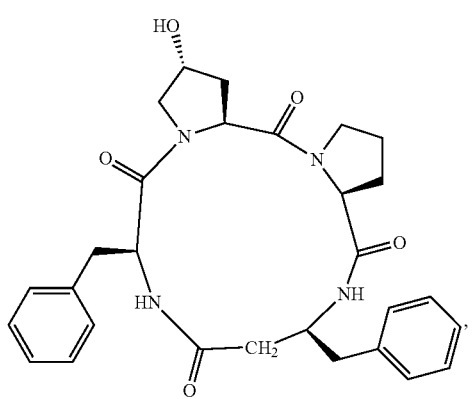
I-S
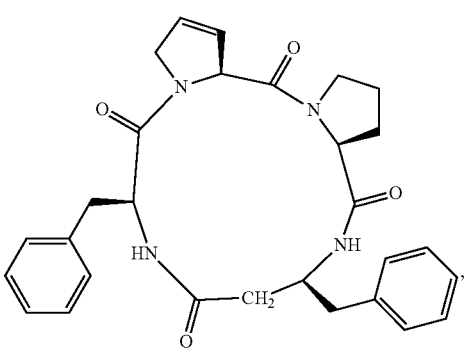
I-T
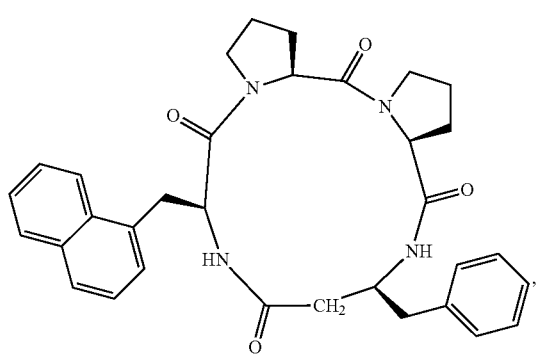
I-U
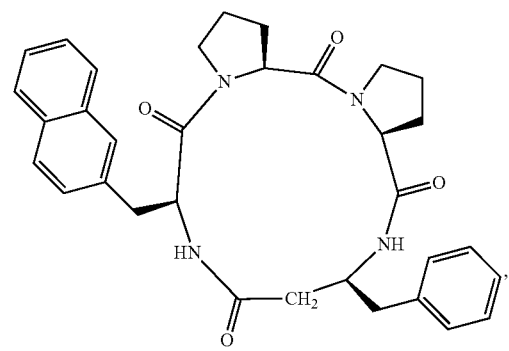
I-V
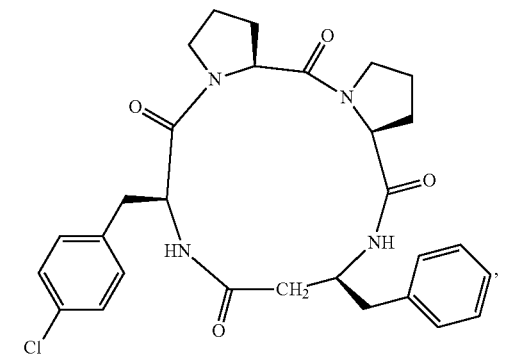

-continued
I-W
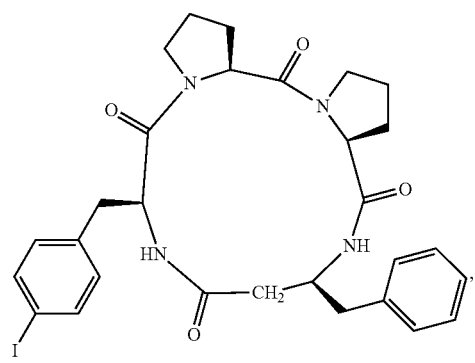
I-X
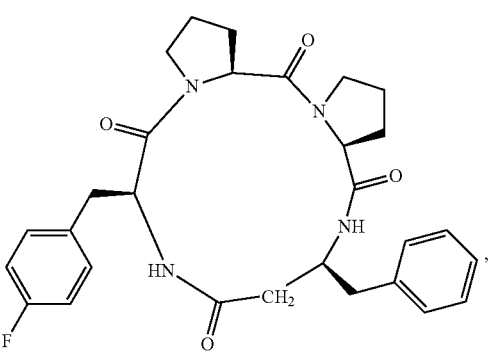
I-Y
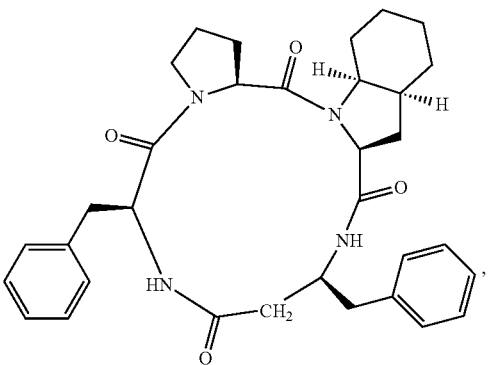
I-Z
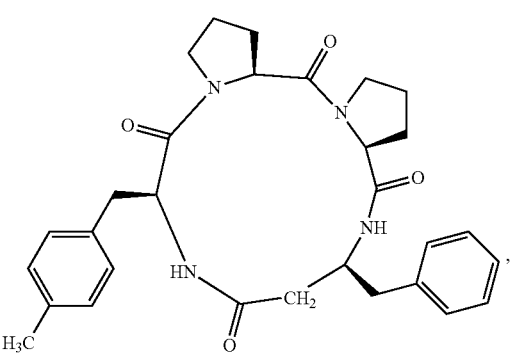
-continued
I-AA
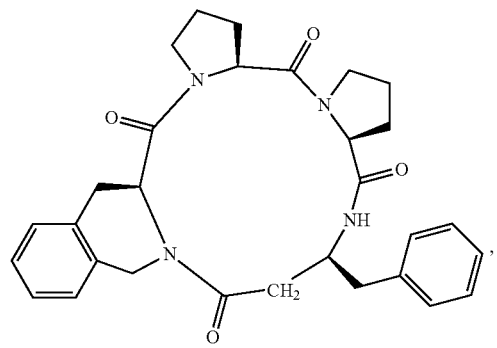
I-AB
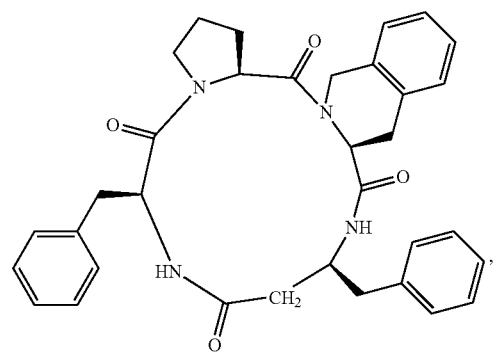
I-AC
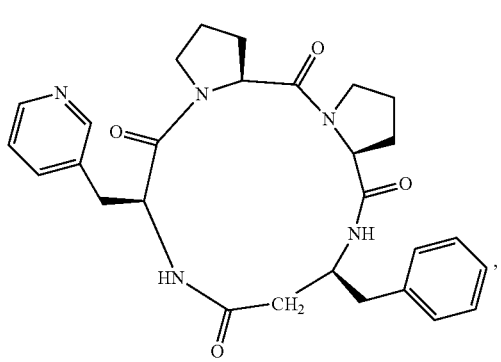
I-AD
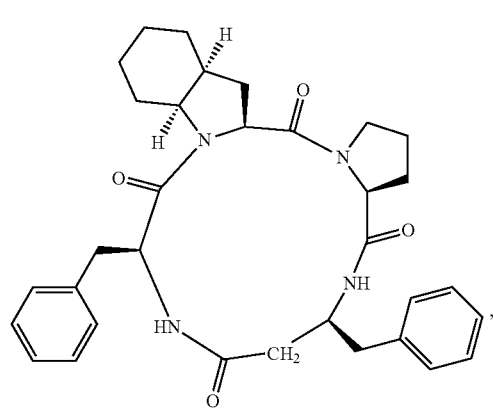

I-AE
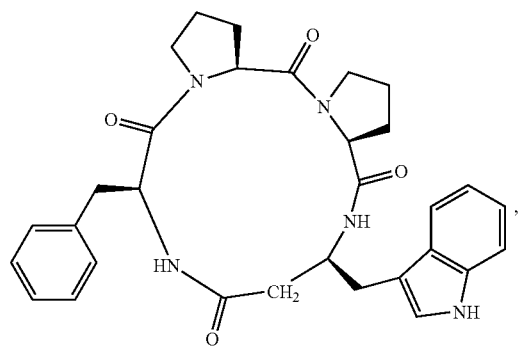
I-AF
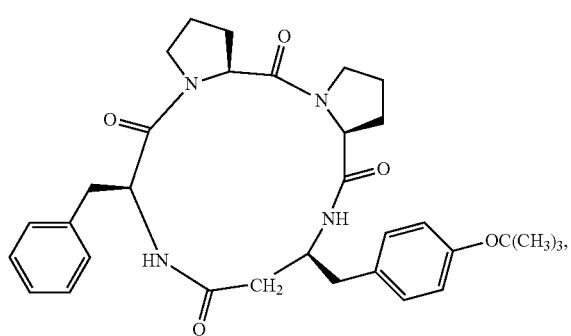
I-AG
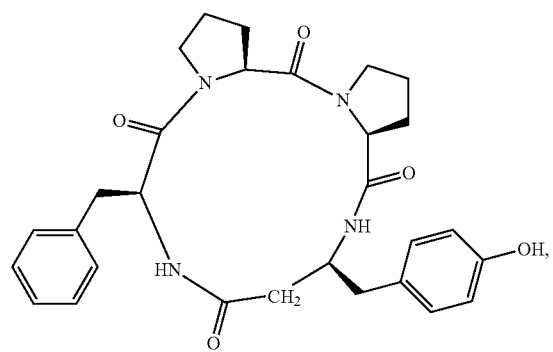
I-AH
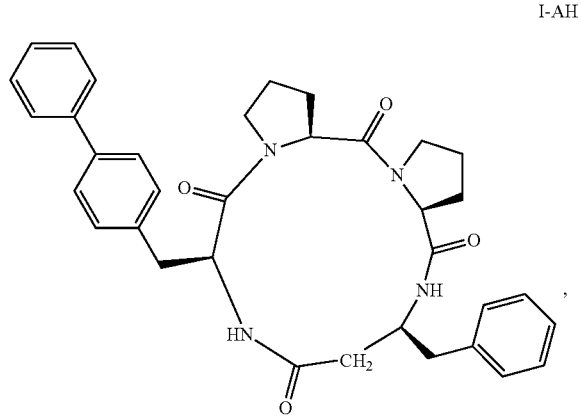
I-AI
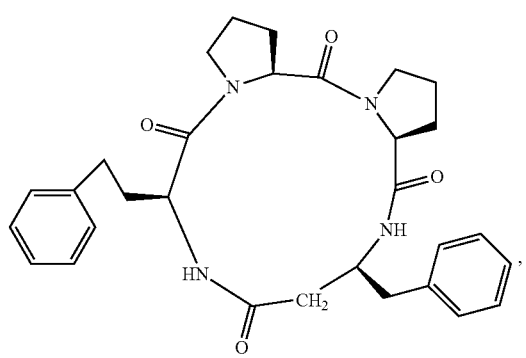
I-AJ
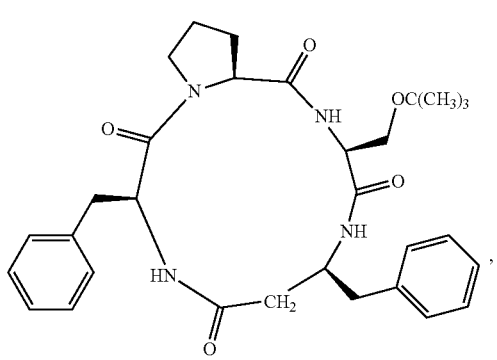
I-AK
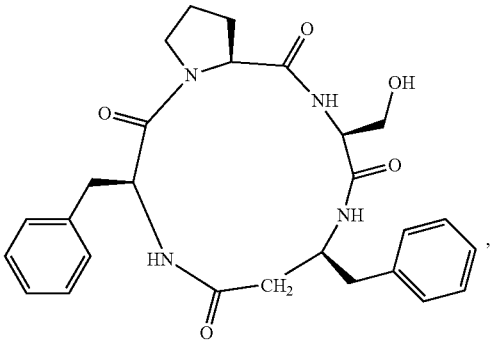
I-AL
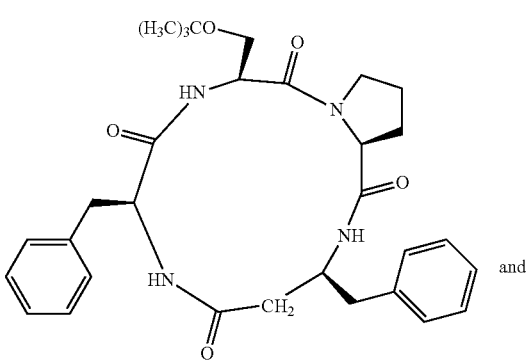
and I-AM
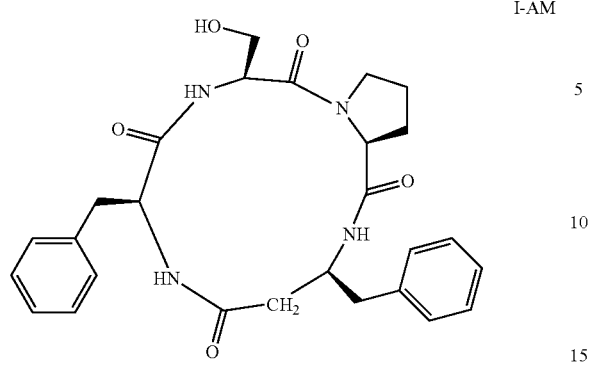
or a pharmaceutically acceptable salt thereof.
5. The method according to claim 4 wherein the compound is of formula I-A, or a pharmaceutically acceptable salt thereof.
* * * * *